United States Patent
Herold et al.

(10) Patent No.: US 7,687,495 B2
(45) Date of Patent: Mar. 30, 2010

(54) SUBSTITUTED PIPERIDINES

(75) Inventors: Peter Herold, Basel (CH); Robert Mah, Muttenz (CH); Vincenzo Tschinke, Binningen (CH); Christiane Marti, Rheinfelden (CH); Stefan Stutz, Basel (CH); Stjepan Jelakovic, Freiburg (DE); Zenon D. Konteatis, Chatham Township, NJ (US); Jennifer L. Ludington, Lansdale, PA (US); Michael Quirmbach, Basel (CH); Aleksandar Stojanovic, Basel (CH); Dirk Behnke, Grenzach-Wyhlen (DE); Frank Hollinger, Wayne, PA (US)

(73) Assignee: Speedel Experimenta AG, Allschwil (CH)

( * ) Notice: Subject to any disclaimer, the term of this patent is extended or adjusted under 35 U.S.C. 154(b) by 0 days.

(21) Appl. No.: 12/076,221

(22) Filed: Mar. 14, 2008

(65) Prior Publication Data

US 2008/0171748 A1 Jul. 17, 2008

Related U.S. Application Data

(62) Division of application No. 11/887,227, filed as application No. PCT/EP2006/061197 on Mar. 30, 2006.

(60) Provisional application No. 60/750,853, filed on Dec. 16, 2005, provisional application No. 60/666,556, filed on Mar. 31, 2005.

(51) Int. Cl.
*C07D 401/02* (2006.01)
*A61K 31/50* (2006.01)
*A61K 31/4965* (2006.01)

(52) U.S. Cl. .................. 514/230.5; 544/90; 544/105

(58) Field of Classification Search .............. 544/90, 544/105; 514/230.5
See application file for complete search history.

(56) References Cited

U.S. PATENT DOCUMENTS

| | | |
|---|---|---|
| 6,197,959 B1 | 3/2001 | Breu et al. |
| 6,376,672 B1 | 4/2002 | Breu et al. |

FOREIGN PATENT DOCUMENTS

| | | |
|---|---|---|
| WO | 97/09311 | 3/1997 |
| WO | 00/64873 | 11/2000 |
| WO | 00/64887 | 11/2000 |
| WO | 2004/089903 | 10/2004 |

OTHER PUBLICATIONS

Chalmers (TiPS vol. 17, pp. 166-172 Apr. 1996.*
International Search Report issued Oct. 10, 2006 in the International (PCT) Application of which the present application is the U.S. National Stage.
International Preliminary Report on Patentability for PCT/EP2006/061197, (2007).
H.P. Märki et al., "Piperidine renin inhibitors: from leads to drug candidates", IL Farmaco, Rome, Italy, pp. 21-27, XP002317172, ISSN: 0014-827X, 2001.
Rolf Güller et al., "Piperidine-Renin Inhibitors Compounds with Improved Physicochemical Properties", Bioorganic & Medicinal Chemistry Letters, Oxford, Great Britain, vol. 9, No. 10, pp. 1403-1408, XP004164901, ISSN: 0960-894X, May 17, 1999.

* cited by examiner

*Primary Examiner*—Kahsay T Habte
(74) *Attorney, Agent, or Firm*—Wenderoth, Lind & Ponack, L.L.P.

(57) ABSTRACT

Substituted piperidines of formulae (I) and (II) with the substituent definitions as explained in the specification. The compounds are suitable in particular as renin inhibitors and are highly potent.

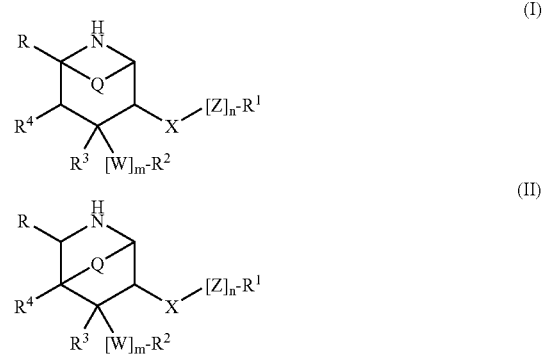

12 Claims, No Drawings

SUBSTITUTED PIPERIDINES

CROSS REFERENCE TO RELATED APPLICATIONS

The present application is a divisional application of Ser. No. 11/887,227, filed Sep. 2, 2009, which is a 371 application of PCT/EP2006/061197, filed Mar. 30, 2006, claiming the benefit of U.S. Provisional Application No. 60/666,556, filed Mar. 31, 2005 and U.S. Provisional Application No. 60/750,853, filed Dec. 16, 2005.

FIELD OF THE INVENTION

The present invention relates to novel substituted piperidines, to processes for their preparation and to the use of the compounds as medicaments, in particular as renin inhibitors.

BACKGROUND OF THE INVENTION

Piperidine derivatives for use as medicaments are disclosed, for example, by WO 97/09311. However, with regard especially to renin inhibition, there is still a need for highly potent active ingredients. In this context, the improvement of the pharmacokinetic properties is at the forefront. These properties directed to better bioavailability are, for example, absorption, metabolic stability, solubility or lipophilicity.

DETAILED DESCRIPTION OF THE INVENTION

The invention therefore provides substituted piperidines of the general formulae (I) and (II)

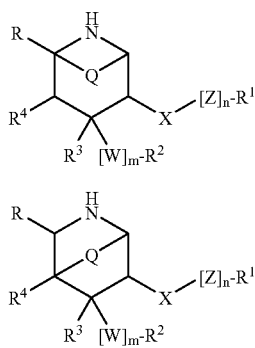

where

R is $C_{2-8}$-alkenyl, $C_{1-8}$-alkyl, $C_{2-8}$-alkynyl, $C_{0-8}$-alkyl-carbonyl-amino-$C_{1-8}$-alkyl, $C_{3-8}$-cycloalkyl-$C_{0-8}$-alkyl, $C_{1-8}$-alkyl-sulfonyl-$C_{1-8}$-alkyl, optionally N-mono- or N,N-di-$C_{1-8}$-alkylated carbamoyl-$C_{0-8}$-alkyl, optionally O—$C_{1-8}$-alkylated carboxyl-$C_{0-8}$-alkyl, optionally N and/or N' mono-, di- or tri-$C_{1-8}$-alkylated ureido-$C_{1-8}$-alkyl or heterocyclylcarbonyl-$C_{0-8}$-alkyl, each of said radicals may be substituted, preferably by 1-4 $C_{1-8}$-alkoxy, $C_{1-8}$-alkoxy-$C_{1-8}$-alkoxy, $C_{1-8}$-alkoxycarbonyl-(N—$C_{1-8}$-alkyl)-amino, $C_{1-8}$-alkyl, $C_{1-8}$-alkyl-carbonyl-(N—$C_{1-8}$-alkyl)-amino, $C_{1-8}$-alkyl-sulfanyl, $C_{1-8}$-alkyl-sulfinyl, aryl-$C_{0-8}$-alkoxy, which is optionally substituted by 1 or 2 aryl or $C_{1-8}$-alkoxy radicals, aryl, which is optionally substituted by 1 or 2 aryl or $C_{1-8}$-alkoxy radicals, aryl-amino, cyano, $C_{3-8}$-cycloalkoxy, halogen, heterocyclyl-$C_{0-8}$-alkyl, heterocycyl-$C_{0-8}$-alkoxy, heterocycyl-$C_{0-8}$-alkyl-amino, heterocycyl-carbonyl, hydroxyl, optionally N-mono- or N,N-di-$C_{1-8}$-alkylated amino, optionally, N-mono- or N,N-di-$C_{1-8}$-alkylated carbamoyl-$C_{0-8}$-alkyl, optionally N-mono- or N,N-di-$C_{1-8}$-alkylated carbamoyloxy, optionally N-mono- or N,N-di-$C_{1-8}$-alkylated sulfamoyl, optionally N-arylated or N-heterocycyl-substituted carbamoyl, oxo, trifluoromethoxy or trifluoromethyl;

$R^1$ is aryl or heterocyclyl;

$R^2$ is acenaphthyl, cyclohexyl, diazinyl, furyl, imidazolyl, naphthyl, oxadiazolyl, oxazolyl, phenyl, pyrazinyl, pyridyl, pyrimidinyl, pyrrolyl, oxopyridinyl, tetrazolyl, thienyl, or triazolyl, each of said radicals may be substituted by 1-3 $C_{1-8}$-alkanoyloxy-$C_{1-8}$-alkyl, $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxycarbonyl, $C_{1-8}$-alkoxycarbonyloxy-$C_{1-8}$-alkyl, $C_{1-8}$-alkyl, carboxy-$C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{1-8}$-alkylsulfanyl-$C_{1-8}$-alkyl, cyano, cyano-$C_{1-8}$-alkyl, $C_{3-8}$-cycloalkyl-$C_{0-6}$-alkoxy-$C_{1-8}$-alkoxy, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{0-6}$-alkoxy-$C_{1-8}$-alkyl, halo-$C_{1-8}$-alkyl, halogen, hydroxy-$C_{1-8}$-alkyl, hydroxyl, oxide, trifluoromethoxy or trifluoromethyl groups, or a $C_{1-8}$-alkylenedioxy group, and/or by an L1-T1-L 2-T2-L3-T3-L4-T4-L5-U radical;

L1, L2, L3, L4 and L5 are each independently a bond, $C_{1-8}$-alkylene, $C_{2-8}$-alkenylene or $C_{2-8}$-alkynylene, $C_{3-8}$-cycloalkene or are absent;

T1, T2, T3 and T4 are each independently (a) a bond, or are absent, or are one of the groups (b) —CH(OH)—

(c) —CH($OR^6$)—

(d) —CH($NR^5R^6$)—

(e) —CO—

(f) —$CR^7R^8$—

(g) —O— or —$NR^6$—

(h) —S(O)$_{0-2}$—

(i) —SO$_2$$NR^6$—

(j) —$NR^6$SO$_2$—

(k) —CON$R^6$—

(l) —$NR^6$CO—

(m) —O—CO—

(n) —CO—O—

(o) —O—CO—O—

(p) —O—CO—$NR^6$—

(q) —N($R^6$)—CO—N($R^6$)—

(r) —N($R^6$)—CO—O—

(s) pyrrolidinylene, piperidinylene or piperazinylene (t) —C($R^{11}$)($R^{12}$)—, where the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;

$R^3$ is hydrogen, hydroxyl, $C_{1-8}$-alkoxy or $C_{2-8}$-alkenyloxy;

$R^4$ is hydrogen, $C_{2-8}$-alkenyl, $C_{1-8}$-alkoxy, $C_{1-8}$-alkoxy-$C_{1-8}$-alkyl, $C_{1-8}$-alkoxy-$C_{1-8}$-alkoxy, $C_{1-8}$-alkyl, optionally (N—$C_{1-8}$-alkyl)-$C_{1-8}$-alkoxycarbonyl-amino-$C_{1-8}$-alkoxy, optionally (N—$C_{1-8}$-alkyl)-$C_{1-8}$-alkylcarbonyl-amino-$C_{1-8}$-alkoxy, optionally (N-mono- or N,N-di-$C_1$-$C_8$-alkyl)amino-$C_{1-8}$-alkoxy, benzyl, $C_{3-8}$-cycloalkyloxy, $C_{3-8}$-cycloalkyloxy-$C_{1-8}$-alkoxy, heterocyclyl-$C_{0-8}$-alkoxy, heterocyclyloxy-$C_{1-8}$-alkoxy, hydroxy, hydroxy-$C_{1-8}$-alkoxy-$C_{1-8}$-alkoxy, hydroxy-$C_{1-8}$-alkyl, oxo or a $R^{4a}$-Z1-X1- group where $R^{4a}$ is
(a) H—
(b) $C_{1-8}$-alkyl-
(c) $C_{2-8}$-alkenyl-
(d) hydroxy-$C_{1-8}$-alkyl-
(e) polyhydroxy-$C_{1-8}$-alkyl-
(f) $C_{1-8}$-alkyl-O—$C_{1-8}$-alkyl-
(g) aryl-
(h) heterocyclyl-
(i) arylalkyl-
(j) heterocyclylalkyl-
(k) aryloxyalkyl-
(l) heterocyclyloxyalkyl-
(m) $(R^5,R^6)N$—$(CH_2)_{1-3}$—
(n) $(R^5,R^6)N$—
(o) $C_{1-8}$-alkyl-$S(O)_{0-2}$—
(p) aryl-$S(O)_{0-2}$—
(q) heterocyclyl-$S(O)_{0-2}$—
(r) HO—$SO_3$— or salts thereof
(s) $H_2N$—C(NH)—NH—
(t) NC— and the bonds starting from (n)-(t) lead to a carbon atom of the adjacent group and this carbon atom is saturated if the bond starts from a heteroatom;

Z1
(a) is a bond, is absent, or is one of the groups
(b) —$C_{1-8}$-alkylene-
(c) —$C_{2-8}$-alkenylene-
(d) —O—, —N($R^{11}$)—, —S(O)$_{0-2}$—
(e) —CO—
(f) —O—CO—
(g) —O—CO—O—
(h) —O—CO—N($R^{11}$)—
(i) —N($R^{11}$)—CO—O—
(j) —CO—N($R^{11}$)—
(k) —N($R^{11}$)—CO—
(l) —N($R^{11}$)—CO—N($R^{11}$)—
(m) —CH(O$R^9$)— and the bonds starting from (d) and (f)-(m) lead to a carbon atom of the adjacent group and this carbon atom is saturated if the bond starts from a heteroatom;

X1
(a) is a bond, is absent, or is one of the groups
(b) —O—
(c) —N($R^{11}$)—
(d) —S(O)$_{0-2}$—
(e) —$(CH_2)_{1-3}$—;

or $R^3$ and $R^4$ in formula (I) together are a bond;

$R^5$ and $R^6$ are each independently hydrogen, $C_{1-8}$-alkyl, $C_{2-8}$-alkenyl, aryl-$C_{1-8}$-alkyl or acyl, or, together with the nitrogen atom to which they are bonded, are a 5- or 6-membered heterocyclic ring which may contain an additional nitrogen, oxygen or sulfur atom or a —SO— or —$SO_2$— group, and the additional nitrogen atom may optionally be substituted by $C_{1-8}$-alkyl radicals;

$R^7$ and $R^8$, together with the carbon atom to which they are bonded, are a 3-7-membered ring which may contain one or two —O— or —S— atoms or —SO— or —$SO_2$— groups;

$R^9$ is hydrogen, $C_{1-8}$-alkyl, $C_{1-8}$-alkoxy-$C_{1-8}$-alkyl, acyl or arylalkyl;
$R^{10}$ is carboxyalkyl, alkoxycarbonylalkyl, alkyl or hydrogen;
$R^{11}$ is hydrogen or $C_{1-8}$-alkyl;
$R^{12}$ is hydrogen or $C_{1-8}$-alkyl;
Q is ethylene or is absent (formula I) or is ethylene or methylene (formula II);

U is hydrogen, $C_{1-8}$-alkyl, cyano, optionally substituted $C_{3-8}$-cycloalkyl, aryl or heterocyclyl;
W is oxygen or sulfur;
X is a bond, oxygen or sulfur, or is a >CH—$R^{11}$, >CHO$R^9$, —O—CO—, >CO, >C=NO$R^{10}$, —O—CH$R^{11}$— or —O—CH$R^{11}$—CO—N$R^9$— group and the bond starting from an oxygen or sulfur atom leads to a saturated carbon atom of the Z group or to $R^1$;
Z is $C_{1-8}$-alkylene, $C_{2-8}$-alkenylene, hydroxy-$C_{1-8}$-alkylidene, —O—, —S—, —O-alk-, —S-alk-, -alk-O—, -alk-S— or -alk-N$R^9$—, where alk is $C_{1-8}$-alkylene; and where
(a) if Z is —O— or —S—, X is >CH—$R^{11}$ and either $R^2$ contains an L1-T1-L2-T2-L3-T3-L4-T4-L5-U substituent or $R^4$ is a substituent other than hydrogen as defined above;
(b) if Z is —O-alk- or —S-alk-, X is >CH—$R^{11}$; and
(c) if X is a bond, Z is $C_{2-8}$-alkenylene, -alk-O— or -alk-S—;
m is 0 or 1;
n is 0 or 1;
and salts thereof.

Examples of alkyl and alkoxy radicals, which may be linear or branched, are $C_{1-8}$-alkyl and $C_{1-8}$-alkoxy radicals such as methyl, ethyl, n-propyl, isopropyl, n-butyl, isobutyl, sec-butyl, tert-butyl, pentyl, hexyl, and methoxy, ethoxy, propoxy, isopropoxy, butoxy, isobutoxy, sec-butoxy and tert-butoxy respectively, in addition $C_0$-alkoxy designates —O—. $C_{1-8}$-alkylenedioxy radicals are preferably methylenedioxy, ethylenedioxy and propylenedioxy. Examples of $C_{1-8}$-alkanoyl radicals, which may be linear or branched, are acetyl, propionyl and butyryl. Cycloalkyl is a saturated, cyclic hydrocarbon radical having 3-12 carbon atoms, i.e. cyclopropyl, cyclobutyl, cyclopentyl, cyclohexyl, cycloheptyl, bicyclo[2.2.1]heptyl, cyclooctyl, bicyclo[2.2.2]octyl and adamantyl. $C_{1-8}$-alkylene radicals, which may be linear or branched, are, for example, methylene, ethylene, propylene, 2-methylpropylene, 2-methylbutylene, 2-methylbutyl-2-ene, butyl-2-ene, butyl-3-ene, propyl-2-ene, tetra-, penta- and hexamethylene. $C_{2-8}$-alkenylene radicals, which may be linear or branched, are, for example, vinylene and propenylene. $C_{2-8}$-alkynylene radicals, which may be linear or branched, are, for example, ethynylene; acyl radicals are alkanoyl radicals, preferably $C_{1-8}$-alkanoyl radicals, or aroyl radicals such as benzoyl. Aryl denotes mono- or polycyclic aromatic radicals which may be mono- or polysubstituted, for example phenyl, substituted phenyl, naphthyl, substituted naphthyl, tetrahydronaphthyl or substituted tetrahydronaphthyl. Examples of substituents on such aryl radicals or on heterocyclyl radicals are $C_{1-8}$-alkyl, trifluoromethyl, trifluoromethoxy, nitro, amino, $C_{2-6}$-alkenyl, $C_{1-8}$-alkoxy, $C_{1-8}$-alkylsulfinyl, $C_{1-8}$-alkylcarbonyloxy, hydroxyl, halogen, cyano, carbamoyl, carboxyl and $C_{1-8}$-alkylenedioxy, and also phenyl, phenoxy, phenylthio, phenyl-$C_{1-8}$-alkyl or phenyl-$C_{1-8}$-alkoxy each optionally substituted by halogen, $C_{1-8}$-alkyl, $C_{1-8}$-alkoxy or dihydroxy-$C_{1-8}$-alkylaminocarbonyl. Further examples of substituents on aryl or on heterocyclyl radicals are oxo, $C_{1-8}$-alkoxycarbonylphenyl, hydroxy-$C_{1-8}$-alkylphenyl, benzyloxy, pyridylcarbonylamino-$C_{1-8}$-alkyl, $C_{2-6}$-alkenyloxy, $C_{1-8}$-alkoxy-$C_{1-8}$-alkoxy, $C_{1-8}$-alkoxy-$C_{1-8}$-alkoxy-$C_{1-8}$-alkyl, hydroxy-$C_{1-8}$-alkoxy, di-$C_{1-8}$-alkylamino, 2,3-dihydroxypropoxy, 2,3-dihydroxypropoxy-$C_{1-8}$-alkoxy, 2,3-dimethoxypropoxy, methoxybenzyloxy, hydroxybenzyloxy, phenethyloxy, methylenedioxybenzyloxy, dioxolanyl-$C_{1-8}$-alkoxy, cyclopropyl-$C_{1-8}$-alkyl, cyclopropyl-$C_{1-8}$-alkoxy, hydroxy-$C_{1-8}$-alkoxy, carbamoyloxy-$C_{1-8}$-alkoxy, pyridylcarbamoyloxy-$C_{1-8}$-alkoxy, benzoyloxy-$C_{1-8}$-alkoxy, picolyloxy, $C_{1-8}$-alkoxycarbonyl, $C_{0-6}$-alkylcarbonylamino, $C_{0-6}$-alkylcarbonylamino-$C_{1-8}$-alkyl, $C_{0-6}$-alkylcarbonylamino-$C_{1-8}$-alkoxy, (N—$C_{1-8}$- alkyl)-$C_{0-6}$-alkylcarbonylamino-$C_{1-8}$-alkyl, (N—$C_{1-8}$-alkyl)-$C_{0-6}$-alkylcarbonylamino-$C_{1-8}$-alkoxy, $C_{3-8}$-cycloalkylcarbonylamino-$C_{1-8}$-alkyl, $C_{3-8}$-cycloalkylcarbonylamino-$C_{1-8}$-alkoxy, $C_{1-8}$-alkoxy-$C_{1-8}$-alkyl, hydroxy-$C_{1-8}$-alkyl, hydroxy-$C_{1-8}$-alkoxy-$C_{1-8}$-alkyl, hydroxy-$C_{1-8}$-alkoxy-$C_{1-8}$-alkoxy, $C_{1-8}$-alkoxycarbonylamino-$C_{1-8}$-alkyl, $C_{1-8}$-alkoxycarbonylamino-$C_{1-8}$-alkoxy, $C_{1-8}$-alkylaminocarbonylamino-$C_{1-8}$-alkyl, $C_{1-8}$-alkylaminocarbonylamino-$C_{1-8}$-alkoxy, $C_{1-8}$-alkylaminocarbonyl-$C_{1-8}$-alkyl, $C_{1-8}$-alkylaminocarbonyl-$C_{1-8}$-alkoxy, $C_{1-8}$-alkylaminocarbonyl-$C_{1-8}$-alkoxy-$C_{1-8}$-alkyl, di-$C_{1-8}$-alkylaminocarbonyl-$C_{1-8}$-alkyl, di-$C_{1-8}$-alkylaminocarbonyl-$C_{1-8}$-alkoxy, $C_{1-8}$-alkoxycarbonyloxy-$C_{1-8}$-alkyl, $C_{1-8}$-alkylcarbonyloxy-$C_{1-8}$-alkyl, $C_{1-8}$-alkylcarbonyloxy-$C_{1-8}$-alkoxy, cyano-$C_{1-8}$-alkyl cyano-$C_{1-8}$-alkoxy, 2-oxooxazolidinyl-$C_{1-8}$-alkyl, 2-oxooxazolidinyl-$C_{1-8}$-alkoxy, $C_{1-8}$-alkoxycarbonyl-$C_{1-8}$-alkyl, $C_{1-8}$-alkoxycarbonyl-$C_{1-8}$-alkoxy, $C_{1-8}$-alkylsulfonylamino-$C_{1-8}$-alkyl, $C_{1-8}$-alkylsulfonylamino-$C_{1-8}$-alkoxy, (N—$C_{1-8}$-alkyl)-$C_{1-8}$-alkylsulfonylamino-$C_{1-8}$-alkyl, (N—$C_{1-8}$-alkyl)-$C_{1-8}$-alkylsulfanylamino-$C_{1-8}$-alkoxy, amino-$C_{1-8}$-alkyl, amino-$C_{1-8}$-alkoxy, $C_{1-8}$-alkylamino-$C_{1-8}$-alkyl $C_{1-8}$-alkylamino-$C_{1-8}$-alkoxy, di-$C_{1-8}$-alkylamino-$C_{1-8}$-alkyl, di-$C_{1-8}$-alkylamino-$C_{1-8}$-alkoxy $C_{1-8}$-alkylsulfonyl-$C_{1-8}$-alkyl, $C_{1-8}$-alkylsulfonyl-$C_{1-8}$-alkoxy, carboxy-$C_{1-8}$-alkyl, carboxy-$C_{1-8}$-alkoxy, carboxy-$C_{1-8}$-alkoxy-$C_{1-8}$-alkyl, $C_{1-8}$-alkoxy-$C_{1-8}$-alkylcarbonyl, acyl-$C_{1-8}$-alkoxy-$C_{1-8}$-alkyl, (N—$C_{1-8}$-alkyl)-$C_{1-8}$-alkoxycarbonylamino, (N-hydroxy)-$C_{1-8}$-alkylaminocarbonyl-$C_{1-8}$-alkyl, (N-hydroxy)-$C_{1-8}$-alkylaminocarbonyl-$C_{1-8}$-alkoxy, (N-hydroxy)aminocarbonyl-$C_{1-8}$-alkyl, (N-hydroxy)aminocarbonyl-$C_{1-8}$-alkoxy, $C_{1-8}$-alkoxyaminocarbonyl-$C_{1-8}$-alkyl, $C_{1-8}$-alkoxyaminocarbonyl-$C_{1-8}$-alkoxy, (N—$C_{1-8}$-alkoxy)-$C_{1-8}$-alkylaminocarbonyl-$C_{1-8}$-alkyl, (N—$C_{1-8}$-alkoxy)-$C_{1-8}$-alkylaminocarbonyl-$C_{1-8}$-alkoxy, (N-acyl)-$C_{1-8}$-alkoxy-$C_{1-8}$-alkylamino, $C_{1-8}$-alkoxy-$C_{1-8}$-alkylcarbamoyl, (N—$C_{1-8}$-alkyl)-$C_{1-8}$-alkoxy-$C_{1-8}$-alkylcarbamoyl, $C_{1-8}$-alkoxy-$C_{1-8}$-alkylcarbonyl, $C_{1-8}$-alkoxy-$C_{1-8}$-alkylcarbonylamino, (N—$C_{1-8}$-alkyl)-$C_{1-8}$-alkoxy-$C_{1-8}$-alkylcarbonylamino, 1-$C_{1-8}$-alkoxy-$C_{1-8}$-alkylimidazol-2-yl, 1-$C_{1-8}$-alkoxy-$C_{1-8}$-alkyltetrazol-5-yl, 5-$C_{1-8}$-alkoxy-$C_{1-8}$-alkyltetrazol-1-yl, 2-$C_{1-8}$-alkoxy-$C_{1-8}$-alkyl-4-oxoimidazol-1-yl, carbamoyl-$C_{1-8}$-alkyl, carbamoyl-$C_{1-8}$-alkoxy, $C_{1-8}$-alkylcarbamoyl, di-$C_{1-8}$-alkylcarbamoyl, $C_{1-8}$-alkylsulfonyl, $C_{1-8}$-alkylamidinyl, acetamidinyl-$C_{1-8}$-alkyl, O-methyloximyl-$C_{1-8}$-alkyl, O,N-dimethylhydroxylamino-$C_{1-8}$-alkyl, $C_{3-8}$-cycloalkyl-$C_{1-8}$-alkanoyl, aryl-$C_{1-8}$-alkanoyl, heterocyclyl-$C_{1-8}$-alkanoyl; and also pyridyl, pyridyloxy, pyridylthio, pyridylamino, pyridyl-$C_{1-8}$-alkyl, pyridyl-$C_{1-8}$-alkoxy, pyrimidinyl, pyrimidinyloxy, pyrimidinylthio, pyrimidinylamino, pyrimidinyl-$C_{1-8}$-alkyl, pyrimidinyl-$C_{1-8}$-alkoxy, thienyl, thienyl-$C_{1-8}$-alkyl thienyl-$C_{1-8}$-alkoxy, furyl, furyl-$C_{1-8}$-alkyl, furyl-$C_{1-8}$-alkoxy each optionally substituted by halogen, $C_{1-8}$-alkyl, $C_{1-8}$-alkoxy or dihydroxy-$C_{1-8}$-alkylaminocarbonyl.

The term heterocyclyl denotes a saturated or unsaturated, 4-8-membered, particularly preferably 5 or 6-membered, monocyclic ring system, a saturated or unsaturated, 7-12-membered, particularly preferably 9- or 10-membered, bicyclic ring system and also a saturated or unsaturated, 7-12-membered tricyclic ring system, in each case having from 1 to 4 nitrogen and/or 1 or 2 sulfur or oxygen atoms and comprising an N, O or S atom in at least one ring, it also being possible for additional N, O or S atoms to be present in the same ring. Said radicals may be unsubstituted or substituted one or more times, e.g. once or twice. It also being possible for a plurality of identical or different substituents to be present. Preferred substituents are (in the case of unsaturated heterocyclyl radicals) alkyl, hydroxyl, alkoxy, cyano, oxide, nitrogen, halogen, and substituents as defined above for aryl radicals, or (in the case of saturated heterocyclyl radicals) alkyl and alkoxy. Examples of heterocyclyl radicals are pyridyl, thienyl, pyrazinyl, triazolyl, imidazolyl, benzothiazolyl, furyl, pyranyl, tetrahydropyranyl, azetidinyl, pyrimidinyl, morpholinyl, quinazolinyl, quinolyl, quinoxalinyl, isoquinolyl, tetrahydroquinolyl, tetrahydroisoquinolyl, benzo[b]thienyl, isobenzofuranyl, benzoimidazolyl, 2-oxobenzoimidazolyl, oxazolyl, thiazolyl, indolyl, 2-oxo-1H-quinolinyl, 2H-chromenyl, 2-oxo-2H-chromenyl, 1,1a,2,7b-tetrahydro-cyclopropa[c]chromenyl, 2-oxo-1a,7b-dihydro-1H-cyclopropa[c]chromenyl, pyrrolyl, 2-oxodihydrobenzo[d][1,3]oxazinyl, 4-oxodihydroimidazolyl, 5-oxo-4H-[1,2,4]triazinyl, 3-oxo-4H-benzo[1,4]thiazinyl, tetrahydroquinoxalinyl, 1,1,3-trioxodihydro-2H-1$\lambda^6$-benzo[1,4]thiazinyl, 1-oxopyridyl, dihydro-2H-benzo[1,4]oxazinyl, 2-oxotetrahydrobenzo[e][1,4]diazepinyl, 2-oxodihydrobenzo[e][1,4]diazepinyl, 1H-pyrrolizinyl, phthalazinyl, 1-oxo-3H-isobenzofuranyl, 4-oxo-3H-thieno[2,3-d]pyrimidinyl, 3-oxo-4H-benzo[1,4]oxazinyl, [1,5]naphthyridyl, dihydro-2H-benzo[1,4]thiazinyl, 1,1-dioxodihydro-2H-benzo[1,4]thiazinyl, 2-oxo-1H-pyrido[2,3-b][1,4]oxazinyl, dihydro-1H-pyrido[2,3-b][1,4]oxazinyl, 1H-pyrrolo[2,3-b]pyridyl, benzo[1,3]dioxolyl, benzooxazolyl, 2-oxobenzooxazolyl, 2-oxo-1,3-dihydroindolyl, 2,3-dihydroindolyl, 2-oxodihydro-1H-quinazolinyl, indazolyl or benzofuranyl. Examples of substituted heterocyclyl radicals are nitrobenzothiazolyl, phenyltetrazolyl, phenyloxadiazolyl, phenylpiperidinyl, phenylpiperazinyl, phenylpyrrolidinyl, thienyloxadiazolyl, furanyloxadiazolyl, benzyloxadiazolyl or phenyloxazolyl. Examples of substituted heterocyclyl radicals are dioxolanyl, dioxanyl, dithiolanyl, dithianyl, pyrrolidinyl, piperidinyl, piperazinyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, tetrahydropyranyl, 2-oxoimidazolidinyl, 2-oxooxazolidinyl, 2-oxopiperidinyl, 2-oxopyrrolidinyl, 2-oxo-[1,3]oxazinyl, 2-oxoazepanyl, 2-oxotetrahydropyrimidinyl and the like.

In the case of $R^1$, $R^{4a}$ and $R^9$, the aryl, aroyl and heterocyclyl radicals may be additionally be substituted by heterocyclylalkyl, heterocyclylalkoxy, heterocyclylalkoxyalkyl or heterocyclyl for example piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, and also alkylaminoalkyl, alkylaminoalkoxy, alkylaminoalkoxyalkyl, mono- and polyhydroxyalkyl, -alkoxy, -alkoxyalkyl and -alkoxyalkoxy, carbamoylalkyloxy, $C_{1-8}$-alkoxy, amino-$C_{1-8}$-alkoxy, hydroxy-$C_{1-8}$-alkoxy, dioxolanyl, dioxanyl, dithiolanyl, dithianyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-C$_{1-8}$-alkoxy-C$_{1-8}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo[1,3]oxazinyl, 2-oxotetrahydropyrimidinyl and the like, or by the —O—CH$_2$CH(OH)CH$_2$NRx radical where NRx is a mono- or di-C$_{1-8}$-alkylamino, piperidino, morpholino, piperazino or N-methylpiperazino radical.

Examples of 5- and 6-membered heterocyclic rings represented by NR$^5$R$^6$ are pyrrolidinyl, piperidinyl, piperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl, 2-oxotetrahydropyrimidinyl and the like. Examples of 3-7-membered rings represented by CR$^7$R$^8$ are cyclopentyl, cyclohexyl, cycloheptyl, 1,3-dioxolanyl, 1,3-dioxanyl, 1,3-dithiolanyl and 1,3-dithianyl.

The term polyhydroxyalkyl denotes C$_{1-7}$-alkyl radicals which may be substituted by 2-6 hydroxyl groups, for example glyceryl, arabityl, sorbityl, etc.

Halogen or halo denotes, for example, fluorine, chlorine or bromine, or a radical singly, multiply or fully substituted by fluorine, chlorine or bromine.

Salts are primarily the pharmaceutically usable or nontoxic salts of compounds of the formula (I) or formula (II). The term "pharmaceutically useable salts" encompasses salts with inorganic or organic acids, such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like.

Salts of compounds having salt-forming groups are in particular acid addition salts, salts with bases, or, in the presence of a plurality of salt-forming groups, in some cases also mixed salts or internal salts.

Such salts are formed, for example, from compounds of the formula (I) or formula (II) with an acidic group, for example a carboxyl or sulfo group, and are, for example, the salts thereof with suitable bases such as non-toxic metal salts derived from metals of group Ia, Ib, IIa and IIb of the Periodic Table of the Elements, for example alkali metal, in particular lithium, sodium, or potassium, salts, alkaline earth metal salts, for example magnesium or calcium salts, and also zinc salts and ammonium salts, including those salts which are formed with organic amines, such as optionally hydroxy-substituted mono-, di- or trialkylamines, in particular mono-, di- or tri(lower alkyl)amines, or with quaternary ammonium bases, e.g. methyl-, ethyl-, diethyl- or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-hydroxy(lower alkyl))amine, such as N N-di-N-dimethyl-N-(2-hydroxyethyl)amine, or N-methyl-D-glucamine, or quaternary ammonium hydroxides such as tetrabutylammonium hydroxide. The compounds of the formula I having a basic group, for example an amino group, may form acid addition salts, for example with suitable inorganic acids, e.g. hydrohalic acid such as hydrochloric acid, hydrobromic acid, sulfuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulfonic or phosphonic acids or N-substituted sulfamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the alpha-amino acids mentioned above, and also methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose 6-phosphate, N-cyclohexylsulfamic acid (with formation of the cyclamates) or with other acidic organic compounds such as ascorbic acid. Compounds of the formula (I) or formula (II) having acidic and basic groups may also form internal salts.

Salts obtained may be converted to other salts in a manner known per se, acid addition salts, for example, by treating with a suitable metal salt such as a sodium, barium or silver salt, of another acid in a suitable solvent in which an inorganic salt which forms is insoluble and thus separates out of the reaction equilibrium, and base salts by release of the free acid and salt reformation.

The compounds of the formula (I) and (II), including their salts, may also be obtained in the form of hydrates or include the solvent used for the crystallization.

For the isolation and purification, pharmaceutically unsuitable salts may also find use.

The compounds of the formulae (I) and (II) also include those compounds in which one or more atoms are replaced by their stable, non-radioactive isotopes; for example a hydrogen atom by deuterium.

The compounds of the formulae (I) or (II) may be prepared in a similar manner to the preparation processes disclosed in the literature. Preferred procedures for the preparation of optically pure compounds of the formula (I) or (II) consist of the construction of the requisite multiply-substituted piperidine scaffolds and their precursors via either (i) a chiral aza-Diels-Alder reaction of an imine derivative with a diene (see Chemistry—A European Journal 2000, 6(13), 2435-2448 and references cited therein) [Scheme 1] or (ii) condensation of a chiral amino acid derivative with Meldrum's acid followed by cyclisation (see Journal of Organic Chemistry 2004, 69(1), 130-141 and references cited therein) [Scheme 2]. In the case of the former approach, the presence of non-stoichiometric amounts of an amine (e.g. triethylamine) is crucial for obtaining products of high optical purities. This amine component may either be present in the commercially available diene (e.g. Danishefsky's diene from Aldrich) or added exogenously. Details on the specific preparation variants can be taken from the examples.

Scheme 1

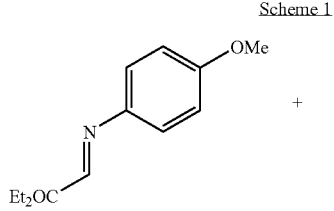

-continued
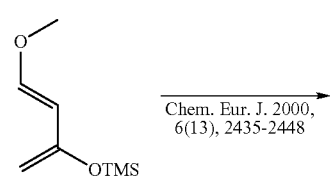
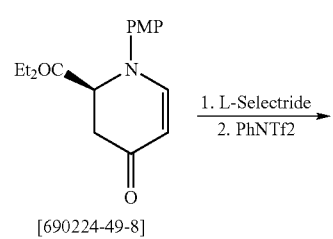
[690224-49-8]
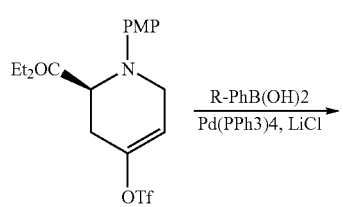
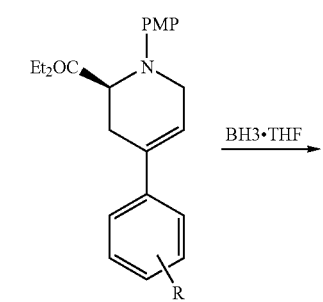
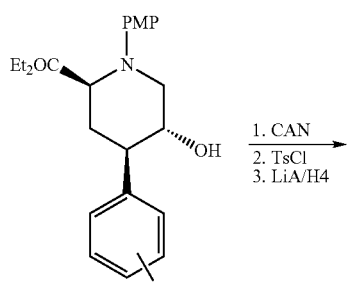
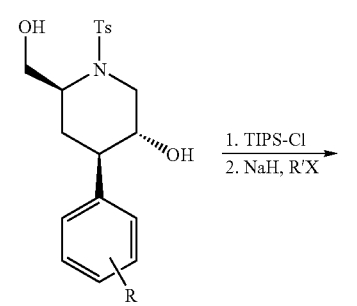
-continued
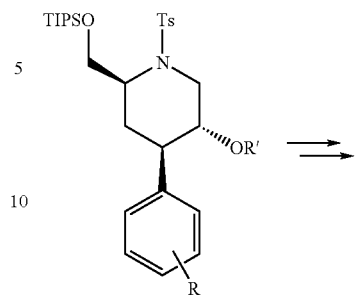
Scheme 2
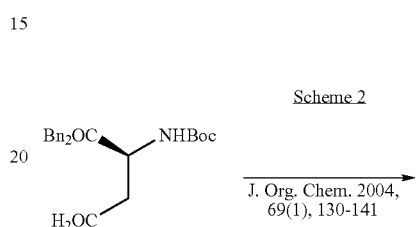
Boc-Asp-OBn
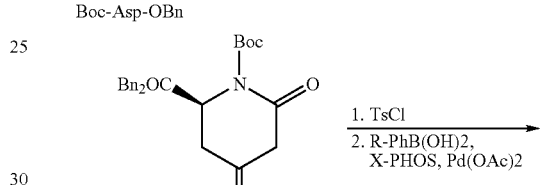
[176436-10-5]
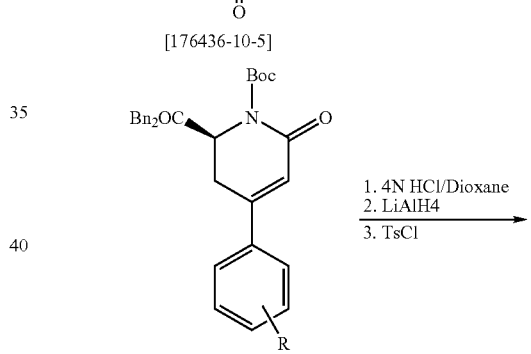
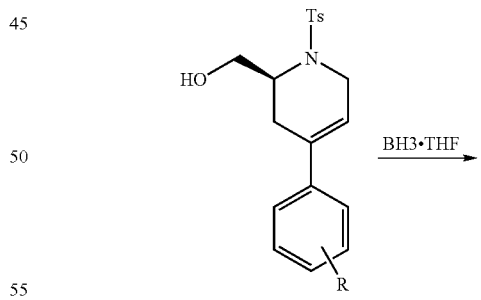
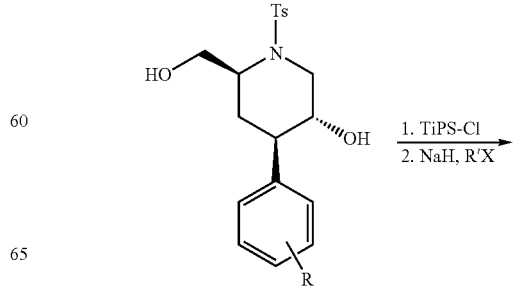

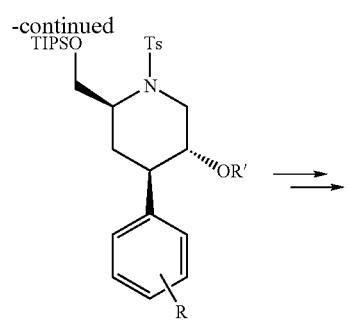

The compounds of the formula (I) or formula (II) have at least three asymmetric carbon atoms and may therefore be in the form of optically pure diastereomers, diastereomeric mixtures, diastereomeric racemates, mixtures of diastereomeric racemates or as meso compounds. The invention encompasses all of these forms. Diastereomeric mixtures, diastereomeric racemates or mixtures of diastereomeric racemates may be separated by customary procedures, for example by column chromatography, thin-layer chromatography, HPLC and the like.

The compounds of the formulae (I) or (II) may also be prepared in optically pure form. The separation into antipodes can be effected by procedures known per se, either preferably at an earlier synthetic stage by salt formation with an optically active acid, for example (+)- or (−)-mandelic acid and separation of the diastereomeric salts by fractional crystallization, or preferably at a relatively late stage by derivatizing with a chiral auxiliary building block, for example (+)- or (−)-camphanoyl chloride, and separation of the diastereomeric products by chromatography and/or crystallization and subsequent cleavage of the bonds to give the chiral auxiliary. The pure diastereomeric salts and derivatives may be analysed to determine the absolute configuration of the piperidine present with common spectroscopic procedures, and X-ray spectroscopy on single crystals constitutes a particularly suitable procedure.

It is possible for the configuration at individual chiral centres in a compound of the formulae (I) or (II) to be inverted selectively. For example, the configuration of asymmetric carbon atoms which bear nucleophilic substituents, such as amino or hydroxyl, may be inverted by second-order nucleophilic substitution, if appropriate after conversion of the bonded nucleophilic substituent to a suitable nucleofugic leaving group and reaction with a reagent which introduces the original substituents, or the configuration at carbon atoms having hydroxyl groups can be inverted by oxidation and reduction, analogously to the process in the European patent application EP-A-0 236 734. Also advantageous is the reactive functional modification of the hydroxyl group and subsequent replacement thereof by hydroxyl with inversion of configuration.

The compounds of the formulae (I) or (II) also include compounds where one or more atoms are replaced by their stable, non-radioactive isotopes (for example hydrogen by deuterium).

Prodrug derivatives of the compounds described in the present context are derivatives thereof which, on in vivo application, release the original compound by a chemical or physiological process. A prodrug may be converted to the original compound, for example, when a physiological pH is attained or by enzymatic conversion. Prodrug derivatives may, for example, be esters of freely available carboxylic acids, S- and O-acyl derivatives of thiols, alcohols or phenols, and the acyl group is as defined in the present context. Preference is given to pharmaceutically useable ester derivatives which are converted by solvolysis in physiological medium to the original carboxylic acid, for example lower alkyl esters, cycloalkyl esters, lower alkenyl esters, benzyl esters, mono- or disubstituted lower alkyl esters such as lower ω-(amino, mono- or dialkylamino, carboxyl, lower alkoxycarbonyl)-alkyl esters or such as lower α-(alkanoyloxy, alkoxycarbonyl or dialkylaminocarbonyl)-alkyl esters; as such, pivaloyloxymethyl esters and similar esters are utilized in a conventional manner.

Owing to the close relationship between a free compound, a prodrug derivative and a salt compound, a certain compound in this invention also encompasses its prodrug derivative and salt form, where these are possible and appropriate.

The compound groups mentioned below are not to be regarded as closed, but rather parts of these compound groups may be exchanged with one another or with the definitions given above or omitted in a sensible manner, for example to replace general by more specific definitions. The definitions are valid in accordance with general chemical principles, such as, for example, the common valences for atoms.

Preferred inventive compounds are those of the general formulae (IA) or (IIA)

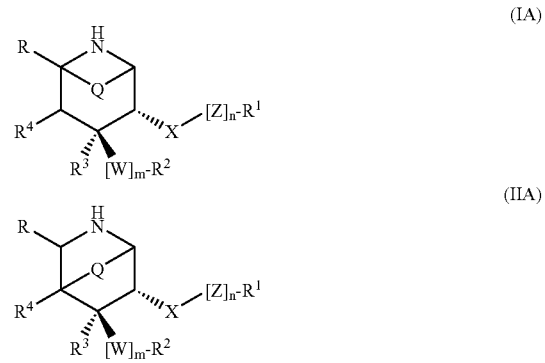

where R, $R^1$, $R^2$, $R^3$, $R^4$, Q, W, X and Z, n and m are each as defined above for the compounds of the formulae (I) and (II).

A further, preferred group of compounds of the formula (I) or (II), or more preferably of the formula (IA) or (IIA), are compounds where R is $C_{2-8}$-alkenyl, $C_{1-8}$-alkyl, $C_{2-8}$-alkynyl, $C_{0-8}$-alkyl-carbonyl-amino-$C_{1-8}$-alkyl, $C_{3-8}$-cycloalkyl-$C_{0-8}$-alkyl, $C_{1-8}$-alkyl-sulfonyl-$C_{0-8}$-alkyl, optionally N-mono- or N,N-di-$C_{1-8}$-alkylated carbamoyl-$C_{0-8}$-alkyl, optionally O—$C_{1-8}$-alkylated carboxyl-$C_{0-8}$-alkyl, optionally N and/or N' mono-, di- or tri-$C_{1-8}$-alkylated ureido-$C_{0-8}$-alkyl or heterocyclylcarbonyl-$C_{0-8}$-alkyl, each of said radicals may be substituted, preferably by 1-4 $C_{1-8}$-alkoxy, $C_{1-8}$-alkoxy-$C_{1-8}$-alkoxy, $C_{1-8}$-alkoxycarbonyl-(N—$C_{1-8}$-alkyl)-amino, $C_{1-8}$-alkyl, $C_{1-8}$-alkyl-carbonyl-(N—$C_{1-8}$-alkyl)-amino, $C_{1-8}$-alkyl-sulfanyl, $C_{1-8}$-alkyl-sulfinyl, aryl-$C_{0-8}$-alkoxy, which is optionally substituted by 1 or 2 aryl or $C_{1-8}$-alkoxy radicals, aryl, which is optionally substituted by 1 or 2 aryl or $C_{1-8}$-alkoxy radials, aryl-amino, cyano, $C_{3-8}$-cycloalkoxy, halogen, heterocyclyl-$C_{0-8}$-alkyl, heterocyclyl-$C_{0-8}$-alkoxy, heterocyclyl-$C_{0-8}$-alkylamino, heterocyclyl-carbonyl, hydroxyl, optionally N-mono- or N,N-di-$C_{1-8}$-alkylated amino, optionally N-mono- or N,N-di-$C_{1-8}$-alkylated carbamoyl-$C_{0-8}$-alkyl, optionally N-monoor N,N-di-$C_{1-8}$-alkylated carbamoyloxy, optionally N-mono- or N,N-di-$C_{1-8}$-alkylated sulfamoyl, optionally N—$C_{1-8}$-alkylated, N-arylated or N-heterocyclyl-substituted carbamoyl, oxo, trifluoromethoxy or trifluoromethyl;

$R^1$ is aryl or heterocyclyl;

$R^2$ is phenyl, cyclohexyl, tetrazolyl, naphthyl or acenaphthyl, each of said radicals may be unsubstituted or substituted, preferably by 1-3 $C_{1-8}$-alkanoyloxy-$C_{1-8}$-alkyl, $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxycarbonyl, $C_{1-8}$-alkoxycarbonyloxy-$C_{1-8}$-alkyl, $C_{1-8}$-alkyl, carboxy-$C_{1-8}$-alkyl, $C_{1-8}$-alkoxy-$C_{1-8}$-alkylsulfanyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{1-8}$-alkylsulfanyl-$C_{1-8}$-alkyl, cyano, cyano-$C_{1-8}$-alkyl, $C_{3-8}$-cycloalkyl-$C_{0-6}$-alkoxy-$C_{1-8}$-alkoxy, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{0-6}$-alkoxy-$C_{1-8}$-alkyl, halo-$C_{1-8}$-alkyl, halogen, hydroxy-$C_{1-8}$-alkyl, hydroxyl, oxide, trifluoromethoxy or trifluoromethyl groups, or a $C_{1-8}$-alkylenedioxy group, and/or by an L1-T1-L2-T2-L3-T3-L4-T4-L5-U radical;

L1, L2, L3, L4 and L5 are each independently a bond, $C_{1-8}$-alkylene, $C_{2-8}$-alkenylene or $C_{2-8}$-alkynylene, $C_{3-8}$-cycloalkene or are absent;

T1, T2, T3 and T4 are each independently (a) a bond, or are absent, or are one of the groups (b) —CH(OH)—

(c) —CH($OR^6$)—

(d) —CH($NR^5R^6$)—

(e) —CO—

(f) —$CR^7R^8$—

(g) —O— or —$NR^6$—

(h) —$S(O)_{0-2}$—

(l) —$SO_2NR^6$—

(j) —$NR^6SO_2$—

(k) —$CONR^6$—

(l) —$NR^6CO$—

(m) —O—CO—

(n) —CO—O—

(o) —O—CO—O—

(p) —O—CO—$NR^6$—

(q) —N($R^6$)—CO—N($R^6$)—

(r) —N($R^6$)—CO—O—

(s) pyrrolidinylene, piperidinylene or piperazinylene (t) —C($R^{11}$)($R^{12}$)—, where the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;

$R^3$ is hydrogen, hydroxyl, $C_{1-8}$-alkoxy or $C_{2-8}$-alkenyloxy;

$R^4$ is hydrogen, $C_{1-8}$-alkoxy, $C_{1-8}$-alkoxy-$C_{1-8}$-alkoxy, $C_{1-8}$-alkoxy-$C_{1-8}$-alkyl, $C_{1-8}$-alkyl, optionally (N—$C_{1-8}$-alkyl)-$C_{1-8}$-alkoxycarbonyl-amino-$C_{1-8}$-alkoxy, optionally (N—$C_{1-8}$-alkyl)-$C_{1-8}$-alkylcarbonylamino-$C_{1-8}$-alkoxy, optionally (N-mono- or N,N-di-$C_1$-$C_8$-alkyl)-amino-$C_{1-8}$-alkoxy, $C_{3-8}$-cycloalkyloxy, $C_{3-8}$-cycloalkyloxy-$C_{1-8}$-alkoxy, heterocyclyl-$C_{0-8}$-alkoxy, heterocyclyloxy-$C_{1-8}$-alkoxy, hydroxy, oxo or hydroxy-$C_{1-8}$-alkoxy-$C_{1-8}$-alkoxy;

$R^5$ and $R^6$ are each independently hydrogen, $C_{1-8}$-alkyl or acyl, or, together with the nitrogen atom to which they are bonded, are a 5- or 6-membered heterocyclic ring which may contain an additional nitrogen, oxygen or sulfur atom;

$R^7$ and $R^8$, together with the carbon atom to which they are bonded, are a 3-7-membered ring which may contain one or two —O— or —S— atoms;

$R^9$ is hydrogen, $C_{1-8}$-alkyl, acyl or arylalkyl;

U is hydrogen, $C_{1-8}$-alkyl, $C_{3-8}$-cycloalkyl, cyano, aryl or heterocyclyl;

Q is ethylene or is absent (formula (I)) and is ethylene or methylene (formula (II));

X is a bond, oxygen, sulfur or is a >$CHR^{11}$, >$CHOR^9$, —O—CO—, >CO or —O—CH—$R^{11}$—CO—$NR^9$— group;

W is oxygen or sulfur if $R^3$ is hydrogen;

Z is $C_{1-8}$-alkylene or -alk-O—;

where, if X is a bond, Z is -alk-O—;

n is 0 or 1;

m is 0 or 1;

and pharmaceutically useable salts thereof.

Preference is further given to compounds of the formulae (I), (IA), (II) and (IIA) in which W is absent (m is 0), and to those of the formulae (I) and (IA) in which Q is absent.

Preferred R radicals are $C_{1-8}$-alkyl, $C_{0-8}$-alkyl-carbonylamino-$C_{1-8}$-alkyl, $C_{1-8}$-alkyl-sulfonyl-$C_{1-8}$-alkyl, optionally N-mono- or N,N-di-$C_{1-8}$-alkylated carbamoyl-$C_{0-8}$-alkyl, optionally N and/or N' mono-, di- or tri-$C_{1-8}$-alkylated ureido-$C_{0-8}$-alkyl, heterocyclyl-$C_{0-8}$-alkyl, or heterocyclylcarbonyl-$C_{0-8}$-alkyl, each of said radicals may be substituted, preferably by 1-4 $C_{1-8}$-alkoxy, $C_{1-8}$-alkoxy-$C_{1-8}$-alkoxy, $C_{1-8}$-alkoxycarbonyl-(N—$C_{1-8}$-alkyl)-amino, $C_{1-8}$-alkyl, $C_{1-8}$-alkyl-carbonyl-(N—$C_{1-8}$-alkyl)-amino, $C_{1-8}$-alkyl-sulfanyl, aryl-$C_{0-8}$-alkoxy, which is optionally substituted by 1 or 2 aryl or $C_{1-8}$-alkoxy radicals, aryl, which is optionally substituted by 1 or 2 aryl or $C_{1-8}$-alkoxy radials, cyano, halogen, heterocyclyl, heterocyclyl-$C_{0-8}$-alkyl-amino, heterocyclyl-carbonyl, optionally N-mono- or N,N-di-$C_{1-8}$-alkylated carbamoyl-$C_{0-8}$-alkyl, optionally N-mono- or N,N-di-$C_{1-8}$-alkylated carbamoyloxy, hydroxyl, optionally N-mono- or N,N-di-$C_{1-8}$-alkylated amino, trifluoromethoxy and trifluoromethyl.

Preferred $R^1$ radicals are phenyl and phenyl substituted by 1-3 radicals selected from $C_{1-8}$-alkyl, $C_{1-8}$-alkoxy, halogen, hydroxyl, hydroxy-$C_{1-8}$-alkoxy, $C_{1-8}$-alkoxy-$C_{1-8}$-alkoxy, $C_{1-8}$-alkylsulfinyl, carbamoyl, cyano, trifluoromethyl, trifluoromethoxy, carboxyl, $C_{1-8}$-alkoxycarbonyl, $C_{1-8}$-alkoxy-$C_{1-8}$-alkoxy-$C_{1-8}$-alkyl, $C_{0-6}$-alkylcarbonylamino, $C_{0-6}$-alkylcarbonylamino-$C_{1-8}$-alkyl, $C_{0-6}$-alkylcarbonylamino-$C_{1-8}$-alkoxy, (N—$C_{1-8}$-alkyl)-$C_{0-6}$-alkylcarbonylamino-$C_{1-8}$-alkyl, (N—$C_{1-8}$-alkyl)-$C_{0-6}$-alkylcarbonylamino-$C_{1-8}$-alkoxy, $C_{3-8}$-cycloalkylcarbonylamino-$C_{1-8}$-alkyl, $C_{3-8}$-cycloalkylcarbonylamino-$C_{1-8}$-alkoxy, $C_{1-8}$-alkoxy-$C_{1-8}$-alkyl, hydroxy-$C_{1-8}$-alkyl, hydroxy-$C_{1-8}$-alkoxy-$C_{1-8}$-alkyl, hydroxy-$C_{1-8}$-alkoxy-$C_{1-8}$-alkoxy, $C_{1-8}$-alkoxycarbonylamino-$C_{1-8}$-alkyl, $C_{1-8}$-alkoxycarbonylamino-$C_{1-8}$-alkoxy, $C_{1-8}$-alkylaminocarbonylamino-$C_{1-8}$-alkyl, $C_{1-8}$-alkylaminocarbonylamino-$C_{1-8}$-alkoxy, $C_{1-8}$-alkylaminocarbonyl-$C_{1-8}$-alkyl, $C_{1-8}$-alkylaminocarbonyl-$C_{1-8}$-alkoxy, $C_{1-8}$-alkylaminocarbonyl-$C_{1-8}$-alkoxy-$C_{1-8}$-alkyl, di-$C_{1-8}$-alkylaminocarbonyl-$C_{1-8}$-alkyl, di-$C_{1-8}$-alkylaminocarbonyl-$C_{1-8}$-alkoxy, $C_{1-8}$-alkylcarbonyloxy-$C_{1-8}$-alkyl, $C_{1-8}$-alkylcarbonyloxy-$C_{1-8}$-alkoxy, cyano-$C_{1-8}$-alkyl, cyano-$C_{1-8}$-alkoxy, 2-oxooxazolidinyl-$C_{1-8}$-alkyl, 2-oxooxazolidinyl-$C_{1-8}$-alkoxy, $C_{1-8}$-alkoxycarbonyl-$C_{1-8}$-alkyl, $C_{1-8}$-alkoxycarbonyl-$C_{1-8}$-alkoxy, $C_{1-8}$-alkylsulfonylamino-$C_{1-8}$-alkyl, $C_{1-8}$-alkylsulfonylamino-$C_{1-8}$-alkoxy, (N—$C_{1-8}$-alkyl)-$C_{1-8}$-alkylsulfonylamino-$C_{1-8}$-alkyl, (N—$C_{1-8}$-alkyl)-$C_{1-8}$-alkylsulfonylamino-$C_{1-8}$-alkoxy, amino-$C_{1-8}$-alkyl, amino-$C_{1-8}$-alkoxy, $C_{1-8}$-alkylamino-$C_{1-8}$-alkyl, $C_{1-8}$-alkylamino-$C_{1-8}$-alkoxy, di-$C_{1-8}$-alkylamino-$C_{1-8}$-alkyl, di-$C_{1-8}$-alkylamino-$C_{1-8}$-alkoxy, $C_{1-8}$-alkylsulfonyl-$C_{1-8}$-alkyl, $C_{1-8}$-alkylsulfonyl-$C_{1-8}$-alkoxy, carboxy-$C_{1-8}$-alkyl, carboxy-$C_{1-8}$-alkoxy, carboxy-$C_{1-8}$- alkoxy-$C_{1-8}$-alkyl, $C_{1-8}$-alkoxy-$C_{1-8}$-alkylcarbonyl, acyl-$C_{1-8}$-alkoxy-$C_{1-8}$-alkyl, (N—$C_{1-8}$-alkyl)-$C_{1-8}$-alkoxycarbonylamino, (N-hydroxy)-$C_{1-8}$-alkylaminocarbonyl-$C_{1-8}$-alkyl, (N-hydroxy)-$C_{1-8}$-alkylaminocarbonyl-$C_{1-8}$-alkoxy, (N-hydroxy)aminocarbonyl-$C_{1-8}$-alkyl, (N-hydroxy)aminocarbonyl-$C_{1-8}$-alkoxy, $C_{1-8}$-alkoxyaminocarbonyl-$C_{1-8}$-alkyl, $C_{1-8}$-alkoxyaminocarbonyl-$C_{1-8}$-alkoxy, (N—$C_{1-8}$-alkoxy)-$C_{1-8}$-alkylaminocarbonyl-$C_{1-8}$-alkyl, (N—$C_{1-8}$-alkoxy)-$C_{1-8}$-alkylaminocarbonyl-$C_{1-8}$-alkoxy, (N-acyl)-$C_{1-8}$-alkoxy-$C_{1-8}$-alkylamino, $C_{1-8}$-alkoxy-$C_{1-8}$-alkylcarbamoyl, (N—$C_{1-8}$-alkyl)-$C_{1-8}$-alkoxy-$C_{1-8}$-alkylcarbamoyl, $C_{1-8}$-alkoxy-$C_{1-8}$-alkylcarbonyl, $C_{1-8}$-alkoxy-$C_{1-8}$-alkylcarbonylamino, (N—$C_{1-8}$-alkyl)-$C_{1-8}$-alkoxy-$C_{1-8}$-alkylcarbonylamino, 1-$C_{1-8}$-alkoxy-$C_{1-8}$-alkylimidazol-2-yl, 1-$C_{1-8}$-alkoxy-$C_{1-8}$-alkyltetrazol-5-yl, 5-$C_{1-8}$-alkoxy-$C_{1-8}$-alkyltetrazol-1-yl, 2-$C_{1-8}$-alkoxy-$C_{1-8}$-alkyl-oxoimidazol-1-yl, carbamoyl-$C_{1-8}$-alkyl, carbamoyl-$C_{1-8}$-alkoxy, $C_{1-8}$-alkylcarbamoyl, di-$C_{1-8}$-alkylcarbamoyl, $C_{1-8}$-alkylsulfonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-8}$-alkoxy-$C_{1-8}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo[1,3]oxazinyl and 2-oxotetrahydropyrimidinyl.

$R^1$ radicals which are likewise preferred are benzofuranyl, benzoimidazolyl, 4H-benzo[1,4]oxazinyl, benzoxazolyl, 2- and 5-benzo[b]thienyl, 3,4-dihydro-2H-benzo[1,4]oxazinyl, 1,3-dihydroindolyl, 2,3-dihydroindolyl, indazolyl, indolyl, 1H-quinolinyl, 2H-chromenyl, 1,1a,2,7b-tetrahydro-cyclopropa[c]chromenyl, 1a,7b-dihydro-1H-cyclopropa[c]chromenyl, 6- and 7-isoquinolyl, pyridyl, pyrimidinyl, 6- and 7-quinazolyl, 6- and 7-quinolyl, 6-quinoxalinyl, 6- and 7-tetrahydroisoquinolyl, 6- and 7-tetrahydroquinolyl, each of which is substituted by 1-3 radicals selected from hydroxyl, oxo, oxide, halogen, cyano, trifluoromethyl, trifluoromethoxy, carbamoyl, carboxyl, $C_{1-8}$-alkyl, $C_{1-8}$-alkoxy, hydroxy-$C_{1-8}$-alkoxy, $C_{1-8}$-alkoxy-$C_{1-8}$-alkoxy, di-$C_{1-8}$-alkylamino, 2,3-dihydroxypropoxy, 2,3-dihydroxypropoxy-$C_{1-8}$-alkoxy, 2,3-dimethoxypropoxy, methoxybenzyloxy, hydroxybenzyloxy, phenethyloxy, methylenedioxybenzyloxy, dioxolanyl-$C_{1-8}$-alkoxy, cyclopropyl-$C_{1-8}$-alkoxy, -hydroxy-$C_{1-8}$-alkoxy, pyridylcarbamoyloxy-$C_{1-8}$-alkoxy, 3-morpholino-2-hydroxypropoxy, benzyloxy-$C_{1-8}$-alkoxy, picolyloxy, $C_{1-8}$-alkoxycarbonyl, $C_{1-8}$-alkoxy-$C_{1-8}$-alkoxy-$C_{1-8}$-alkyl, $C_{1-8}$-alkoxycarbonylamino, $C_{0-6}$-alkylcarbonylamino-$C_{1-8}$-alkyl, $C_{0-6}$-alkylcarbonylamino-$C_{1-8}$-alkoxy, (N—$C_{1-8}$-alkyl)-$C_{0-6}$-alkylcarbonylamino-$C_{1-8}$-alkyl, (N—$C_{1-8}$-alkyl)-$C_{0-6}$-alkylcarbonylamino-$C_{1-8}$-alkoxy, $C_{3-8}$-cycloalkylcarbonylamino-$C_{1-8}$-alkyl, $C_{3-8}$-cycloalkylcarbonylamino-$C_{1-8}$-alkoxy, $C_{1-8}$-alkoxy-$C_{1-8}$-alkyl, hydroxy-$C_{1-8}$-alkyl, hydroxy-$C_{1-8}$-alkoxy-$C_{1-8}$-alkyl, hydroxy-$C_{1-8}$-alkoxy-$C_{1-8}$-alkoxy, $C_{1-8}$-alkoxycarbonylamino-$C_{1-8}$-alkyl, $C_{1-8}$-alkoxycarbonylamino-$C_{1-8}$-alkoxy, $C_{1-8}$-alkylaminocarbonylamino-$C_{1-8}$-alkyl, $C_{1-8}$-alkylaminocarbonylamino-$C_{1-8}$-alkoxy, $C_{1-8}$-alkylaminocarbonyl-$C_{1-8}$-alkyl, $C_{1-8}$-alkylaminocarbonyl-$C_{1-8}$-alkoxy, $C_{1-8}$-alkylaminocarbonyl-$C_{1-8}$-alkoxy-$C_{1-8}$-alkyl, di-$C_{1-8}$-alkylaminocarbonyl-$C_{1-8}$-alkyl, di-$C_{1-8}$-alkylaminocarbonyl-$C_{1-8}$-alkoxy, $C_{1-8}$-alkylcarbonyloxy-$C_{1-8}$-alkyl, $C_{1-8}$-alkylcarbonyloxy-$C_{1-8}$-alkoxy, cyano-$C_{1-8}$-alkyl, cyano-$C_{1-8}$-alkoxy, 2-oxooxazolidinyl-$C_{1-8}$-alkyl, 2-oxooxazolidinyl-$C_{1-8}$-alkoxy, $C_{1-8}$-alkoxycarbonyl-$C_{1-8}$-alkyl, $C_{1-8}$-alkoxycarbonyl-$C_{1-8}$-alkoxy, $C_{1-8}$-alkylsulfonylamino-$C_{1-8}$-alkyl, $C_{1-8}$-alkylsulfonylamino-$C_{1-8}$-alkoxy, (N—$C_{1-8}$-alkyl)-$C_{1-8}$-alkylsulfonylamino-$C_{1-8}$-alkyl, (N—$C_{1-8}$-alkyl)-$C_{1-8}$-alkylsulfonylamino-$C_{1-8}$-alkoxy, amino-$C_{1-8}$-alkyl, amino-$C_{1-8}$-alkoxy, $C_{1-8}$-alkylamino-$C_{1-8}$-alkyl, $C_{1-8}$-alkylamino-$C_{1-8}$-alkoxy, di-$C_{1-8}$-alkylamino-$C_{1-8}$-alkyl, di-$C_{1-8}$-alkylamino-$C_{1-8}$-alkoxy, $C_{1-8}$-alkylsulfonyl-$C_{1-8}$-alkyl, $C_{1-8}$-alkylsulfonyl-$C_{1-8}$-alkoxy, carboxy-$C_{1-8}$-alkyl, carboxy-$C_{1-8}$-alkoxy, carboxy-$C_{1-8}$-alkoxy-$C_{1-8}$-alkyl, $C_{1-8}$-alkoxy-$C_{1-8}$-alkylcarbonyl, acyl-$C_{1-8}$-alkoxy-$C_{1-8}$-alkyl, (N—$C_{1-8}$-alkyl)-$C_{1-8}$-alkoxycarbonylamino, (N-hydroxy)-$C_{1-8}$-alkylaminocarbonyl-$C_{1-8}$-alkyl, (N-hydroxy)-$C_{1-8}$-alkylaminocarbonyl-$C_{1-8}$-alkoxy, (N-hydroxy)-aminocarbonyl-$C_{1-8}$-alkyl, (N-hydroxy)aminocarbonyl-$C_{1-8}$-alkoxy, $C_{1-8}$-alkoxyaminocarbonyl-$C_{1-8}$-alkyl, $C_{1-8}$-alkoxyaminocarbonyl-$C_{1-8}$-alkoxy, (N—$C_{1-8}$-alkoxy)-$C_{1-8}$-alkylaminocarbonyl-$C_{1-8}$-alkyl, (N—$C_{1-8}$-alkoxy)-$C_{1-8}$-alkylaminocarbonyl-$C_{1-8}$-alkoxy, (N-acyl)-$C_{1-8}$-alkoxy-$C_{1-8}$-alkylamino, $C_{1-8}$-alkoxy-$C_{1-8}$-alkylcarbamoyl, (N—$C_{1-8}$-alkyl)-$C_{1-8}$-alkoxy-$C_{1-8}$-alkylcarbamoyl, $C_{1-8}$-alkoxy-$C_{1-8}$-alkylcarbonyl, $C_{1-8}$-alkoxy-$C_{1-8}$-alkylcarbonylamino, (N—$C_{1-8}$-alkyl)-$C_{1-8}$-alkoxy-$C_{1-8}$-alkylcarbonylamino, 1-$C_{1-8}$-alkoxy-$C_{1-8}$-alkylimidazol-2-yl, 1-$C_{1-8}$-alkoxy-$C_{1-8}$-alkyltetrazol-5-yl, 5-$C_{1-8}$-alkoxy-$C_{1-8}$-alkyltetrazol-1-yl, 2-$C_{1-8}$-alkoxy-$C_{1-8}$-alkyl-4-oxoimidazol-1-yl, carbamoyl-$C_{1-8}$-alkyl, carbamoyl-$C_{1-8}$-alkoxy, $C_{1-8}$-alkylcarbamoyl, di-$C_{1-8}$-alkylcarbamoyl, $C_{1-8}$-alkylsulfonyl, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperazinoalkoxyalkyl, [1,2,4]-triazol-1-ylalkyl, [1,2,4]-triazol-1-ylalkoxy, [1,2,4]-triazol-4-ylalkyl, [1,2,4]-triazol-4-ylalkoxy, [1,2,4]-oxadiazol-5-ylalkyl, [1,2,4]-oxadiaol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyltetrazol-1-ylalkyl, 5-methyltetrazol-1-ylalkoxy, thiazol-4-ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy, N-methylpiperazinoalkyl, N-methylpiperazinoalkoxy, N-methylpiperazinoalkoxyalkyl, pyrrolidinyl, piperidinyl, piperazinyl, pyrrolyl, 4-methylpiperazinyl, morpholinyl, thiomorpholinyl, 2-hydroxymethylpyrrolidinyl, 3-hydroxypyrrolidinyl, 3,4-dihydroxypyrrolidinyl, 3-acetamidomethylpyrrolidinyl, 3-$C_{1-8}$-alkoxy-$C_{1-8}$-alkylpyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl, 2-oxoimidazolidinyl, 2-oxooxazolidinyl, 2-oxopyrrolidinyl, 2-oxo-[1,3]oxazinyl and 2-oxotetrahydropyrimidinyl.

Examples of particularly preferred $R^1$ radicals are phenyl, pyridyl, 3-$C_{1-8}$-alkylindolyl, benzofuranyl, 4H-benzo[1,4]oxazin-3-onyl, 3,4-dihydro-2H-benzo[1,4]oxazinyl, 3,4-dihydro-2H-benzo[1,4]thiazinyl, 3,3-di-$C_{1-8}$-alkyl-1,3-dihydroindol-2-onyl, 3,3-di-$C_{1-8}$-alkyl-1,3-dihydroindolyl, indazolyl, indolyl, 1H-quinolinyl, 2H-chromenyl, 1,1a,2,7b-tetrahydro-cyclopropa[c]chromenyl, 1a,7b-dihydro-1H-cyclopropa[c]chromenyl, and spiro[cyclopropane-1,3']-2,3-dihydro-1H-indolyl which may be substituted as specified above, especially by at least one substituent selected from halogen, oxide, oxo, $C_{1-8}$-alkoxy, $C_{1-8}$-alkoxy-$C_{1-8}$-alkoxy, $C_{1-8}$-alkoxy-$C_{1-8}$-alkyl, $C_{1-8}$-alkoxycarbonylamino-$C_{1-8}$-alkoxy, $C_{1-8}$-alkoxycarbonylamino-$C_{1-8}$-alkyl, $C_{1-8}$-alkyl, $C_{0-6}$-alkylcarbonylamino-$C_{1-8}$-alkoxy, $C_{0-6}$-alkylcarbonylamino-$C_{1-8}$-alkyl, N-acetyl-$C_{1-8}$-alkoxy-$C_{1-8}$-alkylamino, $C_{1-8}$-alkanoylamido-$C_{1-8}$-alkyl, N—$C_{1-8}$-alkyl-$C_{1-8}$-alkanoylamido-$C_{1-8}$-alkyl, $C_{1-8}$-alkoxy-$C_{1-8}$-alkoxy-$C_{1-8}$-alkyl, triazol-1-yl-$C_{1-8}$-alkyl, tetrazol-1-yl-$C_{1-8}$-alkyl, tetrazol-2-yl-$C_{1-8}$-alkyl, tetrazol-5-yl-$C_{1-8}$-alkyl, $C_{1-8}$-alkoxycarboxyl-$C_{1-8}$-alkyl, pyrrolidinonyl-$C_{1-8}$-alkyl, imidazolyl-$C_{1-8}$-alkyl, cyano-$C_{1-8}$-alkyl, carboxy-$C_{1-8}$-alkyl, carboxy-$C_{1-8}$-alkoxy, $C_{1-8}$-alkoxycarbonyl-$C_{0-6}$-alkyl, $C_{1-8}$-alkylsulfonamidyl-$C_{1-8}$-alkyl, $C_{1-8}$-alkoxy-$C_{1-8}$-alkanoylamido, $C_{1-8}$-alkoxy-$C_{1-8}$-alkanoylamido-$C_{1-8}$-alkyl, N—($C_{1-8}$-alkyl)-$C_{1-8}$-alkoxy-$C_{1-8}$-alkanoylamido, N—$C_{1-8}$-alkylcarbamoyl-$C_{1-8}$-alkyl, $C_{3-8}$-cycloalkanoylamido-$C_{1-8}$-alkyl, $C_{1-8}$-alkylaminocarbonylamino-$C_{1-8}$-alkyl, $C_{1-8}$-alkanoylamidomethylpyrrolidinyl, N—($C_{1-8}$-alkoxy-$C_{1-8}$-alkyl)carbamoyl, N—($C_{1-8}$-alkoxy-$C_{1-8}$-alkyl)-N—($C_{1-8}$-alkyl)carbamoyl, N—($C_{1-8}$-alkoxy-$C_{1-8}$-alkyl)imidazol-2-yl, hydroxy-$C_{1-8}$-alkyl, hydroxy-$C_{1-8}$-alkoxy, hydroxy-$C_{1-8}$-alkoxy-$C_{1-8}$-alkyl, $C_{1-8}$-alkoxycarbonylamido-$C_{1-8}$-alkyl, amino-$C_{1-8}$-alkyl and $C_{1-8}$-alkylamino-$C_{1-8}$-alkyl.

Examples of very particularly preferred $R^1$ radicals are phenyl, pyridyl, or a bicyclic heterocyclyl, consisting of a phenyl-ring annulated to a 5-6 membered, saturated or unsaturated, heterocyclic ring, having from 1 to 3 nitrogen and/or 1 sulfur or oxygen atoms, such as 4H-benzo[1,4]oxazin-3-on-6-yl, 3,4-dihydro-2H-benzo[1,4]oxazin-6-yl, 3,4-dihydro-2H-benzo[1,4]thiazin-6-yl, 2,2-dimethyl-3,4-dihydro-2H-benzo[1,4]oxazin-6-yl, 2,2-dimethyl-4H-benzo[1,4]oxazin-3-on-6-yl, 4,4-dimethyl-1,4-dihydrobenzo[d][1,3]oxazin-2-on-8-yl, 3,3-dimethyl-1,3-dihydroindol-2-on-6-yl, 3,3-dimethyl-1,3-dihydroindol-2-on-7-yl, 3,3-dimethyl-1,3-dihydroindol-6-yl, 3-methylindol-6-yl, 1-methyl-indazol-5-yl, 3,4-dihydro-1H-quinolin-2-on-7-yl, 4,4-dimethyl-3,4-dihydro-1H-quinolin-2-on-8-yl, 1H-quinolinyl, 2H-chromenyl, 1,1a,2,7b-tetrahydro-cyclopropa[c]chromenyl, 1a,7b-dihydro-1H-cyclopropa[c]chromenyl, and spiro[cyclopropane-1,3']-2,3-dihydro-1H-indol-6-yl, which may be substituted as specified above, especially by at least one substituent selected from $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxycarbonylamino-$C_{1-8}$-alkoxy, $C_{1-8}$-alkoxycarbonylamino-$C_{1-8}$-alkyl, $C_{1-8}$-alkyl, $C_{0-6}$-alkylcarbonylamino-$C_{1-8}$-alkoxy, $C_{0-6}$-alkylcarbonylamino-$C_{1-8}$-alkyl, halogen, oxide, triazol-1-yl-$C_{1-8}$-alkyl, and oxo, and, preferably, where, in the case that $R^1$ is a bicyclic heterocyclyl, the phenyl-ring of the bicyclic system is bonded to Z or, in case n is 0, is bonded to X and at least the non-phenyl-ring is substituted as specified.

Preferred $R^2$ radicals are phenyl and phenyl substituted by halogen, hydroxyl, cyano, trifluoromethoxy, trifluoromethyl, $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{3-8}$-cycloalkylsulfanyl-$C_{1-8}$-alkyl, $C_{3-8}$-cycloalkyl-$C_{0-6}$-alkoxy, $C_{3-8}$-cycloalkyl-$C_{0-6}$-alkoxy-$C_{1-8}$-alkyl, $C_{3-8}$-cycloalkyl-$C_{0-6}$-alkoxy-$C_{1-8}$-alkoxy, heterocyclyl-$C_{0-6}$-alkoxy, heterocyclyl-$C_{0-6}$-alkoxy-$C_{1-8}$-alkyl, halo-$C_{1-8}$-alkyl, hydroxy-$C_{1-8}$-alkyl, cyano-$C_{1-8}$-alkyl, carboxy-$C_{1-8}$-alkyl, $C_{1-8}$-alkylcarbonyloxy-$C_{1-8}$-alkyl, $C_{1-8}$-alkoxycarbonyloxy-$C_{1-8}$-alkyl, $C_{1-8}$-alkoxycarbonyl or $C_{1-8}$-alkylenedioxy.

$R^2$ radicals which are likewise preferred are phenyl and halophenyl substituted by an L1-T1-L2-T2-L3-T3-L4-T4-L5-U radical where L1 and L2 are preferably absent or $C_{1-8}$-alkylene and L3 is absent and U is hydrogen, $C_{1-8}$-alkyl, $C_{3-8}$-cycloalkyl, phenylpiperidinyl, phenylpiperazinyl, phenylpyrrolidinyl, phenyl, is phenyl or phenylpyrrolidinyl each substituted by $C_{1-8}$-alkyl, $C_{1-8}$-alkoxy, $C_{1-8}$-alkylthio, $C_{1-8}$-alkylsulfinyl, $C_{1-8}$-alkylenedioxy, halogen, benzoyl-$C_{1-8}$-alkyl, halogen-$C_{1-8}$-alkyl, $C_{1-8}$-alkanoyloxy or hydroxyl, or is naphthyl, pyridyl, thienyl, pyrazinyl, triazolyl, imidazolyl, phenyloxadiazolyl, thienyloxadiazolyl, furyloxadiazolyl, phenyloxazolyl, benzthiazolyl, furyl, pyrimidinyl, nitrobenzthiazolyl, phenyltetrazolyl, piperidinyl, tetrahydropyranyl, morpholinyl or indolyl.

In the groups T1-T4, preference is given to the definitions (a)-(c), (e)-(h), (k)-(n) and (r)-(t).

Examples of particularly preferred $R^2$ radicals are unsubstituted phenyl and phenyl and halophenyl each substituted by $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxy-$C_{1-8}$-alkyl-amino-$C_{1-8}$-alkyl, $C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{3-8}$-alkylsulfanyl-$C_{1-8}$-alkyl, $C_{1-8}$-alkylsulfonyl-$C_{1-8}$-alkoxy-$C_{1-8}$-alkyl, $C_{3-8}$-cycloalkyl-$C_{0-6}$-alkoxy, $C_{3-8}$-cycloalkyl-$C_{0-6}$-alkoxy-$C_{1-8}$-alkoxy, $C_{3-8}$-cycloalkyl-$C_{0-6}$-alkoxy-$C_{1-8}$-alkyl, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{1-8}$-alkylamino-$C_{1-8}$-alkyl, halogen, heterocyclyl-$C_{0-6}$-alkoxy, heterocyclyl-$C_{0-6}$-alkoxy-$C_{1-8}$-alkyl, $C_{1-8}$-alkoxy-$C_{1-8}$-alkylamino-$C_{1-8}$-alkyl, N-(halophenyl)pyrrolidinyloxy, N-(halo-phenyl)pyrrolidinyloxy-$C_{1-8}$-alkyl, $C_{1-8}$-alkoxybenzyloxy-$C_{1-8}$-alkoxy, $C_{1-8}$-alkoxyphenoxy-$C_{1-8}$-alkoxy, $C_{1-8}$-alkoxyphenoxy-$C_{1-8}$-alkyl, $C_{1-8}$-alkoxyphenyl-$C_{1-8}$-alkoxy-$C_{1-8}$-alkoxy, halobenzyloxy-$C_{1-8}$-alkoxy, halophenoxy-$C_{1-8}$-alkoxy, halophenoxy-$C_{1-8}$-alkoxy-$C_{1-8}$-alkyl, halophenoxy-$C_{1-8}$-alkyl, halophenyl-$C_{1-8}$-alkoxy-$C_{1-8}$-alkoxy or $C_{1-8}$-alkylbenzyloxy-$C_{1-8}$-alkoxy.

Examples of very particularly preferred $R^2$ radicals are phenyl and halophenyl each substituted by $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxy-$C_{1-8}$-alkyl-amino-$C_{1-8}$-alkyl, $C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{3-8}$-alkylsulfanyl-$C_{1-8}$-alkyl, $C_{1-8}$-alkylsulfonyl-$C_{1-8}$-alkoxy-$C_{1-8}$-alkyl, $C_{3-8}$-cycloalkyl-$C_{0-6}$-alkoxy, $C_{3-8}$-cycloalkyl-$C_{0-6}$-alkoxy-$C_{1-8}$-alkoxy, $C_{3-8}$-cycloalkyl-$C_{0-6}$-alkoxy-$C_{1-8}$-alkyl, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{1-8}$-alkylamino-$C_{1-8}$-alkyl, halogen, heterocyclyl-$C_{0-6}$-alkoxy, heterocyclyl-$C_{0-6}$-alkoxy-$C_{1-8}$-alkyl, $C_{1-8}$-alkoxy-$C_{1-8}$-alkylamino-$C_{1-8}$-alkyl, N-(halo-phenyl)pyrrolidinyloxy, N-(halo-phenyl)pyrrolidinyloxy-$C_{1-8}$-alkyl, $C_{1-8}$-alkoxybenzyloxy-$C_{1-8}$-alkoxy, $C_{1-8}$-alkoxyphenoxy-$C_{1-8}$- alkoxy, $C_{1-8}$-alkoxyphenoxy-$C_{1-8}$-alkyl, $C_{1-8}$-alkoxyphenyl-$C_{1-8}$-alkoxy-$C_{1-8}$-alkoxy, halobenzyloxy-$C_{1-8}$-alkoxy, halophenoxy-$C_{1-8}$-alkoxy, halophenoxy-$C_{1-8}$-alkoxy-$C_{1-8}$-alkyl, halophenoxy-$C_{1-8}$-alkyl, halophenyl-$C_{1-8}$-alkoxy-$C_{1-8}$-alkoxy or $C_{1-8}$-alkylbenzyloxy-$C_{1-8}$-alkoxy.

Also very particularly preferred $R^2$ radicals are phenyl and halophenyl each substituted as defined above whereby at least one substituent is in the para-position relative to the bond of $R^2$ to the rest of the molecule. Preferred substituents—in the para-position relative to the bond of $R^2$ to the rest of the molecule—on $R^2$ are fluoro, ethyl, propyl, butyl, isobutyl, pentyl, methylsulfanyl, 2-methoxyethylsulfanyl, 3-methoxypropylsulfanyl, 4-methoxybutylsulfanyl, 4-methoxy-3-methyl-butylsulfanyl, allyloxy, methoxy, ethoxy, propoxy, 4-methoxybutoxy, 3-methoxypropoxy, 2-methoxyethoxy, 3-cyclopropyloxypropoxy, (2-methoxy-cyclopropyl)methoxymethyl, (2-methoxymethyl-cyclopropyl)methoxymethyl, 3-methylsulfanylpropoxy, methoxymethyl, 2-methoxyethoxymethyl, 3-methoxypropoxymethyl, 2-methyl-3-methylsulfanyl-propoxymethyl, cyclopropylmethoxymethyl, ethoxymethyl, 2-methoxyethyl, 3-methoxy-2-methyl-propoxymethyl, 2-methylsulfanylethoxymethyl, methylsulfanylmethyl, 2-methoxyethylsulfanylmethyl, 3-methoxypropylsulfanylmethyl and cyclopropylsulfanylmethyl.

Examples of preferred X radicals are oxygen, methylene, —O—$CH_2$—CO—NH—, —O—$CH_2$—CO—N($CH_3$)— and —O—CH($CH_3$)—CO—NH—.

Particularly preferred for X are, a bond, methylene and oxygen.

Particularly preferred Z radicals are alkylene, —$(CH_2)_{1-2}$—O— and —CH($CH_3$)—;
where, if X is a bond, Z is —$(CH_2)_{1-2}$—O—

A group of very particularly preferred compounds of the formula (I) or (II), or more preferably of the formula (IA) or (IIA), are compounds where R is $C_{1-8}$-alkyl, $C_{0-8}$-alkyl-carbonyl-amino-$C_{1-8}$-alkyl, $C_{1-8}$-alkyl-sulfonyl-$C_{1-8}$-alkyl, optionally N-mono- or N,N-di-$C_{1-8}$-alkylated carbamoyl-$C_{0-8}$-alkyl, optionally N and/or N' mono-, di- or tri-$C_{1-8}$-alkylated ureido-$C_{0-8}$-alkyl, heterocyclyl-$C_{0-8}$-alkyl, or heterocyclylcarbonyl-$C_{0-8}$-alkyl, each of said radicals may be substituted, preferably by 1-4 $C_{1-8}$-alkoxy, $C_{1-8}$-alkoxy-$C_{1-8}$-alkoxy $C_{1-8}$-alkoxycarbonyl-(N—$C_{1-8}$-alkyl)-amino, $C_{1-8}$-alkyl, $C_{1-8}$-alkyl-carbonyl-(N—$C_{1-8}$-alkyl)-amino, $C_{1-8}$-alkyl-sulfanyl, aryl-$C_{0-8}$-alkoxy, which is optionally substituted by 1 or 2 aryl or $C_{1-8}$-alkoxy radicals, aryl, which is optionally substituted by 1 or 2 aryl or $C_{1-8}$-alkoxy radials, cyano, halogen, heterocyclyl, heterocyclyl-$C_{0-8}$-alkyl-amino, heterocyclyl-carbonyl, optionally N-mono- or N,N-di-$C_{1-8}$-alkylated carbamoyl-$C_{0-8}$-alkyl, optionally N-mono- or N,N-di-$C_{1-8}$-alkylated carbamoyloxy, hydroxyl, optionally N-mono- or N,N-di-$C_{1-8}$-alkylated amino, trifluoromethoxy or trifluoromethyl;

$R^1$ is phenyl, pyridyl, 4H-benzo[1,4]oxazin-3-on-6-yl, 3,4-dihydro-2H-benzo[1,4]oxazin-1-yl, 3,4-dihydro-2H-benzo[1,4]thiazin-1-yl, 2,2-dimethyl-3,4-dihydro-2H-benzo[1,4]oxazinyl, 2,2-dimethyl-4H-benzo[1,4]oxazin-3-on-4-yl, 4,4-dimethyl-1,4-dihydrobenzo[d][1,3]oxazin-2-n8-yl, 3,3-dimethyl-1,3-dihydroindol-2-on-6-yl, 3,3-dimethyl-1,3-dihydroindol-2-on-7-yl, 3,3-dimethyl-1,3-dihydroindolyl, 3-methylindol-6-yl, 1-methyl-indazol-5-yl, 3,4-dihydro-1H-quinolin-2-on-7-yl, 4,4-dimethyl-3,4-dihydro-1H-quinolin-2-on-8-yl, 1H-quinolinyl, 2H-chromenyl, 1,1a,2,7b-tetrahydro-cyclopropa[c]chromenyl, 1a,7b-dihydro-1H-cyclopropa[c]chromenyl, or spiro[cyclopropane-1,3']-2,3-dihydro-1H-indol-6-yl which may be substituted as specified above, especially by at least one substituent selected from $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxycarbonylamino-$C_{1-8}$-alkoxy, $C_{1-8}$-alkoxycarbonylamino-$C_{1-8}$-alkyl, $C_{1-8}$-alkyl, $C_{0-6}$-alkylcarbonylamino-$C_{1-8}$-alkoxy, $C_{0-6}$-alkylcarbonylamino-$C_{1-8}$-alkyl, halogen, oxide, triazol-1-yl-$C_{1-8}$-alkyl, or oxo;

$R^2$ is phenyl or halophenyl each substituted by $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxy-$C_{1-8}$-alkyl-amino-$C_{1-8}$-alkyl, $C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{3-8}$-cycloalkylsulfanyl-$C_{1-8}$-alkyl, $C_{1-8}$-alkylsulfonyl-$C_{1-8}$-alkoxy-$C_{1-8}$-alkyl, $C_{3-8}$-cycloalkyl-$C_{0-6}$-alkoxy, $C_{3-8}$-cycloalkyl-$C_{0-6}$-alkoxy-$C_{1-8}$-alkoxy, $C_{3-8}$-cycloalkyl-$C_{0-6}$-alkoxy-$C_{1-8}$-alkyl, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{1-8}$-alkylamino-$C_{1-8}$-alkyl, halogen, heterocyclyl-$C_{0-6}$-alkoxy, heterocyclyl-$C_{0-6}$-alkoxy-$C_{1-8}$-alkyl, $C_{1-8}$-alkoxy-$C_{1-8}$-alkylamino-$C_{1-8}$-alkyl, N-(halophenyl)pyrrolidinyloxy, N-(halo-phenyl)pyrrolidinyloxy-$C_{1-8}$-alkyl, $C_{1-8}$-alkoxybenzyloxy-$C_{1-8}$-alkoxy, $C_{1-8}$-alkoxyphenoxy-$C_{1-8}$-alkoxy, $C_{1-8}$-alkoxyphenoxy-$C_{1-8}$-alkyl, $C_{1-8}$-alkoxyphenyl-$C_{1-8}$-alkoxy-$C_{1-8}$-alkoxy, halobenzyloxy-$C_{1-8}$-alkoxy, halophenoxy-$C_{1-8}$-alkoxy, halophenoxy-$C_{1-8}$-alkoxy-$C_{1-8}$-alkyl, halophenoxy-$C_{1-8}$-alkyl, halophenyl-$C_{1-8}$-alkoxy-$C_{1-8}$-alkoxy or $C_{1-8}$-alkylbenzyloxy-$C_{1-8}$-alkoxy, whereby at least one substituent is in the para-position relative to the bond of $R^2$ to the rest of the molecule. Preferred substituents—in the para-position relative to the bond of $R^2$ to the rest of the molecule—on $R^2$ are fluoro, ethyl, propyl, butyl, isobutyl, pentyl, methylsulfanyl, 2-methoxyethylsulfanyl, 3-methoxypropylsulfanyl, 4-methoxybutylsulfanyl, 4-methoxy-3-methyl-butylsulfanyl, allyloxy, methoxy, ethoxy, propoxy, 4-methoxybutyloxy, 3-methoxypropoxy, 2-methoxyethoxy, 3-cyclopropyloxypropoxy, (2-methoxy-cyclopropyl)methoxymethyl, (2-methoxymethyl-cyclopropyl)methoxymethyl, 3-methylsulfanylpropoxy, methoxymethyl, 2-methoxyethoxymethyl, 3-methoxypropoxymethyl, 2-methyl-3-methylsulfanyl-propoxymethyl, cyclopropylmethoxymethyl, ethoxymethyl, 2-methoxyethyl, 3-methoxy-2-methyl-propoxymethyl, 2-methylsulfanylethoxymethyl, methylsulfanylmethyl, 2-methoxyethylsulfanylmethyl, 3-methoxyptopylsulfanylmethyl and cyclopropylsulfanylmethyl;

$R^3$ is hydrogen;
$R^4$ is hydrogen;
Q is absent;
X is a bond, methylene or oxygen;
Z is alkylene, —$(CH_2)_{1-2}$—O— and —CH($CH_3$)—;
where, if X is a bond, Z is —$(CH_2)_{1-2}$—O—
m=0 and
n=1.

The compounds of the formulae (I) and (II), or preferably of the formula (IA) or (IIA), and their pharmaceutically useable salts have inhibiting action on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II increases the blood pressure both directly by arterial constriction and indirectly by the release of the hormone aldosterone which inhibits the release of the sodium ion from the adrenal glands, which is associated with a rise in the extracellular liquid volume. This rise can be attributed to the action of angiotensin II itself or of the heptapeptide angiotensin III formed therefrom as a cleavage product. Inhibitors of the enzymatic activity of renin bring about a reduction in the formation of angiotensin I and, as a consequence thereof, the formation of a smaller amount of angiotensin II. The reduced concentration of this active peptide hormone is the immediate cause of the hypotensive action of renin inhibitors.

One experimental procedure of detecting the action of renin inhibitors is by means of in vitro tests, in which the reduction of the formation of angiotensin I in different systems (human plasma, purified human renin together with synthetic or natural renin substrate) is measured.

One in vitro test which is used is the one according to Nussberger et. al (1987) J. Cardiovascular Pharmacol., Vol. 9, p. 39-44 which follows. This test measures the formation of angiotensin I in human plasma. The amount of angiotensin I formed is determined in a subsequent radioimmunoassay. Which action inhibitors have on the formation of angiotensin I is tested in this system by the addition of different concentrations of these substances. The $IC_{50}$ refers to that concentration of the particular inhibitor which reduces the formation of angiotensin I by 50%. The compounds of the present invention exhibit inhibiting actions in the in vitro systems at minimum concentrations of about $10^{-3}$ to about $10^{-10}$ mol/l.

Illustrative of the invention, the compounds of examples 10, 12, 21, 33, 40, 53, and 120 inhibit the formation of angiotensin I with $IC_{50}$ values in the range of about $10^{-5}$ to about $10^{-7}$ mol/l.

In salt-depleted animals, renin inhibitors bring about a blood pressure decrease. Human renin differs from renin of other species. To test inhibitors of human renin, primates (marmosets, *Callithrix jacchus*) are used, because human renin and primate renin are substantially homologous in the enzymatically active region. One in vivo test which is used is as follows: the test compounds are tested on normotensive marmosets of both genders and having a body weight of about 350 g which are conscious, able to move freely and in their normal cages. Blood pressure and heart rate are measured using a catheter in the descending aorta and recorded radiometrically. The endogenous release of renin is stimulated by the combination of a 1-week low-salt diet with a single intramuscular injection of furosemide (5-(aminosulfonyl)-4-chloro-2-[(2-furanylmethyl)amino]benzoic acid) (5 mg/kg). 16 hours after the injection of furosemide, the test substances are administered either directly into the femoral artery by means of an injection cannular or into the stomach by gavage as a suspension or solution, and their effect on blood pressure and heart rate was evaluated. The compounds of the present invention effectively reduce blood pressure in the in vivo test described at doses of about 0.003 to about 0.3 mg/kg i.v. and at doses of about 0.3 to about 30 mg/kg p.o.

The compounds of the formulae (I) or (II), or preferably of the formula (IA) or (IIA), and their pharmaceutically useable salts may find use as medicaments, for example in the form of pharmaceutical preparations. The pharmaceutical preparations may be administered enterally, such as orally, for example in the form of tablets, coated tablets, sugar-coated tablets, hard and soft gelatine capsules, solutions, emulsions or suspensions, nasally, for example in the form of nasal sprays, rectally, for example in the form of suppositories, or transdermally, for example in the form of ointments or patches. The administration may also be parenteral, such as intramuscular or intravenous, for example in the form of injection solutions.

To prepare tablets, coated tablets, sugar-coated tablets and hard gelatine capsules, the compounds of the formulae (I) or (II), or preferably of the formula (IA) or (IIA), and pharmaceutically useable salts thereof, may be processed with pharmaceutically inert, inorganic or organic excipients. Such excipients used, for example for tablets, coated tablets and hard gelatine capsules, may be lactose, corn starch, or derivatives thereof, talc, stearic acid or salts thereof etc.

Suitable excipients for soft gelatine capsules are, for example, vegetable oils, waxes, fats, semisolid and liquid polyols, etc.

Suitable excipients for preparing solutions and syrups are, for example, water, polyols, sucrose, invert sugar, glucose, etc.

Suitable excipients for injection solutions are, for example, water, alcohols, polyols, glycerol, vegetable oils, bile adds, lecithin, etc.

Suitable excipients for suppositories are, for example, natural or hardened oils, waxes, fats, semisolid or liquid polyols, etc.

The pharmaceutical preparations may additionally also comprise preservatives, solubilizers, viscosity-increasing substances, stabilizers, wetting agents, emulsifiers, sweeteners, colorants, flavourings, salts for altering the osmotic pressure, buffers, coatings or antioxidants. They may also comprise other therapeutically valuable substances.

The present invention further provides the use of the compounds of the formulae (I) or (II), or preferably of the formula (IA) or (IIA), and the pharmaceutically useable salts thereof, in the treatment or prevention of hypertension and heart failure, and also glaucoma, cardiac infarction, kidney failure and restenoses of mammals, especially of human beings.

The compounds of the formulae (I) or (II), or preferably of the formula (IA) or (IIA), and the pharmaceutically useable salts thereof, may also be administered in combination with one or more agents having cardiovascular action, for example α- and β-blockers such as phentol-amine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexylene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane-synthetase inhibitors; neutral endopeptidase inhibitors (NEP inhibitors); angiotensin II antagonists; and also diuretics such as hydrochlorothiazide, chlorothiazide, acetazolamide, amiloride, bumetanide, benzthiazide, ethacrynic acid, furosemide; indacrinone, metolazone, spironolactone, triamteren, chlorthalidone etc.; sympatholytics such as methyldopa, clonidine, guanabenz, reserpine; and other agents which are suitable for the treatment of hypertension, heart failure or vascular diseases in humans and animals which are associated with diabetes or renal disorders such as acute or chronic renal failure. Such combinations may be employed separately or in preparations which comprise a plurality of components.

Further substances which can be used in combination with the compounds of the formulae (I) or (II), or preferably of the formula (IA) or (IIA), are the compounds of classes (i) to (ix) on page 1 of WO 02/40007 (and also the preferences and examples further listed therein) and the substances specified on pages 20 and 21 of WO 03/027091.

The dose may vary within wide limits and has of course to be adapted to the individual circumstances in each individual case. In general, for oral administration, a daily dose of about 3 mg to about 3 g, preferably about 10 mg to about 1 g, for example about 300 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

EXAMPLES

The examples which follow illustrate the present invention. All temperatures are reported in degrees Celsius, pressures in mbar. Unless stated otherwise, the reactions take place at room temperature. The abbreviation "Rf=xx (A)" means, for example, that the Rf value xx is obtained in the solvent system A. The ratio of the solvents relative to one another is always reported in parts by volume. Chemical names of end products and intermediates were obtained with the aid of the program AutoNom 2000 (Automatic Nomenclature).

HPLC gradient on Hypersil BDS C-18 (5 μm); column: 4×125 mm

90% water*/10% acetonitrile* to 0% water*/100% acetonitrile* in 5 minutes+2.5 minutes (1.5 ml/min); *: containing 0.1% trifluoroacetic acid The following abbreviations are used:

Rf ratio of distance which a substance travels to distance of the eluent front from the start point in thin layer chromatography Rt retention time of a substance in HPLC (in minutes)

m.p. melting point (temperature)

General Procedure A (N-Tos-deprotection)

To a stirred solution of 0.09 mmol "tosylamide" in 10 ml of methanol are added 0.44 mmol sodiumdihydrogenphosphate and 0.90 mmol of sodium amalgam (10% Na) at room temperature. The reaction mixture is stirred for 2-18 hours, diluted with water and extracted with ethyl acetate. The organic phases are combined, washed with brine and dried over sodium sulfate. The solvent is concentrated under reduced pressure and the residue is purified by flash chromatography ($SiO_2$ 60 F) to afford the title compound.

General Procedure B: (N-p-Methoxyphenyl Deprotection)

To a stirred solution of 0.5 mmol "p-methoxyanilin" in 10 ml of acetonitrile/water (1:1) is added a solution of 1.43 mol of ceric ammonium nitrate in 5.0 ml of water at 0° C. The mixture is stirred for 30 min, followed by addition of 1.0 g of sodium sulfite. After additional 30 min, the mixture is diluted with water and extracted with tert-butyl methyl ether. The organic phase is dried and concentrated under reduced pressure. The residue is purified by flash chromatography ($SiO_2$ 60 F) to afford the title compound.

General Procedure C: ($BH_3$-Reduction)

To a stirred solution of 1 mmol of "lactam" in 3 ml of tetrahydrofuran is admixed with 2-4 mmol of borane tetrahydrofuran (1M in tetrahydrofuran) and heated to 50° C. for 28 hours.

The reaction mixture is quenched by addition of 10 ml of methanol and concentrated under reduced pressure. The title compound is obtained from the residue by means of flash chromatography ($SiO_2$ 60 F).

General Procedure D: (Amide-Formation)

To a stirred solution of 1.0 mmol of "acid" and "1.0 mmol of "amin" in 20 ml of dichloromethane are added 5.0 mmol of triethylamine and 1.0 mmol of tri-propylphosphonic acid cyclic anhydride [68957-94-8] (50% in ethyl acetate) at room temperature. The reaction mixture is stirred for 13 hours, diluted with dichloromethane, washed with 1N hydrochloric acid and brine. The organic phases are combined, dried over sodium sulfate and the solvent is concentrated under reduced pressure. The residue is purified by flash chromatography ($SiO_2$ 60 F) to afford the title compound.

General Procedure E: (Hydrogenation)

To a stirred solution of 1 mmol of "substrate" in 15 ml of tetrahydrofuran are added 100-200 mg Pd/C 10% and the reaction mixture is hydrogenated at 15-20° C. The reaction mixture is filtered and concentrated under reduced pressure. The residue is purified by flash chromatography ($SiO_2$ 60 F) to afford the title compound.

General Procedure F: (Mesylation)

To a stirred solution of 1 mmol of "alcohol" in 10 ml of dichloromethane are added 5 mmol of triethylamine and 2 mmol of methanesulfonyl chloride at 0° C. The reaction mixture is allowed to stir for 1 hour, diluted with dichloromethane, washed with 1N hydrochloric acid, and dried over sodium sulfate. The solvent is concentrated under reduced pressure and the residue is purified by flash chromatography ($SiO_2$ 60 F) to afford the title compound or is directly used in the next step without any further purification.

Example 1

{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-methanol

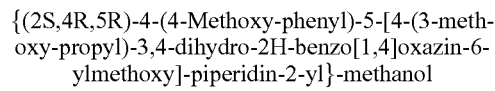

To a stirred solution of 0.10 g of (2S,4R,5R)-4-(4-methoxy-phenyl)-5-[4-(3-methoxy-propyl)-3,4-dihydro-2H-benzo[1,4]oxazin-6-ylmethoxy]-piperidine-2-carboxylic acid ethyl ester in 10 ml of tetrahydrofuran are added 17.0 mg of lithium aluminium hydride at 0° C. The reaction mixture is stirred for 1 hour at this temperature, diluted with tert-butyl methyl ether and quenched by addition of 2.0 ml of aqueous saturated sodium sulfate solution. The mixture is allowed to warm to room temperature, filtered and dried over sodium sulfate. The solvent is concentrated under reduced pressure and the residue is purified by flash chromatography ($SiO_2$ 60 F) to afford the title compound.

The starting materials are prepared as follows:

a) (2S,4R,5R)-4-(4-Methoxy-phenyl)-5-[4-(3-methoxy-propyl)-3-oxo-3,4-dihydro-2H-benzo[1,4]oxazin-6-ylmethoxy]-piperidine-2-carboxylic acid ethyl ester

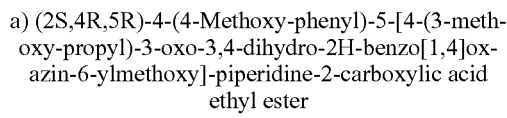

According to general procedure B, 0.3 g of (2S,4R,5R)-1,4-bis-(4-methoxy-phenyl)-5-[4-(3-methoxy-propyl)-3-oxo-3,4-dihydro-2H-benzo[1,4]oxazin-6-ylmethoxy]-piperidine-2-carboxylic acid ethyl ester are used to afford the title compound as a yellow oil. Rf=0.15 (dichlormethane-methanol-25% ammonia conc. 200:10:1); Rt=3.53.

b) (2S,4R,5R)-1,4-Bis-(4-methoxy-phenyl)-5-[4-(3-methoxy-propyl)-3-oxo-3,4-dihydro-2H-benzo[1,4]oxazin-6-ylmethoxy]-piperidine-2-carboxylic acid ethyl ester

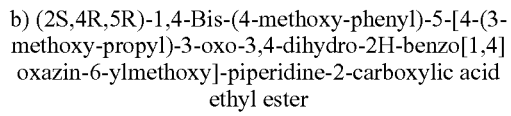

To a stirred solution of 5.20 g of (2S,4R,5R)-5-hydroxy-1,4-bis(4-methoxy-phenyl)piperidine-2-carboxylic acid ethyl ester and 5.62 g of 2,2,2-trichloro-acetimidic acid 4-(3-methoxy-propyl)-3-oxo-3,4-dihydro-2H-benzo[1,4]oxazin-6-ylmethyl ester in 150 ml of dichloromethane is added 1.1 ml of trifluoromethanesulfonic acid at −0° C. The reaction mixture is allowed to stir for another hour at this temperature and then allowed to warm to 0° C. within 2 hours. The mixture is quenched by addition of 2N sodium hydroxide, extracted with dichlormethane, dried over sodium sulfate and concentrated under reduced pressure. The residue is purified by flash chromatography (SiO$_2$ 60 F) to afford the title compound as a brown oil. Rf=0.15 (EtOAc-heptane 1:1); Rt=4.73.

c) (2S,4R,5R)-5-Hydroxy-1,4-bis(4-methoxy-phenyl)piperidine-2-carboxylic acid ethyl ester To a stirred solution of 19.5 g of (S)-1,4-bis-(4-methoxy-phenyl)-1,2,3,6-tetrahydro-pyridine-2-carboxylic acid ethyl ester in 400 ml of tetrahydrofuran are added 56 ml of a solution of borane-tetrahydrofuran (1M) at room temperature. The reaction mixture is heated to 40° C. for 2-6 hours, cooled to room temperature, and quenched by the addition of 50 ml of 2N sodium hydroxide solution and 100 ml of 30% hydrogen peroxide solution. The organic phase is separated, dried over sodium sulfate and concentrated under reduced pressure. The residue is purified by flash chromatography (SiO$_2$ 60 F) to afford the title compound as a yellow solid. Rf=0.33 (EtOAc-heptane 1:1); Rt=3.58.

d) (S)-1,4-Bis-(4-methoxy-phenyl)-1,2,3,6-tetrahydro-pyridine-2-carboxylic acid ethyl ester To a suspension of 38.0 g of (S)-1-(4-methoxy-phenyl)-4-trifluoromethanesulfonyloxy-1,2,3,6-tetrahydropyridine-2-carboxylic acid ethyl ester, 18.1 g of 4-methoxyphenylboronic acid, 6.45 g of lithiumchloride in 300 ml of dimethoxyethan are added 100 ml of ethanol, 160 ml of 2N sodium carbonate solution and 2.22 g of tetrakis(triphenylphosphine)palladium. The reaction mixture is heated to 75° C. for 3-6 hours and allowed to cool to room temperature overnight. The reaction mixture is filtered and the filtercake is redissolved in dichloromethane and water. The suspension is filtered again and the organic phase is concentrated under reduced pressure to afford the title compound as a colourless solid. Rf=0.25 (EtOAc-heptane 1:4); Rt=5.00.

e) (S)-1-(4-Methoxy-phenyl)-4-trifluoromethane-sulfonyloxy-1,2,3,6-tetrahydropyridine-2-carboxylic acid ethyl ester To a stirred solution of 0.94 g (S)-1-(4-methoxy-phenyl)-4-oxo-1,2,3,4-tetrahydro-pyridine-2-carboxylic acid ethyl ester [690224-49-8] in 20 ml tetrahydrofuran is added a solution of 3.7 ml of L-selectride (0.5M, Aldrich 17, 849-7) at −78° C. The mixture is stirred for 1 hour and a solution of 1.18 g N-phenyltrifluoromethanesulfonimide (Fluka 78175) in 8 ml of tetrahydrofuran is added and the mixture is allowed to warm to room temperature overnight. The reaction mixture is concentrated under reduced pressure and the residue is purified by flash chromatography (aluminium oxide, Fluka 06290) to afford the title compound as a brown solid. Rf=0.2 (EtOAc-heptane 1:9); Rt=5.14.

f) 2,2,2-Trichloro-acetimidic acid 4-(3-methoxy-propyl)-3-oxo-3,4-dihydro-2H-benzo[1,4]oxazin-6-ylmethyl ester To a stirred solution of 8.50 g of 6-hydroxymethyl-4-(3-methoxy-propyl)-4H-benzo[1,4]oxazin-3-one in 200 ml of diethylether is added 1.28 g of sodium hydride at 0° C. The mixture is stirred for 1 hour and concentrated to dryness under reduced pressure to afford a brown oil, which is not further purified and directly used in the next step. Rf=0.5 (EtOAc-heptane 1:1).

g) 6-Hydroxymethyl-4-(3-methoxy-propyl)-4H-benzo[1,4]oxazin-3-one

A stirred suspension of 1.79 g of 6-hydroxymethyl-4H-benzo[1,4]oxazin-3-one, 2.20 ml of 1-chlor-3-methoxypropane, 10 g of potassium fluoride on aluminium oxide and 0.033 g potassium iodide in 150 ml of acetonitrile is heated to reflux for 72 hours. The reaction mixture is allowed to cool to room temperature, filtered and concentrated under reduced pressure. The residue is purified by flash chromatography (SiO$_2$ 60 F) to afford the title compound. Rf=0.60 (dichlormethane-methanol 9:1); Rt=2.74.

h) 6-Hydroxymethyl-4H-benzo[1,4]oxazin-3-on

To a mixture of 6.9 g of 3-oxo-3,4-dihydro-2H-benzo[1,4] oxazin-6-carboxylic acid methyl ester [604756-32-3] in 230 ml of tetrahydrofuran are added 88.9 ml of diisobutylaluminiumhydride (1.5M in toluene) at −40° C. The reaction mixture is stirred for 1.5 hours at −40° C. to −20° C. and poured into 150 ml of 2N hydrochloric acid. The organic phase is separated, washed with brine, dried over sodium sulfate and concentrated under reduced pressure. The residue is crystallized from ethanol to afford the title compound as a beige solid. Rf=0.16 (EtOAc-heptan 2:1); Rt=2.23, m.p.: 186-187° C.

Example 2

(2S,4R,5R)-4-(4-Methoxy-phenyl)-5-[4-(3-methoxy-propyl)-3,4-dihydro-2H-benzo[1,4]oxazin-6-yl-methoxy]-piperidine-2-carboxylic acid ethyl ester According to general procedure B, 0.1 g of (2S,4R,5R)-1,4-bis-(4-methoxy-phenyl)-5-[4-(3-methoxy-propyl)-3-oxo-3,4-dihydro-2H-benzo[1,4]oxazin-6-ylmethoxy]-piperidine-2-carboxylic acid ethyl ester (from example 1b) are used. The residue is purified by flash chromatography (SiO$_2$ 60 F) to afford the title compound.

Example 3

(2S,4R,5R)-4-(4-Methoxy-phenyl)-5-[4-(3-methoxy-propyl)-3,4-dihydro-2H-benzo[1,4]oxazin-6-yl-methoxy]-piperidine-2-carboxylic acid (biphenyl-3-ylmethyl)-amide According to general procedure E, 0.05 g of (2S,4R,5R)-2-[(biphenyl-3-ylmethyl)-carbamoyl]-4-(4-methoxy-phenyl)-5-[4-(3-methoxy-propyl)-3,4-dihydro-2H-benzo[1,4] oxazin-6-ylmethoxy]-piperidine-1-carboxylic acid benzyl ester are used to afford the title compound.

The starting materials are prepared as follows:

a) (2S,4R,5R)-2-[(Biphenyl-3-ylmethyl)-carbamoyl]-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester According to general procedure D, 0.07 g of (2S,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester and 3-phenylbenzylamine are reacted to afford the title compound as a colourless solid. Rf=0.15 (EtOAc-heptan 1:1:1); Rt=5.62.

b) (2S,4R,5R)-4-(4-Methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester To a solution of 1.5 g of (2S,4R,5R)-4-(4-methoxy-phenyl)-5-[4-(3-methoxy-propyl)-3,4-dihydro-2H-benzo[1,4]oxazin-6-ylmethoxy]-piperidine-2-carboxylic acid ethyl ester (from example 2) in 60 ml of methanol-tetrahydrofuran-water 1:1:1 are added 2.85 ml of a solution of 1N lithiumhydroxide at 0° C. Stirring is continued for an additional 2 hours at room temperature, followed by addition of 40 ml of ethyl acetate, 20 ml of saturated aqueous sodium carbonate solution and 0.42 ml of benzyl chloroformate. The reaction mixture is stirred for 1 hour, diluted with ethyl acetate and the organic phase is dried over sodium sulfate. The organic phase is concentrated under reduced pressure and the residue is purified by flash chromatography ($SiO_2$ 60 F) to afford the title compound as a yellow oil. Rf=0.13 (EtOAc); Rt=4.77.

Example 4

{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-(3-phenyl-pyrrolidin-1-yl)-methanone According to general procedure E, 0.08 g of (2S,4R,5R)-4-(4-methoxy-phenyl)-5-[4-(3-methoxy-propyl)-3,4-dihydro-2H-benzo[1,4]oxazin-6-ylmethoxy]-2-(3-phenyl-pyrrolidine-1-carbonyl)-piperidine-1-carboxylic acid benzyl ester are used to afford the title compound.

The starting material is prepared as follows:

a) (2S,4R,5R)-4-(4-Methoxy-phenyl)-5-[4-(3-methoxy-propyl)-3,4-dihydro-2H-benzo[1,4]oxazin-6-ylmethoxy]-2-(3-phenyl-pyrrolidine-1-carbonyl)-piperidine-1-carboxylic acid benzyl ester According to general procedure D, 0.10 g of (2S,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester (from example 3b) and 3-phenylpyrrolidine are reacted to afford the title compound as a colourless solid. Rf=0.15 (EtOAc-heptane 1:1); Rt=5.47.

Example 5

(2S,4R,5R)-4-(4-Methoxy-phenyl)-5-[4-(3-methoxy-propyl)-3,4-dihydro-2H-benzo[1,4]oxazin-6-ylmethoxy]-piperidine-2-carboxylic acid methylamide According to general procedure E, 0.06 g of (2S,4R,5R)-4-(4-methoxy-phenyl)-5-[4-(3-methoxy-propyl)-3,4-dihydro-2H-benzo[1,4]oxazin-6-ylmethoxy]-2-methylcarbamoyl-piperidine-1-carboxylic acid benzyl ester are used to afford the title compound.

The starting material is prepared as follows:

a) (2S,4R,5R)-4-(4-methoxy-phenyl)-5-[4-(3-methoxy-propyl)-3,4-dihydro-2H-benzo[1,4]oxazin-6-ylmethoxy]-2-methylcarbamoyl-piperidine-1-carboxylic acid benzyl ester According to general procedure D, 0.05 g of (2S,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester (from example 3b) and methylamine-hydrochloride are used to afford the title compound as a yellow oil. Rf=0.50 (dichlormethane-methanol 9:1); Rt=4.52.

Example 6

(2S,4R,5R)-4-(4-Methoxy-phenyl)-5-[4-(3-methoxy-propyl)-3,4-dihydro-2H-benzo[1,4]oxazin-6-ylmethoxy]-piperidine-2-carboxylic acid amide According to the general procedure E, 0.06 g of (2S,4R,5R)-2-carbamoyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting material is prepared as follows:

a) (2S,4R,5R)-2-Carbamoyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester To a solution of 0.51 g of (2S,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester (from example 3b) in 1 ml of dichlormethane are added 1.2 ml of triethylamine and 0.79 ml of isopropyl chloroformate. The reaction mixture is stirred for 10 minutes, followed by addition of 2 ml of conc. ammonia 25%. After an additional 10 minutes the reaction mixture is diluted with dichloromethane, washed with 0.5N hydrochloric acid and the organic phase is dried over sodium sulfate and concentrated under reduced pressure. The residue is purified by flash chromatography ($SiO_2$ 60 F) to afford the title compound as a yellow oil. Rf=0.50 (dichlormethane-methanol 9:1); Rt=4.50.

Example 7

(2S,4R,5R)-4-(4-Methoxy-phenyl)-5-[4-(3-methoxy-propyl)-3,4-dihydro-2H-benzo[1,4]oxazin-6-ylmethoxy]-piperidine-2-carboxylic acid According to general procedure E, 0.05 g of (2S,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester (from example 3b) are used to afford the title compound.

Example 8

(2S,4R,5R)-4-(4-Methoxy-phenyl)-5-[4-(3-methoxy-propyl)-3,4-dihydro-2H-benzo[1,4]oxazin-6-ylmethoxy]-piperidine-2-carboxylic acid dimethylamide According to general procedure E, 28.0 mg of (2S,4R,5R)-2-dimethylcarbamoyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting material is prepared as follows:

a) (2S,4R,5R)-2-Dimethylcarbamoyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester Similar to example 6a, 50.0 mg of (2S,4R,5R)-4-(4-methoxy-phenyl)-5-[4-(3-methoxy-propyl)-3,4-dihydro-2H-benzo[1,4]oxazin-6-ylmethoxy]-piperidin-1,2-dicarboxylic acid 1-benzyl ester (from example 3b) are allowed to react with dimethylamine to afford the title compound as a yellow oil. Rf=0.04 (dichlormethane-methanol 98:2); Rt=4.85.

Example 9

2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-N-methyl-N-quinolin-2-ylmethyl-acetamide According to general procedure E, 50.0 mg of (2S,4R,5R)-4-(4-methoxy-phenyl)-5-[4-(3-methoxy-propyl)-3,4-dihydro-2H-benzo[1,4]oxazin-6-ylmethoxy]-2-[(methyl-quinolin-2-ylmethyl-carbamoyl)-methyl]-piperidine-1-carboxylic acid benzyl ester are used to afford the title compound.

The starting materials are prepared as follows:

a) (2S,4R,5R)-4-(4-Methoxy-phenyl)-5-[4-(3-methoxy-propyl)-3,4-dihydro-2H-benzo[1,4]oxazin-6-ylmethoxy]-2-[(methyl-quinolin-2-ylmethyl-carbamoyl)-methyl]-piperidine-1-carboxylic acid benzyl ester According to general procedure D, 42.0 mg of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester and methylquinolin-2-ylmethyl-amine [136727-11-2] are used to afford the title compound as a yellow oil. Rf=0.50 (dichlormethane-methanol 10:1); Rt=4.69.

b) (2S,4R,5R)-2-Carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester To a solution of 45 mg of (2S,4R,5R)-2-(2-diazo-acetyl)-4-(4-methoxy-phenyl)-5-[4-(3-methoxy-propyl)-3,4-dihydro-2H-benzo[1,4]oxazin-6-ylmethoxy]-piperidin-1-carboxylic acid benzyl ester in 10 ml of tetrahydrofuran and 1 ml of water are added 0.027 ml of triethylamine und 8.0 mg of silver trifluoroacetate at −15° C. The reaction mixture is allowed to warm to room temperature, stirred for another 2 hours, diluted with tert-butyl methyl ether and dried over sodium sulfate. The organic phase is concentrated under reduced pressure and the residue is purified by flash chromatography (SiO$_2$ 60 F) to afford the title compound as a brown oil. Rf=0.25 (EtOAc); Rt=4.82.

c) (2S,4R,5R)-2-(2-Diazo-acetyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester To a solution of 0.1 g of (2S,4R,5R)-4-(4-methoxy-phenyl)-5-[4-(3-methoxy-propyl)-3,4-dihydro-2H-benzo[1,4]oxazin-6-ylmethoxy]-piperidine-1,2-carboxylic acid 1-benzyl ester (from example 3b) in 10 ml of tetrahydrofuran are added 0.023 ml of triethylamine and 0.014 ml of ethyl chloroformate at −15° C. The reaction mixture is allowed to warm to 0° C., stirred for 30 minutes at this temperature and cooled to −10° C., followed by the addition of 20 ml of a solution of diazomethane in diethyl ether (1.5%). The reaction mixture is allowed to warm to room temperature overnight, diluted with tert.-butyl methyl ether and the organic phase is washed with an aqueous solution of saturated sodium bicarbonate, dried over sodium sulfate and concentrated under reduced pressure to afford the title compound after flash chromatography (SiO$_2$ 60 F) as a yellow oil. Rf=0.16 (EtOAc-heptane 1:1); Rt=5.12.

Example 10

2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-N-methyl-acetamide According to general procedure E, 52.0 mg of (2S,4R,5R)-4-(4-methoxy-phenyl)-5-[4-(3-methoxy-propyl)-3,4-dihydro-2H-benzo[1,4]oxazin-6-ylmethoxy]-2-methylcarbamoylmethyl-piperidine-1-carboxylic acid benzyl ester are used to afford the title compound.

The starting material is prepared as follows:

a) (2S,4R,5R)-4-(4-Methoxy-phenyl)-5-[4-(3-methoxy-propyl)-3,4-dihydro-2H-benzo[1,4]oxazin-6-ylmethoxy]-2-methylcarbamoylmethyl-piperidine-1-carboxylic acid benzyl ester Similar to example 6a, 50.0 mg of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 9b) reacted with methylamine to afford the title compound as a yellow oil. Rf=0.35 (dichlormethane-methanol 9:1); Rt=4.57.

Example 11

2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-N,N-dimethyl-cetamide According to general procedure E, 68.0 mg of (2S,4R,5R)-2-dimethylcarbamoylmethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting material is prepared as follows:

a) (2S,4R,5R)-2-Dimethylcarbamoylmethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester Similar to example 6a, 50.0 mg of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 9b) are reacted with dimethylamine to afford the title compound as a yellow oil. Rf=0.40 (dichlormethane-methanol 9:1); Rt=4.82.

Example 12

N-Benzyl-2-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-acetamide According to general procedure E, 50.0 mg of (2S,4R,5R)-2-(benzylcarbamoyl-methyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting material is prepared as follows:

a) (2S,4R,5R)-2-(Benzylcarbamoyl-methyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester According to general procedure D, 50.0 mg of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 9b) are reacted with benzylamine to afford the title compound as yellow oil. Rf=0.50 (dichlormethane-methanol 9:1); Rt=5.17.

Example 13

N-Benzyl-2-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-N-methyl-acetamide According to general procedure E, 50.0 mg of (2S,4R,5R)-2-[(benzyl-methyl-carbamoyl)-methyl]-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting material is prepared as follows:

a) (2S,4R,5R)-2-[(Benzyl-methyl-carbamoyl)-methyl]-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester According to general procedure D, 50.0 mg of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 9b) reacted with benzyl methyl amine to afford the title compound as a yellow oil. Rf=0.11 (EtOAc-heptane 1:1); Rt=5.47.

Example 14

N-(1H-Indol-3-ylmethyl)-2-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-N-methyl-acetamide According to general procedure E, 50.0 mg of (2S,4R,5R)-2-{[(1H-Indol-3-ylmethyl)methyl-carbamoyl]-methyl}-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting material is prepared as follows:

a) (2S,4R,5R)-2-{[(1H-Indol-3-ylmethyl)-methyl-carbamoyl]-methyl}-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester According to general procedure D, 50.0 mg of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 9b) are reacted with (1H-Indol-3-ylmethyl)-methyl-amine [36284-95-4] to afford the title compound as a colourless oil. Rf=0.20 (EtOAc-heptane 2:1); Rt=5.23.

Example 15

2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-ethanol According to general procedure E, 70.0 mg of (2S,4R,5R)-2-(2-hydroxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting material is prepared as follows:

a) (2S,4R,5R)-2-(2-Hydroxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester To a solution of 0.10 g of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1 carboxylic acid benzyl ester (from example 9b) in 8.0 ml of tetrahydrofuran are added 0.31 ml of a solution of borane tetrahydrofuran (1M) at 50° C. The reaction mixture is stirred for 2 hours at this temperature, allowed to cool to room temperature and quenched by addition of methanol. The mixture is concentrated under reduced pressure and the obtained residue is purified by flash chromatography ($SiO_2$ 60 F) to afford the title compound as a colourless oil. Rf=0.50 (EtOAc-heptane 5:1); Rt=4.95.

Example 16

2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-N-methyl-N-(1-methyl-1H-benzoimidazol-2-ylmethyl)-acetamide According to general procedure E, 45.0 mg of (2S,4R,5R)-4-(4-methoxy-phenyl)-5-[4-(3-methoxy-propyl)-3,4-dihydro-2H-benzo[1,4]oxazin-6-ylmethoxy]-2-{[methyl-(1-methyl-1H-benzoimidazol-2-ylmethyl)-carbamoyl]-methyl}-piperidine-1-carboxylic acid benzyl ester are used to afford the title compound.

The starting material is prepared as follows:

a) (2S,4R,5R)-4-(4-Methoxy-phenyl)-5-[4-(3-methoxy-propyl)-3,4-dihydro-2H-benzo[1,4]oxazin-6-ylmethoxy]-2-{[methyl-(1-methyl-1H-benzoimidazol-2-ylmethyl)-carbamoyl]-methyl}piperidine-1-carboxylic acid benzyl ester According to general procedure D, 50.0 mg of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 9b) are reacted with methyl-(1-methyl-1H-benzoimidazol-2-ylmethyl)-amine [137898-62-5] to afford the title compound as a yellow oil. Rf=0.65 (dichlormethane-methanol 9:1); Rt=4.59.

Example 17

2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-N-quinolin-2-ylmethyl-acetamide According to general procedure E, 64.0 mg of (2S,4R,5R)-4-(4-methoxy-phenyl)-5-[4-(3-methoxy-propyl)-3,4-dihydro-2H-benzo[1,4]oxazin-6-ylmethoxy]-2-[(methyl-quinolin-2-ylmethyl-carbamoyl)-methyl]piperidine-1-carboxylic acid benzyl ester are used to afford the title compound.

The starting material is prepared as follows:

a) (2S,4R,5R)-4-(4-ethoxy-phenyl)-5-[4-(3-methoxy-propyl)-3,4-dihydro-2H-benzo[1,4]oxazin-6-ylmethoxy]-2-[(methyl-quinolin-2-ylmethyl-carbamoyl)-methyl]-piperidine-1-carboxylic acid benzyl ester According to general procedure D, 50.0 mg of (2S,4R,5R)-2-carboxymethyl-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 9b) are reacted with methyl-quinolin-2-ylmethyl-amine [5760-20-3] to afford the title compound as a yellow solid. Rf=0.25 (dichlormethane-methanol 9:1); Rt=4.52.

Example 18

6-[(3R,4R,6S)-6-(2-Methoxy-ethyl)-4-(4-methoxy-phenyl)-piperidin-3-yloxymethyl]-4-(3-methoxy-propyl)-3,4-dihydro-2H-benzo[1,4]oxazine According to general procedure E, 47.0 mg of (2S,4R,5R)-2-(2-methoxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting materials are prepared as follows:

a) (2S,4R,5R)-2-(2-Methoxy-ethyl)-4-(4-methoxy-phenyl)-5-[4-(3-methoxy-propyl)-3,4-dihydro-2H-benzo[1,4]oxazin-6-ylmethoxy]-piperidine-1 carboxylic acid benzyl ester To a solution of 0.10 g of (2S,4R,5R)-2-(2-methanesulfonyloxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester in 2.0 ml of N,N-dimethylformamide are added 0.060 ml of a 5M solution of sodium methoxide in methanol at room temperature. The reaction mixture is stirred for 5 hours, diluted with tert-butyl methyl ether, washed with 1N hydrochloric acid and the organic phase is dried over sodium sulfate. The organic phase is concentrated under reduced pressure and the residue is purified by flash chromatography ($SiO_2$ 60 F) to afford the title compound as a slightly brown oil. Rf=0.25 (EtOAc-heptane 1:1); Rt=5.47.

b) (2S,4R,5R)-2-(2-Methanesulfonyloxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester According to general procedure F, 0.35 g of (2S,4R,5R)-2-(2-hydroxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 15a) are used to afford the title compound as a slightly brown oil. Rf=0.15 (dichlormethane-methanol 10:1); Rt=5.16.

Example 19

3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-methyl-propionamide According to general procedure-E, 70.0 mg of (2R,4R,5R)-4-(4-methoxy-phenyl)-5-[4-(3-methoxy-propyl)-3,4-dihydro-2H-benzo[1,4]oxazin-6-ylmethoxy]-2-(2-methylcarbamoyl-ethyl)-piperidine-1-carboxylic acid benzyl ester are used to afford the title compound.

The starting materials are prepared as follows:

a) (2R,4R,5R)-4-(4-Methoxy-phenyl)-5-[4-(3-methoxy-propyl)-3,4-dihydro-2H-benzo[1,4]oxazin-6-ylmethoxy]-2-(2-methylcarbamoyl-ethyl)-piperidine-1 carboxylic acid benzyl ester Similar to example 6a, 80.0 mg of (2R,4R,5R)-2-(2-carboxy-ethyl)-4-(4-methoxy-phenyl)-5-[4-(3-methoxy-propyl)-3,4-dihydro-2H-benzo[1,4]oxazin-6-ylmethoxy]-piperidine-1 carboxylic acid benzyl ester are reacted with methylamine to afford the title compound as a yellow oil. Rf=0.35 (dichlormethane-methanol 9:1); Rt=4.69.

b) (2R,4R,5R)-2-(2-Caboxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester A stirred solution of 0.90 g of (2R,4R,5R)-2-(2-cyano-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester in 20 ml of ethanol and 20 ml of 2N sodium hydroxide is heated to 85° C. overnight. The reaction mixture is allowed to cool to room temperature, acidified by addition of 1N hydrochloric acid solution and extracted with ethyl acetate. The organic phase is dried over sodium sulfate and concentrated under reduced pressure. The residue is purified by flash chromatography (SiO$_2$ 60 F) to afford the title compound as a colourless oil. Rf=0.50 (dichlormethane-methanol 10:1); Rt=4.85.

c) (2R,4R,5R)-2-(2-Cyano-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester To a stirred solution of 0.90 g of (2S,4R,5R)-2-(2-methanesulfonyloxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 18b) in 10 ml of dimethylsulfoxide are added 0.25 g of sodium cyanide and the mixture is heated to 50° C. for 4 hours. The reaction mixture is diluted with water, extracted with ethyl acetate, dried over sodium sulfate and concentrated under reduced pressure. The residue is purified by flash chromatography (SiO$_2$ 60 F) to afford the title compound as a colourless oil. Rf=0.30 (EtOAc-heptane 1:1); Rt=5.20.

Example 20

3{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-N-phenyl-propionamide According to general procedure E, 0.11 g of (2R,4R,5R)-4-(4-methoxy-phenyl)-5-[4-(3-methoxy-propyl)-3,4-dihydro-2H-benzo[1,4]oxazin-6-ylmethoxy]-2-(2-phenylcarbamoyl-ethyl)-piperidine-1-carboxylic acid benzyl ester are used to afford the title compound.

The starting material is prepared as follows:

a) (2R,4R,5R)-4-(4-Methoxy-phenyl)-5-[4-(3-methoxy-propyl)-3,4-dihydro-2H-benzo[1,4]oxazin-6-ylmethoxy]-2-(2-phenylcarbamoyl-ethyl)-piperidine-1-carboxylic acid benzyl ester According to general procedure D, 0.10 g of (2R,4R,5R)-2-(2-carboxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 19b) and aniline are reacted to afford the title compound as a colourless oil. Rf=0.50 (dichlormethane-methanol 10:1); Rt=5.40.

Example 21

N-(2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-ethyl-benzamide According to general procedure E, 50.0 mg of (2S,4R,5R)-2-(2-benzoylamino-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are used to afford the title compound.

The starting materials are prepared as follows:

a) (2S,4R,5R)-2-(2-Benzoylamino-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester According to general procedure D, 50.0 mg of (2S,4R,5R)-2-(2-amino-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester are reacted with benzoic acid to afford the title compound after flash chromatography (SiO$_2$ 60 F) as a colourless oil. Rf=0.50 (dichlormethane-methanol 10:1); Rt=5.33.

b) (2S,4R,5R)-2-(2-Amino-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester To a solution of 70.0 mg of (2S,4R,5R)-2-(2-azido-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester in 4.0 ml of tetrahydrofuran and 0.4 ml of water are added 30 mg of triphenyl-phosphine. The reaction mixture is stirred for 2 days at room temperature; concentrated under reduced pressure and the residue is purified by flash chromatography (SiO$_2$ 60 F) to afford the title compound as a colourless oil. Rf=0.05 (dichlormethane-methanol 10:1); Rt=4.27.

c) (2S,4R,5R)-2-(2-Azido-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester To a solution of 98.0 mg of (2S,4R,5R)-2-(2-methanesulfonyloxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 18b) in N,N-dimethylformamide are added 94 mg of sodium azide and the resulting mixture is stirred for 24 hours at room temperature. The reaction mixture is diluted with water, extracted with tert-butyl methyl ether, dried over sodium sulfate and concentrated under reduced pressure. The residue is purified by flash chromatography (SiO$_2$ 60 F) to afford the title compound as a colourless oil. Rf=0.47 (EtOAc-heptane 1:1); Rt=5.65.

Example 22

3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-N,N-dimethyl-propionamide According to general procedure E, 75 mg of (2R,4R,5R)-2-(2-dimethylcarbamoyl-ethyl)-4-(4-methoxy-phenyl)-5-[4-

(3-methoxy-propyl)-3,4-dihydro-2H-benzo[1,4]oxazin-6-ylmethoxy]-piperidine-1-carboxylic acid benzyl ester are used to afford the title compound.

The starting material is prepared as follows:

a) (2R,4R,5R)-2-(2-Dimethylcarbamoyl-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester Similar to example 6a, 80.0 mg of (2R,4R,5R)-2-(2-carboxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 19b) are reacted with dimethylamine to afford the title compound as a yellow oil. Rf=0.35 (dichlormethane-methanol 9:1); Rt=4.93.

Example 23

6-[(3R,4R,6R)-4-(4-Methoxy-phenyl)-6-(3-phenoxy-propyl)-piperidin-3-yloxymethyl]-4-(3-methoxy-propyl)-3,4-dihydro-2H-benzo[1,4]oxazine According to general procedure E, 90.0 mg of (2R,4R,5R)-4-(4-methoxy-phenyl)-5-[4-(3-methoxy-propyl)-3,4-dihydro-2H-benzo[1,4]oxazin-6-ylmethoxy]-2-(3-phenoxy-propyl)-piperidine-1 carboxylic acid benzyl ester are used to afford the title compound.

The starting materials are prepared as follows:

a) (2R,4R,5R)-4-(4-Methoxy-phenyl)-5-[4-(3-methoxy-propyl)-3,4-dihydro-2H-benzo[1,4]oxazin-6-ylmethoxy]-2-(3-phenoxy-propyl)-piperidine-1-carboxylic acid benzyl ester To a stirred solution of 120 mg of (2R,4R,5R)-2-(3-hydroxy-propyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester in 8 ml of tetrahydrofuran are added 36.5 mg of triphenylphosphine and 0.052 ml of diisopropylazodicarboxylate at room temperature. The reaction mixture is stirred for 1 hour and concentrated under reduced pressure. The residue is purified by flash chromatography (SiO$_2$ 60 F) to afford the title compound as a colourless oil. Rf=0.30 (EtOAc-heptane 1:2); Rt=6.06.

b) (2R,4R,5R)-2-(3-Hydroxy-propyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester Similar to example 15a, 0.2 g of (2R,4R,5R)-2-(2-carboxy-ethyl)-4-(4-methoxy-phenyl)-5-[4-(3-methoxy-propyl)-3,4-dihydro-2H-benzo[1,4]oxazin-6-ylmethoxy]-piperidine-1-carboxylic acid benzyl ester (from example 19b) are used to afford the title compound as a colourless oil. Rf=0.50 (EtOAc-heptane 5:1); Rt=4.91.

Example 24

6-[(3R,4R,6S)-4-(4-Methoxy-phenyl)-6-(3-phenyl-propoxymethyl)-piperidin-3-yloxymethyl]-4-(3-methoxy-propyl)-3,4-dihydro-2H-benzo[1,4]oxazine According to general procedure A, 128 mg of 6-[(3R,4R,6S)-4-(4-methoxy-phenyl)-6-(3-phenyl-propoxymethyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6S)-4-(4-Methoxy-phenyl)-6-(3-phenyl-propoxymethyl)-1-(toluene-4-sulfonyl)-piperidin-3-yloxymethyl]-4-(3-methoxy-propyl)-3,4-dihydro-2H-benzo[1,4]oxazine To a solution of 158 mg of [(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-methanol in 8 ml of N,N-dimethylformamide are added 104 mg of sodium hydride, 0.048 ml of 1-brom-3-phenylpropane and 193 mg of tetrabutylammoniumiodide at room temperature. The reaction mixture is stirred overnight, diluted with water, extracted with tert-butyl methyl ether and the organic phase is dried over sodium sulfate. The organic phase is concentrated under reduced pressure and the residue is purified by flash chromatography (SiO$_2$ 60 F) to afford the title compound as a colourless oil. Rf=0.30 (EtOAc-heptane 1:2); Rt=6.11.

b) [(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-methanol Similar to example 1, 0.45 g of (2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidine-2-carboxylic acid ethyl ester are reacted with lithium aluminium hydride to afford the title compound as a yellow oil. Rf=0.3 (EtOAc-heptane 2:1); Rt=4.82.

c) (2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidine-2-carboxylic acid ethyl ester To a solution of 1.51 g of (2S,4R,5R)-4-(4-methoxy-phenyl)-5-[4-(3-methoxy-propyl)-3,4-dihydro-2H-benzo[1,4]oxazin-6-ylmethoxy]-piperidine-2-carboxylic acid ethyl ester (from example 1a) in 25 ml of dichlormethane are added 1.97 ml of triethylamine, 3.5 mg of 4-dimethylaminopyridine and 0.57 g of 4-toluenesulfonylchloride at 0° C. The reaction mixture is allowed to warm to room temperature overnight, diluted with water and 1N hydrochloric acid and the organic phase is separated and dried over sodium sulfate. The organic phase is concentrated under reduced pressure and the residue is purified by flash chromatography (SiO$_2$ 60 F) to afford the title compound as a colourless oil. Rf=0.50 (EtOAc-heptane 1:1); Rt=5.44.

Alternative synthesis for example 24b:

[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-methanol To a stirred solution of 17.09 g of 6-[(3R,4R,6S)-4-(4-methoxy-phenyl)-1-(toluene-4-sulfonyl)-6-triisopropylsilanyloxymethyl-piperidin-3-yloxymethyl]-4-(3-methoxy-propyl)-3,4-dihydro-2H-benzo[1,4]oxazine in 200 ml of tetrahydrofuran are added 42 ml of a 1N solution of tetrabutyl-ammonium fluoride in tetrahydrofuran at room temperature. The reaction mixture is stirred for 2 hours at room temperature, diluted with water and extracted with tert-butyl methyl ether. The combined organic phases are dried over sodium sulfate and concentrated under reduced pressure. The crude product is purified by flash chromatography (SiO₂ 60 F) to afford the title compound as a clear yellow oil. Rf=0.30 (EtOAc-heptane 2:1); Rt=4.82.

The starting materials are prepared as follows:

a) 6-[(3R,4R,6S)-4-(4-Methoxy-phenyl)-1-(toluene-4-sulfonyl)-6-triisopropylsilanyloxymethyl-piperidin-3-yloxymethyl]-4-(3-methoxy-propyl)-3,4-dihydro-2H-benzo[1,4]oxazine According to general procedure C, 19.0 g of 6-[(3R,4R,6S)-4-(4-methoxy-phenyl)-1-(toluene-4-sulfonyl)-6-triisopropylsilanyloxymethyl-piperidin-3-yloxymethyl]-4-(3-methoxy-propyl)-4H-benzo[1,4]oxazin-3-one are used to afford the title compound after flash chromatography as a gold yellow oil. Rf=0.50 (EtOAc-heptane 1:2); Rt=6.44.

b) 6-[(3R,4R,6S)-4-(4-Methoxy-phenyl)-1-(toluene-4-sulfonyl)-6-triisopropylsilanyloxymethyl-piperidin-3-yloxymethyl]-4-(3-methoxy-propyl)-4H-benzo[1,4]oxazin-3-one To a stirred solution of 22.65 g of (3R,4R,6S)-4-(4-methoxy-phenyl)-1-(toluene-4-sulfonyl)-6-triisopropylsilanyloxymethyl-piperidin-3-ol, 11.6 g of 6-bromomethyl-4-(3-methoxy-propyl)-4H-benzo[1,4]oxazin-3-one and 16.56 g of tetrabutyl ammonium iodide in 200 ml of N,N-dimethylformamide are added 1.63 g of sodium hydride at room temperature. The reaction mixture is stirred for 2 hours at room temperature, poured into ice water and extracted with tert-butyl methyl ether. The organic phases are combined, dried over sodium sulfate and concentrated under reduced pressure. The crude product is purified by flash chromatography (SiO₂ 60 F) to afford the title compound as a clear yellow oil. Rf=0.50 (EtOAc-heptane 1:1); Rt=6.74.

c) (3R,4R,6S)-4-(4-Methoxy-phenyl)-1-(toluene-4-sulfonyl)-6-triisopropylsilanyloxymethyl-piperidin-3-ol To a stirred solution of 19.3 g of (3R,4R,6S)-6-hydroxymethyl-4-(4-methoxy-phenyl)-1-(toluene-4-sulfonyl)-piperidin-3-ol in 400 ml of N,N-dimethylformamide is added 10.9 g of imidazole and 6.79 g of triisopropylchlorosilane at room temperature. The reaction mixture is stirred overnight, diluted with 1N hydrochloric acid and extracted with tert-butyl methyl ether. The organic phases are combined, dried over sodium sulfate and concentrated under reduced pressure. The crude product is purified by flash chromatography (SiO₂ 60 F) to afford the title compound as a light yellow oil. Rf=0.60 (EtOAc-heptane 1:1); Rt=6.39.

d) (3R,4R,6S)-6-Hydroxymethyl-4-(4-methoxy-phenyl)-1-(toluene-4-sulfonyl)-piperidin-3-ol To a stirred solution of 108.1 g of [(S)-4-(4-methoxy-phenyl)-1-(toluene-4-sulfonyl)-1,2,3,6-tetrahydro-pyridin-2-yl]-methanol in 1000 ml of tetrahydrofuran are added 504 ml of a solution of borane-tetrahydrofuran (1M) at room temperature. The reaction mixture is heated to 40° C. for 2-6 hours, cooled to room temperature, and quenched by the addition of 150 ml of 2N sodium hydroxide solution and 150 ml of 30% hydrogen peroxide solution. The organic phase is separated, dried over sodium sulfate and concentrated under reduced pressure. The residue is purified by flash chromatography (SiO₂ 60 F) to afford the title compound as a white solid. Rf=0.19 (EtOAc-heptane 1:1); Rt=3.67.

e) [(S)-4-(4-methoxy-phenyl)-1-(toluene-4-sulfonyl)-1,2,3,6-tetrahydro-pyridin-2-yl]-methanol To a solution of 72.0 g of [(S)-4-(4-methoxy-phenyl)-1,2,3,6-tetrahydro-pyridin-2-yl]-methanol in 1.5 l of ethyl acetate and 1.5 l of 2N aqueous sodium carbonate are added 57.7 g of p-toluenesulfonyl chloride at 0° C. The reaction mixture is stirred overnight, extracted with ethyl acetate and the combined organic phases are dried over sodium sulfate and concentrated under reduced pressure. The crude product is used for the next step without any further purification. Rf=0.1 (EtOAc-heptane 1:1); Rt=4.20.

f) [(S)-4-(4-Methoxy-phenyl)-1,2,3,6-tetrahydro-pyridin-2-yl]-methanol

To a stirred suspension of 10.9 g of lithium aluminium hydride in 1 l of tetrahydrofuran is added a solution of 43 g of (S)-4-(4-methoxy-phenyl)-6-oxo-1,2,3,6-tetrahydro-pyridine-2-carboxylic acid benzyl ester in 1 l of tetrahydrofuran at 70° C. The reaction mixture is stirred for another 3-4 hours at this temperature, cooled to 0° C. and quenched by the slow addition of 12.4 ml of water, 12.4 ml of 2N sodium hydroxide and 37 ml of water. The mixture is filtered and the filtrate is concentrated under reduced pressure. The residue is purified by flash chromatography (SiO₂ 60 F) to afford the title compound as a white solid. Rf=0.17 (dichloromethane-methanol-25% ammonia conc. 90:10:1); Rt=2.55.

g) (S)-4-(4-Methoxy-phenyl)-6-oxo-1,2,3,6-tetrahydro-pyridine-2-carboxylic acid benzyl ester To a solution of 1.8 g of (S)-4-(4-methoxy-phenyl)-6-oxo-3,6-dihydro-2H-pyridine-1,2-dicarboxylic acid 2-benzyl ester 1-tert-butyl ester in 15 ml of 1,4 dioxane are added 1.2 ml of 4N hydrochloric acid in 1,4 dioxane at room temperature. The reaction mixture is stirred for 1 hour and concentrated under reduced pressure to afford the title compound as an off white solid. Rf=0.1 (EtOAc-heptane 1:1); Rt=3.94.

h) (S)-4-(4-Methoxy-phenyl)-6-oxo-3,6-dihydro-2H-pyridine-1,2-dicarboxylic acid 2-benzyl ester 1-tert-butyl ester To a solution of 2.75 g of 6-oxo-4-(toluene sulfonyloxy)-3,6-dihydro-2H-pyridine-1,2-dicarboxylic acid 2-benzyl ester 1-tert-butyl ester in 18 ml of tetrahydrofuran are added 1.4 g of 4-methoxyphenylboronic acid, 3.15 g of potassium phosphate, 0.12 g of 'ic'cl'hexyl-(2',4',6'-triisopropyl-biphenyl-2-yl)-phosphane (X-PHOS) and 22 mg of palladium acetate under argon. The reaction mixture is heated to 80° C. for 2 hours, cooled to room temperature, diluted with ethyl acetate and the organic phase is washed with water and dried over sodium sulfate. The residue is purified by flash chromatography (SiO₂ 60 F) to afford the title compound as a brown solid. Rf=0.35 (EtOAc-heptane 1:2); Rt=4.95.

i) (S)-6-oxo-4-(toluene-4-sulfonyloxy)-3,6-dihydro-2H-pyridine-1,2-dicarboxylic acid 2-benzyl ester 1-tert-butyl ester Similar to example 24c, 9.43 g of (2S)-4,6-dioxo-piperidine-1,2-dicarboxylic acid 2-benzyl ester 1-tert-butyl ester [176436-10-5] are reacted with p-toluene sulfonyl chloride to afford the title compound as a yellow oil Rf=0.64 (EtOAc-heptane 1:1); Rt=5.20.

j) 6-Bromomethyl-4-(3-methoxy-propyl)-4H-benzo[1,4]oxazin-3-one

To a solution of 74.0 g of 6-hydroxymethyl-4-(3-methoxy-propyl)-4H-benzo[1,4]oxazin-3-one (from example 1 g) in 600 ml of chloroform are added 58 ml of bromotrimethylsilane at room temperature. The reaction mixture is stirred for 30 minutes and concentrated under reduced pressure. The residue is purified by flash chromatography (SiO$_2$ 60 F) to afford the title compound as an off white solid. Rf=0.46 (EtOAc-heptane 1:1); Rt=4.03.

Example 25

N-(2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-ethyl)-acetamide According to general procedure A, 50 mg of N-{2-[(2R,4R,5R)-4-(4-methoxy-phenyl)-5-[4-(3 methoxy-propyl)-3,4-dihydro-2H-benzo[1,4]oxazin-6-ylmethoxy]-1-(toluene-4-sulfonyl)-piperidin-2-yl]-ethyl}-acetamide are used to afford the title compound.

The starting materials are prepared as follows:

a) N-{2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl}-acetamide To a solution of 131 mg of 2-[(2R,4R,5R)-4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethylamine in 3 ml dichloromethane are added 0.124 ml triethylamine and 0.015 ml acetyl chloride. The reaction mixture is stirred at room temperature for 30 minutes and diluted with dichloromethane and water. The phases are separated and the organic phase is dried over sodium sulfate. The residue is purified by flash chromatography (SiO$_2$ 60 F) to afford the title compound as a brown oil. Rt=4.67.

b) 2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethylamine To a stirred solution of 189 mg 6-[(3R,4R,6R)-6-(2-azido-ethyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine in 20 ml of methanol are added 3.2 mg Pd/C 10% and the reaction mixture is hydrogenated at room temperature for 1.5 hours. The reaction mixture is filtered and concentrated under reduced pressure. The residue is purified by flash chromatography (SiO$_2$ 60 F) to afford the title compound as a yellow oil. Rt=4.30.

c) 6-[(3R,4R,6R)-6-(2-Azido-ethyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine Similar to example 21c, 235 mg of methanesulfonic acid 2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl ester are reacted with sodium azide to afford the title compound as a yellow oil. Rf=0.46 (EtOAc-heptane 1:1); Rt=5.53.

d) Methanesulfonic acid 2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl ester According to general procedure F, 200 mg of 2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]ethanol are reacted to afford the title compound as a yellow oil. Rf=0.20 (EtOAc-heptane 1:1); Rt=5.12.

e) 2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene 4-sulfonyl)-piperidin-2-yl]-ethanol Similar to example 15a, 0.75 g of [(2R,4R,5R)-4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid are reduced to afford the title compound obtained as a colourless foam. Rf=0.1 (EtOAc-heptane 1:1); Rt=4.83.

f) [(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid Similar to example 19b, 0.5 g of [(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetonitrile are used to afford the title compound as a green foam. Rf=0.33 (EtOAc-heptane 5:1); Rt=4.76.

g) [(2S,4R,5R)-5-[4-Methoxy-phenyl)-5-(4-(3-methoxy-propyl)-3,4-dihydro-2H-benzo[1,4]oxazin-6-ylmethoxy]-1-(toluol-4-sulfonyl)-piperidin-2-yl]-acetonitril Similar to example 19c, 0.5 g of (2S,4R,5R)-methanesulfonic acid 4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl ester are used to afford the title compound. Rf=0.26 (EtOAc-heptane 1:1); Rt=5.20.

h) (2S,4R,5R)-Methanesulfonic acid 4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl ester According to general procedure F, 225 mg of [(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-methanol (from example 24b) are used to afford the title compound. Rf=0.45 (EtOAc-heptane 1:1); Rt=5.15.

Example 26

6-[(3R,4R,6S)-6-Benzyloxymethyl-4-(4-methoxy-phenyl)-piperidin-3-yloxymethyl]-4-(3-methoxy-propyl)-3,4-dihydro-2H-benzo[1,4]oxazine According to general procedure A, 74 mg of 6-[(3R,4R,6S)-6-benzyloxymethyl-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6S)-6-Benzyloxymethyl-4-(4-methoxy-phenyl)-1-(toluene-4-sulfonyl)-piperidin-3-yloxymethyl]-4-(3-methoxy-propyl)-3,4-dihydro-2H-benzo[1,4]oxazine Similar to example 24a, 80 mg of [(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidine-2-yl]-methanol (from example 24b) are reacted with benzylbromide to afford after flash chromatography (SiO$_2$ 60 F) the title compound as a white oil. Rf=0.38 (EtOAc-heptane 1:1); Rt=5.91.

Example 27

6-[(3R,4R,6S)-4-(4-Methoxy-phenyl)-6-phenoxymethyl-piperidin-3-yloxymethyl]-4-(3-methoxy-propyl)-3,4-dihydro-2H-benzo[1,4]oxazine According to general procedure A, 72.0 mg of 6-[(3R,4R,6S)-4-(4-methoxy-phenyl)-6-phenoxymethyl-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6S)-4-(4-Methoxy-phenyl)-6-phenoxymethyl-1-(toluene-4-sulfonyl)-piperidin-3-yloxymethyl]-4-(3-methoxy-propyl)-3,4-dihydro-2H-benzo[1,4]oxazine To a stirred solution of 76.0 mg of (2S,4R,5R)-methanesulfonic acid 4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl ester (from example 25 h) in 2 ml of N,N-dimethylformamide are added 9.0 mg of sodium hydride and 42.0 mg of phenol. The reaction mixture is warmed to 90° C. for 3 hours, allowed to cool to room temperature, diluted with water and extracted with tert-butyl methyl ether. The organic phases are combined, dried over sodium sulfate and concentrated under reduced pressure. The residue is purified by flash chromatography (SiO$_2$ 60 F) to afford the title compound as a yellow oil. Rf=0.28 (EtOAc-heptane 1:2); —Rt=5.90.

Example 28

6-[(3R,4R,6S)-6-(3-Methoxy-phenoxymethyl)-4-(4-methoxy-phenyl)-piperidin-3-yloxymethyl]-4-(3-methoxy-propyl)-3,4-dihydro-2H-benzo[1,4]oxazine According to general procedure A, 9.6 mg of 6-[((3R,4R,6S)-6-(3-methoxy-phenoxymethyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6S)-6-(3-Methoxy-phenoxymethyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine Similar to example 27a, 54 mg of (2S,4R,5R)-methanesulfonic acid 4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl ester (from example 25 h) are reacted with 3-methoxyphenol to afford the title compound as a yellow oil. Rf=0.24 (EtOAc-Heptan 1:2); Rt=5.82.

Example 29

(R,S)-1-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-propan-2-ol (diastereomeric mixture)

According to general procedure A, 54 mg of (R,S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-ol (diastereomeric mixture) are used to afford the title compound as mixture of diastereomers.

The starting materials are prepared as follows:

a) (R,S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-ol (diastereomeric mixture)

To a stirred solution of 0.5 g of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-one in 8.0 ml of tetrahydrofuran are added 1.5 ml of a 1M solution of borane tetrahydrofuran complex at room temperature. The reaction mixture is stirred for 3 hours, quenched with 60 ml of methanol and concentrated under reduced pressure. The residue is purified by flash chromatography (SiO$_2$ 60 F) to afford the title compound as a yellow oil. Rf=0.53 (EtOAc-heptane 5:1); Rt=4.95 and 5.06.

b) 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-one To a stirred solution of 0.79 g of N-methoxy-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide in 10 ml of tetrahydrofuran are added 1.3 ml of a 3M solution of methyl magnesium bromide in tetrahydrofuran at 0° C. The reaction mixture is stirred for 1 hour, diluted with an aqueous solution of 1N potassium hydrogen sulfate, extracted with tert-butyl methyl ether. The organic phases are combined and dried over sodium sulfate. The residue is purified by flash chromatography (SiO$_2$ 60 F) to afford the title compound as a yellow oil. Rf=0.20 (EtOAc-heptane 1:1); Rt=5.14.

c) N-Methoxy-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide According to general procedure D, 0.79 g of [(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid (from example 25f) are reacted with N,O-dimethylhydroxylamine hydrochloride to afford the title compound as a colourless foam. Rf=0.44 (EtOAc-heptane 5:1); Rt=5.00.

Example 30

6-[((3R,4R,6R)-4-(4-Methoxy-phenyl)-6-((R,S)-2-methoxy-propyl)-piperidin-3-yloxymethyl]-4-(3-methoxy-propyl)-3,4-dihydro-2H-benzo[1,4]oxazine (diastereomeric mixture)

According to general procedure A, 77.0 mg of 6-[(3R,4R,6R)-4-(4-methoxy-phenyl)-6-((R,S)-2-methoxy-propyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6R)-4-(4-Methoxy-phenyl)-6-((R,S)-2-methoxy-propyl)-1-(toluene-4-sulfonyl)-piperidin-3-yloxymethyl]-4-(3-methoxy-propyl)-3,4-dihydro-2H-benzo[1,4]oxazine (diastereomeric mixture)

To a solution of 87 mg of (R,S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-ol (diastereomeric mixture) (from example 29a) in 2.0 ml of N,N-dimethylformamide are added 59 mg of sodium hydride and 0.110 ml of methyl iodide at 0° C. The reaction mixture is stirred for 1 hour, diluted with 1N hydrochloric acid and extracted with tert-butyl methyl ether. The organic phases are combined, dried over sodium sulfate and concentrated under reduced pressure. The residue is purified by flash chromatography (SiO$_2$ 60 F) to afford the title compound as a yellow oil. Rf=0.30 (EtOAc-heptane 1:1); Rt=5.50.

Example 31

(R,S)-3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2-methyl-propionitrile (diastereomeric mixture)

According to general procedure A, 72.0 mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionitrile (diastereomeric mixture) are used to afford the title compound.

The starting materials are prepared as follows:

a) (R,S)-3-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionitrile (diastereomeric mixture)

Similar to example 19c, 249 mg of methanesulfonic acid (R,S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (diastereomeric mixture) are used to afford the title compound as a slightly red oil. Rf=0.25 (EtOAc-heptane 1:1); Rt=5.25.

b) Methanesulfonic acid (R,S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (diastereomeric mixture)

According to general procedure F, 210 mg of (R,S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-ol (diastereomeric mixture) (from example 29a) are used to afford the title compound as a yellow oil. Rf=0.27 (EtOAc-heptane 1:1); Rt=5.23.

Example 32

6-[(3R,4R,6R)-6-(2-Benzyloxy-ethyl)-4-(4-methoxy-phenyl)-piperidin-3-yloxymethyl]-4-(3-methoxy-propyl)-3,4-dihydro-2H-benzo[1,4]oxazine According to general procedure A, 66 mg of 6-[(3R,4R,6R)-6-(2-benzyloxy-ethyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is, prepared as follows:

a) 6-[(3R,4R,6R)-6-(2-Benzyloxy-ethyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine Similar to example 24a, 80 mg of 2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethanol (from example 25e) are reacted with benzylbromide to afford the title compound as a yellow oil. Rf=0.3 (EtOAc-heptane 1:2); Rt=5.85.

Example 33

N-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-ethyl)-N-methyl-acetamide According to general procedure A, 72 mg of N-{2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl}-N-methyl-acetamide are used to afford the title compound.

The starting material is prepared as follows:

a) N-{2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl}-N-methyl-acetamide To a solution of 82 mg of N-{2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl}-acetamide (from example 25a) in 2.0 ml of N,N-dimethylformamide are added 59 mg of sodium hydride and 0.110 ml of methyl iodide at 0° C. The reaction mixture is stirred for 1 hour, diluted with 1N hydrochloric acid and extracted with tert-butyl methyl ether. The organic phases are combined, dried over sodium sulfate and concentrated under reduced pressure. The residue is purified by flash chromatography (SiO$_2$ 60 F) to afford the title compound as a yellow oil. Rf=0.49 (dichlormethane-methanol 10:1); Rt=4.83.

Example 34

6-[(3R,4R,6R)-4-(4-Methoxy-phenyl)-6-((R)-2-methoxy-propyl)-piperidin-3-yloxymethyl]-4-(3-methoxy-propyl)-3,4-dihydro-2H-benzo[1,4]oxazine According to general procedure A, 61 mg of 6-[(3R,4R,6R)-4-(4-methoxy-phenyl)-6-((R)-2-methoxy-propyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6R)-4-(4-Methoxy-phenyl)-6-((R)-2-methoxy-propyl)-1-(toluene-4-sulfonyl)-piperidin-3-yloxymethyl]-4-(3-methoxy-propyl)-3,4-dihydro-2H-benzo[1,4]oxazine According to example 30a, 63 mg of 1-[4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-(R)-2-ol (diastereomer 1) are used to afford the title compound as a yellow oil. Rt=5.58.

b) (R)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-ol (diastereomer 1)

and (S)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-ol (diastereomer 2)

Similar to example 29a, 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-one (from example 29b) are used to afford the title compound. The diastereomers are separated by flash chromatography (SiO$_2$ 60 F).

Diastereomer 1: yellow oil; Rf=0.18 (EtOAc-heptan 1:1); Rt=5.10.
Diastereomer 2: yellow oil; Rf=0.09 (EtOAc-heptan 1:1); Rt=4.98.

Example 35

6-[(3R,4R,6R)-4-(4-Methoxy-phenyl)-6-((S)-2-methoxy-propyl)-piperidin-3-yloxymethyl]-4-(3-methoxy-propyl)-3,4-dihydro-2H-benzo[1,4]oxazine According to general procedure A, 6-[(3R,4R,6R)-4-(4-methoxy-phenyl)-6-((S)-2-methoxy-propyl)-1-(toluene-4-sulfonyl)-piperidin-3-yloxymethyl]-4-(3-methoxy-propyl)-3,4-dihydro-2H-benzo[1,4]oxazine is used to afford the title compound.

The starting material is prepared as follows:

a) 6-[(3R,4R,6R)-4-(4-Methoxy-phenyl)-6-((S)-2-methoxy-propyl)-1-(toluene-4-sulfonyl)-piperidin-3-yloxymethyl]-4-(3-methoxy-propyl)-3,4-dihydro-2H-benzo[1,4]oxazine Similar to example 30a, 1-[(3R,4R,6R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-(S)-2-ol (diastereomer 2) (from example 34b) is used to afford the title compound as a yellow oil. Rt=5.54.

Example 36

6-[(3R,4R,6R)-4-(4-Methoxy-phenyl)-6-((R)-2-methylsulfanyl-propyl)-piperidin-3-yloxymethyl]-4-(3-methoxy-propyl)-3,4-dihydro-2H-benzo[1,4]oxazine (diastereomer 1)

To a solution of 92 mg of 6-[(3R,4R,6R)-4-(4-methoxy-phenyl)-6-((R)-2-methylsulfanyl-propyl)-1-(toluene-4-sulfonyl)-piperidin-3-yloxymethyl]-4-(3-methoxy-propyl)-3,4-dihydro-2H-benzo[1,4]oxazine (diastereomer 1) in 2.0 ml of dimethoxyethane are added 100 mg of naphthalene and 20 mg of sodium. The reaction mixture is sonicated for 10 minutes, diluted with water and extracted with dichloromethane. The organic phases are combined, dried over sodium sulfate and concentrated under reduced pressure. The residue is purified by flash chromatography (SiO$_2$ 60 F) to afford the title compound.

The starting materials are prepared as follows:

a) 6-[(3R,4R,6R)-4-(4-Methoxy-phenyl)-6-((R)-2-methylsulfanyl-propyl)-1-(toluene-4-sulfonyl)-piperidin-3-yloxymethyl]-4-(3-methoxy-propyl)-3,4-dihydro-2H-benzo[1,4]oxazine To a solution of 103 mg of methanesulfonic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester in 2.0 ml of N,N-dimethylformamide are added 19.5 mg of sodium methanethiolate and the resulting mixture is heated to 70° C. overnight. The reaction mixture is cooled to room temperature, diluted with water, and extracted with dichloromethane. The organic phases are combined, dried over sodium sulfate and concentrated under reduced pressure. The residue is purified by flash chromatography (SiO$_2$ 60 F) to afford the title compound as an orange oil. Rf=0.53 (EtOAc-heptane 5:1); Rt=5.81.

b) Methanesulfonic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester According to general procedure F, 0.58 g of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-(S)-2-ol (diastereomer 2) (from example 34b) are used to afford the title compound as a brown oil. Rf=0.53 (EtOAc-Heptan 5:1); Rt=5.28.

Example 37

N—((R)-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1-methyl-ethyl)-acetamide According to general procedure A, 70 mg of N—{(R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-acetamide are used to afford the title compound.

The starting materials are prepared as follows:

a) N—{(R)-2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-acetamide According to general procedure D, 80 mg of (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethylamine are reacted with acetic acid to afford the title compound as a brown oil. Rf=0.17 (EtOAc-heptane 5:1); Rt=4.67.

b) (R)-2-[(2R,4R,5R)-4-(4-Methoxy-phenyl)-5-[4-(3-methoxy-propyl)-3,4-dihydro-2H-benzo[1,4]oxazin-4-ylmethoxy]-1-(toluene-4-sulfonyl)-piperidin-2-yl]-1-methyl-ethylamine Similar to example 21b, 90 mg of 6-[(3R,4R,6R)-6-((R)-2-azido-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are reduced to afford the title compound as a dark oil. Rf=0.17 (EtOAc-heptane 5:1); Rt=4.42.

c) 6-[(3R,4R,6R)-6-((R)-2-Azido-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine Similar to example 21c, 150 mg of methanesulfonic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (diastereomer 2) (from example 36b) are used to afford the title compound as a green oil. Rf=0.24 (EtOAc-heptane 1:2); Rt=5.76.

Example 38

6-[(3R,4R,6R)-4-(4-Methoxy-phenyl)-6-((S)-2-methylsulfanyl-propyl)-piperidin-3-yloxymethyl]-4-(3-methoxy-propyl)-3,4-dihydro-2H-benzo[1,4]oxazine According to general procedure A, 48 mg of 6-[(3R,4R,6R)-4-(4-methoxy-phenyl)-6-((S)-2-methylsulfanyl-propyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6R)-4-(4-Methoxy-phenyl)-6-((S)-2-methylsulfanyl-propyl)-1-(toluene-4-sulfonyl)-piperidin-3-yloxymethyl]-4-(3-methoxy-propyl)-3,4-dihydro-2H-benzo[1,4]oxazine Similar to example 36a, 108 mg of methanesulfonic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester are used to afford the title compound as an orange oil. Rf=0.53 (EtOAc-heptane 5:1); Rt=5.80.

b) Methanesulfonic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester Similar to example 36b, 0.36 g of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-(R)-2-ol (diastereomer 1) (from example 34b) are used to afford the title compound as a brown oil. Rf=0.53 (EtOAc-heptane 5:1); Rt=5.28.

Example 39

6-[(3R,4R,6R)-6-((R)-2-Ethylsulfanyl-propyl)-4-(4-methoxy-phenyl)-piperidin-3-yloxymethyl]-4-(3-methoxy-propyl)-3,4-dihydro-2H-benzo[1,4]oxazin According to general procedure A, 60 mg of 6-[(3R,4R,6R)-6-(6-(R)-2-ethylsulfanyl-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6R)-6-((R)-2-Ethylsulfanyl-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazin Similar to example 36a, 90 mg of methanesulfonic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1 methyl-ethyl ester (from example 36a) are reacted with sodium ethanethiolate to afford the title compound as a slightly yellow oil. Rf=0.50 (EtOAc-heptane 1:1); Rt=5.96.

Example 40

((R)-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1-methyl-ethyl)-dimethyl-amine According to general procedure A, 58 mg of {(R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluol-4-sulfonyl)-piperidin-2-yl]-1-methyl-ethyl}-dimethyl-amine are used to afford the title compound.

The starting material is prepared as follows:

a) {(R)-2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-dimethyl-amine To a solution of 40 mg of (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluol-4-sulfonyl)-piperidin-2-yl]-1-methyl-ethylamine (from example 37b) in 1 ml of tetrahydrofuran are added 0.065 ml of formic acid and 0.065 ml of aqueous formaldehyde solution (37%) and the resulting reaction mixture is heated to 80° C. for 1 hour. The reaction mixture is diluted with ethyl acetate, washed with saturated sodium bicarbonate and the combined organic phases are separated and dried over sodium sulfate. The residue is purified by flash chromatography (SiO$_2$ 60 F) to afford the title compound as a brown oil. Rf=0.20 (EtOAc-Heptan 1:1); Rt=4.58.

Example 41

N—((R)-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1-methyl-ethyl)-2,2-dimethyl-propionamide According to general procedure A, 8.0 mg of N—{(R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-2,2-dimethyl-propionamide are used to afford the title compound.

The starting material is prepared as follows:

a) N—{(R)-2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-2,2-dimethyl-propionamide To a solution of 50 mg of (R)-2-[(2R,4R,5R)-4-methoxy-phenyl)-5-[4-(3-methoxy-propyl)-3,4-dihydro-2H-benzo[1,4]oxazin-6-ylmethoxy]-1-(toluol-4-sulfonyl)-piperidin-2-yl]-1-methyl-ethylamine (from example 37b) in 5.0 ml of dichlormethane are added 0.057 ml of N,N-diisopropylethylamine and 0.010 ml of pivaloylchloride at room temperature. The reaction mixture is stirred overnight, concentrated under reduced pressure and the residue is purified by flash chromatography (SiO$_2$ 60 F) to afford the title compound as a colourless foam. Rf=0.50 (EtOAc-heptane 5:1); Rt=5.26.

Example 42

6-[(3R,4R,6R)-6-((R)-2-Imidazol-1-yl-propyl)-4-(4-methoxy-phenyl)-piperidin-3-yloxymethyl]-4-(3-methoxy-propyl)-3,4-dihydro-2H-benzo[1,4]oxazine According to general procedure A, 18 mg of 6-[(3R,4R,6R)-6-((R)-2-imidazol-1-yl-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine used to afford the title compound.

The starting material is prepared as follows:

a) 6-[(3R,4R,6R)-6-((R)-2-Imidazol-1-yl-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine To a solution of 50 mg of methanesulfonic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (diastereomer 2) (from example 36b) in 0.2 ml of N-methylpyrrolidine are added 48 mg of imidazole and the reaction mixture is heated for 3 days at 70° C. The reaction mixture is concentrated under reduced pressure and the residue is purified by flash chromatography (SiO$_2$ 60 F) to afford the title compound as a colourless oil. Rf=0.40 (dichlormethane-methanol 10:1); Rt=4.58.

Example 43

6-[(3R,4R,6R)-4-(4-Methoxy-phenyl)-6-((R,S)-2-pyrrolidin-1-yl-propyl)-piperidin-3-yloxymethyl]-4-(3-methoxy-propyl)-3,4-dihydro-2H-benzo[1,4]oxazine (diastereomeric mixture)

According to general procedure A, 130 mg of 6-[(3R,4R,6R)-4-(4-methoxy-phenyl)-6-((R,S)-2-pyrrolidin-1-yl-propyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6R)-4-(4-methoxy-phenyl)-6-((R,S)-2-pyrrolidin-1-yl-propyl)-1-(toluene-4-sulfonyl)-piperidin-3-yloxymethyl]-4-(3-methoxy-propyl)-3,4-dihydro-2H-benzo[1,4]oxazine To a solution of 100 mg of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-one (from example 29b) in 5 ml of ethanol are added 0.026 ml of pyrrolidine, 0.009 ml of acetic acid and 31 mg of sodium cyanoborohydride. The reaction mixture is stirred overnight, diluted with dichloromethane and washed with aqueous 1N sodium hydroxide. The organic phases are combined, dried over sodium sulfate and concentrated under reduced pressure. The residue is purified by flash chromatography (SiO$_2$ 60 F) to afford the title compound as a colourless oil. Rf=0.50 (dichloromethane-methanol 2:1); Rt=4.67.

According to the processes described in example 43, the following compounds are prepared in an analogous manner:

Examples 58 6-[(3R,4R,6R)-4-(4-Methoxy-phenyl)-6-((R,S)-2-morpholin-4-yl-propyl)-piperidin-3-yloxymethyl]-4-(3-methoxy-propyl)-3,4-dihydro-2H-benzo[1,4]oxazine 59 Diethyl-((R,S)-2-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-1-methyl-ethyl)-amine 63 Isobutyl-((R,S)-2-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-1-methyl-ethyl)-methyl-amine Example 44

Isopropyl-(2-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-ethyl)-amine According to general procedure A, 110 mg of isopropyl-{2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl}-amine are used to afford the title compound.

The starting materials are prepared as follows:

a) Isopropyl-{2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl}-amine To a solution of 100 mg of 2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethylamine in 3 ml of ethanol are added 0.006 ml of acetone, 0.009 ml of acetic acid and 0.032 g of sodium cyano borohydride. The reaction mixture is stirred overnight at room temperature, diluted with tert-butyl methyl ether, washed with 1N sodium hydroxide and the organic phases are combined and dried over sodium sulfate. The crude product is obtained as a turbid yellow oil, which is used in the next step without any further purification. Rf=0.23 (EtOAc-heptane 2:1); Rt=4.59.

b) 2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethylamine To a solution of 1.9 g of [(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetonitrile (from example 25 g) in 30 ml of tetrahydrofuran are added 11.0 ml of a 1M solution of borane tetrahydrofuran. The reaction mixture is stirred overnight, quenched with methanol and concentrated under reduced pressure. The residue is purified by flash chromatography (SiO$_2$ 60 F) to afford the title compound as a yellow oil. Rf=0.09 (dichlormethane-methanol-25% ammonia conc. 200:10:1); Rt=4.32.

Example 45

N-(2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-ethyl)-2-(tetrahydro-pyran-4-yl)-isobutyramide According to general procedure A, 160 mg of N-{2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl}-2-(tetrahydro-pyran-4-yl)-isobutyramide are used to afford the title compound.

The starting material is prepared as follows:

a) N-{2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl}-2-(tetrahydro-pyran-4-yl)-isobutyramide According to general procedure D, 100 mg of 2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethylamine (from example 44b) are reacted with 2-methyl-2-(tetrahydro-pyran-4-yl)-propionic acid [16386-97-3] to afford the title compound as a yellow oil. Rf=0.40 (dichlormethane-methanol-25% ammonia conc. 200:20:1); Rt=3.87.

Example 46

6-[(3R,4R,6R)-6-((S)-2-Imidazol-1-yl-propyl)-4-(4-methoxy-phenyl)-piperidin-3-yloxymethyl]-4-(3-methoxy-propyl)-3,4-dihydro-2H-benzo[1,4]oxazine According to general procedure A, 40 mg of 6-[(3R,4R,6R)-6-((S)-2-imidazo-1-yl-propyl)-4-(4-methoxy-phenyl)-piperidin-3-yloxymethyl]-4-(3-methoxy-propyl)-3,4-dihydro-2H-benzo[1,4]oxazine are used to afford the title compound.

The starting material is prepared as follows:

a) (3R,4R,6R)-6-((S)-Imidazol-1-yl-propyl)-4-(4-methoxy-phenyl)-piperidin-3-yloxymethyl]-4-(3-methoxy-propyl)-3,4-dihydro-2H-benzo[1,4]oxazine Similar to example 42a, methanesulfonic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (from example 38b) are reacted with imidazol to afford the title compound as a colourless oil. Rf=0.22 (dichlormethane-methanol 10:1); Rt=4.60.

Example 47

6-[(3R,4R,6R)-4-(4-Methoxy-phenyl)-6-((R)-2-[1,2,4]triazol-1-yl-propyl)-piperidin-3-yloxymethyl]-4-(3-methoxy-propyl)-3,4-dihydro-2H-benzo[1,4]oxazine According to general procedure A, 100 mg of 6-[(3R,4R,6R)-4-(4-methoxy-phenyl)-1-(toluene-4-sulfonyl)-6-((R)-2-[1,2,4]triazol-1-yl-propyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6R)-4-(4-Methoxy-phenyl)-1-(toluene-4-sulfonyl)-6-((R)-2-[1,2,4]triazol-1-yl-propyl)-piperidin-3-yloxymethyl]-4-(3-methoxy-propyl)-3,4-dihydro-2H-benzo[1,4]oxazine To a solution of 0.126 g of 1,2,4 triazole sodium salt in N,N-dimethylformamide are added 0.1 g of methanesulfonic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (diastereomer 2) (from example 36b) and the resulting mixture is stirred for 2 days at room temperature. The reaction mixture is diluted with water, extracted with ethyl acetate and the organic phase is separated and dried over sodium sulfate. The organic phase is concentrated under reduced pressure and the residue is purified by flash chromatography (SiO$_2$ 60 F) to afford the title compound as a colourless oil. Rf=0.50 (EtOAc-heptane 5:1); Rt=4.76.

Example 48

6-[(3R,4R,6R)-4-(4-Methoxy-phenyl)-6-((S)-2-[1,2,4]triazol-1-yl-propyl)-piperidin-3-yloxymethyl]-4-(3-methoxy-propyl)-3,4-dihydro-2H-benzo[1,4]oxazine According to general procedure A, 6-[(3R,4R,6R)-4-(4-methoxy-phenyl)-1-(toluene-4-sulfonyl)-6-((S)-2-[1,2,4]triazol-1-yl-propyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6R)-4-(4-Methoxy-phenyl)-1-(toluene-4-sulfonyl)-6-((S)-2-1,2,4]triazol-1-yl-propyl)-piperidin-3-yloxymethyl]-4-(3-methoxy-propyl)-3,4-dihydro-2H-benzo[1,4]oxazine Similar to example 47a, using methanesulfonic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (from example 38b) to afford the title compound as a colourless oil. Rf=0.13 (EtOAc-heptane 5:1); Rt=4.84.

Example 49

6-{(3R,4R,6S)-4-(4-Methoxy-phenyl)-6-[(R)-2-(1H-tetrazol-5-yl)-propyl]-piperidin-3-yloxymethyl}-4-(3-methoxy-propyl)-3,4-dihydro-2H-benzo[1,4]oxazine According to general procedure A, 26.0 mg of 6-[(3R,4R,6S)-4-(4-methoxy-phenyl)-6-[(R)-2-(1H-tetrazol-5-yl)-propyl]-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6S)-4-(4-Methoxy-phenyl)-6-[(R)-2-(1H-tetrazol-5-yl)-propyl]-1-(toluene-4-sulfonyl)-piperidin-3-yloxymethyl]-4-(3-methoxy-propyl)-3,4-dihydro-2H-benzo[1,4]oxazine To a stirred solution of 0.12 g of (R)-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionitrile and 0.0043 g dibutyltin oxide in 4.0 ml of toluene is added 0.44 ml of trimethylsilylazide. The reaction mixture is heated to 125° C. overnight, concentrated under reduced pressure and the residue is purified by flash chromatography (SiO$_2$ 60 F) to afford the title compound as a brown oil. Rf=0.7 (dichloromethane-methanol 9:1); Rt=4.71 b) (R)-3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionitrile Similar to example 31, using methanesulfonic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (diastereomer 2) (from example 36b) to afford the title compound as a brown oil. Rf=0.58 (EtOAc-heptane 2:1); Rt=5.18.

Example 50

6-{(3R,4R,6S)-4-(4-Methoxy-phenyl)-6-[(S)-2-(1H-tetrazol-5-yl)-propyl]-piperidin-3-yloxymethyl}-4-(3-methoxy-propyl)-3,4-dihydro-2H-benzo[1,4]oxazine According to general procedure A, 0.096 g 6-[(3R,4R,6S)-4-(4-methoxy-phenyl)-6-[(S)-2-(1H-tetrazol-5-yl)-propyl]-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6S)-4-(4-Methoxy-phenyl)-6-[(S)-2-(1H-tetrazol-5-yl)-propyl]-1-(toluene-4-sulfonyl)-piperidin-3-yloxymethyl]-4-(3-methoxy-propyl)-3,4-dihydro-2H-benzo[1,4]oxazine Similar to example 49, 0.1 g of (S)-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionitrile are used, to afford the title compound as a brown oil. Rf=0.7 (dichloromethane-methanol 9:1); Rt=4.71 b) (S)-3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionitrile Similar to example 31, using methanesulfonic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (from example 38b) to afford the title compound as a brown oil. Rf=0.58 (EtOAc-heptane 2:1); Rt=5.18.

Example 51

1-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2-methyl-propan-2-ol According to general procedure A, 0.095 g of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol are used to afford the title compound.

The starting materials are prepared as follows:

a) 1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol 0.34 ml of a methyl magnesium bromide solution (3M in ether) are added to a solution of 0.17 g of [(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid methyl ester in 3 ml of tetrahydrofuran at 0° C. The reaction mixture is worked up after 3 hours by quenching with 1N aqueous potassium bisulfate solution and extracting with tert-butyl methyl ether (3×). The combined organic layers are washed with brine, dried over sodium sulfate and concentrated under reduced pressure. The residue is purified by flash chromatography (SiO$_2$ 60 F) to afford the title compound as a turbid yellow oil. Rf=0.12 (EtOAc-heptane 1:1); Rt=5.11.

b) [(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid methyl ester 4 ml of a solution of diazomethane in ether (0.2M) are added dropwise to a solution of 0.12 g of [(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid (from example 25f) in 2 ml of methanol at 0° C. The reaction mixture is worked up after 3.5 hours by quenching with solid magnesium sulfate to decompose any excess diazomethane, filtering and concentrating under reduced pressure to afford the crude title compound as a pale yellow solid with was used in the next step without any further purification. Rf=0.78 (EtOAc); Rt=5.26.

Example 52

(S)-1-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-3-methyl-butan-2-ol According to general procedure A, 0.058 g of (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-butan-2-ol (diastereomer 1) are used to afford the title compound.

The starting materials are prepared as follows:

a) (S)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-butan-2-ol (diastereomer 1)

and (R)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-butan-2-ol (diastereomer 2)

Similar to example 34b, 0.16 g of 1-[(2R,4R,5R)-4-(4-methoxy-phenyl)-5-[4 (3-methoxy-propyl)-3,4-dihydro-2H-benzo[1,4]oxazin-6-ylmethoxy]-1-(toluene-4-sulfonyl)-piperidin-2-yl]-3-methyl-butan-2-one are reduced to provide the title compounds.

Diastereomer 1: colourless oil; Rf=0.26 (EtOAc-heptan 1:1); Rt=5.40.

Diastereomer 2: colourless oil; Rf=0.1 g (EtOAc-heptan 1:1); Rt=5.50.

b) 1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-butan-2-one A mixture of 0.19 g of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-but-3-en-2-one and 0.044 g of 10% Pd/C in 5 ml of ethanol is hydrogenated at room temperature for 30 minutes. The reaction mixture is clarified by filtration and concentrated to afford the crude title compound as a light brown oil which is used in the next step without any further purification. Rf=0.30 (EtOAc-heptane 1:1); Rt=5.54.

c) 1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-but-3-en-2-one Similar to example 29b, 0.20 g of N-methoxy-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide (from example 29c) are reacted with isopropenyl magnesium bromide (0.5M in tetrahydrofuran) to afford the crude title compound as a yellow-brown oil which is used in the next step without any further purification. Rf=0.22 (EtOAc-heptane 1:1); Rt=5.49.

Example 53

(R)-1-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-3-methyl-butan-2-ol According to general procedure A, 0.024 g of (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-butan-2-ol (diastereomer 2) (from example 52a) are used to afford the title compound.

Example 54

6-[(3R,4R,6R)-4-(4-Methoxy-phenyl)-6-((S)-2-pyrazol-1-yl-propyl)-piperidin-3-yloxymethyl]-4-(3-methoxy-propyl)-3,4-dihydro-2H-benzo[1,4]oxazine According to general procedure A, 100 mg of 6-[(3R,4R,6R)-4-(4-methoxy-phenyl)-6-((S)-2-pyrazol-1-yl-propyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6R)-4-(4-Methoxy-phenyl)-6-((S)-2-pyrazol-1-yl-propyl)-1-(1-toluene-4-sulfonyl)-piperidin-3-yloxymethyl]-4-(3-methoxy-propyl)-3,4-dihydro-2H-benzo[1,4]oxazine Similar to example 42a, methanesulfonic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (from example 38b) is reacted with the sodium salt of pyrazole to afford the title compound as a colourless solid. Rf=0.62 (EtOAc); Rt=5.07.

Example 55

6-{(3R,4R,6R)-4-(4-Methoxy-phenyl)-6-[(R)-2-(5-methyl-tetrazol-2-yl)-propyl]-piperidin-3-yloxymethyl}-4-(3-methoxy-propyl)-3,4-dihydro-2H-benzo[1,4]oxazine According to general procedure A, 62 mg of 6-[(3R,4R,6R)-4-(4-methoxy-phenyl)-6-[(R)-2-(5-methyl-tetrazol-2-yl)propyl]-1-(toluene-4-sulfonyl)-piperidin-3-yloxymethyl]-4-(3-methoxy-propyl)-3,4-dihydro-2H-benzo[1,4]oxazine (regioisomer 1) are used to afford the title compound.

The starting material is prepared as follows:

a) 6-[(3R,4R,6R)-4-(4-Methoxy-phenyl)-6-[(R)-2-(5-methyl-tetrazol-2-yl)-propyl]-1-(toluene-4-sulfonyl)-piperidin-3-yloxymethyl]-4-(3-methoxy-propyl)-3,4-dihydro-2H-benzo[1,4]oxazine (regioisomer 1)

and

6-[(3R,4R,6R)-4-(4-Methoxy-phenyl)-6-[(R)-2-(5-methyl-tetrazol-1-yl)-propyl]-1-(toluene-4-sulfonyl)-piperidin-3-yloxymethyl]-4-(3-methoxy-propyl)-3,4-dihydro-2H-benzo[1,4]oxazine (regioisomer 2)

Similar to example 42a, methanesulfonic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (diastereomer 2) (from example 36b) is reacted with the sodium salt of 5-methyltetrazole to afford a mixture of regioisomers consisting of the title compounds and subsequent separation of the regioisomers by flash chromatography (SiO$_2$ 60 F).

Regioisomer 1: colourless oil; Rf=0.25 (EtOAc-heptane 1:1); Rt=5.07.

Regioisomer 2: crystalline solid; Rf=0.08 (EtOAc-heptane 1:1); Rt=4.92.

Example 56

6-{(3R,4R,6R)-4-(4-Methoxy-phenyl)-6-[(R)-2-(5-methyl-tetrazol-1-yl)-propyl]-piperidin-3-yloxymethyl}-4-(3-methoxy-propyl)-3,4-dihydro-2H-benzo[1,4]oxazine According to general procedure A, 44 mg of 6-[(3R,4R,6R)-4-(4-methoxy-phenyl)-6-[(R)-2-(5-methyl-tetrazol-1-yl)-propyl]-1-(toluene-4-sulfonyl)-piperidin-3-yloxymethyl]-4-(3-methoxy-propyl)-3,4-dihydro-2H-benzo[1,4]oxazine (regioisomer 2) (from example 55a) are used to afford the title compound.

Example 57

6-[(3R,4R,6R)-6-[2-(2-Methoxy-ethoxy)-2-methyl-propyl]-4-(4-methoxy-phenyl)-piperidin-3-yloxymethyl]-4-(3-methoxy-propyl)-3,4-dihydro-2H-benzo[1,4]oxazine According to general procedure A, 64.2 mg of 6-[(3R,4R,6R)-6-[2-(2-methoxyethoxy)-2-methyl-propyl]-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are used to afford the title compound as a yellow oil. Rf=0.28 (dichloromethane-methanol-25% ammonia conc. 200:20:1); Rt=4.56.

The starting materials are prepared as follows:

a) 6-[(3R,4R,6R)-6-[2-(2-Methoxy-ethoxy)-2-methyl-propyl]-4-(4-methoxy-phenyl)-1-(toluene-4-sulfonyl)-piperidin-3-yloxymethyl]-4-(3-methoxy-propyl)-3,4-dihydro-2H-benzo[1,4]oxazine To a solution of 100 mg of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol in 0.7 ml of tetrahydrofuran are added 35 mg sodium hydride (55% dispersion in oil). The reaction mixture is stirred for 30 minutes and then 47 μl 2-chloroethyl methyl ether and 10 mg tetrabutyl ammonium iodide is added. The mixture is stirred at 70° C. for 5 hours. During this time, the addition of sodium hydride and 2-chloroethyl methyl ether is repeated (5×). The mixture is treated with 2 ml water and extracted with 50 ml ethyl acetate (2×). The combined organic layers are washed with brine and dried with sodium sulfate. The organic layer is filtered and evaporated under reduced pressure. The residue is purified by flash chromatography (SiO$_2$ 60 F) to afford the title compound as a yellow oil. Rf=0.13 (EtOAc-heptane 1:1); Rt=5.58.

b) 1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol To a solution of 700 mg of [(2R,4R,5R)-4-(4-methoxy-phenyl)-[4-(3-methoxy-propyl)-3,4-dihydro-2H-benzo[1,4]oxazin-6-ylmethoxy]-1-(toluene-4-sulfonyl)-piperidin-2-yl]-acetic acid methyl ester in 10 ml of tetrahydrofuran at 0° C. is added 1.43 ml of methyl magnesium bromide (3M solution in ether). After 2.5 hours the reaction mixture is treated with 1N aqueous potassium bisulfate and extracted with 60 ml ethyl acetate (2×). The combined organic layers are washed with brine and dried with sodium sulfate. The organic layer is filtered and evaporated under reduced pressure to afford the title compound as a white foam. Rf=0.10 (EtOAc-heptane 1:1); Rt=5.11.

c) [(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid methyl ester To a solution of 2.03 g of [(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid (from example 25f) in 50 ml of methanol at 0° C. is added a 0.1M solution of diazomethane in ether until the conversion to the methyl ester is complete. The reaction mixture is treated with magnesium sulfate to destroy the excess of diazomethane. The solids are removed by filtration and the organic layer is concentrated under reduced pressure. The residue is purified by flash chromatography (SiO$_2$ 60 F) to afford the title compound as a yellow oil. Rf=0.24 (EtOAc-heptane 1:1); Rt=5.24.

Example 60

Dimethyl-carbamic acid 2-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-1,1-dimethyl-ethyl ester According to general procedure A, 35 mg of dimethyl-carbamic acid 2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethyl ester are used to afford the title compound.

The starting material is prepared as follows:

a) Dimethyl-carbamic acid 2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethyl ester To a solution of 120 mg of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol (from example 57b) in 0.5 ml of tetrahydrofuran are added 80 mg potassium hydride (35% dispersion in oil). The reaction mixture is stirred for 1 hour and then 163 µl dimethylcarbamoyl chloride are added. The mixture is stirred at room temperature for 18 hours. The mixture is treated with 2 ml water and extracted with 50 ml ethyl acetate (2×). The combined organic layers are washed with brine and dried with sodium sulfate. The organic layer is filtered and evaporated under reduced pressure. The residue is purified by flash chromatography (SiO$_2$ 60 F) to afford the title compound as a yellow solid. Rf=0.45 (EtOAc-heptane 2:1); Rt=5.59.

According to the processes described in example 60, the following compounds are prepared in an analogous manner:

Examples

70 Dimethyl-carbamic acid (S)-1-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-ylmethyl}-propyl ester starting from (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol (diastereomer 2) (from example 64d).

71 Dimethyl-carbamic acid (R)-1-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-ylmethyl}-propyl ester starting from (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol (diastereomer 1) (from example 64d).

86 Dimethyl carbamic acid (S)-1-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-ylmethyl}-2-methyl-propyl ester starting from (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-butan-2-ol (diastereomer 1) (from example 52a).

87 Dimethyl-carbamic acid (R)-1-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-ylmethyl}-2-methyl-propyl ester starting from (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-butan-2-ol (diastereomer 2) (from example 52a).

Example 61

1-((R,S)-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1-methyl-ethyl)-pyrrolidin-2-one According to general procedure A, 0.035 g of 1-{(R,S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-pyrrolidin-2-one are used to afford the title compound.

The starting materials are prepared as follows:

a) 1-{(R,S)-2-[(2R,4R,5R)-4-(4-Methoxy-phenyl)-5-[4-(3-methoxy-propyl)-3,4-dihydro 2H-benzo[1,4] oxazin-6-ylmethoxy]-1-(toluene-4-sulfonyl)-piperidin-2-yl]-1-methyl-ethyl}-pyrrolidin-2-one According to general procedure D, 0.116 g of 4-{(R,S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethylamino}-butyric acid are used to afford the title compound as a yellow oil. Rf=0.23 (dichloromethane-methanol 9:1); Rt=4.90.

b) 4-{(R,S)-2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethylamino}-butyric acid Analogously to example 43a, 0.100 g of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-one (from example 29b) and 0.164 g of 4-aminobutyric acid are reacted to afford the title compound as a yellow "paste". Rf=0.02 (methanol); Rt=4.40.

According to the processes described in example 61, the following compound is prepared in an analogous manner:

Example 62 1-((R or S)-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1-methyl-ethyl)-pyrrolidin-2-one Example 64

6-{(3R,4R,6S)-4-(4-Methoxy-phenyl)-6-[(R)-2-(1H-tetrazol-5-yl)-butyl]-piperidin-3-yloxymethyl}-4-(3-methoxy-propyl)-3,4-dihydro-2H-benzo[1,4]oxazine According to general procedure A, 184 mg of 6-[(3R,4R,6S)-4-(4-methoxy-phenyl)-6-[(R)-2-(1H-tetrazol-5-yl)-butyl]-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6S)-4-(4-Methoxy-phenyl)-6-[(R)-2-(1H-tetrazol-5-yl)-butyl]-1-(toluene-4-sulfonyl)-piperidin-3-yloxymethyl]-4-(3-methoxy-propyl)-3,4-dihydro-2H-benzo[1,4]oxazine Similar to example 49a, using (R)-2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-butyronitrile to afford the title compound as a yellow oil. Rf=0.25 (dichloromethane-methanol 10:1); —Rt=4.76.

b) (R)-2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-butyronitrile Similar to example 19c, 363 mg of methanesulfonic acid (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propyl ester in the presence of 274 mg of tetrabutylammonium cyanide are used to afford the title compound as a colourless oil. Rf=0.35 (EtOAc-heptane 1:1); Rt=5.26.

c) Methanesulfonic acid (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propyl ester According to general procedure F, 100 mg of (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol (diastereomer 2) are used to afford the title compound as a brown oil. Rt=5.22.

d) (R)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol (diastereomer 1)

and (S)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol (diastereomer 2)

Similar to example 29a, 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-one are used to afford the title compounds. The diastereomers are separated by flash chromatography (SiO$_2$ 60 F).

Diastereomer 1: colourless oil; Rf=0.60 (EtOAc-heptan 5:1); Rt=5.11;

Diastereomer 2: colourless oil; Rf=0.50 (EtOAc-heptan 1:1); Rt=5.01;

e) 1-[(2R,4R,5R)-4-(4-Methoxy-phenyl)-5-[4-(3-methoxy-propyl)-3,4-dihydro 2H-benzo[1,4]oxazin-6-ylmethoxy]-1-(toluene-4-sulfonyl)-piperidin-2-yl]-butan-2-one Similar to example 29b by, 1.0 g of N-methoxy-2-[4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide (from example 29c) in the presence of ethyl magnesium bromide are used to afford the title compound after flash chromatography (SiO$_2$ 60 F) as a colourless oil. Rf=0.20 (EtOAc-heptane 1:1); Rt=5.13.

According to the processes described in example 64, the following compound is prepared in an analogous manner:

Example 91 6-{(3R,4R,6S)-4-(4-Fluoro-phenyl)-6-[(R)-2-(1H-tetrazol-5-yl)-butyl]-piperidin-3-yloxymethyl}-4-(3-methoxy-propyl)-3,4-dihydro-2H-benzo[1,4]oxazine Example 65

N-Ethyl-3-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2,2-dimethyl-propionamide According to general procedure A, 100 mg of N-ethyl-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionamide are used to afford the title compound.

The starting materials are prepared as follows:

a) N-Ethyl-3-[(2S,4R,5R)-4-(4-ethoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionamide According to general procedure D, 150 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid and 1.0 g of ethylamine are used to afford the title compound as a brown oil. Rf=0.13 (EtOAc-heptane 1:1); Rt=5.14.

b) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid To a solution of 8.62 g of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid methyl ester in 20 ml tetrahydrofuran and 50 ml ethanol are added 60 ml of a 20% sodium hydroxide solution. The reaction mixture is stirred for 4 hours at 65° C. The organic solvents are evaporated under reduced pressure and the remaining solution is acidified with 6M aqueous hydrochloric acid until pH 2. This mixture is extracted with 200 ml ethyl acetate (3×). The combined organic layers are washed with brine and dried with sodium-sulfate. The organic layer is filtered and evaporated under reduced pressure. The residue is purified by flash chromatography (SiO$_2$ 60 F) to afford the title compound as a colourless foam. Rf=0.27 (EtOAc-heptane 3:1); Rt=5.10.

c) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid methyl ester To a solution of 5.75 ml methyl isobutyrate in 28 ml tetrahydrofuran at −78° C. are added 100 ml of a 0.5M lithium-diisopropyl amide solution and the reaction mixture is stirred for 30 minutes at −78° C. Then 17.74 ml hexamethylphosphoramide is added at −78° C. and the mixture is stirred for further 30 minutes. A solution of 8.66 g 6-[(3R,4R,6S)-6-bromomethyl-4-(4-methoxy-phenyl)-1-(toluene-4-sulfonyl)-piperidin-3-yloxymethyl]-4-(3-methoxy-propyl)-3,4-dihydro-2H-benzo[1,4]oxazine in 28 ml tetrahydrofuran is then added dropwise to the "enolate" at −78° C. and the solution is stirred for 30 minutes. The reaction mixture is allowed to warm to −12° C. and stirred at this temperature for additional 40 minutes. The solution is quenched with 1M aqueous hydrochloric acid and extracted with 200 ml ethyl acetate (3×). The combined organic layers are washed with brine and dried with sodium sulfate. The organic layer is filtered and evaporated under reduced pressure. The residue is purified by flash chromatography (SiO$_2$ 60 F) to afford the title compound as a colourless foam. Rf=0.29 (EtOAc-heptane 1:1); Rt=5.65.

d) 6-[(3R,4R,6S)-6-Bromomethyl-4-(4-methoxy-phenyl)-1-(toluene-4-sulfonyl)-piperidin-3-yloxymethyl]-4-(3-methoxy-propyl)-3,4-dihydro-2H-benzo[1,4]oxazine To a solution of 11.18 g of methanesulfonic acid (2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl ester (from example 25 h) in 40 ml dimethylformamide is added 13.78 g lithium bromide and the reaction mixture is stirred for 14 hours at 65° C. The reaction mixture is allowed to warm to room temperature and 50 ml water is added. This mixture is extracted with 300 ml tert-butyl methyl ether (3×). The combined organic layers are washed with brine and dried with sodium sulfate. The organic layer is filtered and evaporated under reduced pressure. The residue is purified by flash chromatography (SiO$_2$ 60 F) to afford the title compound as a colourless foam. Rf=0.39 (EtOAc-heptane 1:1); Rt=5.68.

Example 66

6-{(3R,4R,6S)-4-(4-Methoxy-phenyl)-6-[(S)-2-(1H-tetrazol-5-yl)-butyl]-piperidin-3-yloxymethyl}-4-(3-methoxy-propyl)-3,4-dihydro-2H-benzo[1,4]oxazine According to general procedure A, 34 mg of 6-[(3R,4R,6S)-4-(4-methoxy-phenyl)-6-[(S)-2-(1H-tetrazol-5-yl)-butyl]-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6S)-4-(4-Methoxy-phenyl)-6-[(S)-2-(1H-tetrazol-5-yl)-butyl]-1-(toluene-4-sulfonyl)-piperidin-3-yloxymethyl]-4-(3-methoxy-propyl)-3,4-dihydro-2H-benzo[1,4]oxazine Similar to example 49a, (S)-2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-butyronitrile is used to afford the title compound as a yellow oil. Rf=0.22 (dichloromethane-methanol 10:1); Rt=4.77.

b) (S)-2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-butyronitrile Similar to example 19c, 123 mg of methanesulfonic acid (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-toluene-4-sulfonyl)-piperidin-2-ylmethyl]-propyl ester in the presence of 93 mg of tetrabutylammonium cyanide are used to afford the title compound as a colourless oil. Rf=0.32 (EtOAc-heptane 1:1); Rt=5.28.

c) Methanesulfonic acid (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propyl ester According to general procedure F, 100 mg of (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene- 4-sulfonyl)-piperidin-2-yl]-butan-2-ol (diastereomer 1) (from example 64d) are used to afford the title compound as a brown oil. Rt=5.38.

According to the processes described in example 66, the following compound is prepared in an analogous manner:

Example 89 6-{(3R,4R,6S)-4-(4-Fluoro-phenyl)-6-[(S)-2-(1H-tetrazol-5-yl)-butyl]-piperidin-3-yloxymethyl}-4-(3-methoxy-propyl)-3,4-dihydro-2H-benzo[1,4]oxazine Example 67

Dimethyl-carbamic acid (R)-2-{(2R,4R,5R)-4-(4-methoxy-phenyl)-5-[4-(3-methoxy-prolyl)-3,4-dihydro-2H-benzo[1,4]oxazin-6-ylmethoxy]-piperidin-2-yl}-1-methyl-ethyl ester According to general procedure A, 112 mg of dimethyl-carbamic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester are used to afford the title compound.
The starting material is prepared as follows:

a) Dimethyl-carbamic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (diastereomer 1)

To a solution of 100 mg of (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-ol (diastereomer 1) (from example 34b) in 10 ml tetrahydrofuran, are added 35 mg of potassium hydride and 0.14 ml of N,N-dimethylcarbamoyl chloride at room temperature. The reaction mixture is stirred for one additional hour, diluted with water and extracted with tert-butyl methyl ether. The combined organic phases are dried and concentrated under reduced pressure to afford the crude title compound. The residue is purified by flash chromatography (SiO₂ 60 F) to afford the title compound as a yellow oil. Rf=0.37 (EtOAc-heptane 2:1); Rt=5.44.

Example 68

Dimethyl-carbamic acid (S)-2-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-1-methyl-ethyl ester According to general procedure A, 100 mg of dimethyl-carbamic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester are used to afford the title compound.
The starting material is prepared as follows:

a) Dimethyl-carbamic acid (S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester To a solution of 100 mg of (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-ol (diastereomer 2) (from example 34b) in 10 ml tetrahydrofuran are added 34 mg of potassium hydride and 0.14 ml of N,N-dimethylcarbamoyl chloride at room temperature. The reaction mixture is stirred for one additional hour, diluted with water and extracted with tert-butyl methyl ether. The combined organic phases are dried and concentrated under reduced pressure to afford the crude title compound. The residue is purified by flash chromatography (SiO₂ 60 F) to afford the title compound as a yellow oil. Rf=0.41 (EtOAc-heptane 2:1); Rt=5.47.

Example 69

6-{(3R,4R,6S)-4-(4-Methoxy-phenyl)-6-[(S)-3-methyl-2-(1H-tetrazol-5-yl)-butyl]-piperidin-3-yloxymethyl}-4-(3-methoxy-propyl)-3,4-dihydro 2H-benzo[1,4]oxazine (diastereomer 1)

According to general procedure A, 100 mg of 6-[(3R,4R,6S)-4-(4-methoxy-phenyl)-6-[(S)-3-methyl-2-(1H-tetrazol-5-yl)-butyl]-1-(toluene-4-sulfonyl)-piperidin-3-yloxymethyl]-4-(3-methoxy-propyl)-3,4-dihydro-2H-benzo[1,4]oxazine (diastereomer 1) are used to afford the title compound.

The starting materials are prepared as follows:

a) 6-[(3R,4R,6S)-4-(4-Methoxy-phenyl)-6-[(S)-3-methyl-2-(1H-tetrazol-5-yl)-butyl]-1-toluene-4-sulfonyl)-piperidin-3-yloxymethyl]-4-(3-methoxy-propyl)-3,4-dihydro-2H-benzo[1,4]oxazine Similar to example 49a, using (S)-2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-3-methyl-butyronitrile to afford the title compounds as a slightly brown oil. Rf=0.20 (EtOAc-heptane 1:1); Rt=4.86.

b) (S)-2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-3-methyl-butyronitrile Similar to example 19c, 370 mg of methanesulfonic acid (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-2-methyl-propyl ester in the presence of 275 mg of tetrabutylammonium cyanide in acetonitrile are used to afford the title compound as a yellow oil. Rf=0.30 (EtOAc-heptane 1:1); Rt=5.38.

c) Methanesulfonic acid (R)-1-(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl-2-methyl-propyl ester According to general procedure F, are 400 mg of (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-3-methyl-butan-2-ol

Example 72

3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-propionic acid According to general procedure A, 100 mg of 3-[(2S,4R,5R)-4-(4-methoxyphenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) are used to afford the title compound.

Example 73

6-[(3R,4R,6R)-4-(4-Methoxy-phenyl)-6-((R)-[1,2,4]triazol-1-yl-butyl)-piperidin-3-yloxymethyl]-4-(3-methoxy-propyl)-3,4-dihydro-2H-benzo[1,4]oxazine According to general procedure A, 46 mg of 6-[(3R,4R,6R)-4-(4-methoxy-phenyl)-1-(toluene-4-sulfonyl)-6-((R)-2-[1,2,4]triazol-1-yl-butyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6R)-4-(4-Methoxy-phenyl)-1-(toluene-4-sulfonyl)-6-((R)-2-[1,2,4]triazol-1-yl-butyl)-piperidin-3-yloxymethyl]-4-(3-methoxy-propyl)-3,4-dihydro-2H-benzo[1,4]oxazine Similar to example 55a, 90 mg of methanesulfonic acid (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propyl ester (from example 64c) and 116 mg of the sodium salt of 1,2,4 triazole in 1 ml N,N-dimethylformamide are stirred at 40° C. overnight. The reaction mixture is diluted with water and extracted with ethyl acetate. The organic phases are combined, dried and concentrated under reduced pressure. The residue is purified by flash chromatography (SiO$_2$ 60 F) to afford the title compound as a yellow oil. Rf=0.20 (EtOAc-heptane 2:1); Rt=4.85.

According to the processes described in example 73, the following compounds are prepared in an analogous manner:

Examples 88 6-[(3R,4R,6R)-4-(4-Fluoro-phenyl)-6-((R)-2-[1,2,4]triazol-1-yl-butyl)-piperidin-3-yloxymethyl]-4-(3-methoxy-propyl)-3,4-dihydro-2H-benzo[1,4]oxazine 75 6-[(3R,4R,6R)-4-(4-Methoxy-phenyl)-6-((S)-2-[1,2,4]triazol-1-yl-butyl)-piperidin-3-yloxymethyl]-4-(3-methoxy-propyl)-3,4-dihydro-2H-benzo[1,4]oxazine starting from methansulfonic acid (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propyl ester (from example 66c).

According to the processes described in example 75, the following compound is prepared in an analogous manner:

Example 94 6-[(3R,4R,6R)-4-(4-Fluoro-phenyl)-6-((S)-2-[1,2,4]triazol-1-yl-butyl)-piperidin-3-yloxymethyl]-4-(3-methoxy-propyl)-3,4-dihydro-2H-benzo[1,4]oxazine

Example 74

(R,S)-3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2-methyl-propionic acid (diastereomeric mixture)

According to general procedure A, 150 mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionic acid are used to afford the title compound after flash chromatography as a yellow oil. Rf=0.07 (dichloromethane-methanol-25% ammonia conc. 100:20:1); Rt=3.66 and 3.77.

The starting material is prepared as follows:

a) (R,S)-3-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionic acid (diastereomeric mixture)

A stirred solution of 1.1 g of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionitrile (diastereomeric mixture) (from example 31a) in 20 ml of ethanol and 2N sodium hydroxide is heated to 80° C. for 2 days. After complete hydrolysis the reaction mixture is acidified by the addition of 2N hydrochloric acid and extracted with dichloromethane. The organic phases are combined, dried and concentrated under reduced pressure. The residue is purified by flash chromatography (SiO$_2$ 60 F) to afford the title compound as a yellow oil. Rf=0.20 (EtOAc-heptane 2:1); Rt=4.85.

Example 76

(R,S)-3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2-methyl-N-(tetrahydro-pyran-4-yl)-propionamide (diastereomeric mixture)

According to general procedure A, 104 mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-N-tetrahydro-pyran-4-yl)-propionamide (diastereomeric mixture) are used to afford the title compound.

The starting material is prepared as follows:

a) (R,S)-3-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-N-(tetrahydro-pyran-4-yl)-propionamide (diastereomeric mixture)

According to general procedure D, 85 mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene- (from example 53) used to afford the title compound as a colourless oil. Rf=0.29 (EtOAc-heptane 1:1); Rt=5.34.

4-sulfonyl)-piperidin-2-yl]-2-methyl-propionic acid (diastereomeric mixture) (from example 74a) and 14 mg of 4-aminotetrahydrofuran are used to afford the title compound after flash chromatography (SiO$_2$ 60 F) as a yellow oil. Rf=0.23 (EtOAc-heptane 2:1); Rt=4.91.

Example 77

(R,S)-3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2-methyl-N—[(S)-1-(tetrahydro-furan-2-yl)-methyl]-propionamide (diastereomeric mixture)

According to general procedure A, 100 mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-N—[(S)-1-(tetrahydro-furan-2-yl)-methyl]-propionamide (diastereomeric mixture) are used to afford the title compound.

The starting material is prepared as follows:

a) (R,S)-3-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-N—[(S)-1-(tetrahydro-furan-2-yl) methyl]-propionamide (diastereomeric mixture)

According to general procedure D, 100-mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionic acid (diastereomeric mixture) (from example 74a) and 16 mg of (S)-tetrahydrofurfurylamine are used to afford the title compound after flash chromatography (SiO$_2$ 60 F) as a yellow oil. Rf=0.22 and 0.19 (EtOAc-heptane 4:1); Rt=5.06.

Example 78

(R,S)—N-(2-Carbamoyl-2-methyl-propyl)-3-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2-methyl-propionamide (diastereomeric mixture)

According to general procedure A, 93 mg of (R,S)—N-(2-carbamoyl-2-methyl-propyl)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionamide (diastereomeric mixture) are used to afford the title compound.

The starting material is prepared as follows:

a) (R,S)—N-(2-Carbamoyl-2-methyl-propyl)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionamide (diastereomeric mixture)

According to general procedure D, 100 mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionic acid (diastereomeric mixture) (from example 74a) and 19 mg of 3-amino-2,2-dimethyl-propionamide are used to afford the title compound as a yellow oil. Rf=0.16 (EtOAc); Rt=4.62.

Example 79

3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-N—[(S)-1-(tetrahydro-furan-2-yl)-methyl]-propionamide According to general procedure A, 97 mg of 3-[(2S,5R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-N—[(S)-1-(tetrahydro-furan-2-yl)-methyl]-propionamide are used to afford the title compound.

The starting material is prepared as follows:

a) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-N—[(S)-1-(tetrahydro-furan-2-yl)-methyl]-propionamide According to general procedure D, 110 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) and 20 mg (S)-tetrahydrofurfurylamine are used to afford the title compound as a yellow oil. Rf=0.35 (EtOAc-heptane 8:1); Rt=5.12.

According to the processes described in example 79, the following compounds are prepared in an analogous manner:

Examples 80 3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-N-(tetrahydro-pyran-4-yl)-propionamide 85 3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-1-morpholin-4-yl-propan-1-one 132 N-(2-Dimethylamino-ethyl)-3-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2,2-dimethyl-propionamide 133 N-(3-Dimethylamino-propyl)-3-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2,2-dimethyl-propionamide

Example 81

3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-propionitrile According to general procedure A (at 0° C.), 100 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionitrile are used to afford the title compound.

The starting material is prepared as follows:

a) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionitrile A suspension of 500 mg 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b), 111.2 mg ammonium chloride and 0.7 ml triethylamine in 5 ml tetrahydrofuran are cooled to −10° C. and 1.21 ml of a T3P® solution (50% in ethyl acetate) is added dropwise. The reaction mixture is warmed to room temperature and stirred for 8 hours. The resulting suspension is stirred at 70° C. for 2 days. During this time, the addition of 111.2 mg ammonium chloride, 0.7 ml triethylamine and 1.21 ml of a T3P® solution (50% in ethyl acetate) is repeated twice. The reaction mixture is quenched by addition of 5 ml of water and extracted with 50 ml ethyl acetate (3×). The combined organic layers are washed with brine and dried with sodium sulfate. The organic layer is filtered and evaporated under reduced pressure. The residue is purified by flash chromatography (SiO$_2$ 60 F) to afford the title compound as a colourless foam. Rf=0.12 (EtOAc-heptane 1:2); Rt=5.42.

Example 82

6-{(3R,4R,6S)-4-(4-Methoxy-phenyl)-6-[2-methyl-2-(1H-tetrazol-5-yl)-propyl]-piperidin-3-yloxymethyl}-4-(3-methoxy-propyl)-3,4-dihydro-2H-benzo[1,4]oxazine According to general procedure A, 45.7 mg of 6-[(3R,4R,6S)-4-(4-methoxy-phenyl)-6-[2-methyl-2-(1H-tetrazol-5-yl)-propyl]-1-(toluene 4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6S)-4-(4-Methoxy-phenyl)-6-[2-methyl-2-(1H-tetrazol-5-yl)-propyl]-1-(toluene-4-sulfanyl)-piperidin-3-yloxymethyl]-4-(3-methoxy-propyl)-3,4-dihydro-2H-benzo[1,4]oxazine To a solution of 140 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionitrile (from example 81a) in 3 ml toluene are added 0.55 ml trimethylsilyl azide and 5.3 mg dibutyl tin oxide and the mixture is refluxed for 24 hours. During this time, the addition of 0.55 ml trimethylsilyl azide and 5.3 mg dibutyl tin oxide is repeated twice. The reaction mixture is warmed to room temperature and hydrolyzed with 2 ml 1N aqueous hydrochloric acid. This mixture is extracted with 50 ml dichloroethane (3×) and the combined organic layers are washed with brine and dried with sodium sulfate. The organic layer is filtered and evaporated under reduced pressure. The residue is purified by flash chromatography (SiO$_2$ 60 F) to afford the title compound as a yellow oil. Rf=0.15 (EtOAc-heptane 3:1); Rt=4.87.

Example 83

6-{(3R,4R,6S)-4-(4-Methoxy-phenyl)-6-[2-(1H-tetrazol-5-yl)-ethyl]-piperidin-3-yloxymethyl}-4-(3-methoxy-propyl)-3,4-dihydro-2H-benzo[1,4]oxazine According to general procedure A, 150 mg of 6-[(3R,4R,6S)-4-(4-methoxy-phenyl)-6-[2-(1H-tetrazol-5-yl)-ethyl]-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6S)-4-(4-Methoxy-phenyl)-6-[2-(1H-tetrazol-5-yl)-ethyl]-1-(toluene-4-sulfonyl)-piperidin-3-yloxymethyl]-4-(3-methoxy-propyl)-3,4-dihydro-2H-benzo[1,4]oxazine Similar to example 49a, 200 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfanyl)-piperidin-2-yl]-propionitrile are used to afford the title compound as a viscous yellow oil. Rf=0.10 (EtOAc heptane 4:1); Rt=4.71.

b) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propionitrile Similar to example 19c, 2.75 g of methanesulfonic acid 2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethyl ester (from example 25d) are used to afford the title compound as a colourless oil.

Example 84

(R,S)-3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2-methyl-1-morpholinyl-4-yl-propan-1-one (diastereomeric mixture)

According to general procedure A, 108 mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-1-morpholin-4-yl-propan-1-one (diastereomeric mixture) are used to afford the title compound.

The starting material is prepared as follows:

a) (R,S)-3-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-1-morpholin-4-yl-propan-1-one (diastereomeric mixture)

According to general procedure D, 100 mg of (R,S)-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propionic acid (diastereomeric mixture) (from example 74a) and 14 mg of morpholine are used to afford the title compound as a yellow oil. Rf=0.23 (EtOAc-heptane 4:1); Rt=5.01 and 5.08.

Example 90

6-{(3R,4R,6S)-4-[4-(3-Methoxy-propoxy)-phenyl]6-[(R)-2-(1H-tetrazol-5-yl)-propyl]-piperidin-3-yloxymethyl}-4-(3-methoxy-propyl)-3,4-dihydro-2H-benzo[1,4]oxazine According to general procedure A, 50 mg of 6-[(3R,4R,6S)-4-[4-(3-methoxy-propoxy)-phenyl]-6-[(R)-2-(1H-tetrazol-5-yl)-propyl]-1-(toluene-4-sulfonyl)-piperidin-3-yloxymethyl]-4-(3-methoxy-propyl)-3,4-dihydro-2H-benzo[1,4]oxazine used to afford the title compound.

The starting materials are prepared as follows:

a) 6-[(3R,4R,6S)-4-[4-(3-Methoxy-propoxy)-phenyl]-6-[(R)-2-(1H-tetrazol-5-yl)-propyl]-1-(toluene-4-sulfonyl)-piperidin-3-yloxymethyl]-4-(3-methoxy-propyl)-3,4-dihydro-2H-benzo[1,4]oxazine To a stirred solution of 180 mg of 4-[(2S,4R,5R)-5-[4-(3-methoxy-propyl)-3,4-dihydro-2H-benzo[1,4]oxazin-6-ylmethoxy]-2-[(R)-2-(1H-tetrazol-5-yl)-propyl]-1-(toluene-4-sulfonyl)-piperidin-4-yl]-phenol and 104 mg of 3-methoxypropylchloride in N,N-dimethylformamide is added 147 mg of cesium carbonate. The suspension is heated to 60° C. overnight, diluted with water and extracted with ethyl acetate. The organic phases are combined, dried and concentrated under reduced pressure to afford the crude title compound. The residue is purified by flash chromatography (SiO2 60 F) to afford the title compound as a brown oil. Rf=0.40 (EtOAc-heptane 5:1); Rt=4.81.

b) 4-[(2S,4R,5R)-5-[4-(3-Methoxy-propyl)-3,4-dihydro-2H-benzo[1,4]oxazin-6-ylmethoxy]-2-[(R)-2-(1H-tetrazol-5-yl)-propyl]-1-(toluene-4-sulfonyl)-piperidin-4-yl]-phenol To a stirred solution of 200 mg of 6-[(3R,4R,6S)-4-(4-methoxy-phenyl)-6-[(R)-2-(1H-tetrazol-5-yl)-propyl]-1-(toluene-4-sulfonyl)-piperidin-3-yloxymethyl]-4-(3-methoxy-propyl)-3,4-dihydro 2H-benzo[1,4]oxazine (from example 49a) in N,N-dimethylformamide is added 470 mg of sodium ethanethiolate and the resulting suspension is heated to 130° C. overnight. The reaction mixture is diluted with 1N hydrochloric acid solution and extracted with ethyl acetate. The organic phases are combined, dried and concentrated under reduced pressure to afford the crude title compound. The residue is purified by flash chromatography (SiO₂ 60 F) to afford the title compound as a brown oil. Rf=0.40 (EtOAc-heptane 5:1); Rt=4.81.

Example 92

1-(2{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1,1-dimethyl-ethyl)-3-(tetrahydro-pyran-4-yl)-urea According to general procedure A, 138.7 mg of 1-{2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethyl}-3-(tetrahydro-pyran-4-yl)-urea are used to afford the title compound as a white foam. Rf=0.15 (dichloromethane-methanol-25% conc. ammonia 200:10:1); Rt=3.79.

The starting materials are prepared as follows:

a) 1-{2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethyl}-3-(tetrahydro-pyran-4-yl)-urea To a solution of 150 mg 6-[(3R,4R,6S)-6-(2-isocyanato-2-methyl-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine in 1 ml tetrahydrofuran is added 228 mg 4-amino-tetrahydro-pyran and the mixture is stirred for 2 hours at room temperature. The solvent is evaporated under reduced pressure and the residue is purified by flash chromatography (SiO₂ 60 F) to afford the title compound as a colourless oil. Rf=0.31 (EtOAc-heptane 7:1); Rt=4.91.

b) 6-[(3R,4R,6S)-6-(2-Isocyanato-2-methyl-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine To a solution of 290.2 mg 3-[(2S,4R,5R)-4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) and 0.14 ml triethylamine in 4 ml tetrahydrofuran is added 80 µl ethyl chloroformate at 0° C. and the mixture is stirred for 1 hour at 0° C. Then a solution of 523 mg sodium azide in 2 ml water is added dropwise and the reaction mixture is stirred at 0° C. for further 45 minutes. The mixture is warmed to room temperature and diluted with 2 ml water. This mixture is extracted with 50 ml ethyl acetate (3×) and the combined organic layers are washed with water (2×) and dried with sodium sulfate. The organic layer is filtered and evaporated under reduced pressure. The residue is purified by flash chromatography (SiO₂ 60 F, EtOAc-heptane 1:1) to afford the corresponding acyl azide as colourless oil. The residue is redissolved in 2 ml toluene and heated to 115° C. for 1 hour. The toluene is evaporated under reduced pressure yielding the crude title compound as a brown oil. Rt=5.77.

According to the processes described in example 92, the following compounds are prepared in an analogous manner:

Examples 93 3-(2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1,1-dimethyl-ethyl)-1,1-dimethyl-urea 99 Morpholine-4-carboxylic acid (2-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-1,1-dimethyl-ethyl)-amide

Example 95

6-[(3R,4R,6S)-4-(4-Methoxy-phenyl)-6-phenylmethanesulfonylmethyl-piperidin-3-yloxymethyl]-4-(3-methoxy-propyl)-3,4-dihydro-2H-benzo[1,4]oxazine According to general procedure C, 60 mg of 6-[(3R,4R,6S)-4-(4-methoxy-phenyl)-6-phenyl-methanesulfanylmethyl-piperidin-3-yloxymethyl]-4-(3-methoxy-propyl)-4H-benzo[1,4]oxazin-3-one are used to afford the title compound.

The starting materials are prepared as follows:

a) 6-[(3R,4R,6S)-4-(4-Methoxy-phenyl)-6-phenyl-methanesulfonylmethyl-piperidin-3-yloxymethyl]-4-(3-methoxy-propyl)-4H-benzo[1,4]oxazin-3-one According to general procedure A, 157 mg of 6-[(3R,4R,6S)-4-(4-methoxy-phenyl)-6-phenyl-methanesulfonylmethyl-1-(toluene-4-sulfonyl)-piperidin-3-yloxymethyl]-4-(3-methoxy-propyl)-4H-benzo[1,4]oxazin-3-one are used to afford the title compound as a white foam. Rf=0.28 (dichlormethane-methanol 20:1); Rt=3.77.

b) 6-[(3R,4R,6S)-4-(4-Methoxy-phenyl)-6-phenyl-methanesulfonylmethyl-1-(toluene-4-sulfonyl)-piperidin-3-yloxymethyl]4-(3-methoxy-propyl)-4H-benzo[1,4]oxazin-3-one To a solution of 160 mg of 6-[(3R,4R,6S)-6-benzylsulfanylmethyl-4-(4-methoxy-phenyl)-1-(toluene-4-sulfonyl)-piperidin-3-yloxymethyl]-4-(3-methoxy-propyl)-4H-benzo[1,4]oxazin-3-one in chloroform are added 128 mg of 3-chloroperoxybenzoic acid and the resulting mixture is stirred for 1 hour at room temperature. The reaction mixture is diluted with 0.5M aqueous sodium hydroxide (40 ml), extracted with tertbutyl methyl ether. The organic phase is separated, dried with sodium sulfate and concentrated under reduced pressure. The residue is purified by flash chromatography (SiO$_2$ 60 F) to afford the fide compound as a white foam. Rf=0.33 (EtOAc-heptane 2:1); Rt=5.07.

c) 6-[(3R,4R,6S)-6-Benzylsulfanylmethyl-4-(4-methoxy-phenyl)-1-(toluene-4-sulfonyl)-piperidin-3-yloxymethyl]-4-(3-methoxy-propyl)-4H-benzo[1,4]oxazin-3-one To a stirred mixture of 28 mg sodium hydride in 8 ml N,N-dimethylformamide is added 0.070 ml benzyl mercaptan. After 15 minutes, 200 mg of methanesulfonic acid (2S,4R,5R)-4-(4-methoxy-phenyl)-5-[4-(3-methoxy-propyl)-3-oxo-3,4-dihydro-2H-benzo[1,4]oxazin-6-ylmethoxy]-piperidin-2-ylmethyl ester are added and the reaction mixture is stirred for 3 hours at room temperature. The reaction mixture is diluted with 1M aqueous sodium bicarbonate (50 ml), extracted with tert-butyl methyl ether and the organic phase is separated and dried over sodium sulfate. The organic phase is concentrated under reduced pressure and the residue is purified by flash chromatography (SiO$_2$ 60 F) to afford the title compound as a colourless oil. Rf=0.27 (EtOAc-heptane 1:1); Rt=5.75.

d) Methanesulfonic acid (2S,4R,5R)-4-(4-methoxy-phenyl)-5-[4-(3-methoxy-propyl)-3-oxo-3,4-dihydro-2H-benzo[1,4]oxazin-6-ylmethoxy]-piperidin-2-ylmethyl ester According to general procedure F, 5 g of 6-[(3R,4R,6S)-6-hydroxymethyl-4-(4-methoxy-phenyl)-piperidin-3-yloxymethyl]-4-(3-methoxy-propyl)-4H-benzo[1,4]oxazin-3-one are used to afford the title compound as a white foam. Rf=0.27 (EtOAc-heptane 2:1); Rt=4.81.

e) 6-[(3R,4R,6S)-6-Hydroxymethyl-4-(4-methoxy-phenyl)-piperidin-3-yloxymethyl]-4-(3-methoxy-propyl)-4H-benzo[1,4]oxazin-one To a stirred solution of 14.8 g 6-[(3R,4R,6S)-4-(4-methoxy-phenyl)-1-(toluene-4-sulfonyl)-6-triisopropylsilanyloxymethyl-piperidin-3-yloxymethyl]-4-(3-methoxy-propyl)-4H-benzo[1,4]oxazin-3-one (from example 24b-b) in 200 ml of tetrahydrofuran are added 34.6 ml of a 1N solution of tetrabutylammoniumfluoride in tetrahydrofuran at 5° C. The reaction mixture is stirred for 2 hours at room temperature, diluted with water and extracted with tert-butyl methyl ether. The combined organic phases are washed with brine, dried over sodium sulfate and concentrated under reduced pressure. The crude product is purified by flash chromatography (SiO$_2$ 60 F) to afford the title compound as a white foam. Rf=0.20 (EtOAc-heptane 2:1); Rt=4.54.

According to the processes described in example 95, the following compounds are prepared in an analogous manner:

Examples 96 6-[(3R,4R,6S)-6-Methanesulfonylmethyl-4-(4-methoxy-phenyl)-piperidin-3-yloxymethyl]-4-(3-methoxy-propyl)-3,4-dihydro-2H-benzo[1,4]oxazine 97 6-[(3R,4R,6S)-4-(4-Methoxy-phenyl)-6-(2-methyl-propane-2-sulfonylmethyl)-piperidin-3-yloxymethyl]-4-(3-methoxy-propyl)-3,4-dihydro-2H-benzo[1,4]oxazine Example 98

((R)-2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1-methyl-ethyl)-pyridin-2-ylamine According to general procedure A, 73 mg of {(R)-2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-pyridin-2-yl-amine are used to afford the title compound.

The starting material is prepared as follows:

a) {(R)-2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-pyridin-2-yl-amine A stirred mixture of 96 mg (R)-2-[(2S,4R,5R)-4-methoxyphenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethylamine (from example 37b), 21 mg sodium tert-butoxide, 0.022 ml 2-chloro-pyridine and 1.0 ml toluene is placed in a "schlenk tube" under argon. To this mixture is added a solution of 2.7 mg palladium(II)acetate, 5.1 mg 1,3-bis(diphenylphosphino)propane in 0.4 ml toluene. The reaction mixture is stirred for 2 days at 70° C. The resulting mixture is diluted with water (25 ml), extracted with tertbutyl methyl ether and the organic phase is separated and dried over sodium sulfate. The organic phase is concentrated under reduced pressure and the residue is purified by flash chromatography (SiO$_2$ 60 F) to afford the title compound as a yellow oil. Rf=0.09 (dichlormethane-methanol-25% ammonia conc. 200:10:1); Rt=4.62.

Example 100

6-{(3R,4R,6S)-4-(4-Methoxy-phenyl)-6-[(R)-2-((2-methyl-2H-tetrazol-5-yl))-butyl]-piperidin-3-yloxymethyl}-4-(3-methoxy-propyl)-3,4-dihydro-2H-benzo[1,4]oxazine According to general procedure A, 0.099 g of 6-[(3R,4R,6S)-4-(4-methoxy-phenyl)-6-[(R)-2-((2-methyl-2H-tetrazol-5-yl) or (1-methyl-1H-tetrazol-5-yl))-butyl]-1-(toluene-4-sulfonyl)-piperidin-3-yloxymethyl]-4-(3-methoxy-propyl)-3,4-dihydro-2H-benzo[1,4]oxazine (regioisomer 1) are used to afford the title compound.

The starting material is prepared as follows:

a) 6-[(3R,4R,6S)-4-(4-Methoxy-phenyl)-6-[(R)-2-((2-methyl-2H-tetrazol-5-yl))-butyl]-1-(toluene-4-sulfonyl)-piperidin-3-yloxymethyl]-4-(3-methoxy-propyl)-3,4-dihydro-2H-benzo[1,4]oxazine (regioisomer 1)

and

6-[(3R,4R,6S)-4-(4-Methoxy-phenyl)-6-[(R)-2-((1-methyl-1H-tetrazol-5-yl))-butyl]-1-(toluene-4-sulfonyl)-piperidin-3-yloxymethyl]-4-(3-methoxy-propyl)-3,4-dihydro-2H-benzo[1,4]oxazine (regioisomer 2)

A freshly prepared solution of diazomethane/diethylether (from Diazald®) is added dropwise to a solution of 0.201 g of 6-[(3R,4R,6S)-4-(4-methoxy-phenyl)-6-[(R)-2-(1H-tetrazol-5-yl)-butyl]-1-(toluene-4-sulfonyl)-piperidin-3-yloxymethyl]-4-(3-methoxy-propyl)-3,4-dihydro-2H-benzo[1,4]oxazine (from example 64a) in 8 ml of methanol at 0° C. After 2.5 hours, solid magnesium sulfate is added to decompose any excess diazomethane and then the reaction mixture is concentrated. The resulting residue is suspended in dichloromethane, filtered and re-concentrated. The residue is purified by flash chromatography (SiO$_2$ 60 F) to afford the title compound together with its N-methylated regioisomer.

Diastereomer 1, regioisomer 1: brown oil; Rf=0.19 (EtOAc-heptane 2:1); Rt=5.19.

Diastereomer 1, regioisomer 2: yellow oil; Rf=0.26 (EtOAc-heptane 2:1); Rt=5.38.

According to the processes described in example 100, the following compound is prepared in an analogous manner:

Example 101 6-{(3R,4R,6S)-4-(4-Methoxy-phenyl)-6-[(R)-2-((1-methyl-1H-tetrazol-5-yl) or (2-methyl-2H-tetrazol-5-yl))-butyl]-piperidin-3-yloxymethyl}-4-(3-methoxy-propyl)-3,4-dihydro-2H-benzo[1,4]oxazine starting from 6-[(3R,4R,6S)-4-(4-methoxy-phenyl)-6-[(R)-2-((1-methyl-1H-tetrazol-5-yl) or (2-methyl-2H-tetrazol-5-yl))-butyl]-1-(toluene-4-sulfonyl)-piperidin-3-yloxymethyl]-4-(3-methoxy-propyl)-3,4-dihydro-2H-benzo[1,4]oxazine (regioisomer 2) (from example 100a).

Example 102

3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-N-(1-methyl-piperidinyl-4-yl)-propionamide According to general procedure A, 100 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-N-(1-methyl-piperidin-4-yl)-propionamide are used to afford the title compound.

The starting material is prepared as follows:

a) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-N-(1-methyl-piperidin-4-yl)-propionamide According to general procedure D, 196 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) and 37 mg of 1-methyl-piperidin-4-ylamine are used to afford the title compound as a colourless oil. Rf=0.24 (dichloromethane-methanol 10:1); Rt=4.47.

Example 103

3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-N-piperidin-4-yl-propionamide According to general procedure A, 90 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-N-piperidin-4-yl-propionamide are used to afford the title compound.

The starting materials are prepared as follows:

a) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-N-piperidin-4-yl-propionamide According to general procedure E, 160 mg of 4-{3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionylamino}-piperidine-1-carboxylic acid benzyl ester are used to afford the title compound as a yellow oil. Rf=0.50 (dichloromethane-methanol 5:1); Rt=4.55.

b) 4-{3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionylamino}-piperidine-1-carboxylic acid benzyl ester According to general procedure D, 224 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) and 87 mg of 4-amino-piperidine-1-carboxylic acid benzyl ester are used to afford the title compound as a colourless oil. Rf=0.18 (EtOAc-heptane 1:1); Rt=5.53.

Example 104

(S or R)-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1-(2H-tetrazol-5-yl)-ethanol According to general procedure A, 230 mg of (S or R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-(2H-tetrazol-5-yl)-ethanol are used to afford the title compound.

The starting materials are prepared as follows:

a) (S or R)-2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-(2H-tetrazol-5-yl)-ethanol Similar to example 49a, 1.0 g of (R,S)-2-hydroxy-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propionitrile (diastereomeric mixture) are used to afford the title compound as a colourless foam after separation of the diastereomers by flash chromatography (SiO$_2$ 60 F). Rf=0.15 (EtOAc-heptane 11:1); Rt=4.54.

b) (R,S)-2-Hydroxy-3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propionitrile (diastereomeric mixture)

To a stirred solution of 3.7 g of [(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetaldehyde in 50 ml of dichloromethane are added 3.03 g of trimethylsilyl cyanide and 1.36 g of zinc bromide at room temperature. The reaction mixture is stirred overnight, diluted with dichloro-methane and water and the organic phase is separated and dried. The organic phase is concentrated under reduced pressure and the residue is subsequently dissolved in 25 ml of methanol followed by the addition of 2.5 g of potassium fluoride. The reaction mixture is stirred for 2 hours, concentrated under reduced pressure and the residue is purified by flash chromatography (SiO$_2$ 60 F) to afford the title compound as a yellow oil. Rf=0.25 (EtOAc-heptane 1:1); Rt=4.93.

c) [(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetaldehyde To a stirred solution of 4.29 g of 2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethanol (from example 25e) in 6.0 ml of dimethylsulfoxide and 30 ml of dichloromethane at 0° C. are added 4.80 ml of triethylamine and 3.60 g of pyridine sulfur trioxide complex. The reaction mixture is allowed to stir for an additional 3 hours at this temperature and then allowed to warm to room temperature, diluted with water and acidified by the addition of 1N potassium bisulfate solution and subsequently extracted with diethyl ether. The organic phases are dried, concentrated under reduced pressure and the residue is purified by flash chromatography (SiO$_2$ 60 F) to afford the title compound as a colourless oil. Rf=0.21 (EtOAc-heptane 1:1); Rt=4.82.

Example 105

(R,S)-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1(S,R)-(2H-tetrazol-5-yl)-ethanol d(iastereomeric mixture)

According to general procedure A, 950 mg of (R,S)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-(2H-tetrazol-5-yl)-ethanol (diastereomeric mixture) are used to afford the title compound.

The starting material is prepared as follows:

a) (R,S)-2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-(2H-tetrazol-5-yl)-ethanol (diastereomeric mixture)

Similar to example 49a, 1.0 g of 2-hydroxy-3-[(2R,4R,5R)-4-(4-methoxy-phenyl)-5-[4-(3-methoxy-propyl)-3,4-dihydro-2H-benzo[1,4]oxazin-6-ylmethoxy]-1(S,R)-(toluene-4-sulfonyl)-piperidin-2-yl]-propionitrile (diastereomeric mixture) (from example 104b) are used to afford the title compound after flash chromatography (SiO$_2$ 60 F) as a mixture of diastereomers as a brown oil. Rf=0.10 (EtOAc-heptane 1:1); Rt=4.54.

Example 106

3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-1-(4-methyl-piperazin-1-yl)-propan-1-one Similar to example 102, 1-methylpiperazine is reacted with 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) to afford 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-1-(4-methyl-piperazin-1-yl)-propan-1-one which is subsequently deprotected according to general procedure A to afford the title compound.

Example 107

3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-1-piperazin-1-yl-propan-1-one Similar to example 102, piperazine is reacted with 3-[(2S,4R,5R)-4-(4-ethoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) to afford 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-1-piperazin-1-yl-propan-1-one which is subsequently deprotected according to general procedure A to afford the title compound.

Example 108

((S)-2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-1-methyl-ethyl)-(1H-tetrazol-5-yl)-amine According to general procedure A, 159 mg of N-{(S)-2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-4-methyl-N-(1H-tetrazol-5-yl)-benzenesulfonamide are used to afford the title compound.

The starting materials are prepared as follows:

a) N-{(S)-2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-4-methyl-N-(1H-tetrazol-5-yl)-benzenesulfonamide Similar to procedure 49a, 435 mg of N-{(S)-2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-4-methyl-N-(cyano)-benzenesulfonamide are used to afford the title compound as yellow oil. Rf=0.17 (dichloromethane-methanol-25% ammonia conc.=100:10:1); Rt=5.37.

b) N-{(S)-2-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl}-4-methyl-N-(cyano)-benzenesulfonamide To a stirred solution of 399 mg of (S)-2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethylamine in 5 ml of dichloromethane are added 0.12 ml triethylamine and 66 mg of cyanogenbromide at room temperature. The reaction mixture is stirred for 2 hours, followed by the addition of 0.32 ml of triethylamine, 178 mg of 4-toluenesulfonyl chloride and 7 mg of 4-N-dimethylaminopyridine. The reaction mixture is heated to 50° C. for 4 hours and subsequently washed with 1N hydrochloric acid solution and extracted with dichloromethane. The organic phases are combined, dried and concentrated under reduced pressure. The residue is purified by flash chromatography (SiO$_2$ 60 F) to afford the title compound as a yellow oil. Rf=0.16 (EtOAc-heptane 1:1); Rt=–5.71.

c) (S)-2-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethylamine Similar to example 37b, 1.52 g of 6-[(3R,4R,6R)-6-((S)-2-azido-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are reduced to afford the title compound as a colourless oil. Rf=0.45 (dichloromethane-methanol-25% ammonia conc. 200:20:1); Rt=4.41.

d) 6-[(3R,4R,6R)-6-((S)-2-Azido-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine Similar to example 37c, 150 mg of methanesulfonic acid (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethyl ester (from example 38b) are used to afford the title compound as a green oil. Rf=0.33 (EtOAc-heptane 1:1); Rt=5.71.

According to the processes described in example 108, the following compound is prepared in an analogous manner:

Example 109 ((R)-2-{(3R,4R,6R)-4-(4-Methoxy-phenyl)-5-[4-(3-methoxy-propyl)-3,4-dihydro-2H-benzo[1,4]oxazin-6-ylmethoxy]-piperidin-2-yl}-1-methyl-ethyl)-(1H-tetrazol-5-yl)-amine starting from (R)-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1-methyl-ethylamine (from example 37b)

Example 110

(R,S)-1-Methoxy-3-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2-methyl-propan-2-ol (diastereomeric mixture)

According to general procedure A, 200 mg of (R,S)-1-methoxy-3-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2-methyl-propan-2-ol (diastereomeric mixture) are used to afford the title compound.

The starting material is prepared as follows:

a) (R,S)-1-Methoxy-3-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2-methyl-propan-2-ol (diastereomeric mixture)

To a stirred solution of 1.0 g of (R,S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-one (from example 29b) in 15 ml of methanol are added 360 mg of trimethyl-sulfoxoniumiodide and 273 mg of sodium hydroxide and the reaction mixture is heated to 70° C. for 1 day. The reaction mixture is concentrated under reduced pressure and the residue is taken up in water and dichloromethane. The organic phase is dried and concentrated under reduced pressure to afford the crude title compound. The residue is purified by flash chromatography (SiO$_2$ 60 F) to afford the title compound as a yellow oil. Rf=0.39 (EtOAc-heptane 1:1); Rt=5.09.

Example 111

(R,S)-4-Methoxy-1-{(2R,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2-methyl-butan-2-ol (diastereomeric mixture)

According to general procedure A, 65 mg of (R,S)-4-methoxy-1-[(2R,4R,5R)-4-(4-methoxy-phenyl)-5-[4 (3-methoxy-propyl)-3,4-dihydro-2H-benzo[1,4]oxazin-6-yl-methoxy]-1-toluene-4-sulfonyl)-piperidin-2-yl]-2-methyl-butan-2-ol (diastereomeric mixture) are used to afford the title compound.

The starting materials are prepared as follows:

a) (R,S)-4-Methoxy-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-butan-2-ol (diastereomeric mixture)

Similar to example 29b, 4-methoxy-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-one is reacted with methyl magnesium bromide to afford the title compound as a yellow oil. Rf=0.22 (EtOAc-heptane 1:1); Rt=5.12.

b) 4-Methoxy-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-one To a stirred solution of 0.5 g of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-but-3-en-2-one in 1.5 ml of methanol is added 38 mg of 2,8,9-tri-sec-butyl-2,5,8,9-tetraaza-1-phospha-bicyclo[3.3.3]undecane and the reaction mixture is heated to 35° C. for 1 day. The reaction mixture is diluted with 1N hydrochloric acid solution and extracted with ethyl acetate. The organic phases are combined, dried and concentrated under reduced pressure to afford the crude title compound. The residue is purified by flash chromatography (SiO$_2$ 60 F) to afford the title compound as a yellow oil. Rf=0.25 (EtOAc-heptane 2:3); Rt=5.16.

c) 1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-but-3-en-2-one Similar to example 29b, using N-methoxy-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide (from example 29c) and vinyl magnesiumbromide to afford the title compound as a yellow oil. Rf=0.50 (EtOAc-heptane 1:1); Rt=5.23.

Example 112

(R,S)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-3-[1,2,4]triazol-1-yl-propan-2-ol diastereomeric mixture According to general procedure A, 200 mg of (R,S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-3-[1,2,4]triazol-1-yl-propan-2-ol (diastereomeric mixture) are used to afford the title compound.

The starting materials are prepared as follows:

a) (R,S)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-3-[1,2,4]triazol-1-yl-propan-2-ol (diastereomeric mixture)

To a stirred solution of 200 mg of 6-[(3R,4R,6R)-4-(4-methoxy-phenyl)-6-((R,S)-2-methyl-oxiranylmethyl)-1-(toluene-4-sulfonyl)-piperidin-3-yloxymethyl]-4-(3-methoxy-propyl)-3,4-dihydro-2H-benzo[1,4]oxazine (diastereomeric mixture) in 2.0 ml of N,N-dimethylformamide is added 310 mg of the sodium salt of 1,2,4-triazole and the reaction mixture is heated to 40° C. overnight. The reaction mixture is diluted with water and extracted with ethyl acetate. The organic phases are combined, dried and concentrated under reduced pressure to afford the crude title compound. The residue is purified by flash chromatography (SiO$_2$ 60 F) to afford the title compound as a yellow oil. Rf=0.15 (EtOAc-heptane 1:1); Rt=4.61.

b) 6-[(3R,4R,6R)-4-(4-Methoxy-phenyl)-6-((R,S)-2-methyl-oxiranylmethyl)-1-(toluene-4-sulfonyl)-piperidin-3-yloxymethyl]-4-(3-methoxy-propyl)-3,4-dihydro-2H-benzo[1,4]oxazine (diastereomeric mixture)

To a stirred solution of 331 mg of trimethylsulfoxonium iodide in 5.0 ml of dimethylsulfoxide are added 56 mg of sodium hydride followed by the addition of 912 mg of 1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-one (from example 29b) at room temperature. The reaction mixture is stirred for 3 hours, diluted with 1N hydrochloric acid and extracted with tert-butyl methyl ether. The organic phases are dried and concentrated under reduced pressure to afford the crude title compound. The residue is purified by flash chromatography (SiO$_2$ 60 F) to afford the title compound as a yellow oil. Rf=0.19 (EtOAc-heptane 1:1); Rt=5.29.

Example 113

(3-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2-dimethyl-propyl)-(tetrahydro-pyran-4-yl)-amine According to general procedure A, 182 mg of {3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4- sulfonyl)-piperidin-2-yl]-2,2-dimethyl-propyl}-(tetrahydro-pyran-4-yl)-amine are used to afford the title compound.

The starting materials are prepared as follows:

a) {3-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propyl}-(tetrahydro-pyran-4-yl)-amine Similar to example 43a, 430 mg of 3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionaldehyde and 79 mg of 4-aminotetrahydropyran are used to afford the title compound as a yellow oil. Rf=0.05 (EtOAc-heptane 1:1); Rt=4.65.

b) 3-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionaldehyde Similar to example 104c, 390 mg of 3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propan-1-ol are used to afford the title compound as yellow oil. Rt=5.50.

c) 3-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propan-1-ol According to general procedure C, 500 mg of 3-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) are used to afford the title compound as a yellow foam. Rf=0.20 (EtOAc-heptane 1:2); Rt=5.26.

Example 114

6-[(3R,4R,6R)-4-(4-Methoxy-phenyl)-6-(2-morpholin-4-yl-ethyl)-piperidin-3-yloxymethyl]-4-(3-methoxy-propyl)-3,4-dihydro-2H-benzo[1,4]oxazine According to general procedure A, 400 mg of 6-[(3R,4R,6R)-4-(4-methoxy-phenyl)-6-(2-morpholin-4-yl-ethyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting materials are prepared as follows:

a) 6-[(3R,4R,6R)-4-(4-Methoxy-phenyl)-6-(2-morpholin-4-yl-ethyl)-1-(toluene-4-sulfonyl)-piperidin-3-yloxymethyl]-4-(3-methoxy-propyl)-3,4-dihydro-2H-benzo[1,4]oxazine Similar to example 43a, 400 mg of [(3R,4R,6R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetaldehyde and 112 mg of morpholine are used to afford the title compound as a colourless oil. Rf=0.20 (EtOAc-heptane 1:1); Rt=4.44.

b) [(3R,4R,6R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetaldehyde Similar to example 104c, 800 mg of 2-[(3R,4R,6R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-ethanol (from example 25e) are used to afford the title compound as a colourless oil. Rf=0.30 (EtOAc-heptane 1:2); Rt=4.98.

Example 115

3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2,N-trimethyl-propionamide According to general procedure A, 170 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2,N-trimethyl-propionamide are used to afford the title compound.

The starting material is prepared as follows:

a) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2,N-trimethyl-propionamide According to general procedure D, 150 mg of 3-[(2S,4R,5R)-4-(4-methoxy-phenyl)-5-[(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid from (from example 65b) and methylamine are used to afford the title compound as a brown oil. Rf=0.18 (EtOAc-heptane 5:1); Rt=4.97.

According to the processes described in example 115, the following compound is prepared in an analogous manner:

144 N-Ethyl-3-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2,2-dimethyl-propionamide Example 116

N-(2-Methoxy-ethyl)-3-{(2S,4R,6R)-4-(4-methoxy-phenyl)-5-[4-(3-methoxy-propyl)-3,4-dihydro-2H-benzo[1,4]oxazin-6-ylmethoxy]-piperidin-2-yl}-2,2-dimethyl-propionamide According to general procedure A, 180 mg of N-(2-methoxy-ethyl)-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionamide are used to afford the title compound.

The starting material is prepared as follows:

a) N-(2-Methoxy-ethyl)-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionamide According to general procedure D, 150 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) and 2-methoxyethylamine are used to afford the title compound as a brown oil. Rf=0.18 (EtOAc-heptane 5:1); Rt=5.05.

Example 117

(2R,4R,5R)-4-(4-Methoxy-phenyl)-5-[4-(3-methoxy-propyl)-3,4-dihydro-2H-benzo[1,4]-oxazin-6-yl-methoxy]-piperidine-2-carboxylic acid (biphenyl-3-ylmethyl)-amide According to general procedure E, (2R,4R,5R)-(2-[biphenyl-3-ylmethyl)-carbamoyl]-4-(4-methoxy-phenyl)-5-[4-(3-methoxy-propyl)-3,4-dihydro-2H-benzo[1,4]oxazin-6-yl-methoxy]-piperidine-1-carboxylic acid benzyl ester are used to afford the title compound.

The starting materials are prepared as follows:

a) (2R,4R,5R)-2-[(Biphenyl-3-ylmethyl)-carbamoyl]-4-(4-methoxy-phenyl)-5-[4-(3-methoxy-propyl)-3,4-dihydro-2H-4-benzo[1,4]oxazin-6-yl-methoxy]-piperidine-1-carboxylic acid benzyl ester According to general procedure D, 445 mg of (2R,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester and 128 mg of 3-phenylbenzylamine are used to afford the title compound as a colourless foam. Rf=0.23 (EtOAc-heptane 1:1); Rt=5.62.

b) (2R,4R,5R)-4-(4-Methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester A solution of 0.370 g (2R,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester 2-ethyl ester in 18 ml methanol-tetrahydrofuran-water 1:1:1 is cooled to 0° C. Lithiumhydroxide (0.050 g) is added and the mixture is left to warm to room temperature and stirred for 16 hours at this temperature. The mixture is acidified with 1M hydrochloric acid and extracted with dichloromethane (2×). The combined organic phases are dried over sodium sulfate, filtered and concentrated under reduced pressure. The residue is purified via flash chromatography (SiO$_2$ 60 F) to provide the product as a light red wax. Rf=0.25 (EtOAc-heptane-acetic acid 20:10:1); Rt=4.95.

c) (2R,4R,5R)-4-(4-Methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester 2-ethyl ester The title compound is obtained as a light yellow oil according to general procedure C starting from 0.403 g (2R,4R,5R)-4-(4-methoxy-phenyl)-5-[4-(3-methoxy-propyl)-3-oxo-3,4-dihydro-2H-benzo[1,4]oxazin-6-ylmethoxy]-piperidine-1,2-dicarboxylic acid 1-benzyl ester 2-ethyl ester. Rf=0.25 (EtOAc-heptane 1:1); Rt=5.55.

d) (2R,4R,5R)-4-(4-Methoxy-phenyl)-5-[4-(3-methoxy-propyl)-3-oxo-3,4-dihydro-2H-benzo[1,4]oxazin-6-ylmethoxy]-piperidine-1,2-dicarboxylic acid 1-benzyl ester 2-ethyl ester The title compound is prepared according to the procedure described in example 119a starting from 1.150 g (2S,4R,5R)-5-hydroxy-4-(4-methoxy-phenyl)-piperidine-1,2-dicarboxylic acid 1-benzyl ester 2-ethyl ester. The formed diastereomers are separated by flash chromatography (SiO$_2$ F60). The desired diastereomer is obtained as a yellow wax. Rf=0.10 (EtOAc-heptane 1:1), Rt=5.34 e) (2S,4R,5R)-5-hydroxy-4-(4-methoxy-phenyl)-piperidine-1,2-dicarboxylic acid 1-benzyl ester 2-ethyl ester A mixture of 1.2 g (2S,4R,5R)-5-hydroxy-4-(4-methoxy-phenyl)-piperidine-2-carboxylic acid ethyl ester in 40 ml of ethyl acetate, 20 ml of saturated aqueous sodium carbonate solution and 0.42 ml of benzyl chloroformate is stirred for 1 hour at 0° C., diluted with ethyl acetate and the organic phase is dried over sodium sulfate. The organic phase is concentrated under reduced pressure and the residue is purified by flash chromatography (SiO$_2$ 60 F) to afford the title compound as a yellow oil. Rf=0.3 (EtOAc-heptane 1:1); Rt=4.34.

f) (2S,4R,5R)-5-hydroxy-4-(4-methoxy-phenyl)-piperidine-2-carboxylic acid ethyl ester According to general procedure B, (2S,4R,5R)-5-hydroxy-1,4-bis-(4-methoxy-phenyl)-piperidin-2-carboxylic acid ethyl ester (from example 1c) are used to obtain the title compound. Rf=0.1 (dichloromethane-methanol 20:1); Rt=2.66.

Example 118

{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-((R,S)-3-phenyl-pyrrolidin-1-yl)-methanone (diastereomeric mixture)

According to general procedure E, 330 mg of (2R,4R,5R)-4-(4-methoxy-phenyl)-5-[4-(3 methoxy-propyl)-3,4-dihydro-2H-benzo[1,4]oxazin-6-ylmethoxy]-2-((R,S)-3-phenyl-pyrrolidine-1-carbonyl)-piperidine-1-carboxylic acid benzyl ester (diastereomeric mixture) are used to afford the title compound.

The starting material is prepared as follows:

a) (2R,4R,5R)-4-(4-methoxy-phenyl)-5-[4-(3-methoxy-propyl)-3,4-dihydro-2H-benzo[1,4]oxazin-6-ylmethoxy]-2-((R,S)-3-phenyl-pyrrolidine-1 carbonyl)-piperidine-1-carboxylic acid benzyl ester (diastereomeric mixture)

According to general procedure D, 445 mg of (2R,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester (from example 117b) and 135 mg of racemic 3-phenylpyrrolidine are used to afford the title compound as a colourless foam. Rf=0.10 (EtOAc-heptane 1:1); —Rt=5.58.

Example 119

(2R,4R,5R)-4-(4-Methoxy-phenyl)-5-[4-(3-methoxy-propyl)-3-oxo-3,4-dihydro-2H-benzo[1,4]oxazin-6-ylmethoxy]-piperidine-2-carboxylic acid ethyl ester The title compound is prepared according to general procedure B starting from (2R,4R,5R)-1,4-bis-4-(4-methoxy-phenyl)-5-[4-(methoxy-propyl)-3-oxo-3,4-dihydro-2H-benzo[1,4]oxazin-6-ylmethoxy]-piperidine-2-carboxylic acid ethyl ester.

The starting materials are prepared as follows:

a) (2R,4R,5R)-1,4-Bis-4-(4-methoxy-phenyl)-5-[4-(3-methoxy-propyl)-3-oxo-3,4-dihydro-2H-benzo[1,4]oxazin-6-ylmethoxy]-piperidine-2-carboxylic acid ethyl ester A solution of 1.000 g (2S,4R,5R)-5-hydroxy-1,4-bis-(4-methoxy-phenyl)-piperidine-2-carboxylic acid ethyl ester and 0.783 g 6-bromomethyl-4-(3-methoxy-propyl-4H-benzo[1,4]oxazin-3-one in 15 ml dry N,N-dimethylformamide is cooled to −20° C. Sodium hydride 0.100 g, (60% dispersion in oil) is added and the reaction mixture is warmed to room temperature over 8 hours. The reaction is quenched by addition of 1M aqueous hydrochloric acid solution. The precipitated solid is isolated by filtration and further purified by flash chromatography (SiO$_2$ 60 F). Rf=0.29 (EtOAc-heptane 1:1); Rt=5.20.

b) 6-Bromomethyl-4-(3-methoxy-propyl-4H-benzo[1,4]oxazin-3-one

Bromotrimethylsilane (11.7 ml) is added dropwise to a solution of 15.0 g 6-hydroxymethyl-4-(3-methoxy-propyl-4H-benzo[1,4]oxazin-3-one (from example 1 h) in 150 ml chloroform over 10 minutes. The reaction solution is left to stand at room temperature for 30 minutes and is then concentrated under reduced pressure. The residue is purified by flash chromatography (SiO$_2$ 60 F) to provide the title compound as a grey solid. Rf=0.55 (EtOAc-heptane 1:1); Rt=4.09.

Example 120

(2R,4R,5R)-4-(4-Methoxy-phenyl)-5-[4-(3-methoxy-propyl)-3,4-dihydro-2H-benzo[1,4]oxazin-6-yl-methoxy]-piperidin-2-yl}-methanol The title compound is prepared according to example 1, starting from 0.126 g (2R,4R,5R)-4-(4-methoxy-phenyl)-5-[4-(3-methoxy-propyl)-3-oxo-3,4-dihydro-2H-benzo[1,4]oxazin-6-ylmethoxy]-piperidine-2-carboxylic acid ethyl ester (from example 119).

Example 121

(2R,4R,5R)-4-(4-Methoxy-phenyl)-5-[4-(3-methoxy-propyl)-3,4-dihydro-2H-benzo[1,4]oxazin-6-yl-methoxy]-piperidine-2-carboxylic acid The title compound is prepared according to general procedure E starting from 0.035 g (2R,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid benzyl ester (from example 117b).

Example 122

(2R,4R,5R)-4-(4-Methoxy-phenyl)-5-[4-(3-methoxy-propyl)-3,4-dihydro-2H-benzo[1,4]oxazin-6-yl-methoxy]-piperidine-2-carboxylic acid dimethylamide The title compound is prepared according to example 8 starting from 0.051 g (2R,4R,5R)-4-(4-methoxy-phenyl)-5-[4-(3-methoxy-propyl)-3,4-dihydro-2H-benzo[1,4]oxazin-6-ylmethoxy]-piperidin-1,2-dicarboxylic acid 1-benzyl ester (from example 117b).

Example 123

(2R,4R,5R)-4-(4-Methoxy-phenyl)-5-[4-(3-methoxy-propyl)-3,4-dihydro-2H-benzo[1,4]oxazin-6-yl-methoxy]-piperidine-2-carboxylic acid methylamide The title compound is prepared according to example 5 starting from 0.051 g (2R,4R,5R)-4-(4-methoxy-phenyl)-5-[4-(3-methoxy-propyl)-3,4-dihydro-2H-benzo[1,4]oxazin-6-ylmethoxy]-piperidine-1,2-dicarboxylic acid 1-benzyl ester (from example 117b).

Example 124

3-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2,2,N,N-tetramethyl-propionamide According to general procedure A, 170 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2,N,N-tetramethyl-propionamide are used to afford the title compound.

The starting material is prepared as follows:

a) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2,N,N-tetramethyl-propionamide According to general procedure D, 150 mg of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) and dimethylamine are used to afford the title compound as a brown oil. Rf=0.45 (EtOAc-heptane 1:1); Rt=5.27.

According to the processes described in example 124, the following compounds are prepared in an analogous manner.

132 N-(2-Dimethylamino-ethyl)-3-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2,2-dimethyl-propionamide 133 N-(3-Dimethylamino-propyl)-3-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-2,2-dimethyl-propionamide

Example 125

4-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2-methyl-butan-2-ol According to general procedure A, 327 mg of 4-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-butan-2-ol are used to afford the title compound.

The starting materials are prepared as follows:

a) 4-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-butan-2-ol Similar to example 29b, 200 mg of 4-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-one and 0.5 ml of methylmagnesium bromide (1N solution in tetrahydrofuran) are used to afford the title compound as a beige oil. Rf=0.12 (EtOAc-heptane 1:1); Rt=5.14.

b) 4-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-one Similar to example 29b, 1.68 g of N-methoxy-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methylpropionamide and 4.3 ml of methylmagnesium bromide (1N solution in tetrahydrofuran) are used to afford the title compound as a colourless oil. Rf=0.23 (EtOAc-heptane 1:1); Rt=5.25.

c) N-Methoxy-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-propionamide According to general procedure D, 1.65 g of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propionic acid and 271 mg of N,O-dimethylhydroxylamine hydrochloride are used to afford the title compound as a beige oil. Rf=0.18 (EtOAc-heptane 2:1); Rt=5.09.

d) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfanyl)-piperidin-2-yl]-propionic acid Similar to procedure 74b, 1.629 g of 3-[(2S,4R,5R)-4-(4-methoxy-phenyl)-5-[4-(3-methoxy-propyl)-3,4-dihydro-2H-benzo[1,4]oxazin-ylmethoxy]-1-(toluene-4-sulfonyl)-piperidin-2-yl]-propionitrile (from example 81a) are used to afford the title compound as a brown oil. Rf=0.25 (EtOAc); Rt=4.85.

Example 126

6-[(3R,4R,6S)-6-(3(R,S)-Methoxy-butyl)-4-(4-methoxy-phenyl)-piperidin-3-yloxymethyl]-4-(3-methoxy-propyl)-3,4-dihydro-2H-benzo[1,4]oxazine (diastereomeric mixture)

According to general procedure A, 210 mg of 6-[(3R,4R,6S)-6-(3-methoxy-butyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine (diastereomeric mixture) are used to afford the title compound.

The starting materials are prepared as follows:

a) 6-[(3R,4R,6S)-6-(3-Methoxy-butyl)-4-(4-methoxy-phenyl)-1-(toluene-4-sulfonyl)-piperidin-3-yloxymethyl]4-(3-methoxy-propyl)-3,4-dihydro-2H-benzo[1,4]oxazine (diastereomeric mixture)

Similar to example 30a, 550 mg of 4-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol (diastereomeric mixture)_are used to afford the title compound as a yellow oil. Rf=0.30 (EtOAc-heptane 1:1); Rt=5.60.

b) 4-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol (diastereomeric mixture)

Similar to procedure 29a, 800 mg of 4-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-one and 3.0 ml of borane-tetrahydrofuran complex (1N in tetrahydrofuran) are used to afford the title compound as a yellow oil. Rf=0.22 (EtOAc-heptane 2:1); Rt=5.00.

c) 4-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-butan-2-one Similar to example 29b, 1.68 g of N-methoxy-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-propionamide in the presence of methyl magnesium bromide are used to afford the title compound after flash chromatography (SiO$_2$ 60 F) as a colourless oil. Rf=0.23 (EtOAc-heptane 1:1); Rt=5.25.

d) N-Methoxy-3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-propionamide According to general procedure D, 1.65 g of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propionic acid are reacted with N,O-dimethylhydroxylamine hydrochloride to afford the title compound as a grey oil. Rf=0.18 (EtOAc-heptane 5:1); Rt=5.09.

e) 3-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl] propionic acid Similar to example 19b, 1.62 g of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propionitrile (from example 83b) are used to afford the title compound as a brown oil. Rf=0.25 (EtOAc); Rt=4.85.

Example 127

3-{(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-yl}-2,2,N-trimethyl-propionamide According to general procedure A, 290 mg of 3-[(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2,N-trimethyl-propionamide are used to afford the title compound.

The starting materials are prepared as follows:

a) 3-[(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2,N-trimethyl-propionamide According to general procedure D, 250 mg of 3-[(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid are used to afford the title compound as a yellow oil. Rf=0.05 (EtOAc-heptane 1:1); Rt=5.10.

b) 3-[(2S,4R,5R)-4-[4-(3-Methoxy-propoxy)-phenyl]-5-[4-(3-methoxy-propyl)-4-dihydro-2H-benzo[1,4]oxazin-6-ylmethoxy]-1-(toluene-4-sulfonyl)-piperidin-2-yl]-2,2-dimethyl-propionic acid Similar to example 72b, 806 mg of 3-[(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid 3-methoxy-propyl ester are used to afford the title compound as a yellow oil. Rf=0.17 (EtOAc-heptane 1:1); Rt=5.25.

c) 3-[(2S,4R,5R)-4-[4-(3-Methoxy-propoxy)-phenyl-]5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid 3-methoxy-propyl ester To a stirred solution of 702 mg of 3-[(2S,4R,5R)-4-(4-hydroxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic-acid in 5 ml N,N-dimethylformamide is added 1.34 g of cesium carbonate and 890 mg of 3-methoxy-propyl chloride. The reaction mixture is heated to 50° C. overnight diluted with 1N hydrochloric acid and extracted with ethyl acetate. The combined organic phases are dried and concentrated under reduced pressure to afford the crude title compound. The residue is purified by flash chromatography (SiO₂ 60 F) to afford the title compound as a yellow oil. Rt=5.86.

d) 3-[(2S,4R,5R)-4-(4-Hydroxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid To a stirred solution of 1.1 g of 3-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid (from example 65b) in 10 ml N,N-dimethylformamide are added 1.35 g of sodium ethanethiolate and the reaction mixture is heated to 95° C. for 2 days. The reaction mixture is diluted with 1N hydrochloric acid solution and extracted with tert-butyl methyl ether. The organic phases are combined, dried and concentrated under reduced pressure to afford the crude title compound. The residue is purified by flash chromatography (SiO₂ 60 F) to afford the title compound as a colourless oil. Rf=0.10 (EtOAc-heptane 1:1); Rt=4.67.

Example 128

1-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-yl}-2-methyl-propan-2-ol According to general procedure A, 153 mg of 1-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol are used to afford the title compound.

The starting materials are prepared as follows:

a) 1-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol Similar to example 29b, 1.56 g of 1-[4-(4-methoxy-phenyl)-5-[(2S,4R,5R)-4-(3-methoxy-propyl)-3,4-dihydro-2H-benzo[1,4]oxazin-6-ylmethoxy]-1-(toluene-4-sulfonyl)-piperidin-2-yl]-propan-2-one are used to afford the title compound as a yellow oil. Rf=0.18 (EtOAc-heptane 1:1); Rt=5.14.

b) 1-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2-one Similar to example 104c, 3.2 g of 1-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2(R,S)-ol (diastereomeric mixture) are used to afford the title compound as a yellow oil. Rf=0.14 (EtOAc-heptane 1:1).

c) 1-[(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-propan-2(R,S)-ol (diastereomeric mixture)

Similar to example 29b, 4.0 g of [(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetaldehyde are used to afford the title compound as a yellow oil. Rf=0.53 (EtOAc-heptane 5:1); Rt=5.05.

d) [(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetaldehyde To a stirred solution of 8.30 g of (2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetonitrile in 80 ml of dichloromethane are added 18.7 ml of a solution of diisobutyl aluminium hydride (1.0M in dichloromethane) at −30° C. The reaction mixture is allowed to warm to −5° C. over a period of 5 hours and subsequently cooled again to −30° C. overnight. The reaction mixture is diluted with dichloromethane, quenched by the addition of 50 ml of 1N tartaric acid solution and 50 ml of 1N Rochelles salt solution. The mixture is filtered, concentrated under reduced pressure and the residue is purified by flash chromatography (SiO₂ 60 F) to afford the title compound as a brown oil. Rf=0.29 (EtOAc-heptane 1:1); Rt=5.14.

e) [(2S,4R,5R)-4-(4-Methoxy-phenyl)-5-[4-(3-methoxy-propyl)-3,4-dihydro-2H-benzo[1,4]oxazin-6-ylmethoxy]-1-(toluol-4-sulfonyl)-piperidin-2-yl]-acetonitril Similar to example 19c, 0.5 g of methanesulfonic acid (2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl ester (from example 25 h) are used to afford the title compound. Rf=0.26 (EtOAc-heptane 1:1); Rt=5.20.

Example 129

6-[(3R,4R,6S)-6-[2-(2-Methoxy-ethoxy)-2-methyl-propyl]-4-(4-methoxy-phenyl)-piperidin-3-yloxymethyl]-4-(3-methoxy-propyl)-3,4-dihydro-2H-benzo[1,4]oxazine According to general procedure A, 100 mg of 6-[(3R,4R,6S)-6-[2-(2-methoxy-ethoxy)-2-methyl-propyl]-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6S)-6-[2-(2-Methoxy-ethoxy)-2-methyl-propyl]-4-(4-methoxy-phenyl)-1-(toluene-4-sulfonyl)-piperidin-3-yloxymethyl]-4-(3-methoxy-propyl)-3,4-dihydro-2H-benzo[1,4]oxazine Similar to example 30a, 350 mg of 1-[(3R,4R,6S)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol (from example 128a) and 774 mg of 2-chloroethylmethyl ether are used to afford the title compound as a yellow oil. Rf=0.26 (EtOAc-heptane 1:1); Rt=5.69.

Example 130

Dimethyl-carbamic acid 2-{(2S,4R,5R)-4-(4-methoxy-phenyl)-5-[4-(3-methoxy-propyl)-3,4-dihydro-2H-benzo[1,4]oxazin-6-ylmethoxy]-piperidin-2-yl}-1,1-dimethyl-ethyl ester According to general procedure A, 100 mg of dimethyl-carbamic acid 2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethyl ester are used to afford the title compound.

The starting material is prepared as follows:

a) Dimethyl-carbamic acid 2-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethyl ester Similar to example 30a, 335 mg of 1-[(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol (from example 128a) and 0.5 g of N,N-dimethylcarbamoylchloride in the presence of 137 mg of potassium hydride are used to afford the title compound as a yellow oil. Rt=5.62.

Example 131

3-{(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-yl}-2,2,N-trimethyl-propionamide According to general procedure A, 6.60 g 3-[(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-toluene-4-sulfonyl)-piperidin-2-yl]-2,2,N-trimethyl-propionamide are used to afford the title compound.

The starting materials are prepared as follows:

a) 3-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2,N-trimethyl-propionamide According to general procedure D, 7.00 g 3-[(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid are used to afford the title compound as a yellow oil. Rf=0.13 (EtOAc-heptane 5:1); Rt=−4.85.

b) 3-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid According to the procedure described in example 65b-d, 11.92 g 6-[(3R,4R,6S)-6-bromomethyl-4-[4-(2-methoxy-ethoxymethyl)-phenyl]-1-(toluene-4-sulfonyl)-piperidin-3-yloxymethyl]-4-(3-methoxy-propyl)-3,4-dihydro-2H-benzo[1,4]oxazine are used to afford the title compound as a yellow oil. Rf=0.25 (EtOAc); Rt=5.01.

c) 6-[(3R,4R,6S)-6-Bromomethyl-4-[4-(2-methoxy-ethoxymethyl)-phenyl]-1-(toluene-4-sulfon-piperidin-3-yloxymethyl]-4-(3-methoxy-propyl)-3,4-dihydro-2H-benzo[1,4]oxazine According to example 65d, 13.81 g methanesulfonic acid (2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl ester are used to afford the title compound as a yellow oil. Rf=0.34 (EtOAc-heptane 2:1); Rt=5.55.

d) Methanesulfonic acid (2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl ester According to general procedure F, 14.34 g [(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-methanol are used to afford the title compound as a brown oil. Rf=0.22 (EtOAc-heptane 4:1); Rt=5.02.

e) [(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-methanol According to example 24b, 18.14 g 6-[(3R,4R,6S)-4-[4-(2-methoxy-ethoxymethyl)-phenyl]-1-(toluene-4-sulfonyl)-6-triisopropylsilanyloxymethyl-piperidin-3-yloxymethyl]-4-(3-methoxy-propyl)-3,4-dihydro-2H-benzo[1,4]oxazine are used to afford the title compound as a yellow oil. Rf=0.13 (EtOAc-heptane 3:1); Rt=4.76.

f) 6-[(3R,4R,6S)-4-[4-(2-Methoxy-ethoxymethyl)-phenyl]-1-(toluene-4-sulfonyl)-6-triisopropylsilanyloxymethyl-piperidin-3-yloxymethyl]-4-(3-methoxy-propyl)-3,4-dihydro-2H-benzo[1,4]oxazine According to example 57a, 25.83 g {4-[(2S,4R,5R)-5-[4-(3-methoxy-propyl)-3,4-dihydro-2H-benzo[1,4]oxazin-6-ylmethoxy]-1-(toluene-4-sulfonyl)-2-triisopropylsilanyloxymethyl-piperidin-4-yl]-phenyl}-methanol are used to afford the title compound as a yellow oil. Rf=0.31 (EtOAc-heptane 1:1); Rt=6.65.

g) {4-[(2S,4R,5R)-5-[4-(3-Methoxy-propyl)-3,4-dihydro-2H-benzo[1,4]oxazin-6-ylmethoxy]-1-(toluene-4-sulfonyl)-2-triisopropylsilanyloxymethyl-piperidinyl-4-yl]-phenyl}-methanol According to general procedure C, 30.35 g 4-[(2S,4R,5R)-5-[4-(3-methoxy-propyl)-3-oxo-3,4-dihydro-2H-benzo[1,4]oxazin-6-ylmethoxy]-1-(toluene-4-sulfonyl)-2-triisopropylsilanyloxymethyl-piperidin-4-yl]-benzoic acid are used to afford the title compound as a yellow oil. Rf=0.19 (EtOAc-heptane 1:1); Rt=6.03.

h) 4-[(2S,4R,5R)-5-[4-(3-Methoxy-propyl)-3-oxo-3,4-dihydro-2H-benzo[1,4]oxazin-6-ylmethoxy]-1-(toluene-4-sulfonyl)-2-triisopropylsilanyloxymethyl-piperidin-4-yl]-benzoic acid According to example 65b, 33.15 g 4-[(2S,4R,5R)-[(3-methoxy-propyl)-3-oxo-3,4-dihydro-2H-benzo[1,4]oxazin-6-ylmethoxy]-1-(toluene-4-sulfonyl)-2-triisopropylsilanyloxymethyl-piperidin-4-yl]-benzoic acid methyl aster are used to afford the title compound as a white foam. Rf=0.20 (EtOAc-heptane 1:1); Rt=6.30.

i) 4-[(2S,4R,5R)-5-[4-(3-Methoxy-propyl)-3-oxo-3,4-dihydro-2H-benzo[1,4]oxazin-6-ylmethoxy]-1-(toluene-4-sulfonyl)-2-triisopropylsilanyloxymethyl-piperidin-4-yl]-benzoic acid methyl ester According to example 24b (alternative b), 33.24 g 4-[(2S,4R,5R)-5-hydroxy-1-(toluene-4-sulfonyl)-2-triisopropylsilanyloxymethyl-piperidinyl-4-yl]-benzoic acid methyl ester are used to afford the title compound as a yellow oil. Rf=0.43 (EtOAc-heptane 1:1); Rt=6.79.

j) 4-[(2S,4R,5R)-5-Hydroxy-1-(toluene-4-sulfonyl)-2-triisopropylsilanyloxymethyl-piperidin-4-yl]-benzoic acid methyl ester According to example 24b (alternative c), 24.19 g 4-[(2S,4R,5R)-5-hydroxy-2-hydroxymethyl-1-(toluene-4-sulfonyl)-piperidin-4-yl]-benzoic acid methyl ester are used to afford the title compound as a yellow oil. Rf=0.45 (EtOAc-heptane 1:1); Rt=6.46.

k) 4-[(2S,4R,5R)-5-Hydroxy-2-hydroxymethyl-1-(toluene-4-sulfonyl)-piperidin-4-yl]-benzoic acid methyl ester To a solution of 6 g of trifluoro-methanesulfonic acid 4-[(2S,4R,5R)-5-hydroxy-2-hydroxymethyl-1-(toluene-4-sulfonyl)-piperidin-4-yl]-phenyl ester in 42 ml of N,N-dimethylformamide and 32 ml of methanol is added 3.1 ml of triethylamine, 245 mg of palladium(II)acetate and 454 mg of 1,3-bisdiphenylphosphinopropane. The reaction mixture is charged into an autoclave and subjected to a pressure of carbon monoxide of 70 bars and subsequently heated to 70° C. The reaction mixture is kept for 5 hours under those reaction conditions followed by concentrating the mixture under reduced pressure. The residue is purified by flash chromatography ($SiO_2$ 60 F) to afford the title compound as a dark yellow oil. Rf=0.38 (EtOAc-heptane 1:1); Rt=3.75.

l) Trifluoro-methanesulfonic acid 4-[(2S,4R,5R)-5-hydroxy-2-hydroxymethyl-1-(toluene-4-sulfonyl)-piperidin-4-yl]-phenyl ester To a solution of 29.39 g of (3R,4R,6S)-6-hydroxymethyl-4-(4-hydroxy-phenyl)-1-(toluene-4-sulfonyl)-piperidin-3-ol in 170 ml of Dichloromethane are added 29.23 g of N-phenyltrifluoromethane sulfonimide and 11.55 ml of triethylamine. The reaction mixture is stirred for 2 hours at room temperature, diluted with sodium bicarbonate solution and extracted with dichloro-methane. The organic phases are combined, dried and concentrated under reduced pressure. The residue is purified by flash chromatography ($SiO_2$ 60 F) to afford the title compound white solid. Rf=0.27 (EtOAc-heptane 1:1); Rt=4.46.

m) (3R,4R,6S)-6-Hydroxymethyl-4-(4-hydroxy-phenyl)-1-(toluene-4-sulfonyl)-piperidin-3-ol According to example 90b, 25 g (3R,4R,6S)-6-hydroxymethyl-4-(4-methoxy-phenyl)-1-(toluene-4-sulfonyl)-piperidin-3-ol (from example 24b-c) are used to afford the title compound as a white foam. Rf=0.20 (EtOAc-heptane 2:1); Rt=3.22.

According to the processes described in example 131, the following compounds are prepared in an analogous manner:

136 N-Ethyl-3-{(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-piperidin-2-yl}-2,2-dimethyl-propionamide using ethylamine instead of methylamine.

137 3-{(2S,4R,5R)-4-(4-Methoxymethyl-phenyl)-5-[4-(3-methoxy-propyl)-3,4-dihydro-2H-benzo[1,4]oxazin-6-ylmethoxy]-piperidin-2-yl}-2,2,N-trimethyl-propionamide using methyliodide instead of 1-bromo-2-methoxy-ethane.

138 N—((S)-2-Hydroxy-propyl)-3-{(2S,4R,5R)-4-(4-methoxymethyl-phenyl)-5-[4-(3-methoxy-propyl)-3,4-dihydro-2H-benzo[1,4]oxazin-6-ylmethoxy]-piperidin-2-yl}-2,2-dimethyl-propionamide using methyliodide instead of 1-bromo-2-methoxy-ethane and (S)-1-amino-propan-2-ol [2799-17-9] instead of methylamine.

139 N—((R)-2-Hydroxy-propyl)-3-{(2S,4R,5R)-4-(4-methoxymethyl-phenyl)-5-[4-(3-methoxy-propyl)-3,4-dihydro-2H-benzo[1,4]oxazin-6-ylmethoxy]-piperidin-2-yl}-2,2-dimethyl-propionamide using methyliodide instead of 1-bromo-2-methoxy-ethane and (R)-1-amino-propan-2-ol [2799-16-8] instead of methylamine.

140 N-(2-Methoxy-ethyl)-3-{(2S,4R,5R)-4-(4-methoxymethyl-phenyl)-5-[4-(3-methoxy-propyl)-3,4-dihydro-2H-benzo[1,4]oxazin-6-ylmethoxy]-piperidin-2-yl}-2,2-dimethyl-propionamide using methyliodide instead of 1-bromo-2-methoxy-ethane and 2-methoxy-ethylamine [199-87-3] instead of methylamine.

Example 134

(R)-1-{(2R,4R,5R)-4-(Methoxy-phenyl)-5-[4-methoxy-propyl)-3,4-dihydro-2H-benzo[1,4]oxazin-6-ylmethoxy]-piperidin-2-ylmethyl}-propyl)-carbamic acid methyl ester According to general procedure D, {(R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propyl}-carbamic acid methyl ester is used to afford the title compound.

The starting materials are prepared as follows:

a) {(R)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propyl}-carbamic acid methyl ester To a solution of 403 mg of (R)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propylamine in 4 ml of dichloromethane is added 0.4 ml of triethylamine and 0.145 ml of methylchloroformiate at room temperature. The reaction mixture is stirred for 3 hours, diluted with dichloromethane, washed with water and the organic phase is separated, dried and concentrated under reduced pressure to afford the crude material. The crude material is purified by flash chromatography (SiO₂ 60 F) to afford the title compound as yellow oil. Rf=0.47 (EtOAc-heptane 1:1); Rt=5.23.

b) (R)-1-[(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propylamine According to general procedure E, 1.7 g of 6-[(3R,4R,6R)-6-(R)-2-azido-butyl)-4-(4-methoxy-phenyl)-1-(toluene-4-sulfonyl)-piperidin-3-yloxymethyl]-4-(3-methoxy-propyl)-3,4-dihydro 2H-benzo[1,4]oxazine are hydrogenated to afford the title compound after flash chromatography (SiO₂ 60 F) as brown oil. Rf=0.14 (dichloromethane-methanol-25% ammonia conc. 200:10:1); Rt=4.52.

c) 6-[(3R,4R,6R)-6-(R)-2-Azido-butyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine To a solution of 2.55 g of methanesulfonic acid (S)-1-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-propyl ester (diastereomer 2) (from example 64c) in 5.0 ml N,N dimethylformamide is added 1.81 g of sodium azide and the mixture is heated to 80° C. overnight. The reaction mixture is diluted with water and extracted with tert-butyl methyl ether. The organic phase are combined and concentrated under reduced pressure to afford the crude title compound which is purified by flash chromatography (SiO₂ 60 F) to afford the title compound as yellow oil. Rf=0.14 (EtOAc-heptane 1:1); Rt=4.52.

Example 135

6-[(3R,4R,6S)-6-(2-Methoxy-2-methyl-propyl)-4-(4-methoxy-phenyl)-piperidin-3-yloxymethyl]-4-(3-methoxy-propyl)-3,4-dihydro-2H-benzo[1,4]oxazine According to general procedure A, 100 mg of 6-[(3R,4R,6S)-6-(2-methoxy-2-methyl-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine are used to afford the title compound.

The starting material is prepared as follows:

a) 6-[(3R,4R,6S)-6-(2-Methoxy-2-methyl-propyl)-4-(4-methoxy-phenyl)-1-(toluene-4-sulfonyl)-piperidin-3-yloxymethyl]-4-(3-methoxy-propyl)-3,4-dihydro-2H-benzo[1,4]oxazine To a solution of 60 mg of 1-[4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol (from example 128) in N,N-dimethylformamide is added 25 mg of sodium hydride and 0.2 ml of methyl iodide. The reaction mixture is stirred for 2 days at room temperature, acidified with 1 N hydrochloric acid and extracted with tert-butyl methyl ether. The organic phases are combined, dried and concentrated under reduced pressure. The residue is purified by flash chromatography (SiO$_2$ 60 F) to afford the title compound as yellow oil. Rf=0.21 (EtOAc-heptane 1:1); Rt=5.70.

Example 141

6-[(3R,4R,6R)-4-[4-(3-Methoxy-propoxy)-phenyl]-6-((R)-2-[1,2,4]triazol-1-yl-butyl)-piperidin-3-yloxymethyl]-4-(3-methoxy-propyl)-3,4-dihydro-2H-benzo[1,4]oxazine According to general procedure A 300 mg of 6-[(3R,4R,6R)-4-[4-(3-methoxy-propoxy)-phenyl]-1-(toluene-4-sulfonyl)-6-((R)-2-[1,2,4]triazol-1-yl-butyl)-piperidin-3-yloxymethyl]-4-(3-methoxy-propyl)-3,4-dihydro-2H-benzo[1,4]oxazine are used to afford the title compound.
The starting materials are prepared as follows:

a) 6-[(3R,4R,6R)-4-[4-(3-Methoxy-propoxy)-phenyl]-1-(toluene-4-sulfonyl)-6-((R)-2-[1,2,4]triazol-1-yl-butyl)-piperidin-3-yloxymethyl]-4-(3-methoxy-propyl)-3,4-dihydro-2H-benzo[1,4]oxazine Similar to example 127c 500 mg of 4-[(2R,4R,5R)-5-[4-(3-methoxy-propyl)-3,4-dihydro-2H-benzo[1,4]oxazin-6-ylmethoxy]-1-(toluene-4-sulfonyl)-2-((R)-2-[1,2,4]triazol-1-yl-butyl)-piperidin-4-yl]-phenol and 1-Bromo-2-methoxy-ethane are used to afford the title compound as yellow oil. Rf=0.19 (EtOAc-heptane 1:1); Rt=5.08.

b) 4-[(2R,4R,5R)-5-[4-(3-Methoxy-propyl)-3,4-dihydro-2H-benzo[1,4]oxazin-6-ylmethoxy]-1-(toluene-4-sulfonyl)-2-((R)-2-[1,2,4]triazol-1-yl-butyl)-piperidin-4-yl]-phenol Similar to example 90b, 1.8 g 6-[(3R,4R,6R)-4-(4-methoxy-phenyl)-1-(toluene-4-sulfonyl)-6-((R)-2-[1,2,4]triazol-1-yl-butyl)-piperidin-3-yloxymethyl]-4-(3-methoxy-propyl)-3,4-dihydro-2H-benzo[1,4]oxazine (from example 73a) are used to afford the title compound as yellow oil. Rf=0.21 (EtOAc-heptane 1:1); Rt=4.34.

Example 142

6-[(3R,4R,6R)-4-(4-Methoxymethyl-phenyl)-6-((R)-2-[1,2,4]triazol-1-yl-butyl)-piperidin-3-yloxymethyl]-4-(3-methoxy-propyl)-3,4-dihydro-2H-benzo[1,4]oxazine According to general procedure A, 6-[(3R,4R,6R)-4-(4-methoxymethyl-phenyl)-1-(toluene-4-sulfonyl)-6-((R)-2-[1,2,4]triazol-1-yl-butyl)-piperidin-3-yloxymethyl]-4-(3-methoxy-propyl)-3,4-dihydro-2H-benzo[1,4]oxazine is used to afford the title compound.
The starting materials are prepared as follows:

a) 6-[(3R,4R,6R)-4-(4-Methoxymethyl-phenyl)-1-(toluene-4-sulfonyl)-6-((R)-2-[1,2,4]triazol-1-yl-butyl)-piperidin-3-yloxymethyl]-4-(3-methoxy-propyl)-3,4-dihydro-2H-benzo[3,4]oxazine Similar to example 131c, {4-[(2R,4R,5R)-5-[4-(3-methoxy-propyl)-3,4-dihydro-2H-benzo[1,4]oxazin-6-ylmethoxy]-1-(toluene-4-sulfonyl)-2-((R)-2-[1,2,4]triazol-1-yl-butyl)-piperidin-4-yl]-phenyl}-methanol and methyliodide are used to afford the title compound which is identified based on its Rf value.

b) {4-[(2R,4R,5R)-5-[4-(3-Methoxy-propyl)-3,4-dihydro-2H-benzo[1,4]oxazin-6-ylmethoxy]-1-(toluene-4-sulfonyl)-2-((R)-2-[1,2,4]triazol-1-yl-butyl)-piperidin-4-yl]-phenyl}-methanol According to the procedure described in example 131d-g, 4-[(2R,4R,5R)-5-[4-(3-methoxy-propyl)-3,4-dihydro-2H-benzo[1,4]oxazin-6-ylmethoxy]-1-(toluene-4-sulfonyl)-2-((R)-2-[1,2,4]triazol-1-yl-butyl)-piperidin-4-yl]-phenol (from example 141b) is used to afford the title compound which is identified based on its Rf value.

According to the processes described in example 142, the following compound is prepared in an analogous manner:

143 6-[(3R,4R,6R)-4-[4-(2-Methoxy-ethoxymethyl)-phenyl]-6-((R)-2-[1,2,4]triazol-1-yl-butyl)-piperidin-3-yloxymethyl]-4-(3-methoxy-propyl)-3,4-dihydro-2H-benzo[1,4]oxazine using 1-bromo-2-methoxy-ethane instead of methyliodide.

Example 145

Dimethyl-carbamic acid 2-{(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-piperidin-2-yl}-1,1-dimethyl-ethyl ester According to general procedure A, 0.44 g dimethyl-carbamic acid 2-[(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethyl ester are used to afford the title compound.
The starting materials are prepared as follows:

a) Dimethyl-carbamic acid 2-[(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-1,1-dimethyl-ethyl ester According example 60a starting from 0.7 g 1-[(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol are used to afford the title compound as a yellow oil. Rf=0.28 (EtOAc-heptane 1:1); Rt=5.70.

b) 1-[(2R,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2-methyl-propan-2-ol According example 51a, 1.05 g [(2R,4R,5R)-4-[4-(3-methoxy-propoxy)-phenyl]-5-[4-(3 methoxy-propyl)-3,4-dihydro-2H-benzo[1,4]oxazin-6-ylmethoxy]-1-(toluene-4-sulfonyl)-piperidin-2-yl]-acetic acid 3-methoxy-propyl ester are used to afford the title compound as a colorless oil. Rf=0.22 (EtOAc-heptane 1:1); Rt=5.24.

c) [(2R,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid 3-methoxy-propyl ester According to the procedure described in example 90a-b (using 4 equivalents of cesium carbonate and 2.2 equivalents of 3-methoxypropylchloride), 1.17 [(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-acetic acid methyl ester (from example 51b) is used to afford the title compound as a yellow oil. Rt=5.46.

Example 146

(R)-2-{(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-ylmethyl}-N-methyl-butyramide According to the general procedure A, (R)-2-[(2R,4R,5R)-4-[4-(2-methoxy-ethoxymethyl)-phenyl]5-[4-(3-methoxy-propyl)-3,4-dihydro-2H-benzo[1,4]oxazin-6-ylmethoxy]-1-(toluene-4-sulfonyl)-piperidin-2-ylmethyl]-N-methyl-butyramide is used to afford the title compound, which is identified based on its Rf value.

The starting materials are prepared as follows:

a) (R)-2-[(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-N-methyl-butyramide and (S)-2-[(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-N-methyl-butyramide According to the general procedure D, 2-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-butyric acid (diastereomeric mixture) and methylamine (8M in ethanol) are used to afford the title compounds, which are identified based on their Rf values.

b) (R,S)-2-[(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-butyric acid (diastereomeric mixture)

According to example 19b, 2-[(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-butyronitrile (diastereomeric mixture) is used to afford the title compound, which is identified based on its Rf values.

c) 2-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-butyronitrile (diastereomeric mixture)

According to the procedure described in example 64b-e, N-methoxy-2-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide (diastereomeric mixture) is used to afford the title compound, which is identified based on its Rf values.

d) N-Methoxy-2-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide According to example 29c, [(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid is used to afford the title compound, which is identified based on its Rf value.

e) [(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid According to the procedure described in example 19b-c, methanesulfonic acid (2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl ester (from example 131d) is used to afford the title compound, which is identified based on its Rf value.

According to the processes described in example 146, the following compounds are prepared in an analogous manner:

151 (R)-2-{(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-ylmethyl}-N,N-dimethyl-butyramide using dimethylamine instead of methylamine.

152 (R)-2-{(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-ylmethyl}-butyramide instead of conditions from example 146a, conditions from example 6a are used.

158 (R)-2-{(2R,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-ylmethyl}-N-methyl-butyramide starting from [(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid (from example 156f)

168 (R)-2-{(2R,4R,5R)-4-(4-Methoxy-phenyl)-5-[4-(3-methoxy-propyl)-3,4-dihydro-2H-benzo[1,4]oxazin-6-ylmethoxy]-piperidin-2-ylmethyl}-N-methyl-butyramide starting from N-Methoxy-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide (from example 29c).

Example 147

3-{(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-yl}-2,2,N-trimethyl-propionamide According to general procedure A, 3-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2,N-trimethyl-propionamide is used to afford the title compound which is identified based on its Rf value.

The starting materials are prepared as follows:

a) 3-[(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2]-2,2,N-trimethyl-propionamide According to general procedure D, methylamine (8M in ethanol) and 3-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid are used to afford the title compound which is identified based on its Rf value.

b) 3-[(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid According to example 65b, 3-[(2R,4R,5R)-4-[4-(2-methoxy-ethoxyethyl)-phenyl]-5-[4-(3 methoxy-propyl)-3,4-dihydro-2H-benzo[1,4]oxazin-6-ylmethoxy]-1-(toluene-4-sulfonyl)-piperidin-2-yl]-2,2-dimethyl-propionic acid methyl ester is used to afford the title compound which is identified based on its Rf value.

c) 3-[(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-2,2-dimethyl-propionic acid methyl ester To a stirred solution of 0.157 mmol lithiumdiisopropylamide (0.5 M in THF) was added at −78° C. 0.150 mmol 3-[(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid methyl ester (dissolved in 0.3 ml THF). After stirring for 30 minutes 0.11 mmol methyliodide was added at −78° C. and the reaction mixture is allowed to warm to room temperature. This solution was then added again to a solution of 0.157 mmol lithiumdiisopropylamide (0.5 M in THF) at −78° C. and stirred for additional 30 minutes 0.11 mmol methyliodide was added at −78° C. and the reaction mixture is allowed to warm to room temperature. The reaction mixture is hydrolyzed with 0.5M HCl and extracted three times with tert-butyl methyl ether. The combined organic layers are washed with brine, dried with sodium sulfate and the solvent is removed under reduced pressure. The title compound is purified via flash chromatography (SiO$_2$ F60) and is identified based on its Rf value.

d) 3-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid methyl ester According to example 51b, 3-[(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid is used to afford the title compound which is identified based on its Rf value.

e) 3-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid According to the procedure described in example 19b-c, methanesulfonic acid 2-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethyl ester is used to afford the title compound which is identified based on its Rf value.

f) Methanesulfonic acid 2-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethyl ester According to general procedure F, 2-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethanol is used to afford the title compound which is identified based on its Rf value.

g) 2-[(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethanol According to general procedure C, [(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid (from example 146e) is used to afford the title compound which is identified based on its Rf value.

According to the processes described in example 147, the following compounds are prepared in an analogous manner.

148 3-{(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-yl}-2,2,N,N-tetramethyl-propionamide using dimethylamine instead of methylamine.

159 3-{(2R,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-yl}-2,2,N-trimethyl-propionamide starting from 3-[(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid (from example 156c)

160 3-{(2R,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-yl}-2,2,N,N-tetramethyl-propionamide starting from 3-[(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid (from example 156c) and using dimethylamine instead of methylamine.

Example 149

(S)-2-{(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-ylmethyl}-N-methyl-butyramide According to general procedure A, (S)-2-[(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-N-methyl-butyramide is used to afford the title compound.

The starting materials are prepared as follows:

a) (S)-2-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-N-methyl-butyramide and (R)-2-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-N-methyl-butyramide According to the general procedure D, 2-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-butyric acid (diastereomeric mixture) and methylamine (8M in ethanol) are used to afford the title compounds, which are identified based on their Rf values.

b) 2-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-butyric acid (diastereomeric mixture)

According to example 65b, 2-[(2S,4R,5R)-4-[4-(2-methoxy-ethoxymethyl)-phenyl]5-[4-(3 methoxy-propyl)-3,4-dihydro-2H-benzo[1,4]oxazin-6-ylmethoxy]-1-(toluene-4-sulfonyl)-piperidin-2-ylmethyl]-butyric acid methyl ester (diastereomeric mixture) is used to afford the title compound, which is identified based on its Rf values.

c) 2-[(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-butyric acid methyl ester (diastereomeric mixture)

According to example 65c (using methyl butyrate instead of methyl isobutyrate), 6-[(3R,4R,6S)-6-bromomethyl-4-[4-(2-methoxy-ethoxymethyl)-phenyl]-1-(toluene-4-sulfonyl)-piperidin-3-yloxymethyl]-4-(3-methoxy-propyl)-3,4-dihydro-2H-benzo[1,4]oxazine (from example 131c) is used to afford the title compound, which is identified based on its Rf values.

According to the processes described in example 149, the following compounds are prepared in an analogous manner:

155 (S)-2{(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-ylmethyl}-butyramide instead of conditions from example 149a, conditions from example 6a are used.

162 (S)-2-{(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-ylmethyl}-N-methyl-butyramide starting from 2-{(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-piperidin-2-ylmethyl}-butyric acid (diastereomeric mixture).

The starting materials are prepared as follows:

a) 2-{(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-piperidin-2-ylmethyl}butyric acid (diastereomeric mixture)

According to example 65b, 2-{(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-piperidin-2-ylmethyl}-butyric acid 3-methoxy-propyl ester (diastereomeric mixture) is used to afford the title compound which is identified based on its RF values.

b) 2-{(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-ylmethyl}-butyric acid 3-methoxy-propyl ester (diastereomeric mixture)

According to the procedure described in example 90a-b (using 4 equivalents of cesium carbonate and 2.2 equivalents of 3-methoxypropylchloride), 2{(2S,4R,5R)-4-(4-methoxy-phenyl)-5-[4-(3-methoxy-propyl)-3,4-dihydro-2H-benzo[1,4]oxazin-6-ylmethoxy]-piperidin-2-ylmethyl}-butyric acid methyl ester (diastereomeric mixture) is used to afford the title compound which is identified based on its Rf values.

c) 2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-ylmethyl}-butyric acid methyl ester (diastereomeric mixture)

According to example 65c, 6-[(3R,4R,6S)-6-bromomethyl-4-(4-methoxy-phenyl)-1-(toluene-4-sulfonyl)-piperidin-3-yloxymethyl]-4-(3-methoxy-propyl)-3,4-dihydro-2H-benzo[1,4]oxazine (from example 65d) and methyl butyrate are used to afford the title compound which is identified based on its Rf values.

166 (S)-2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-ylmethyl}-N-methyl-butyramide starting from 6-[(3R,4R,6S)-6-bromomethyl-4-(4-methoxy-phenyl)-1-(toluene-4-sulfonyl)-piperidin-3-yloxymethyl]-4-(3-methoxy-propyl)-3,4-dihydro-2H-benzo[1,4]oxazine (from example 65d).

Example 150

(R)-2-{(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-ylmethyl}-N-methyl-butyramide According to general procedure A, (R)-2-[(2S,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-N-methyl-butyramide (from example 149a) is used to afford the title compound.

According to the processes described in example 150 and 149, the following compounds are prepared in an analogous manner:

153 (R)-2-{(2S,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-ylmethyl}-butyramide instead of conditions from example 159a, conditions from example 6a are used.

163 (R)-2-{(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-ylmethyl}-N-methyl-butyramide starting from 2-{(2S,4R,5R)-4-[4-(3-methoxy-propoxy)-phenyl]-5-[4-(3-methoxy-propyl)-3,4-dihydro 2H-benzo[1,4]oxazin-6-ylmethoxy]-piperidin-2-ylmethyl}-butyric acid (diastereomeric mixture) (from example 162a).

165 (R)-2-{(2S,4R,5R)-4-(4-Methoxy-phenyl)-5-[4-(3-methoxy-propyl)-3,4-dihydro-2H-benzo[1,4]oxazin-6-ylmethoxy]-piperidin-2-ylmethyl}-N-methyl-butyramide starting from 6-[(3R,4R,6S)-6-bromomethyl-4-(4-methoxy-phenyl)-1-(toluene-4-sulfonyl)-piperidin-3-yloxymethyl]-4-(3-methoxy-propyl)-3,4-dihydro-2H-benzo[1,4]oxazine (from example 65d).

Example 156

(S)-4-{(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-yl}-butan-2-ol According to general procedure A, (S)-4-[(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol is used to afford the title compound which is identified based on its Rf value.

The starting materials are prepared as follows:

a) (R)-4-[(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol and (S)-4-[(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-butan-2-ol According to general procedure C, 4-[(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-butan-2-one is used to afford the title compounds which are identified based on its Rf value.

b) 4-[(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-butan-2-one According to the procedure described in example 29b-c, 3-[(2S,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid is used to afford the title compound which is identified based on its Rf value.

c) 3-[(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-propionic acid According to the procedure described in example 19b-c, methanesulfonic acid 2-[(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethyl ester is used to afford the title compound which is identified based on its Rf value.

d) Methanesulfonic acid 2-[(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethyl ester According to general procedure F, 2-[(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethanol is used to afford the title compound which is identified based on its Rf value.

e) 2-[(2R,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-ethanol According to general procedure C, [(2R,4R,5R)-4-[4-(3-methoxy-propoxy)-phenyl]-5-[4-(3 methoxy-propyl)-3,4-dihydro-2H-benzo[1,4]oxazin-6-ylmethoxy]1-(toluene-4-sulfonyl)-piperidin-2-yl]-acetic acid is used to afford the title compound which is identified based on its Rf value.

f) [(2R,4R,5R)-4-[4-(3-Methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid According to example 65b, [(2R,4R,5R)-4-[4-(3-methoxy-propoxy)-phenyl]-5-[4-(3-methoxy-propyl)-3,4-dihydro-2H-benzo[1,4]oxazin-6-ylmethoxy]-1-(toluene-4-sulfonyl)-piperidin-2-yl]-acetic acid 3-methoxy-propyl ester (from example 145c) is used to afford the title compound which is identified based on its Rf value.

According to the processes described in example 156, the following compound is prepared in an analogous manner:

157 (R)-4-{(2S,4R,5R)-4-[4-(3-Methoxy-propoxy)-phenyl]-5-[4-(3-methoxy-propyl)-3,4-dihydro-2H-benzo[1,4]oxazin-6-ylmethoxy]-piperidin-2-yl}-butan-2-ol starting from (R)-4-[(2S,4R,5R)-4-[4-(3-methoxy-propoxy)-phenyl]-5-[4-(3-methoxy-propyl)-3,4-dihydro 2H-benzo[1,4]oxazin-6-ylmethoxy]-1-(toluene-4-sulfonyl)-piperidin-2-yl]-butan-2-ol (from example 156a).

Example 164

(S)-2-{(2R,4R,5R)-4-[4-(2-Methoxy-ethoxymethyl)-phenyl]-5-[4-(3-methoxy-propyl)-3,4-dihydro-2H-benzo[1,4]oxazin-6-ylmethoxy]-piperidin-2-ylmethyl}-N-methyl-butyramide According to the general procedure A, (S)-2-[(2R,4R,5R)-4-[4-(2-methoxy-ethoxymethyl)-phenyl]-5-[4-(3-methoxy-propyl)-3,4-dihydro-2H-benzo[1,4]oxazin-6-ylmethoxy]-1-(toluene-4-sulfonyl)-piperidin-2-ylmethyl]-N-methyl-butyramide (from example 146a) is used to afford the title compound, which is identified based on its Rf value.

According to the processes described in example 164 and 146, the following compound is prepared in an analogous manner:

167 (S)-2-{(2R,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl}-N-methyl-butyramide starting from N-Methoxy-2-[(2R,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-yl]-N-methyl-acetamide (from example 29c).

Example 169

6-[(3R,4R,6R)-4-(4-Methoxy-phenyl)-6-(tetrahydro-pyran-4-ylmethyl)-piperidin-3-yloxymethyl]-4-(3-methoxy-propyl)-3,4-dihydro-2H-benzo[1,4]oxazine According to general procedure A, 6-[(3R,4R,6R)-4-(4-methoxy-phenyl)-6-(tetrahydro-pyran-4-ylmethyl)-1-(toluene-4-sulfonyl)-piperidin-3-yloxymethyl]-4-(3-methoxy-propyl)-3,4-dihydro-2H-benzo[1,4]oxazine is used to afford the title compound.

The starting materials are prepared as follows:

a) 6-[(3R,4R,6R)-4-(4-Methoxy-phenyl)-6-(tetrahydro-pyran-4-ylmethyl)-1-(toluene-4-sulfonyl)-piperidin-3-yloxymethyl]-4-(3-methoxy-propyl)-3,4-dihydro-2H-benzo[1,4]oxazine According to general procedure E (using ethanol as solvent), 6-[(3R,4R,6S)-4-(4-methoxy-phenyl)-6-(tetrahydro-pyran-4-ylidenemethyl)-1-(toluene-4-sulfonyl)-piperidin-3-yloxymethyl]-4-(3-methoxy-propyl)-3,4-dihydro-2H-benzo[1,4]oxazine is used to afford the title compound, which is identified based on its Rf value.

b) 6-[(3R,4R,6S)-4-(4-Methoxy-phenyl)-6-(tetrahydro-pyran-4-ylidenemethyl)-1-(toluene-4-sulfonyl)-piperidin-3-yloxymethyl]-4-(3-methoxy-propyl)-3,4-dihydro-2H-benzo[1,4]oxazine A suspension of 2.3 mmol [(2S,4R,5R)-4-(4-methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-triphenyl-phosphonium bromide and 7.5 ml tetrahydrofuran at 0° C. is treated with 3.2 mmol n-butyl-lithium (1.6M in hexane). The reaction mixture is stirred at room temperature for 1 hour, and is then treated with a solution of tetrahydropyranone in 2.5 ml tetrahydrofuran. The reaction mixture is stirred at room temperature for 4 hours, then poured on 1M ammonium-chloride-solution and extracted with tert-butyl methyl ether. The combined organic phases are washed with brine, dried with sodium sulfate and concentrated under reduced pressure. The residue is purified by flash chromatography (SiO$_2$ 60 F) to afford the title compound, which is identified based on its Rf value.

c) [(2S,4R,5R)-4-(4-Methoxy-phenyl)-5-[4-(3-methoxy-propyl)-3,4-dihydro-2H-benzo[1,4]oxazin-6-ylmethoxy]-1-(toluene-4-sulfonyl)-piperidin-2-ylmethyl]-triphenyl-phosphonium bromide A solution of 3 mmol 6-[(3R,4R,6S)-6-bromomethyl-4-(4-methoxy-phenyl)-1-(toluene-4-sulfonyl)-piperidinyl-3-yloxymethyl]-4-(3-methoxy-propyl)-3,4-dihydro-2H-benzo[1,4]oxazine (from example 65d) in 5 ml acetonitrile is treated with 3.6 mmol triphenyl phosphine and stirred at 70° C. for 12 hours. The reaction mixture is cooled to room temperature, and the solid is filtered off to afford the title compound, which is identified based on its Rf value.

| Nr. | Structure | Appearance | R_f (System) | Rt (Procedure) |
| --- | --- | --- | --- | --- |
| 1 | 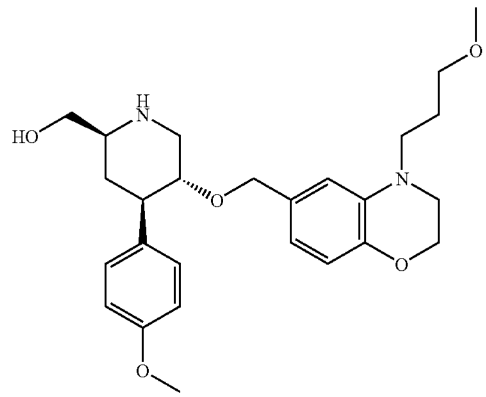 | colourless oil | 0.15 (A) | 3.00 |
| 2 | 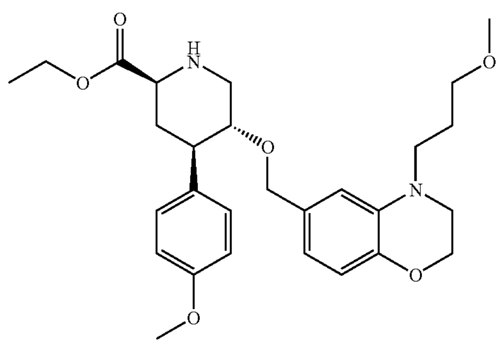 | yellow oil | 0.10 (B) | 3.80 |
| 3 | 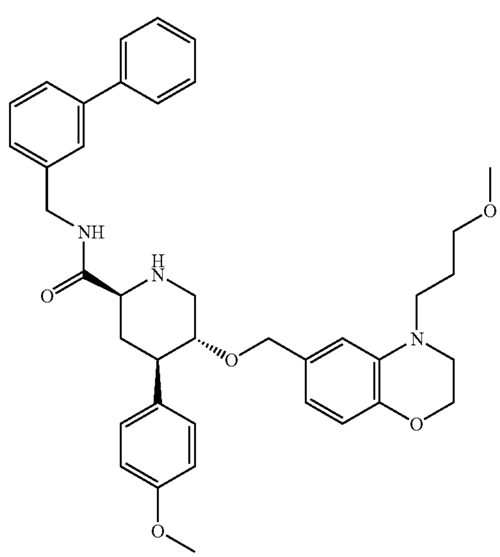 | colourless solid | 0.20 (C) | 4.47 |

-continued

| Nr. | Structure | Appearance | R_f(System) | Rt (Procedure) |
|---|---|---|---|---|
| 4 | 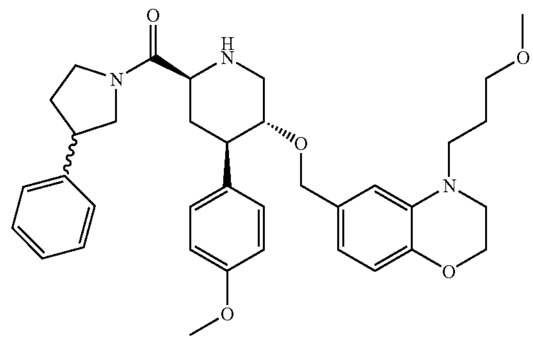 | colourless foam | 0.15 (C) | 4.27 |
| 5 | 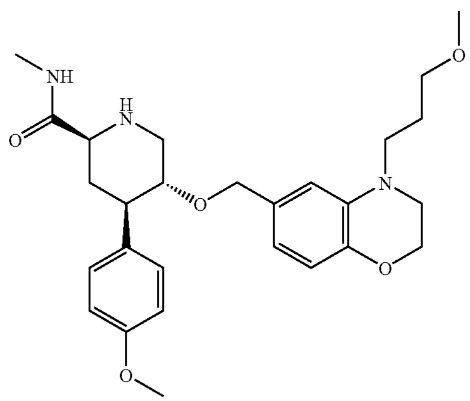 | yellow oil | 0.28 (D) | 3.39 |
| 6 | 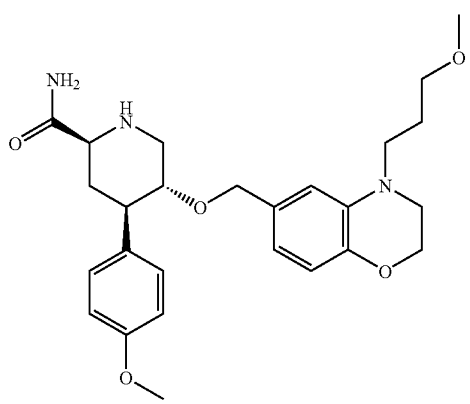 | yellow oil | 0.30 (D) | 3.31 |
| 7 | 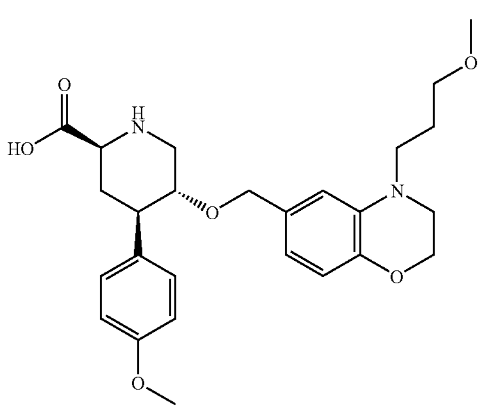 | white solid | 0.64 (E) | 3.44 |

-continued
| Nr. | Structure | Appearance | R$_f$(System) | Rt (Procedure) |
|---|---|---|---|---|
| 8 | 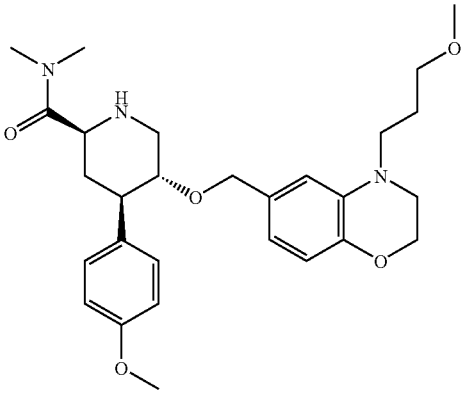 | yellow oil | 0.37 (D) | 3.52 |
| 9 | 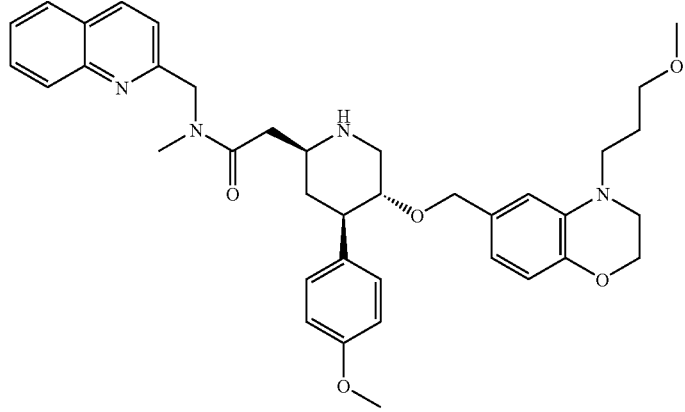 | yellow oil | 0.25 (A) | 3.57 |
| 10 | 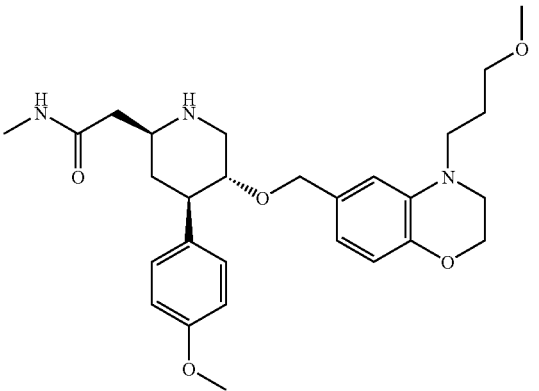 | yellow oil | 0.40 (D) | 3.38 |

-continued
| Nr. | Structure | Appearance | R_f (System) | Rt (Procedure) |
|---|---|---|---|---|
| 11 | 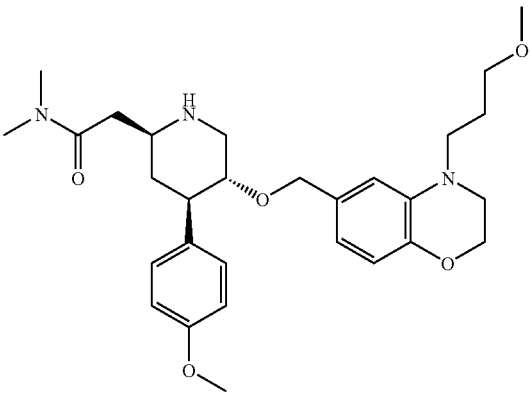 | orange oil | 0.30 (D) | 3.60 |
| 12 | 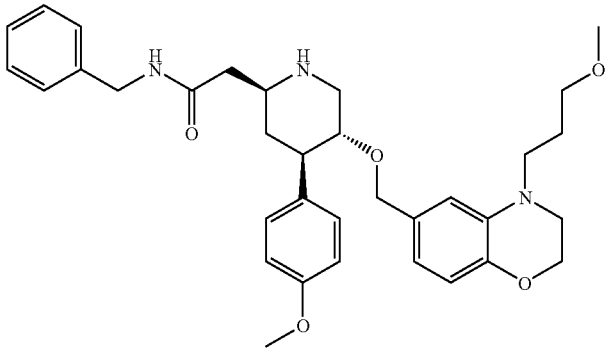 | brown oil | 0.25 (A) | 3.57 |
| 13 | 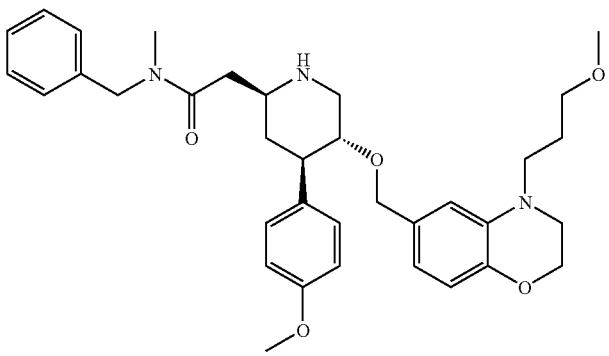 | brown oil | 0.33 (A) | 4.19 |
| 14 | 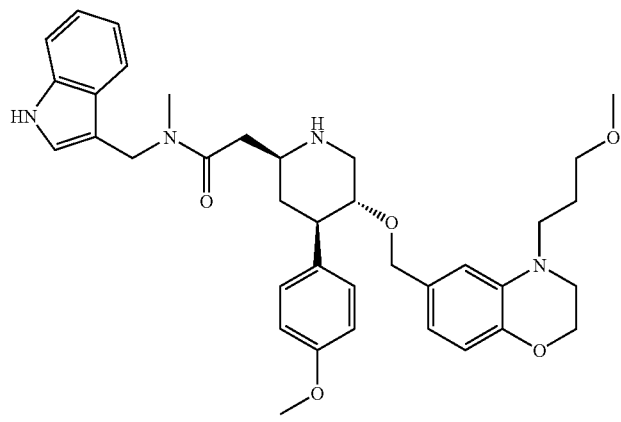 | yellow oil | 0.25 (A) | 4.16 |

-continued
| Nr. | Structure | Appearance | R_f(System) | Rt (Procedure) |
|---|---|---|---|---|
| 15 | 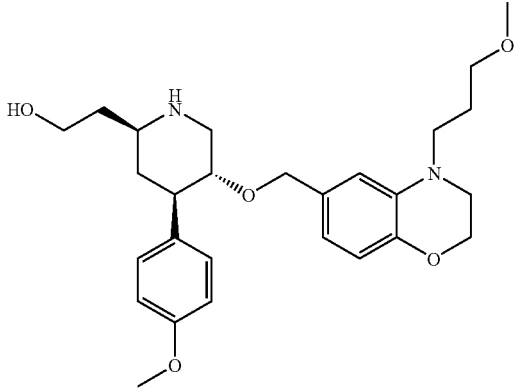 | colourless oil | 0.17 (A) | 3.44 |
| 16 | 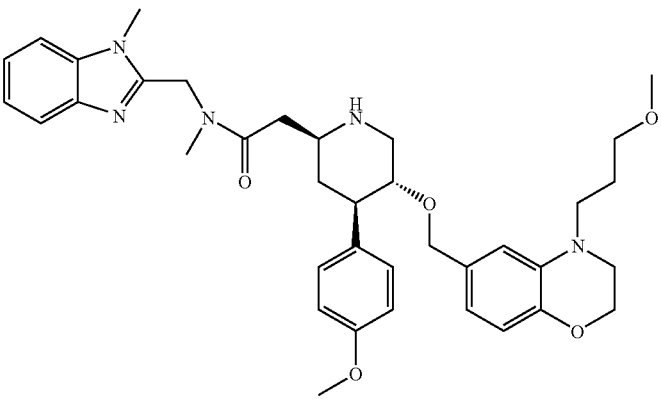 | yellow oil | 0.40 (D) | 3.47 |
| 17 | 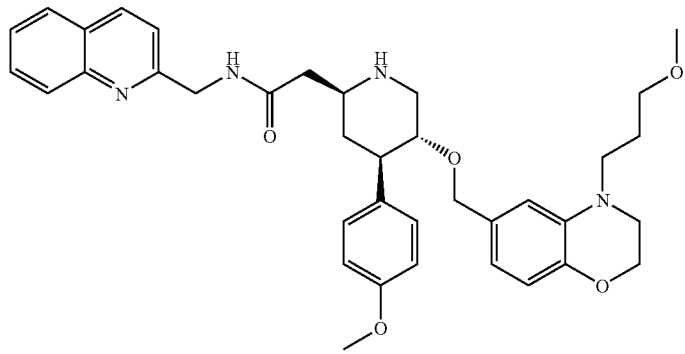 | yellow oil | 0.40 (D) | 3.43 |
| 18 | 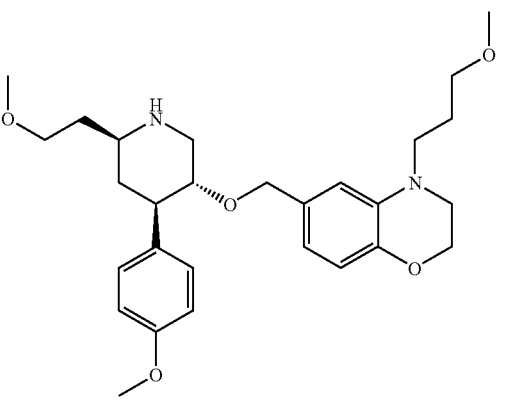 | colourless oil | 0.10 (A) | 3.74 |

-continued

| Nr. | Structure | Appearance | R_f (System) | Rt (Procedure) |
|---|---|---|---|---|
| 19 | 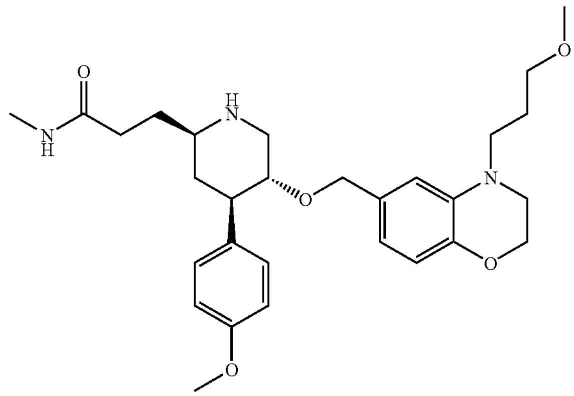 | yellow oil | 0.15 (D) | 3.39 |
| 20 | 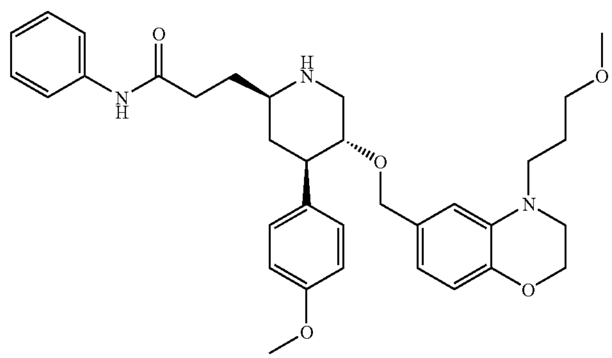 | dark oil | 0.30 (F) | 4.03 |
| 21 | 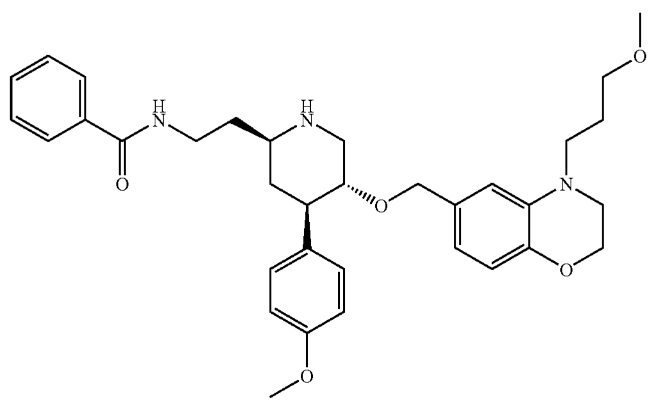 | colourless oil | 0.17 (A) | 3.98 |
| 22 | 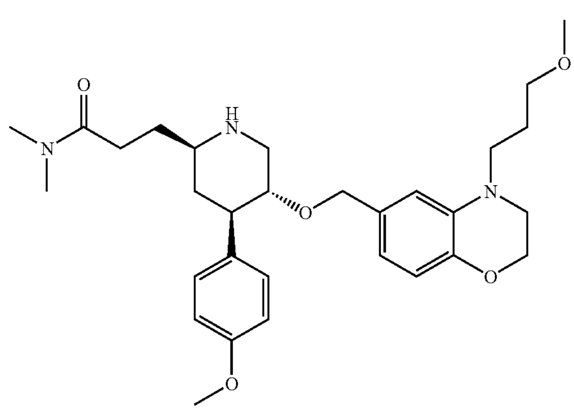 | yellow oil | 0.15 (D) | 3.39 |

-continued

| Nr. | Structure | Appearance | R$_f$(System) | Rt (Procedure) |
|---|---|---|---|---|
| 23 | 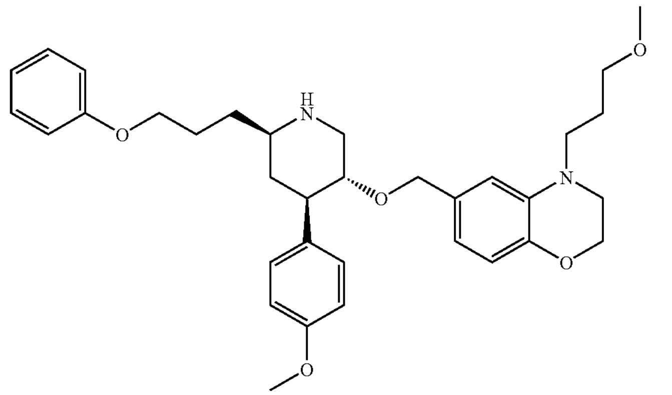 | yellow oil | 0.60 (D) | 4.41 |
| 24 | 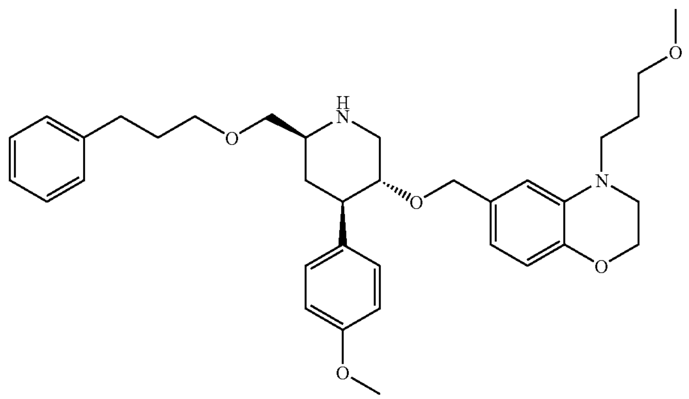 | yellow oil | 0.45 (G) | 4.66 |
| 25 | 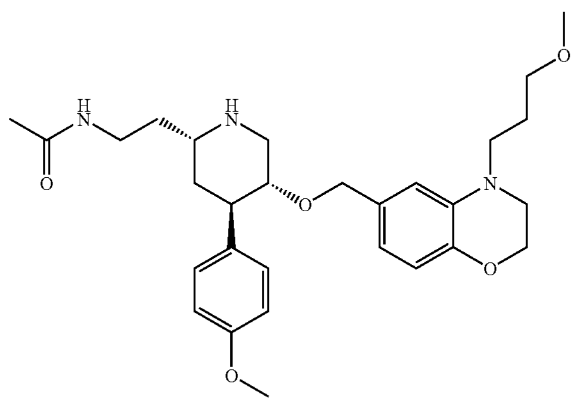 | yellow oil | 0.08 (H) | 3.54 |
| 26 | 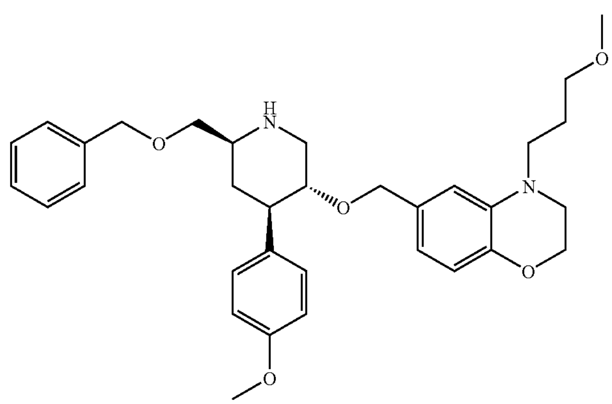 | yellow oil | 0.36 (G) | 4.33 |

-continued

| Nr. | Structure | Appearance | R_f (System) | Rt (Procedure) |
|---|---|---|---|---|
| 27 | 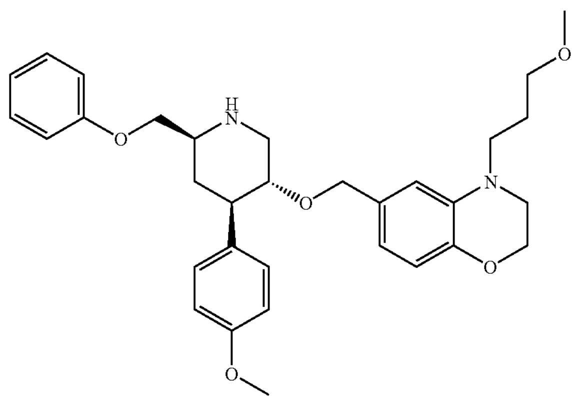 | colourless oil | 0.28 (B) | 4.25 |
| 28 | 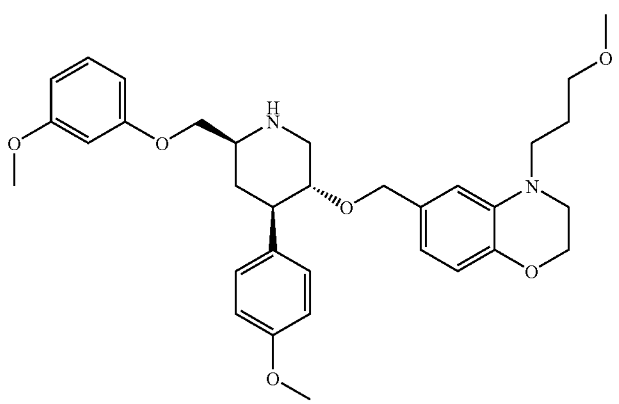 | colourless oil | 0.30 (B) | 4.27 |
| 29 | 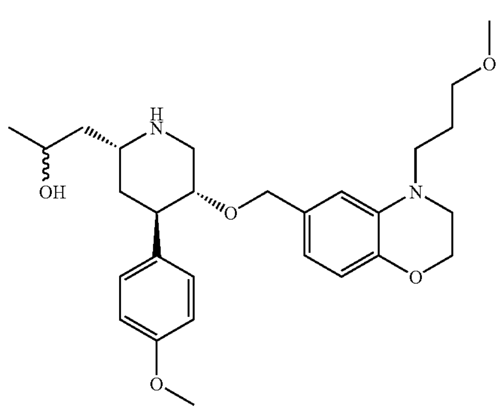 | yellow oil | 0.30 (A) | 3.68/ 3.74 |

-continued

| Nr. | Structure | Appearance | R$_f$(System) | Rt (Procedure) |
|---|---|---|---|---|
| 30 | 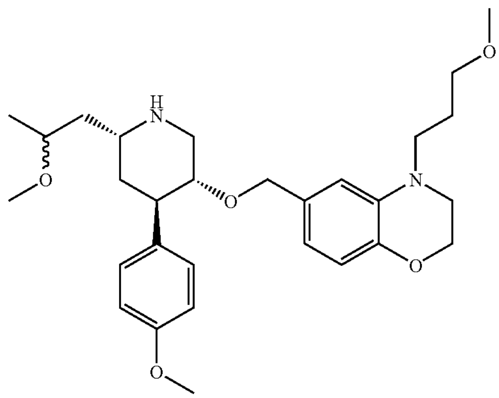 | yellow oil | 0.34 (A) | 4.15 |
| 31 | 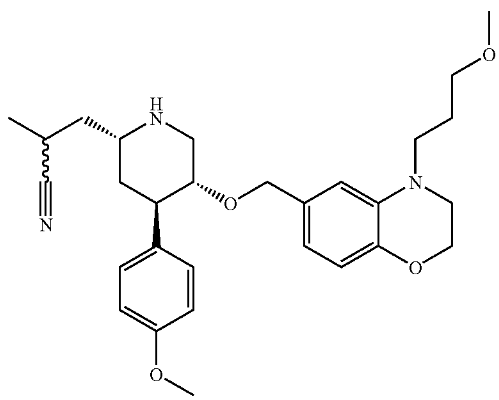 | green oil | 0.17 (F) | 3.98 |
| 32 | 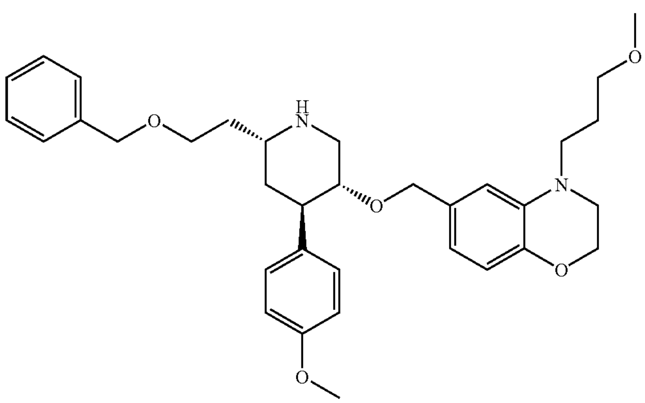 | yellow oil | 0.06 (B) | 4.56 |
| 33 | 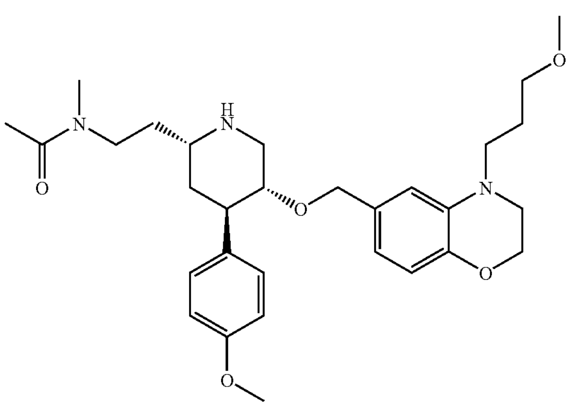 | yellow oil | 0.19 (F) | 3.74 |

-continued

| Nr. | Structure | Appearance | R_f (System) | Rt (Procedure) |
|---|---|---|---|---|
| 34 | 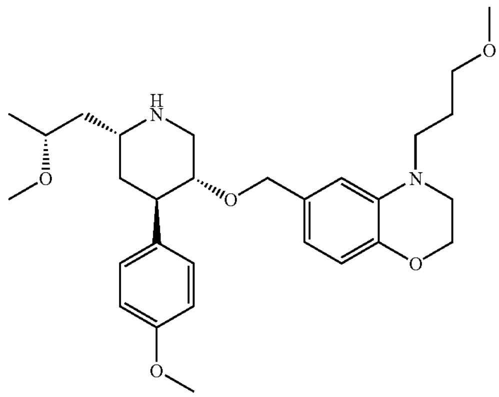 | colourless oil | 0.34 (A) | 4.31 |
| 35 | 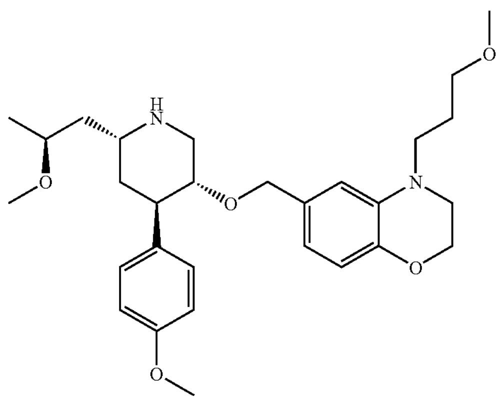 | colourless oil | 0.34 (A) | 4.31 |
| 36 | 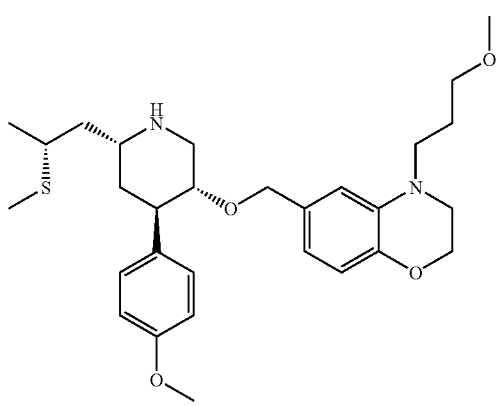 | red oil | 0.04 (C) | 4.43 |

-continued

| Nr. | Structure | Appearance | R$_f$(System) | Rt (Procedure) |
|---|---|---|---|---|
| 37 | 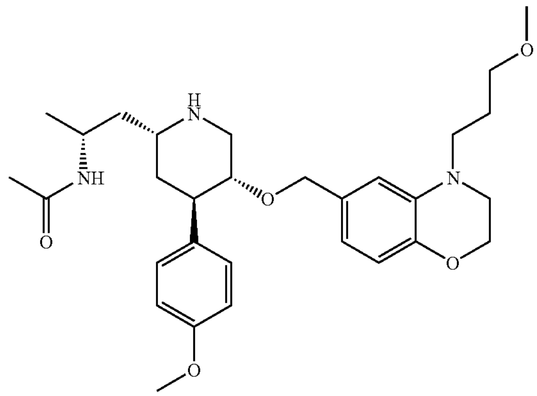 | colourless oil | 0.17 (A) | 3.92 |
| 38 | 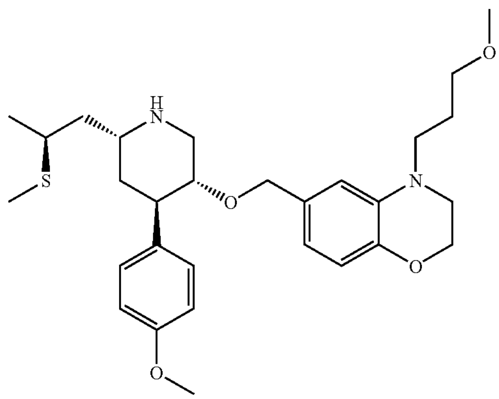 | yellow oil | 0.12 (D) | 4.45 |
| 39 | 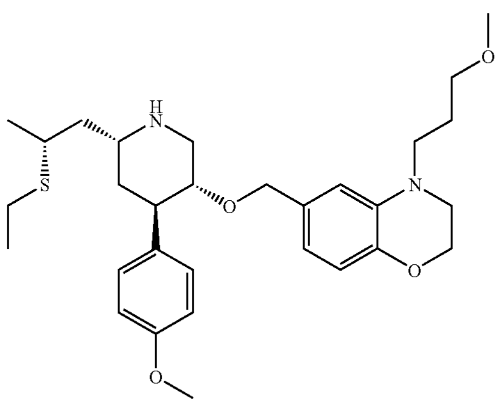 | yellow oil | 0.05 (I) | 4.61 |
| 40 | 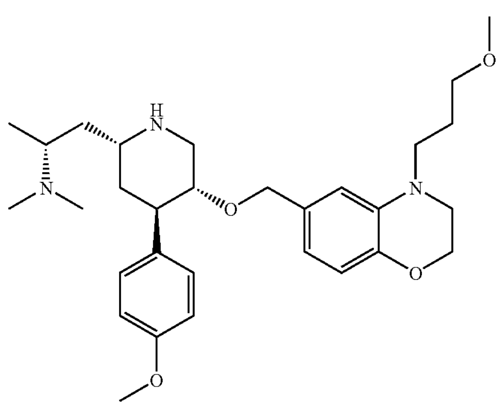 | red oil | 0.01 (B) | 3.21 |

-continued

| Nr. | Structure | Appearance | R$_f$(System) | Rt (Procedure) |
| --- | --- | --- | --- | --- |
| 41 | 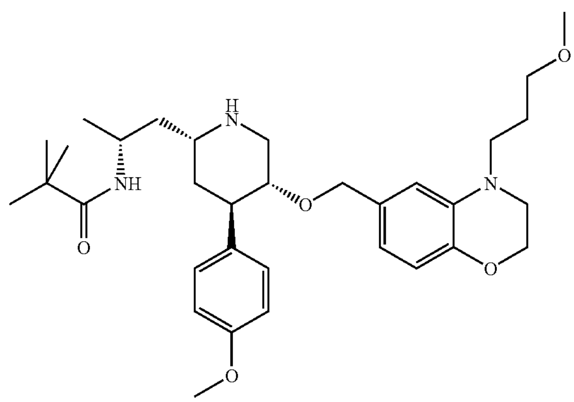 | yellow oil | 0.35 (F) | 4.32 |
| 42 | 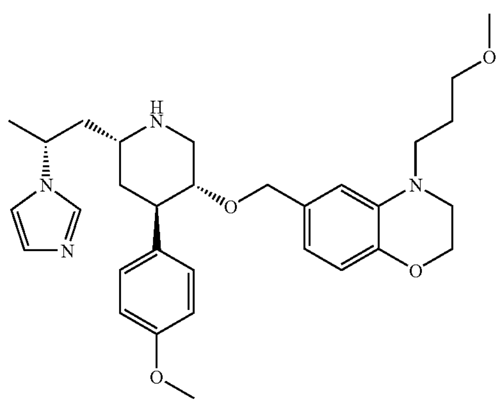 | colourless oil | 0.09 (A) | 3.23 |
| 43 | 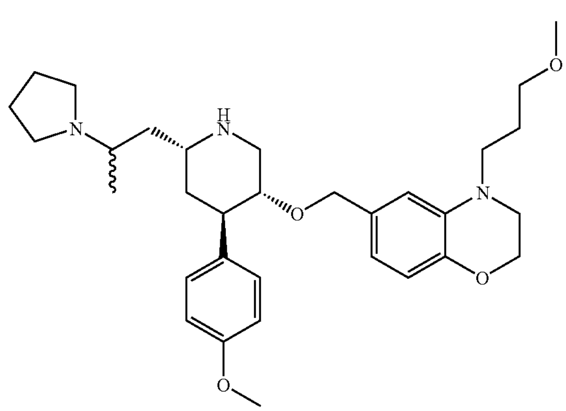 | colourless oil | 0.05 (J) | 3.36 |

-continued
| Nr. | Structure | Appearance | R*f*(System) | Rt (Procedure) |
|---|---|---|---|---|
| 44 | 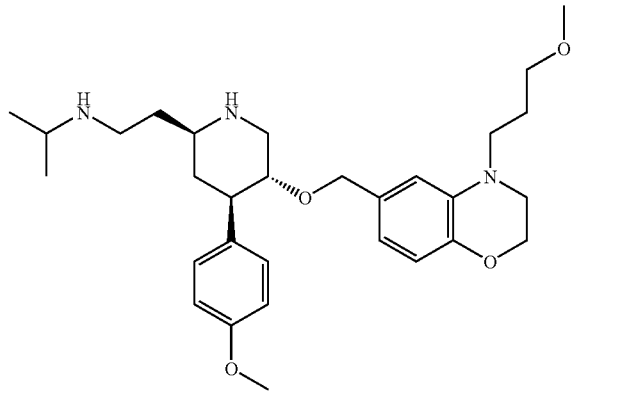 | colourless oil | 0.01 (C) | 3.31 |
| 45 | 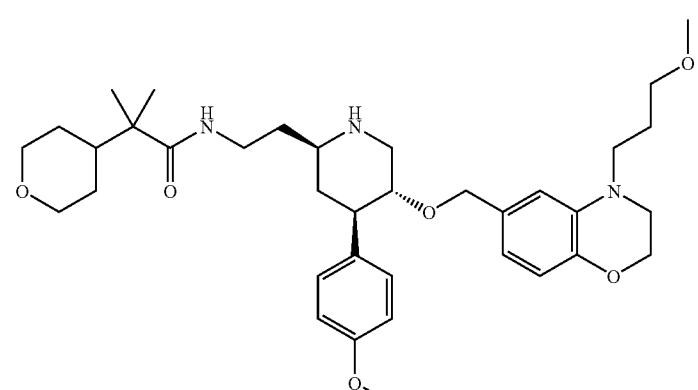 | yellow oil | 0.4 (D) | 3.87 |
| 46 | 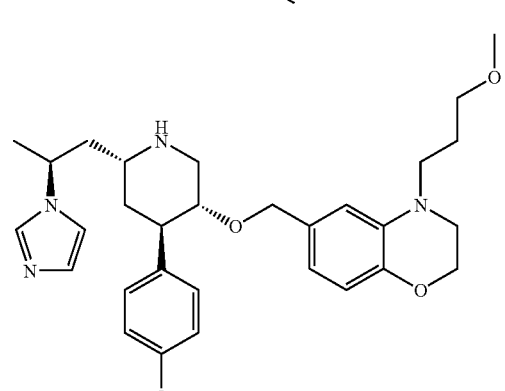 | yellow oil | 0.13 (K) | 3.32 |
| 47 | 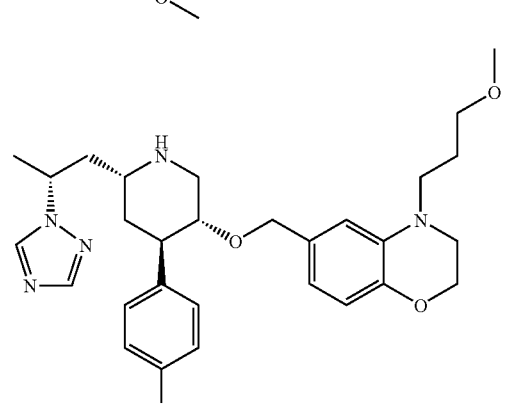 | colourless oil | 0.10 (K) | 3.57 |

-continued
| Nr. | Structure | Appearance | R$_f$(System) | Rt (Procedure) |
|---|---|---|---|---|
| 48 | 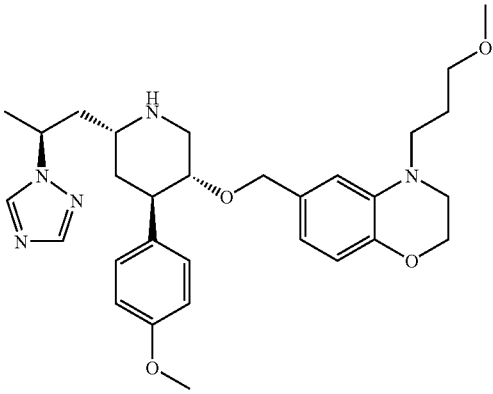 | colourless oil | 0.13 (K) | 3.63 |
| 49 | 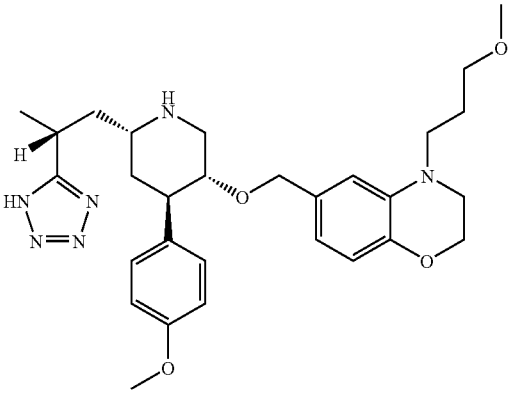 | yellow crystals | 0.10 (L) | 3.60 |
| 50 | 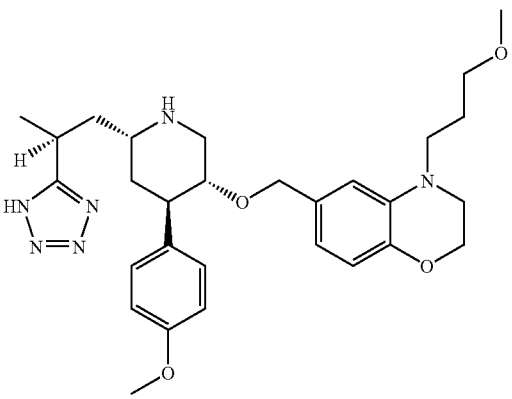 | yellow crystals | 0.10 (L) | 3.60 |

-continued

| Nr. | Structure | Appearance | R_f(System) | Rt (Procedure) |
|---|---|---|---|---|
| 51 | 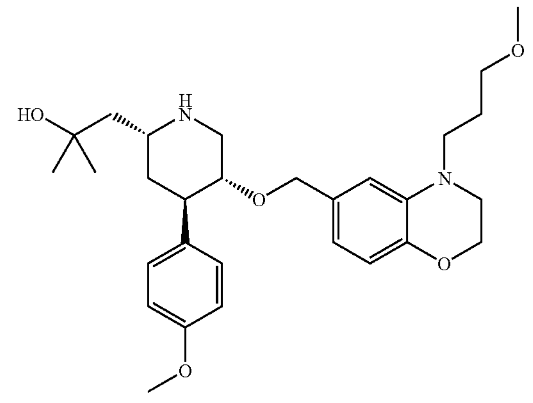 | yellow oil | 0.40 (D) | 3.96 |
| 52 | 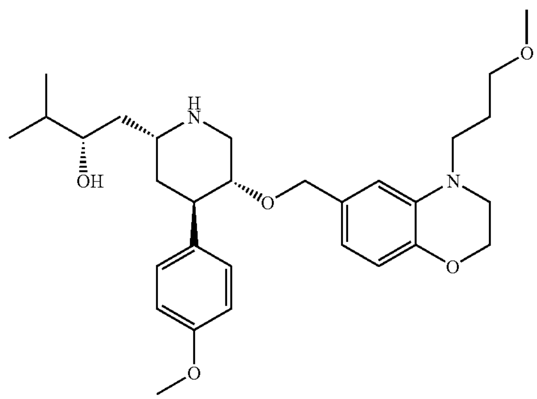 | dark yellow oil | 0.30 (M) | 4.05 |
| 53 | 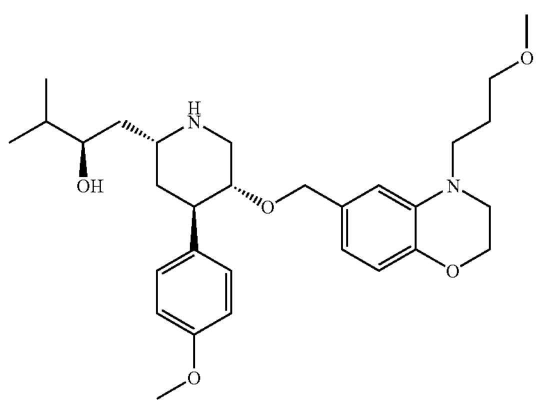 | colorless oil | 0.25 (A) | 4.16 |
| 54 | 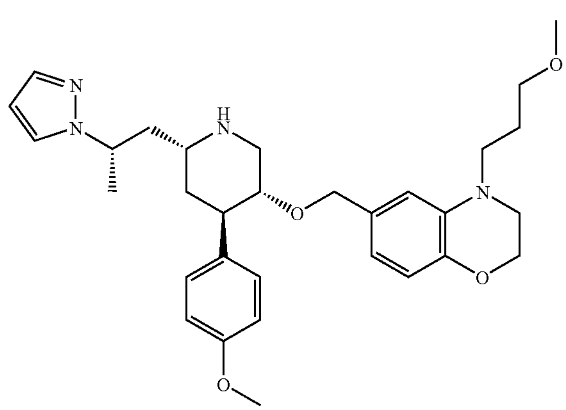 | yellow oil | 0.25 (A) | 3.92 |

-continued

| Nr. | Structure | Appearance | R_f (System) | Rt (Procedure) |
|---|---|---|---|---|
| 55 | 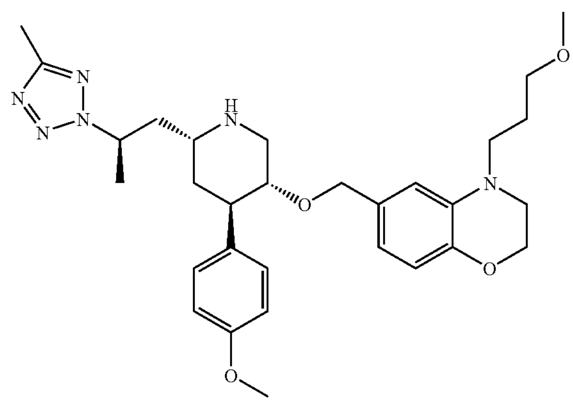 | yellow oil | 0.15 (A) | 3.72 |
| 56 | 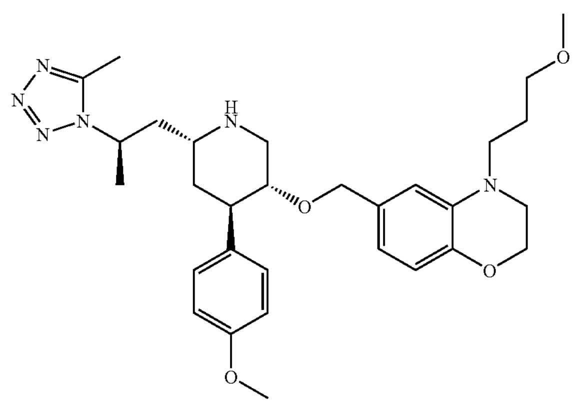 | yellow oil | 0.5 (M) | 3.93 |
| 57 | 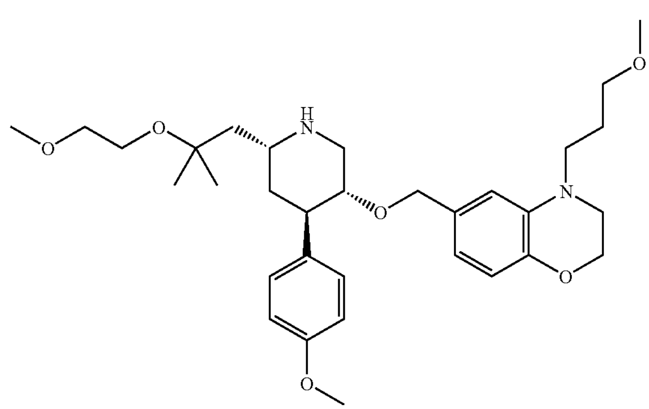 | yellow oil | 0.28 (D) | 4.56 |

-continued

| Nr. | Structure | Appearance | R_f (System) | Rt (Procedure) |
|---|---|---|---|---|
| 58 | 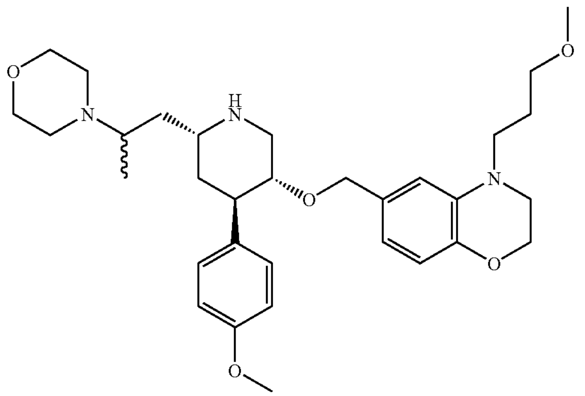 | yellow oil | 0.40 (M) | 3.34 |
| 59 | 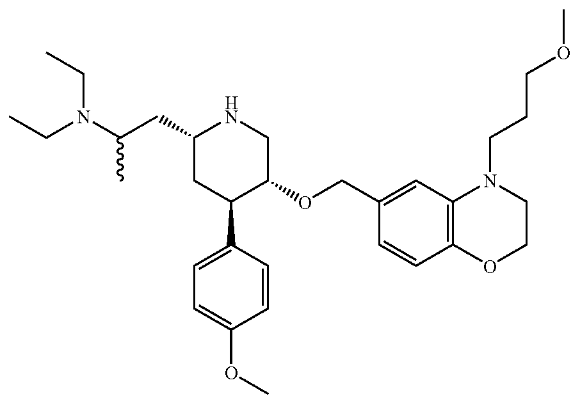 | yellow oil | 0.35 (N) | 3.43 |
| 60 | 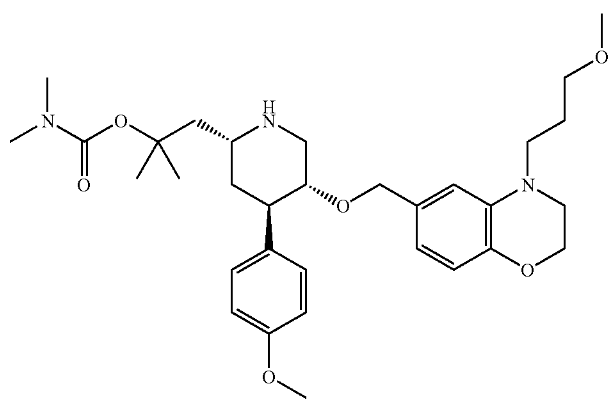 | yellow oil | 0.36 (D) | 4.27 |
| 61 | 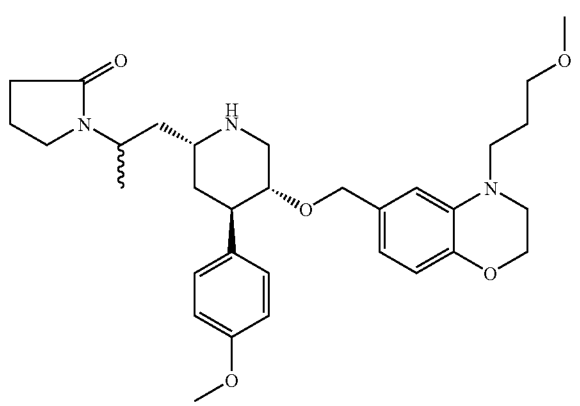 | yellow oil | 0.30 (M) | 3.90 |

-continued

| Nr. | Structure | Appearance | R_f (System) | Rt (Procedure) |
|---|---|---|---|---|
| 62 | 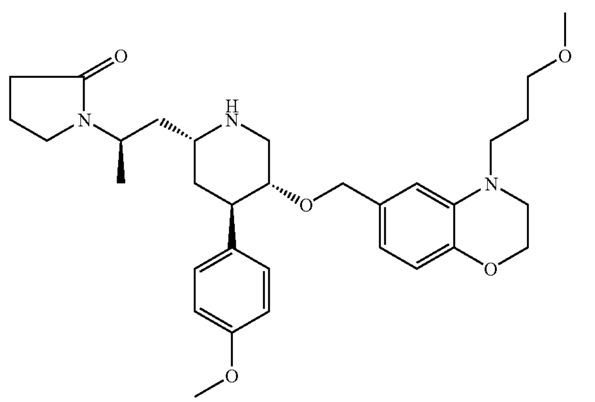 | yellow oil | 0.28 (M) | 3.67 |
| 63 | 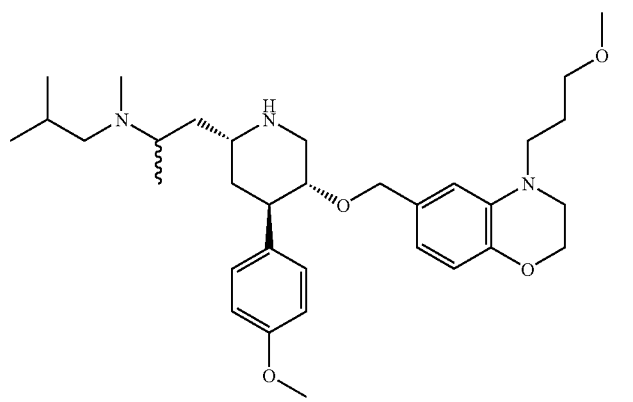 | yellow oil | 0.46 (M) | 3.59 |
| 64 | 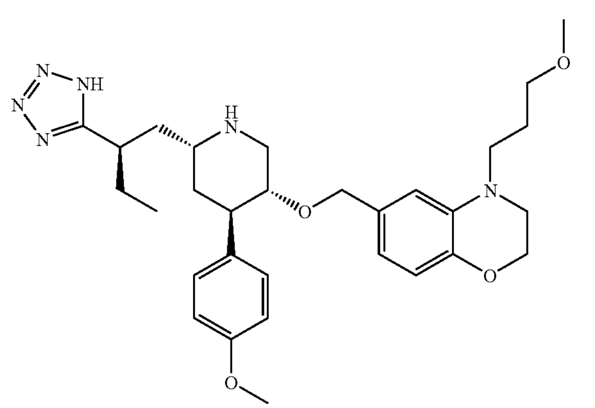 | yellow oil | 0.17 (M) | 3.67 |

-continued

| Nr. | Structure | Appearance | R_f (System) | Rt (Procedure) |
|---|---|---|---|---|
| 65 | 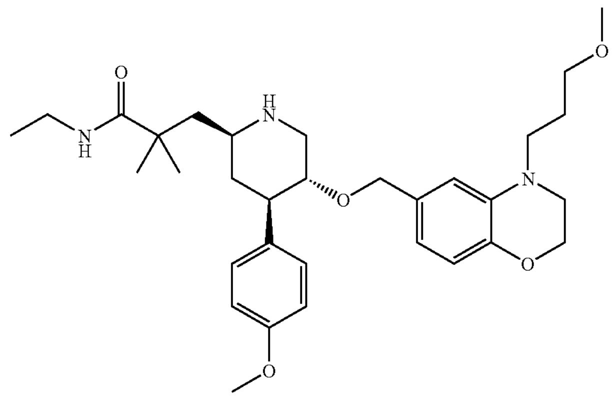 | colorless oil | 0.40 (D) | 3.92 |
| 66 | 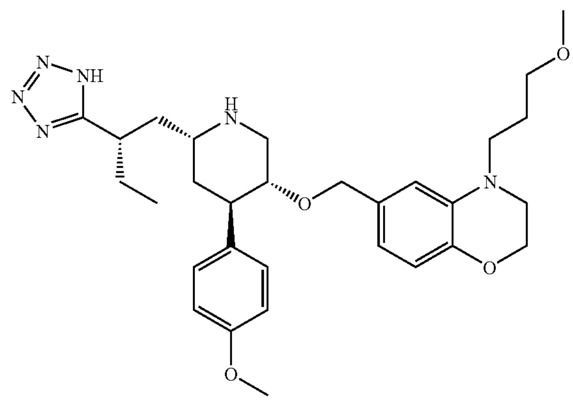 | yellow oil | 0.16 (M) | 3.74 |
| 67 | 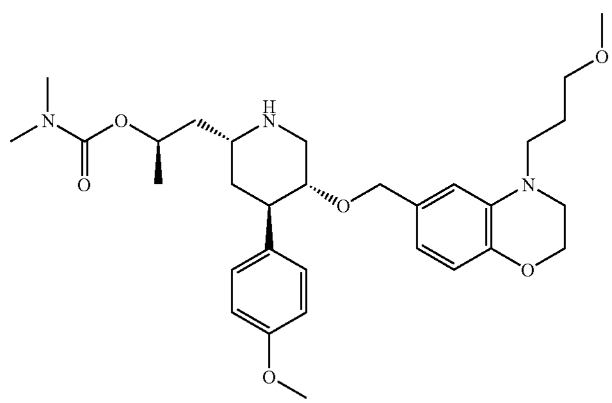 | colourless oil | 0.48 (D) | 4.25 |
| 68 | 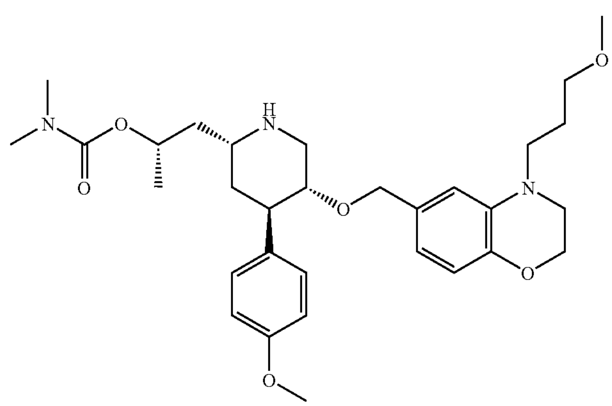 | colourless oil | 0.48 (D) | 4.08 |

-continued

| Nr. | Structure | Appearance | R$_f$(System) | Rt (Procedure) |
|---|---|---|---|---|
| 69 | 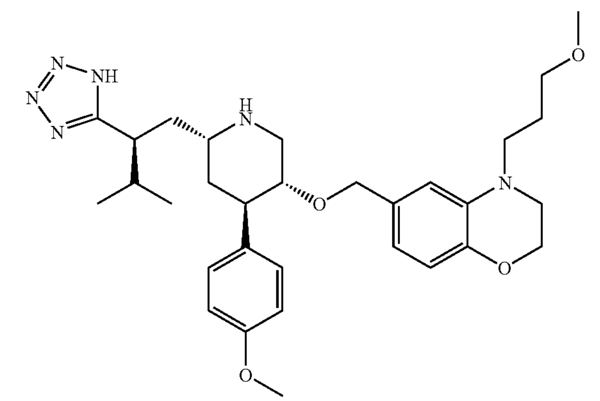 | colourless oil | 0.20 (O) | 3.78 |
| 70 | 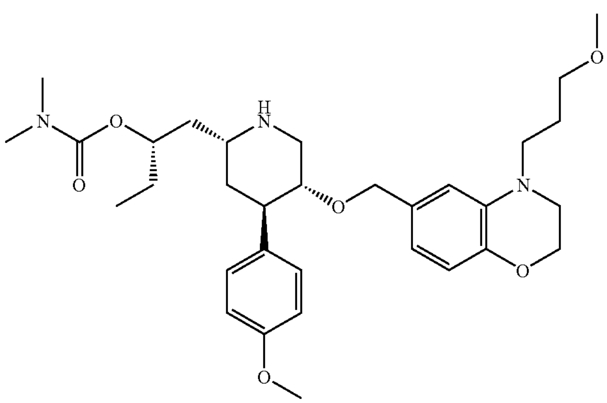 | yellow oil | 0.50 (D) | 4.16 |
| 71 | 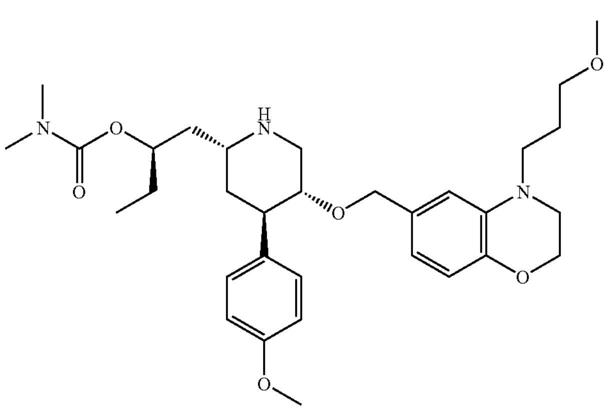 | yellow oil | 0.57 (D) | 4.34 |

-continued

| Nr. | Structure | Appearance | R_f(System) | Rt (Procedure) |
|---|---|---|---|---|
| 72 | 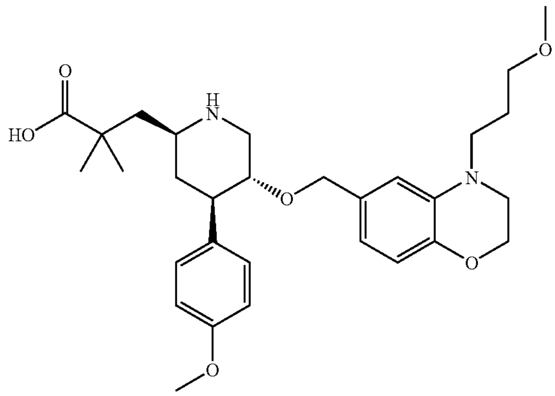 | brown oil | 0.21 (D) | 3.81 |
| 73 | 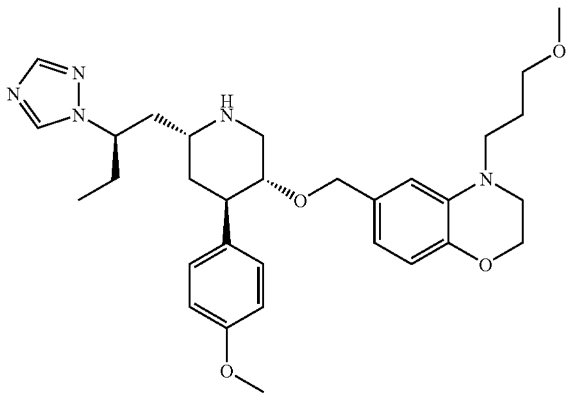 | colourless oil | 0.23 (A) | 3.72 |
| 74 | 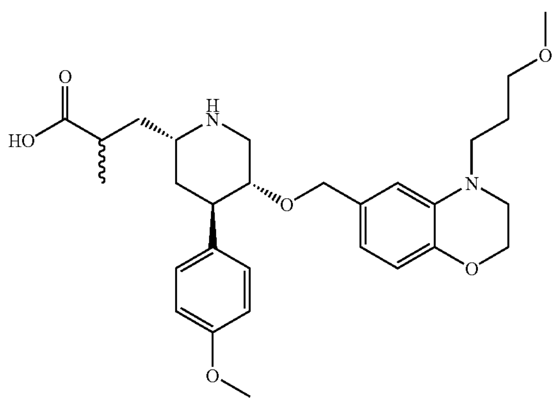 | brown oil | 0.07 (D) | 3.69 |
| 75 | 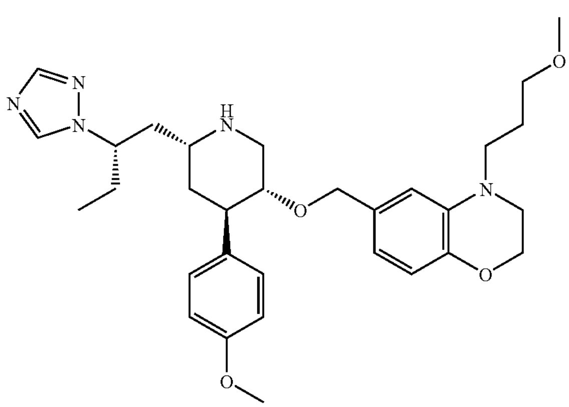 | colourless oil | 0.47 (M) | 3.78 |

-continued

| Nr. | Structure | Appearance | R_f(System) | Rt (Procedure) |
|---|---|---|---|---|
| 76 | 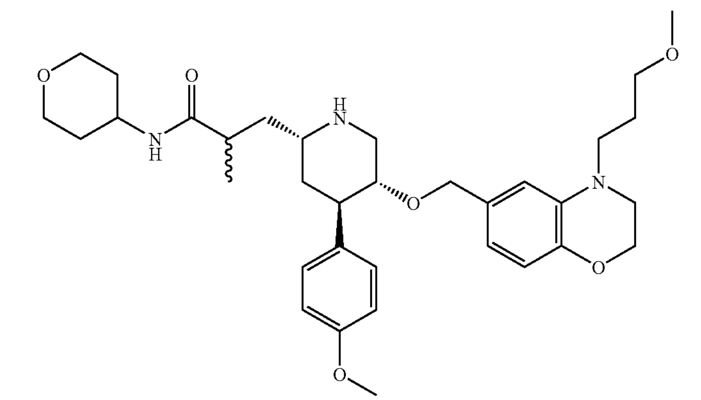 | yellow oil | 0.11 (D) | 3.63 |
| 77 | 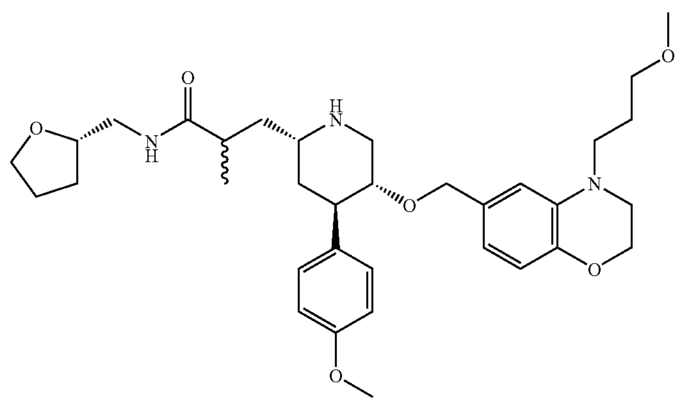 | yellow oil | 0.19 (D) | 3.78 |
| 78 | 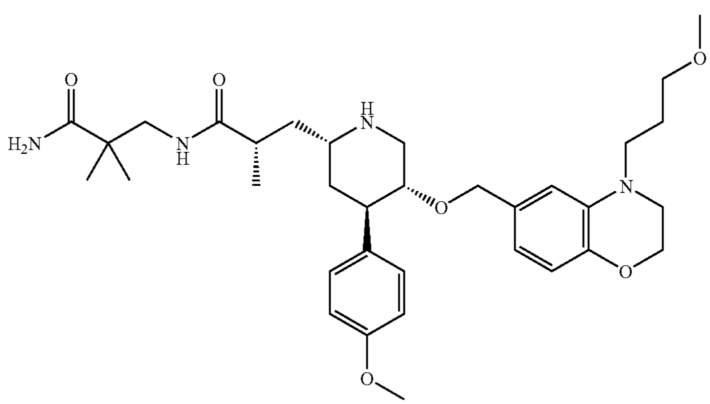 | yellow oil | 0.31 (D) | 3.53 |

-continued

| Nr. | Structure | Appearance | R_f(System) | Rt (Procedure) |
|---|---|---|---|---|
| 79 | 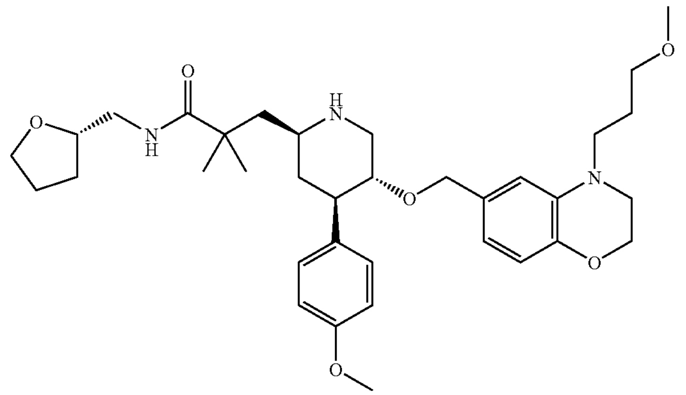 | colourless oil | 0.31 (P) | 4.05 |
| 80 | 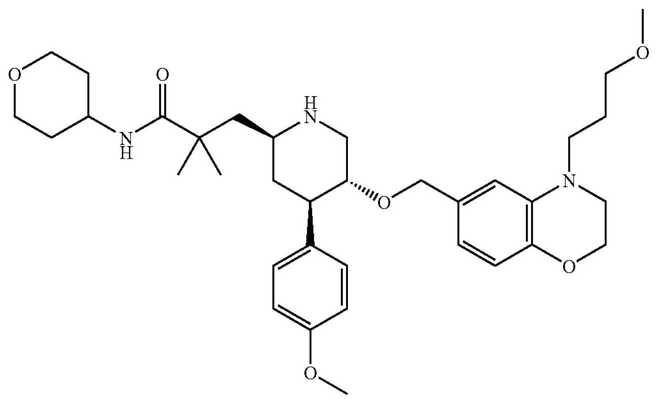 | white foam | 0.31 (P) | 3.89 |
| 81 | 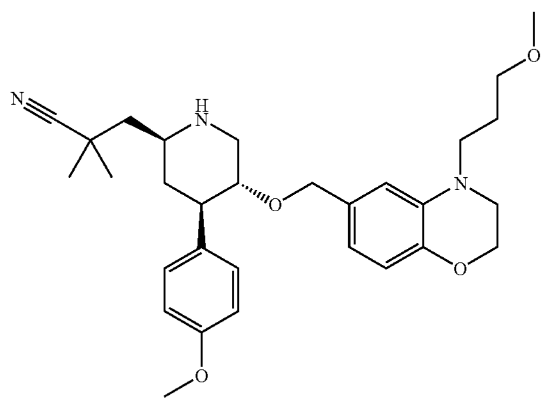 | white foam | 0.34 (D) | 3.98 |
| 82 | 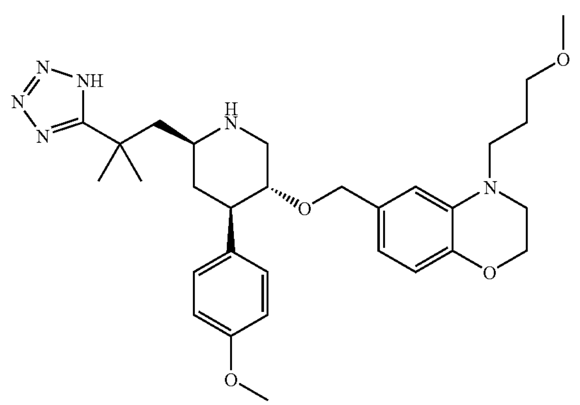 | yellow oil | 0.25 (O) | 3.75 |

| Nr. | Structure | Appearance | Rf (System) | Rt (Procedure) |
| --- | --- | --- | --- | --- |
| 83 | 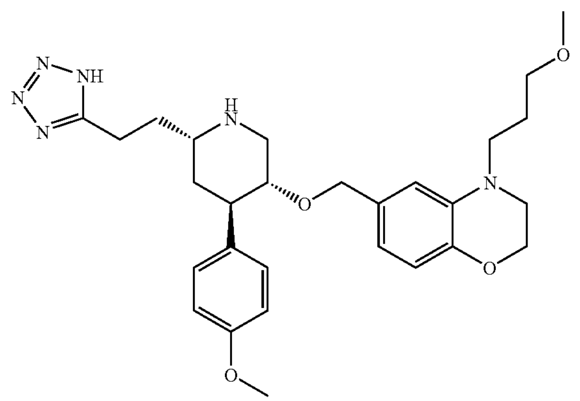 | brown oil | 0.25 (Q) | 3.54 |
| 84 | 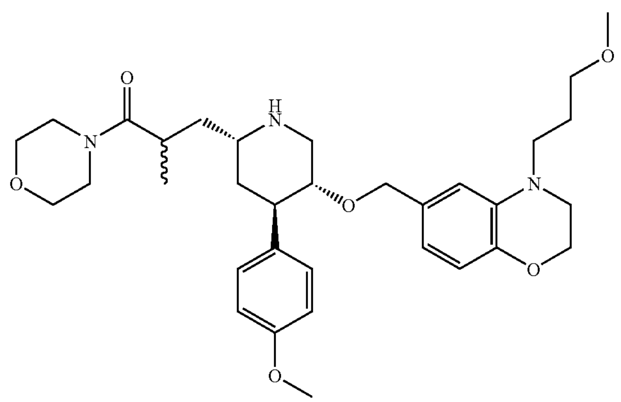 | yellow oil | 0.26 (D) | 3.80 |
| 85 | 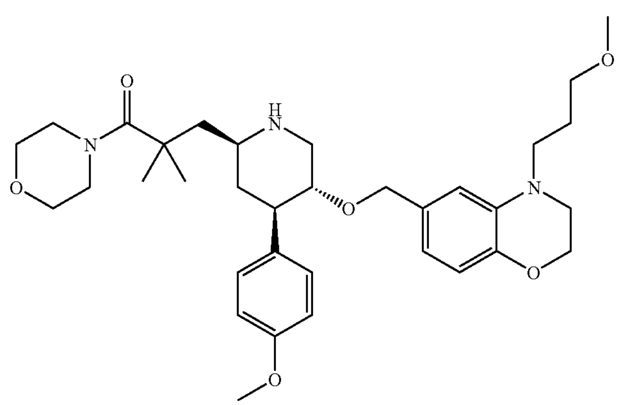 | white foam | 0.16 (D) | 0.16 |

-continued
| Nr. | Structure | Appearance | R$_f$(System) | Rt (Procedure) |
|---|---|---|---|---|
| 86 | 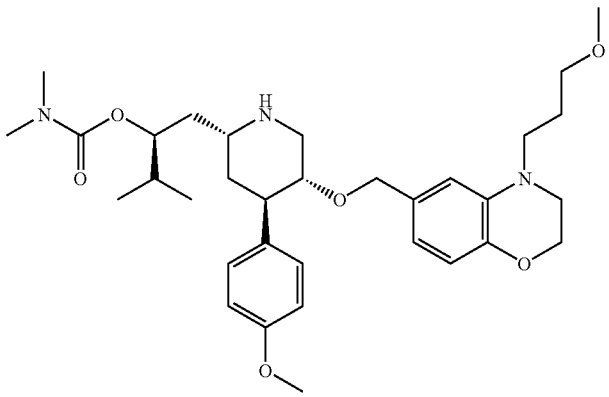 | yellow oil | 0.45 (D) | 4.49 |
| 87 | 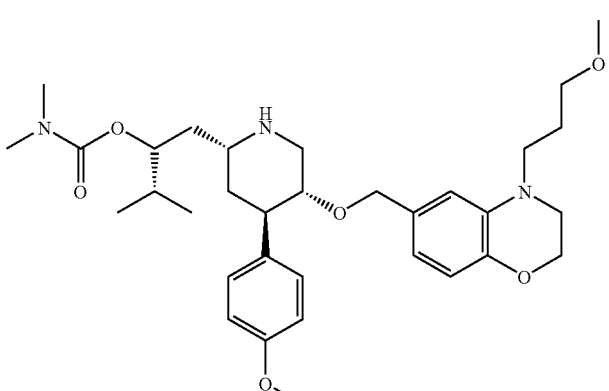 | yellow oil | 0.35 (D) | 4.37 |
| 88 | 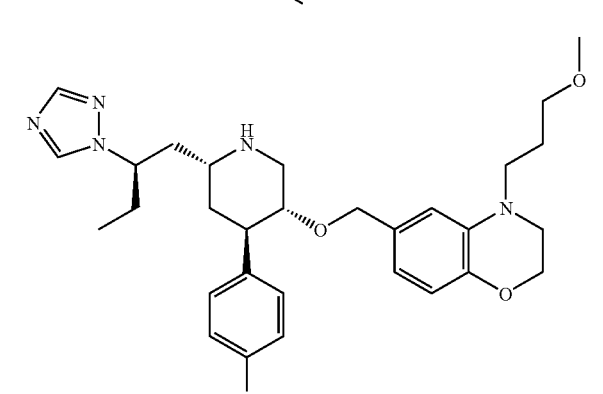 | brown oil | 0.45 (M) | 3.92 |
| 89 | 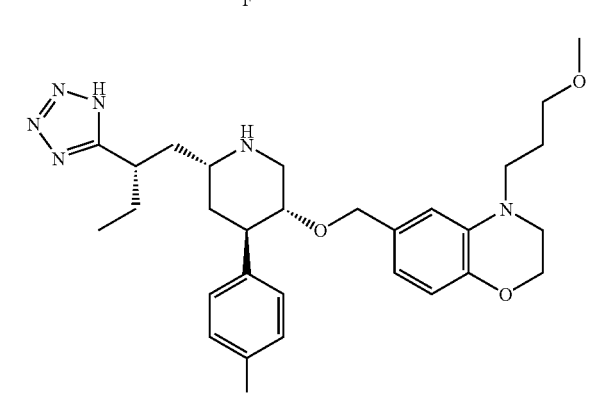 | red oil | 0.20 (M) | 3.90 |

-continued

| Nr. | Structure | Appearance | R_f (System) | Rt (Procedure) |
|---|---|---|---|---|
| 90 | 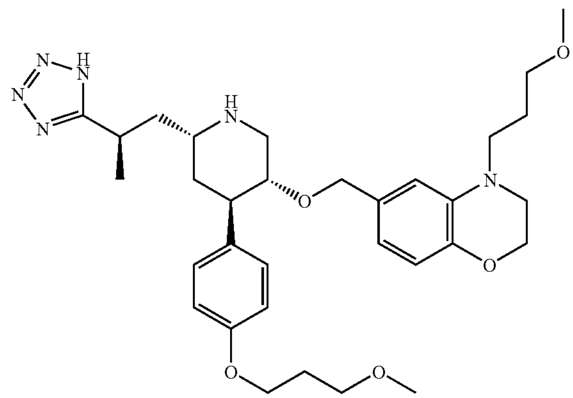 | brown oil | 0.30 (A) | 3.57 |
| 91 | 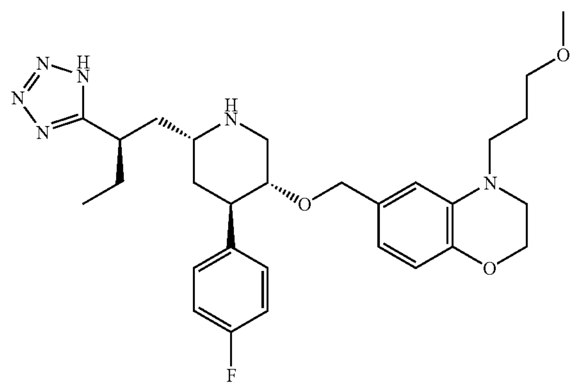 | red oil | 0.29 (M) | 3.85 |
| 92 | 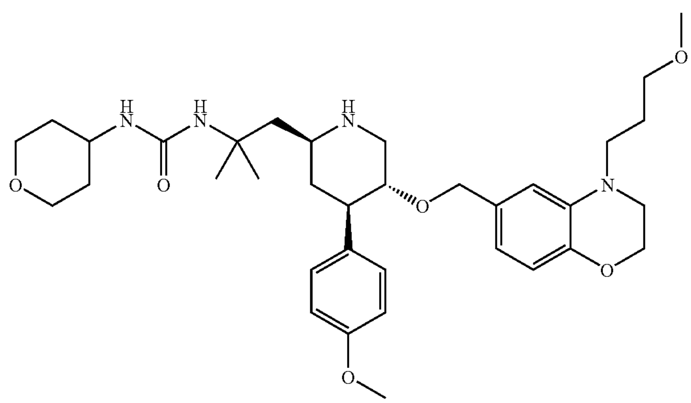 | white foam | 0.15 (D) | 3.79 |
| 93 | 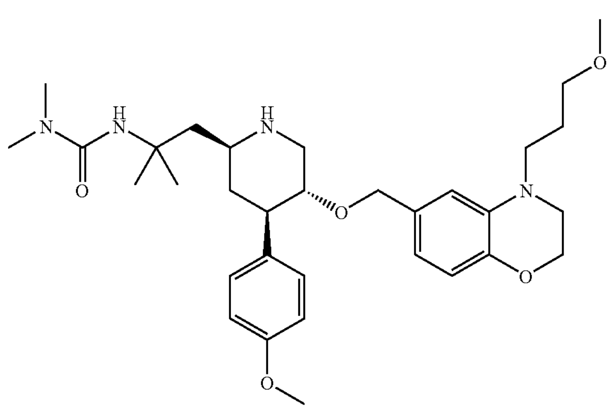 | white foam | 0.38 (D) | 4.02 |

-continued

| Nr. | Structure | Appearance | R$_f$(System) | Rt (Procedure) |
|---|---|---|---|---|
| 94 | 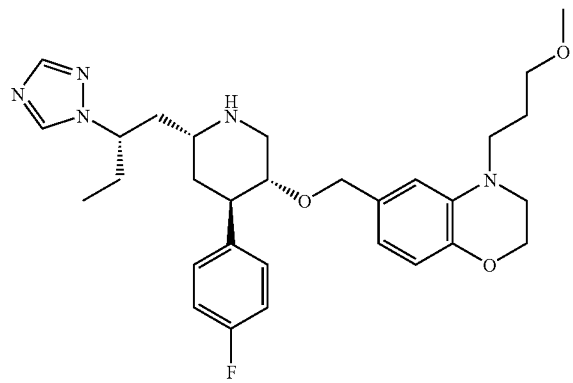 | yellow oil | 0.36 (M) | 3.93 |
| 95 | 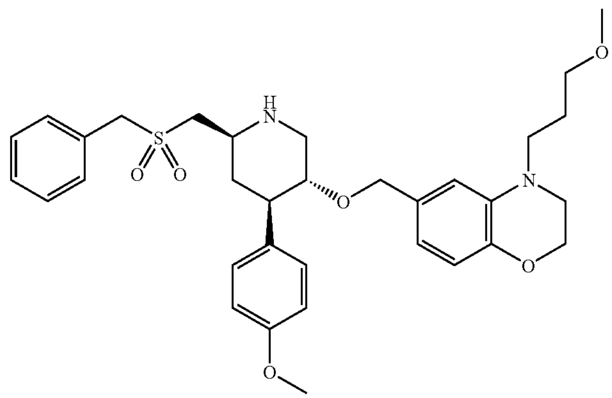 | colourless oil | 0.26 (R) | 4.07 |
| 96 | 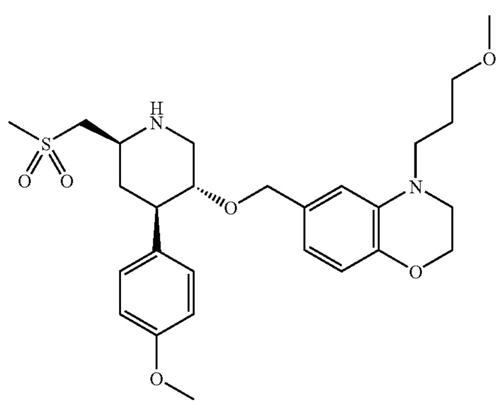 | colourless oil | 0.19 (R) | 3.54 |
| 97 | 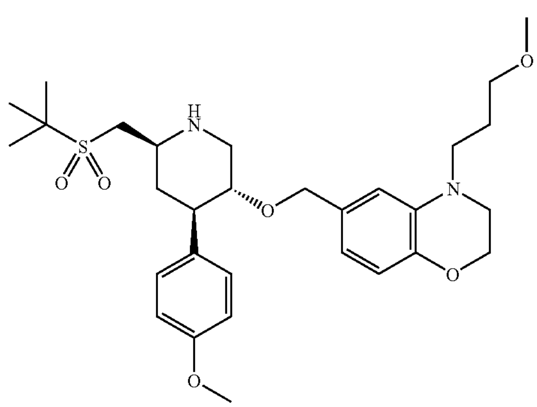 | colourless oil | 0.21 (R) | 3.86 |

-continued

| Nr. | Structure | Appearance | R_f(System) | Rt (Procedure) |
|---|---|---|---|---|
| 98 | 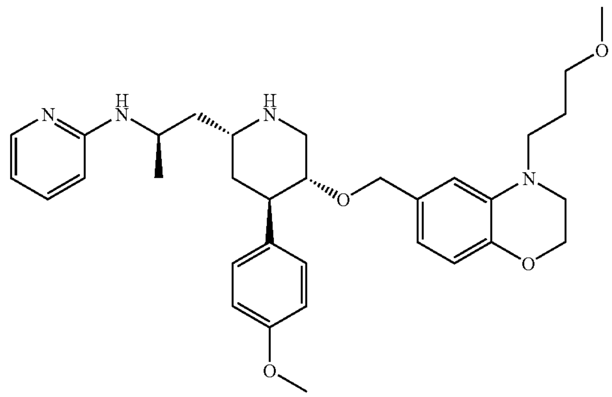 | white foam | 0.11 (S) | 3.42 |
| 99 | 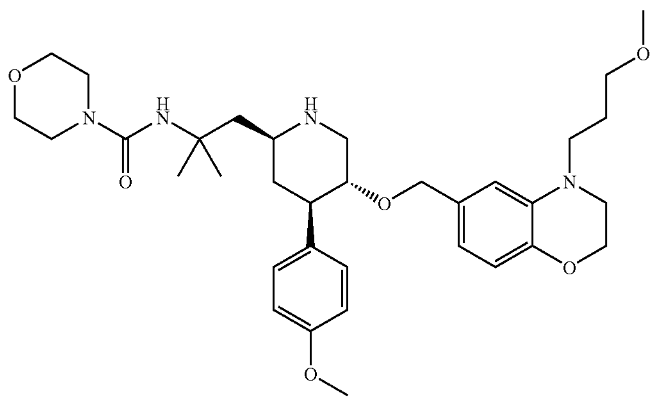 | yellow oil | 0.24 (C) | 3.81 |
| 100 | 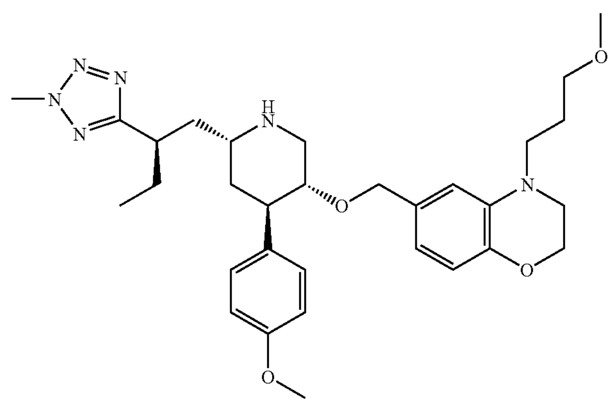 | yellow oil | 0.35 (M) | 3.88 |
| 101 | 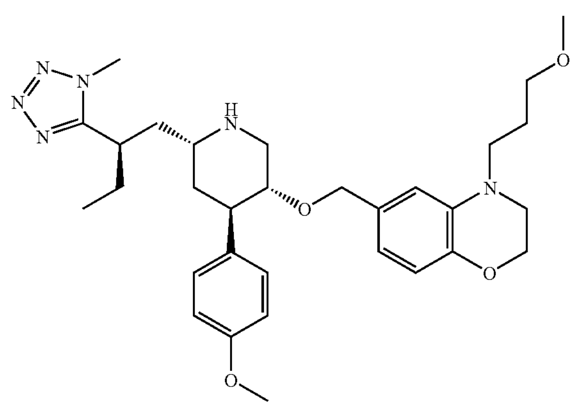 | yellow oil | 0.30 (M) | 4.05 |

-continued

| Nr. | Structure | Appearance | Rf(System) | Rt (Procedure) |
|---|---|---|---|---|
| 102 | 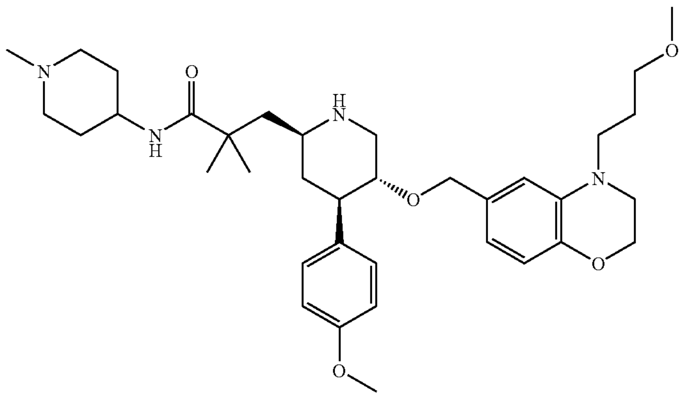 | colourless oil | 0.15 (G) | 3.23 |
| 103 | 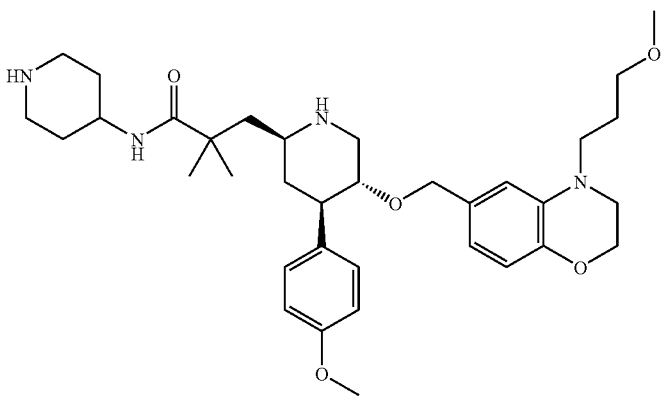 | colourless oil | 0.5 (U) | 3.22 |
| 104 | 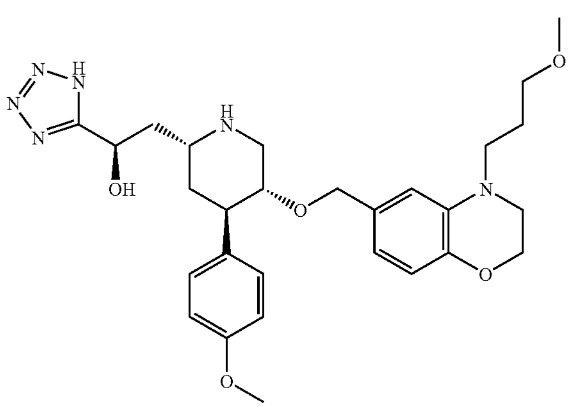 | yellow oil | 0.45 (J) | 3.48 |

-continued

| Nr. | Structure | Appearance | R$_f$(System) | Rt (Procedure) |
|---|---|---|---|---|
| 105 | 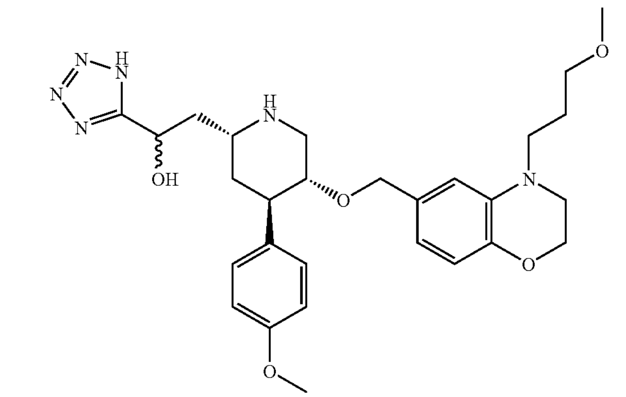 | yellow foam | 0.45 (J) | 3.49 |
| 106 | 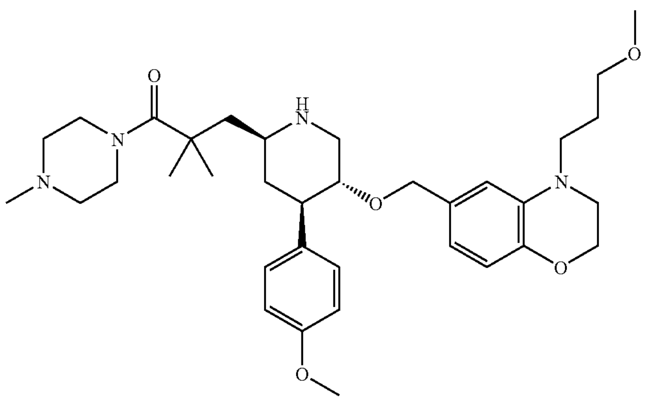 | colourless oil | 0.25 (K) | 3.36 |
| 107 | 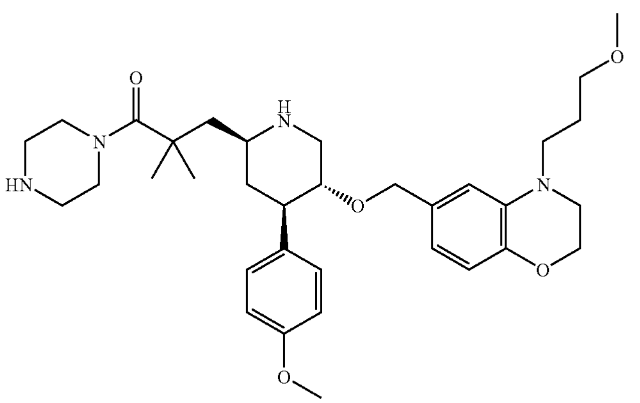 | colourless oil | 0.20 (K) | 3.32 |
| 108 | 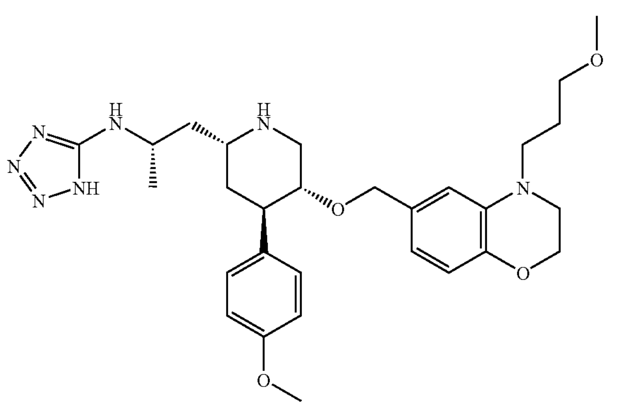 | beige crystals | 0.28 (A) | 3.52 |

-continued

| Nr. | Structure | Appearance | R_f (System) | Rt (Procedure) |
|-----|-----------|------------|--------------|----------------|
| 109 | 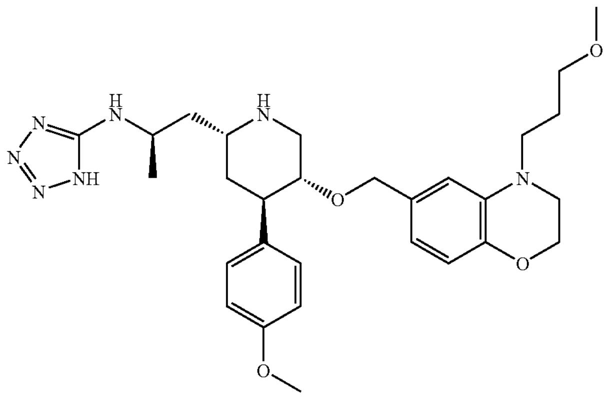 | beige crystals | 0.25 (A) | 3.60 |
| 110 | 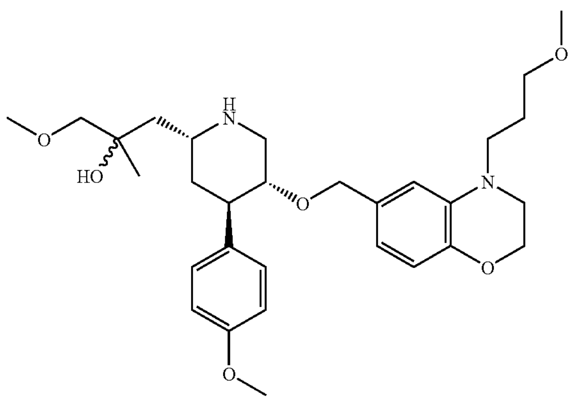 | yellow oil | 0.33 (A) | 3.91 |
| 111 | 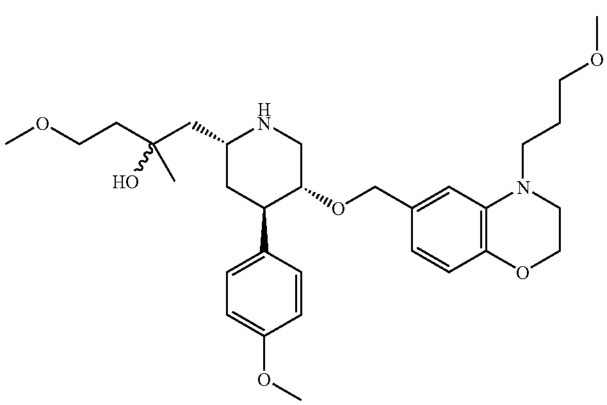 | yellow oil | 0.24 (A) | 4.03 |

-continued

| Nr. | Structure | Appearance | R$_f$(System) | Rt (Procedure) |
|---|---|---|---|---|
| 112 | 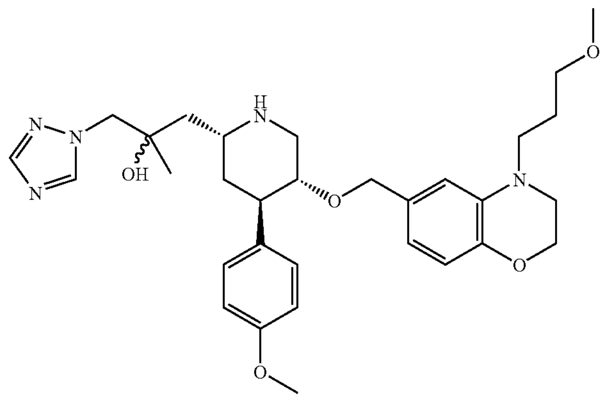 | yellow oil | 0.19 (A) | 3.59 |
| 113 | 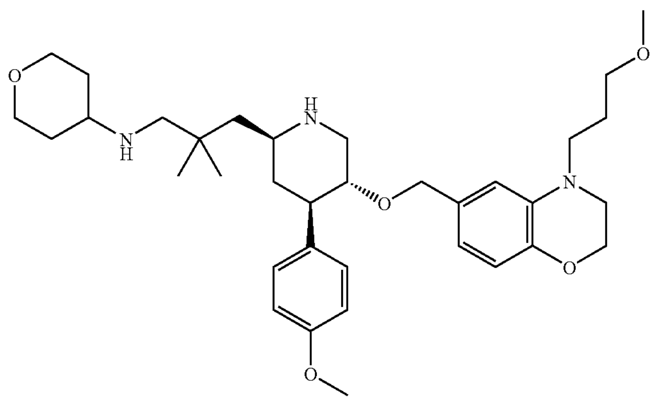 | yellow oil | 0.31 (J) | 3.32 |
| 114 | 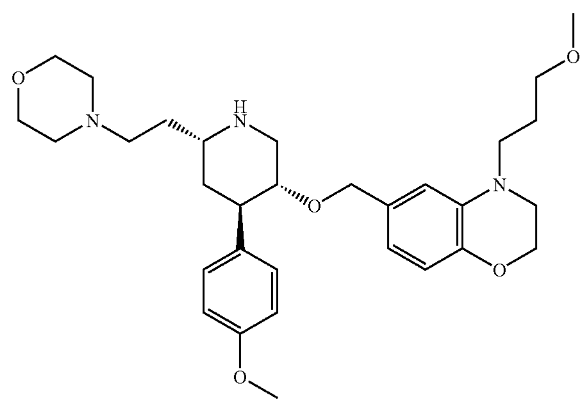 | colourless oil | 0.20 (C) | 3.18 |
| 115 | 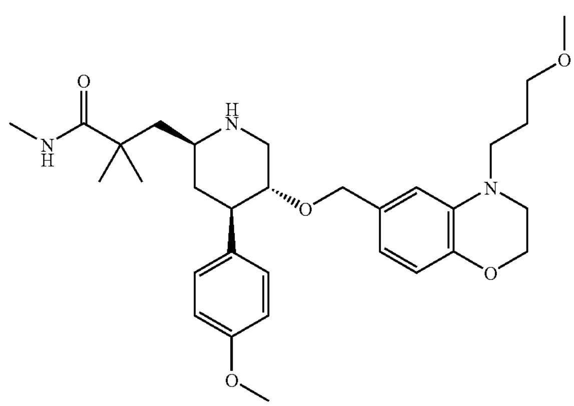 | colourless oil | 0.16 (C) | 3.77 |

-continued

| Nr. | Structure | Appearance | R_f(System) | Rt (Procedure) |
| --- | --- | --- | --- | --- |
| 116 | 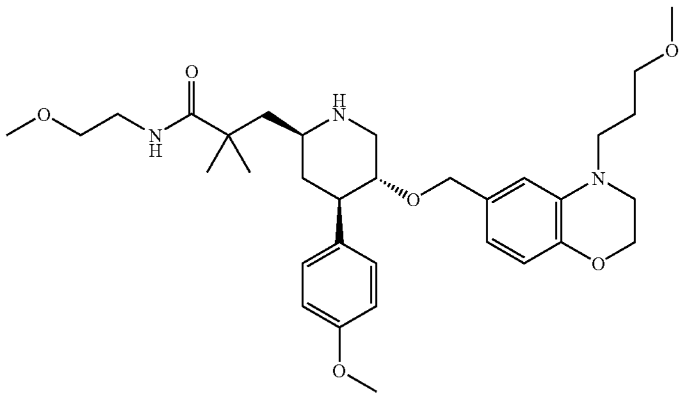 | colourless oil | 0.16 (C) | 3.79 |
| 117 | 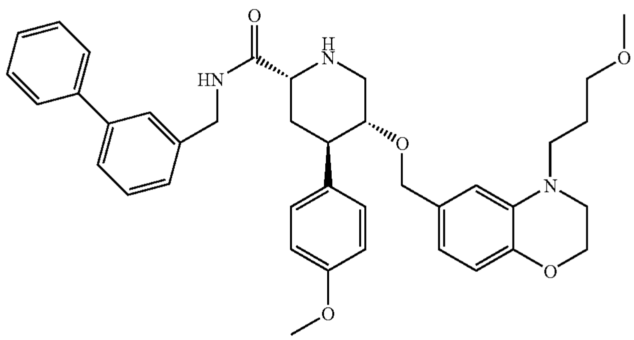 | white foam | 0.20 (C) | 4.55 |
| 118 | 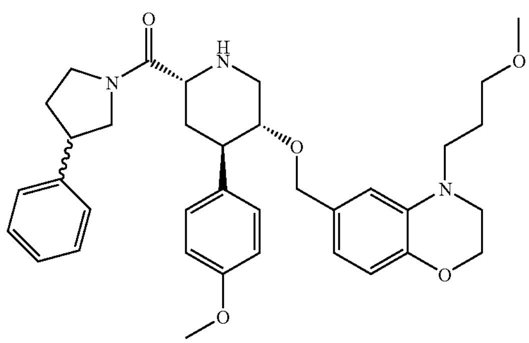 | white foam | 0.15 (C) | 4.33 |
| 119 | 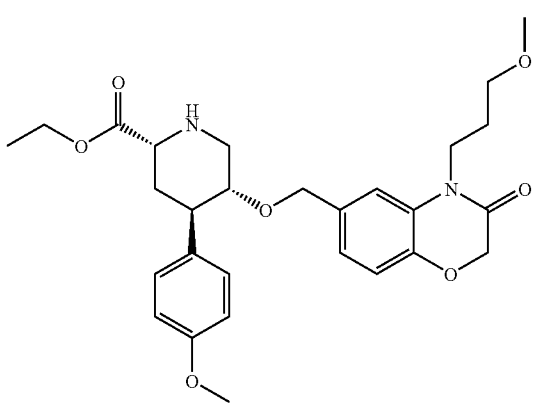 | colourless oil | 0.14 (T) | 3.62 |

-continued

| Nr. | Structure | Appearance | R$_f$(System) | Rt (Procedure) |
|---|---|---|---|---|
| 120 | 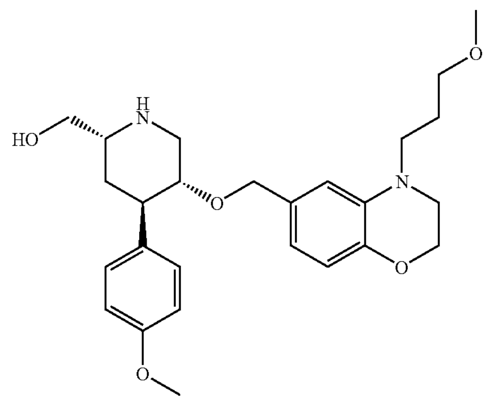 | yellow oil | 0.17 (D) | 3.09 |
| 121 | 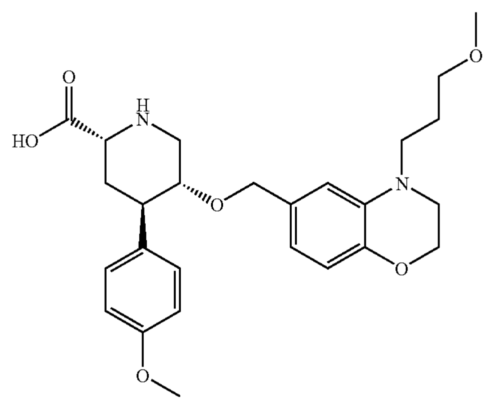 | white solid | 0.41 (E) | 3.43 |
| 122 | 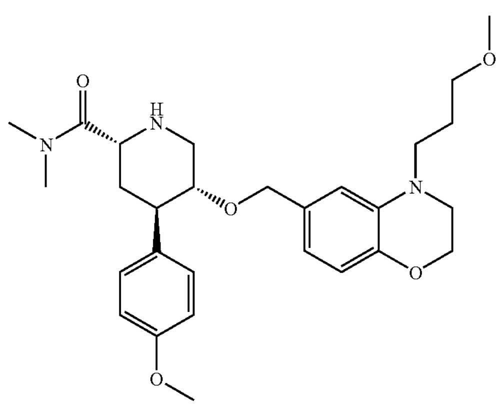 | off white solid | 0.33 (D) | 3.63 |
| 123 | 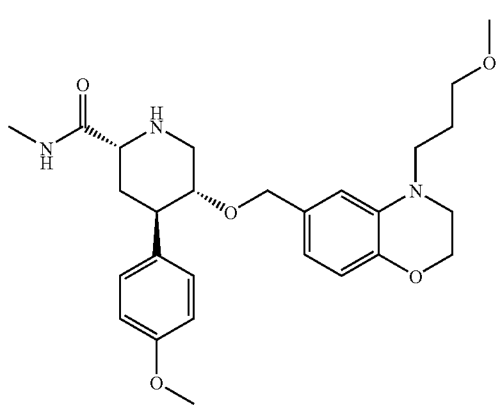 | yellow oil | 0.43 (D) | 3.46 |

-continued

| Nr. | Structure | Appearance | R$_f$(System) | Rt (Procedure) |
|---|---|---|---|---|
| 124 | 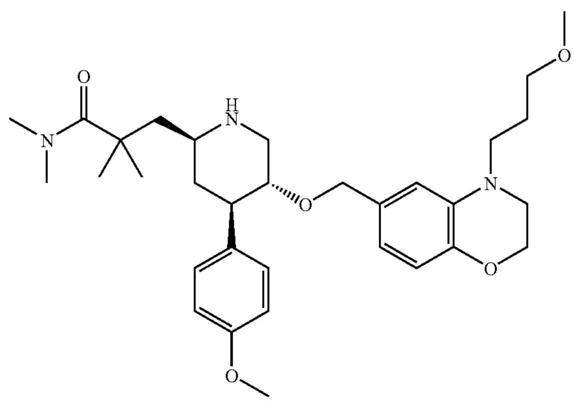 | colourless oil | 0.40 (D) | 4.03 |
| 125 | 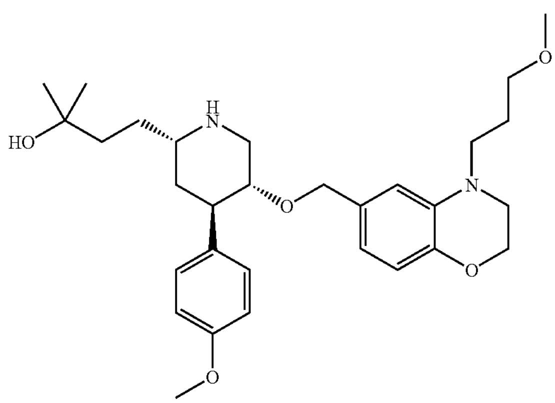 | colourless oil | 0.30 (D) | 3.81 |
| 126 | 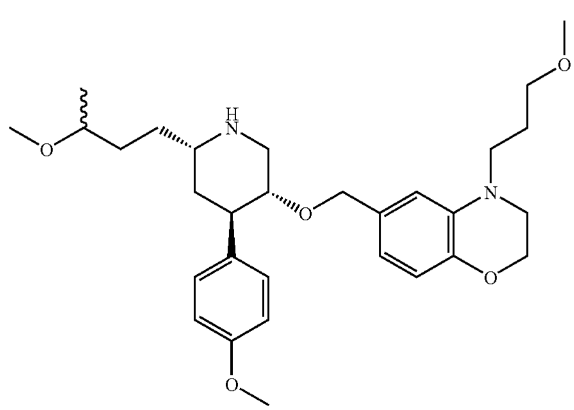 | yellow oil | 0.24 (D) | 4.10 |

-continued

| Nr. | Structure | Appearance | R$_f$(System) | Rt (Procedure) |
|---|---|---|---|---|
| 127 | 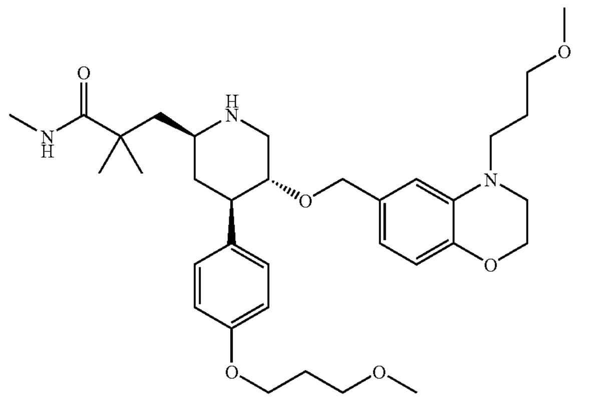 | colourless oil | 0.05 (D) | 3.96 |
| 128 | 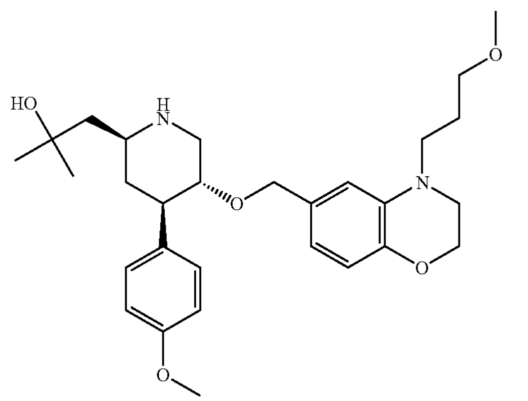 | yellow oil | 0.17 (C) | 3.86 |
| 129 | 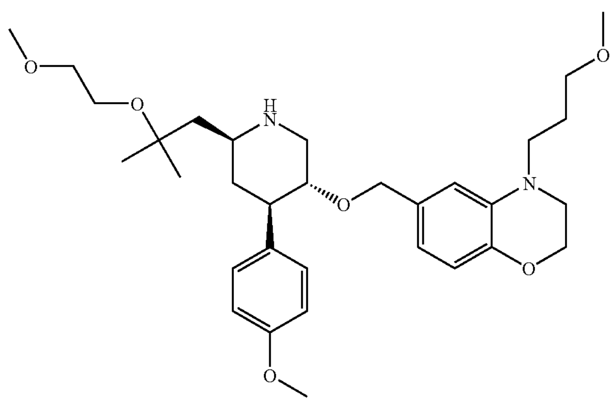 | yellow oil | 0.26 (C) | 4.31 |
| 130 | 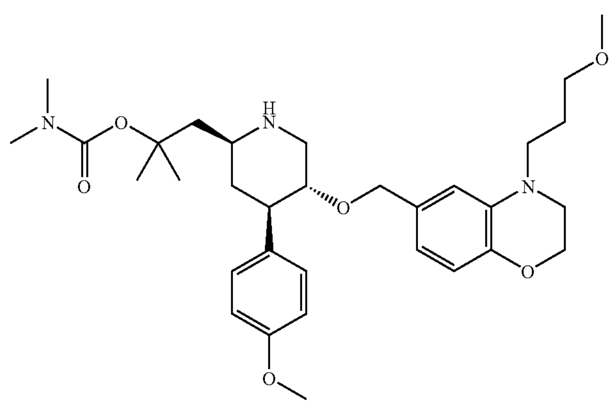 | yellow oil | 0.18 (V) | 4.03 |

-continued

| Nr. | Structure | Appearance | R_f(System) | Rt (Procedure) |
|---|---|---|---|---|
| 131 | 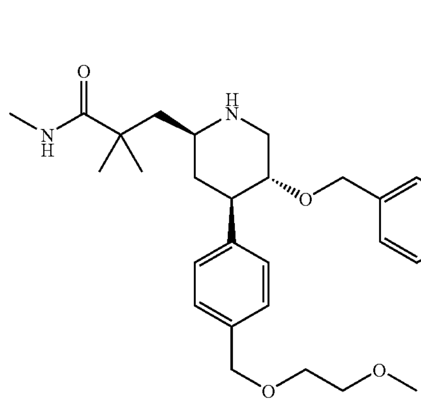 | colorless oil | 0.19 (W) | 3.69 |
| 132 | 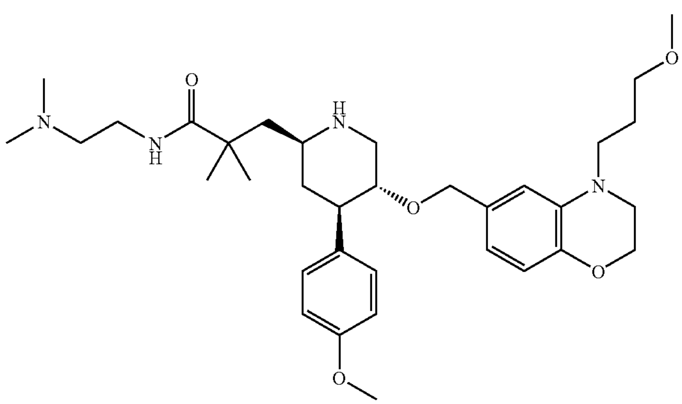 | colourless oil | 0.27 (X) | 3.22 |
| 134 | 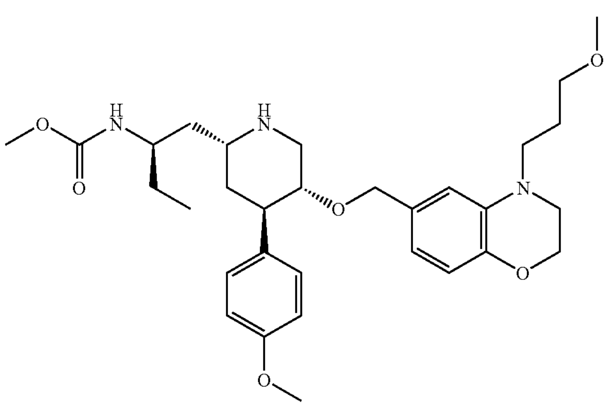 | yellow oil | 0.18 (C) | 4.03 |

-continued

| Nr. | Structure | Appearance | R_f(System) | Rt (Procedure) |
| --- | --- | --- | --- | --- |
| 135 | 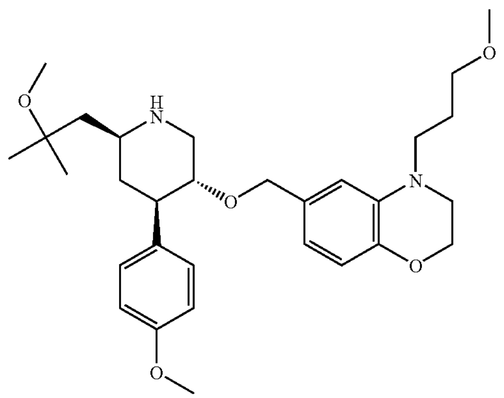 | yellow oil | 0.30 (D) | 4.17 |
| 136 | 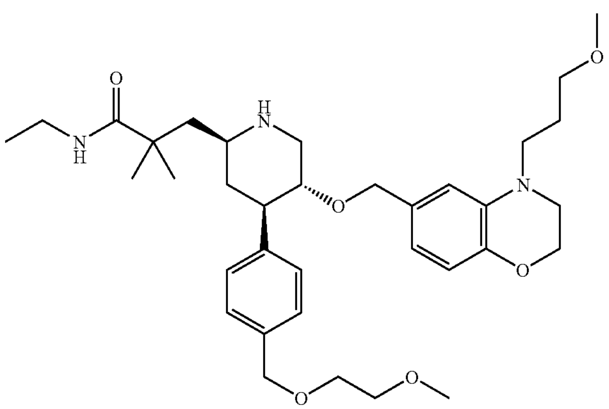 | orange oil | 0.38 (M) | 3.98 |
| 141 | 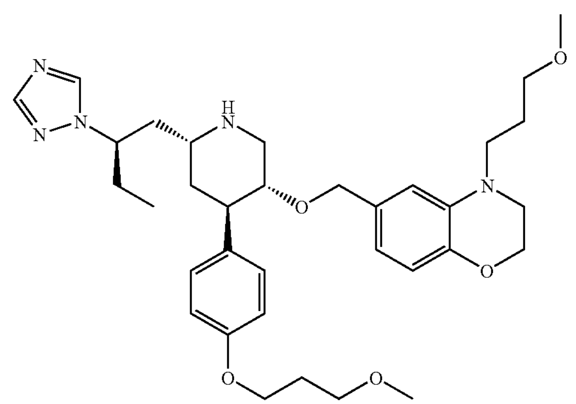 | yellow oil | 0.12 (C) | 3.83 |
| 143 | 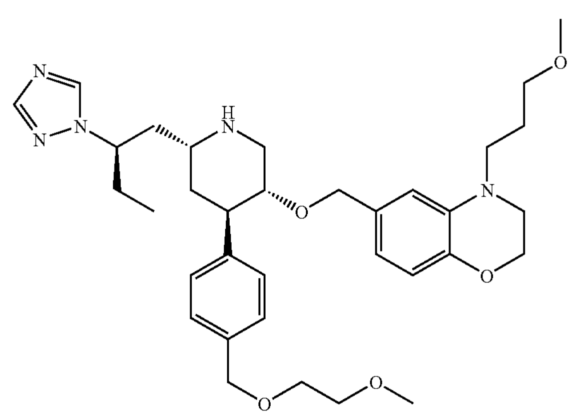 | orange oil | 0.35 (M) | 3.67 |

-continued
| Nr. | Structure | Appearance | R_f(System) | Rt (Procedure) |
| --- | --- | --- | --- | --- |
| 144 | 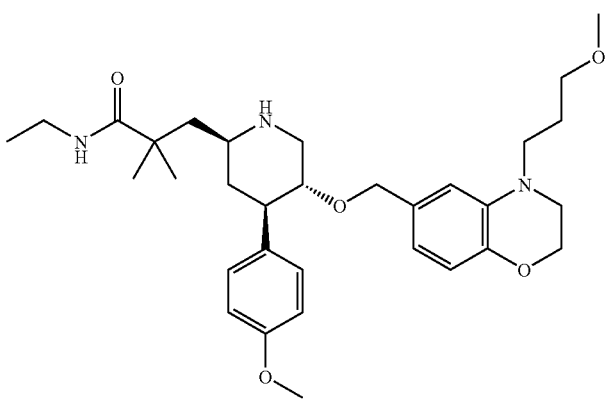 | colourless oil | 0.40 (D) | 3.92 |
| 145 | 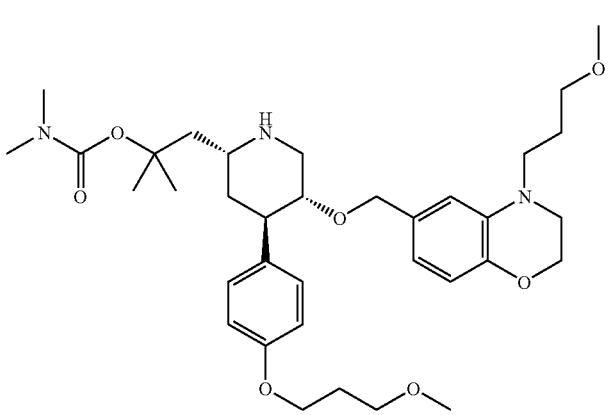 | yellow oil | 0.22 (D) | 4.27 |
| 165 | 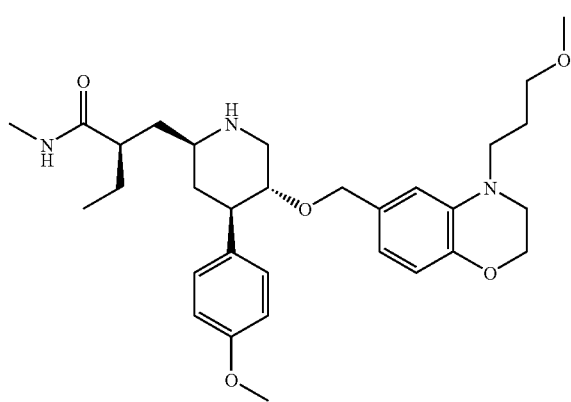 | yellow oil | 0.43 (M) | 3.67 |

-continued

| Nr. | Structure | Appearance | R$_f$(System) | Rt (Procedure) |
|---|---|---|---|---|
| 166 | 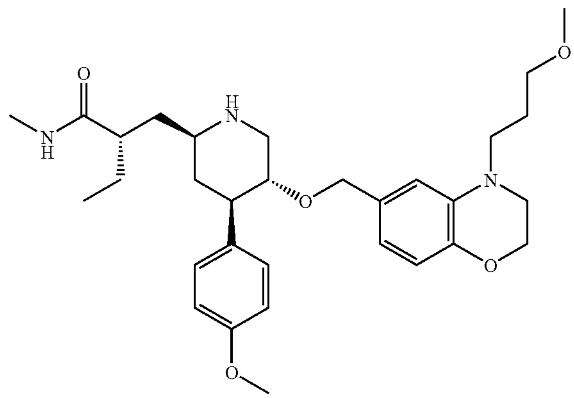 | yellow oil | 0.28 (D) | 3.68 |
| 167 | 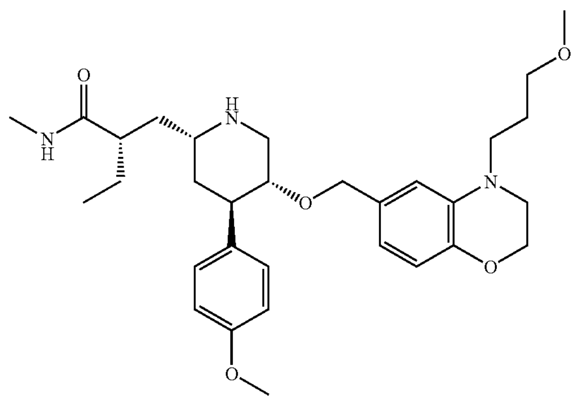 | yellow oil | 0.60 (X) | 3.75 |
| 168 | 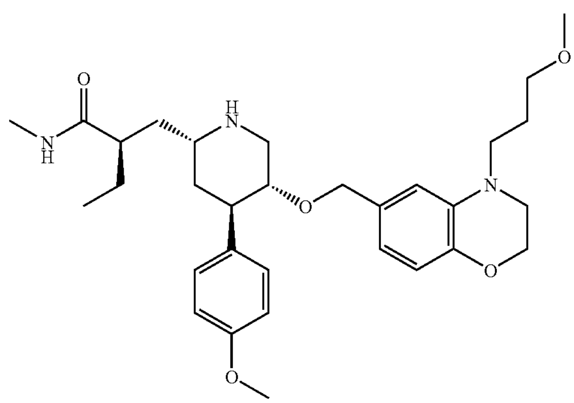 | yellow oil | 0.64 (X) | 3.69 |

Thin Film Chromatography Eluent Systems:
A dichloromethane-methanol=10:1
B EtOAc
C dichloromethane-methanol-25% ammonia conc.=200:10:1
D dichloromethane-methanol-25% ammonia conc.=200:20:1
E dichloromethane-methanol-water-acetic acid conc.=150:54:10:1
F dichloromethane-methanol=20:1
G dichloromethane-methanol=5:1
H dichloromethane-methanol=1:1
I EtOAc-heptane=5:1
J dichloromethane-methanol-25% ammonia conc.=100:10:1
K dichloromethane-methanol-25% ammonia conc.=10:1:0.1
L EtOAc-heptane=1:1
M dichloromethane-methanol=9:1
N dichloromethane-methanol-25% ammonia conc.=40:10:1
O dichloromethane-methanol-conc. acetic acid=100:10:1
P dichloromethane-methanol-25% ammonia conc.=90:10:1
Q dichloromethane-methanol-acetic acid conc.=100:10:2
R dichloromethane-methanol=30:1
S dichloromethane-methanol-25% ammonia conc.=600:20:1
T dichloromethane-methanol-25% ammonia conc.=200:5:1
U dichloromethane-methanol-25% ammonia conc.=5:1:0.1
V toluene-EtOAc-triethylamine=5:3:0.2
W dichloromethane-methanol-25% ammonia conc.=200:15:1

The invention claimed is:
1. A compound of the formula (I)

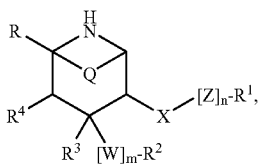

wherein
R is $C_{2-8}$-alkenyl, $C_{1-8}$-alkyl, $C_{2-8}$-alkynyl, $C_{0-8}$-alkyl-carbonyl-amino-$C_{1-8}$-alkyl, $C_{3-8}$-cycloalkyl-$C_{0-8}$-alkyl, $C_{1-8}$-alkyl-sulfonyl-$C_{1-8}$-alkyl, unalkylated or N-mono- or N,N-di-$C_{1-8}$-alkylated carbamoyl-$C_{0-8}$-alkyl, unalkylated or O—$C_{1-8}$-alkylated carboxyl-$C_{0-8}$-alkyl, unalkylated or N and/or N' mono-, di- or tri-$C_{1-8}$-alkylated ureido-$C_{1-8}$-alkyl or heterocyclylcarbonyl-$C_{0-8}$-alkyl, each of said radicals being substituted by 1-4 $C_{1-8}$-alkoxy or hydroxyl;
$R^1$ is benzoxazinyl;
$R^2$ is acenaphthyl, cyclohexyl, diazinyl, furyl, imidazolyl, naphthyl, oxadiazolyl, oxazolyl, phenyl, pyrazinyl, pyridyl, pyrimidinyl, pyrrolyl, oxopyridinyl, tetrazolyl, thienyl, or triazolyl, each of said radicals may be substituted by 1-3 $C_{1-8}$-alkanoyloxy-$C_{1-8}$-alkyl, $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxycarbonyl, $C_{1-8}$-alkoxycarbonyloxy-$C_{1-8}$-alkyl, $C_{1-8}$-alkyl, carboxy-$C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{1-8}$-alkylsulfanyl-$C_{1-8}$-alkyl, cyano, cyano-$C_{1-8}$-alkyl, $C_{3-8}$-cycloalkyl-$C_{0-6}$-alkoxy-$C_{1-8}$-alkoxy, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{0-6}$-alkoxy-$C_{1-8}$-alkyl, halo-$C_{1-8}$-alkyl, halogen, hydroxy-$C_{1-8}$-alkyl, hydroxyl, oxide, trifluoromethoxy or trifluoromethyl groups, or a $C_{1-8}$-alkylenedioxy group, and/or by an L1-T1-L2-T2-L3-T3-L4-T4-L5-U radical;
L1, L2, L3, L4 and L5 are each independently a bond, $C_{1-8}$-alkylene, $C_{2-8}$-alkenylene or $C_{2-8}$-alkynylene, $C_{3-8}$-cycloalkene or are absent;
T1, T2, T3 and T4 are each independently
(a) a bond, or are absent, or are one of the groups
(b) —CH(OH)—;
(c) —CH($OR^6$)—;
(d) —CH($NR^5R^6$)—;
(e) —CO—;
(f) —$CR^7R^8$—;
(g) —O— or —$NR^6$—;
(h) —S(O)$_{0-2}$—;
(i) —SO$_2NR^6$—;
(j) —$NR^6SO_2$—;
(k) —$CONR^6$—;
(l) —$NR^6CO$—;
(m) —O—CO—;
(n) —CO—O—;
(o) —O—CO—O—;
(p) —O—CO—$NR^6$—;
(q) —N($R^6$)—CO—N($R^6$)—;
(r) —N($R^6$)—CO—O—;
(s) pyrrolidinylene, piperidinylene or piperazinylene;
(t) —C($R^{11}$)($R^{12}$)—,
wherein the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;
$R^3$ is hydrogen, hydroxyl, $C_{1-8}$-alkoxy or $C_{2-8}$-alkenyloxy;
$R^4$ is hydrogen, $C_{2-8}$-alkenyl, $C_{1-8}$-alkoxy, $C_{1-8}$-alkoxy-$C_{1-8}$-alkyl, $C_{1-8}$-alkoxy-$C_{1-8}$-alkoxy, $C_{1-8}$-alkyl, optionally (N—$C_{1-8}$-alkyl)-$C_{1-8}$-alkoxycarbonyl-amino-$C_{1-8}$-alkoxy, optionally (N—$C_{1-8}$-alkyl)-$C_{1-8}$-alkylcarbonyl-amino-$C_{1-8}$-alkoxy, optionally (N-mono- or N,N-di-$C_1$-$C_8$-alkyl)-amino-$C_{1-8}$-alkoxy, benzyl, $C_{3-8}$-cycloalkyloxy, $C_{3-8}$-cycloalkyloxy-$C_{1-8}$-alkoxy, heterocyclyl-$C_{0-8}$-alkoxy, heterocyclyloxy-$C_{1-8}$-alkoxy, hydroxy, hydroxy-$C_{1-8}$-alkoxy-$C_{1-8}$-alkoxy, hydroxy-$C_{1-8}$-alkyl, oxo, or a $R^{4a}$-Z1-X1- group, wherein $R^{4a}$ is
(a) H—;
(b) $C_{1-8}$-alkyl-;
(c) $C_{2-8}$-alkenyl-;
(d) hydroxy-$C_{1-8}$-alkyl-;
(e) polyhydroxy-$C_{1-8}$-alkyl-;
(f) $C_{1-8}$-alkyl-O—$C_{1-8}$-alkyl-;
(g) aryl-;
(h) heterocyclyl-;
(i) arylalkyl-;
(j) heterocyclylalkyl-;
(k) aryloxyalkyl-;
(l) heterocyclyloxyalkyl-;
(m) ($R^5,R^6$)N—(CH$_2$)$_{1-3}$—;
(n) ($R^5,R^6$)N—;
(o) $C_{1-8}$-alkyl-S(O)$_{0-2}$—;
(p) aryl-S(O)$_{0-2}$—;
(q) heterocyclyl-S(O)$_{0-2}$—;
(r) HO—SO$_3$— or salts thereof;
(s) H$_2$N—C(NH)—NH—;
(t) NC—,
and the bonds starting from (n)-(t) lead to a carbon atom of the adjacent group and this carbon atom is saturated if the bond starts from a heteroatom;
Z1 is
(a) a bond, is absent, or is one of the groups:
(b) —$C_{1-8}$-alkylene-;
(c) —$C_{2-8}$-alkenylene-;
(d) —O—, —N($R^{11}$)—, —S(O)$_{0-2}$—;
(e) —CO—;
(f) —O—CO—;
(g) —O—CO—O—;
(h) —O—CO—N($R^{11}$)—;
(i) —N($R^{11}$)—CO—O—;
(j) —CO—N($R^{11}$)—;
(k) —N($R^{11}$)—CO—;
(l) —N($R^{11}$)—CO—N($R^{11}$)—;
(m) —CH($OR^9$)—
and the bonds starting from (d) and (f)-(m) lead to a carbon atom of the adjacent group and this carbon atom is saturated if the bond starts from a heteroatom;
X1 is
(a) a bond, is absent, or is one of the groups:
(b) —O—;
(c) —N($R^{11}$)—;
(d) —S(O)$_{0-2}$—;
(e) —(CH$_2$)$_{1-3}$—;
or $R^3$ and $R^4$ in formula (I) together are a bond;

$R^5$ and $R^6$ are each independently hydrogen, $C_{1-8}$-alkyl, $C_{2-8}$-alkenyl, aryl-$C_{1-8}$-alkyl or acyl, or, together with the nitrogen atom to which they are bonded, are a 5- or 6-membered heterocyclic ring which may contain an additional nitrogen, oxygen or sulfur atom or a —SO— or —SO$_2$— group, and the additional nitrogen atom is unsubstituted or substituted by $C_{1-8}$-alkyl radicals;

$R^7$ and $R^8$, together with the carbon atom to which they are bonded, are a 3-7-membered ring which may contain one or two —O— or —S— atoms or —SO— or —SO$_2$— groups;

$R^9$ is hydrogen, $C_{1-8}$-alkyl, $C_{1-8}$-alkoxy-$C_{1-8}$-alkyl, acyl or arylalkyl;

$R^{10}$ is carboxyalkyl, alkoxycarbonylalkyl, alkyl or hydrogen;

$R^{11}$ is hydrogen or $C_{1-8}$-alkyl;

$R^{12}$ is hydrogen or $C_{1-8}$-alkyl;

Q is absent;

U is hydrogen, $C_{1-8}$-alkyl, cyano, unsubstituted or substituted $C_{3-8}$-cycloalkyl, aryl or heterocyclyl;

W is oxygen or sulfur;

X is a bond, oxygen or sulfur, or is a >CH—$R^{11}$, >CHOR$^9$, —O—CO—, >CO, >C=NOR$^{10}$, —O—CHR$^{11}$— or —O—CHR$^{11}$—CO—NR$^9$— group and the bond starting from an oxygen or sulfur atom leads to a saturated carbon atom of the Z group or to $R^1$;

Z is $C_{1-8}$-alkylene, $C_{2-8}$-alkenylene, hydroxy-$C_{1-8}$-alkylidene, —O—, —S—, —O-alk-, —S-alk-, -alk-O—, -alk-S— or -alk-NR$^9$—, where alk is $C_{1-8}$-alkylene; and wherein (a) if Z is —O— or —S—, X is >CH—$R^{11}$ and either $R^2$ contains an L1-T1-L2-T2-L3-T3-L4-T4-L5-U substituent or $R^4$ is a substituent other than hydrogen as defined above;

(b) if Z is —O-alk- or —S-alk-, X is >CH—$R^{11}$; and (c) if X is a bond, Z is $C_{2-8}$-alkenylene, -alk-O— or -alk-S—;

m is 0 or 1;

n is 0 or 1;

or salt or prodrug thereof, or where one or more atoms are replaced by their stable, non-radioactive isotopes.

2. A compound according to claim 1 of the formula (IA)

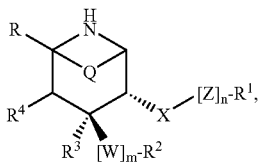

(IA)

wherein R, $R^1$, $R^2$, $R^3$, $R^4$, Q, W, X, Z, n and m are each as defined for the compounds of the formula (I) according to claim 1.

3. A compound according to claim 1, wherein

R is $C_{2-8}$-alkenyl, $C_{1-8}$-alkyl, $C_{2-8}$-alkynyl, $C_{0-8}$-alkyl-carbonyl-amino-$C_{1-8}$-alkyl, $C_{3-8}$-cycloalkyl-$C_{0-8}$-alkyl, $C_{1-8}$-alkyl-sulfonyl-$C_{0-8}$-alkyl, unalkylated or N-mono- or N,N-di-$C_{1-8}$-alkylated carbamoyl-$C_{0-8}$-alkyl, unalkylated or O—$C_{1-8}$-alkylated carboxyl-$C_{0-8}$-alkyl, unalkylated or N and/or N' mono-, di- or tri-$C_{1-8}$-alkylated ureido-$C_{0-8}$-alkyl or heterocyclylcarbonyl-$C_{0-8}$-alkyl, each of said radicals being substituted by 1-4 $C_{1-8}$-alkoxy or hydroxyl;

$R^1$ is benzoxazinyl;

$R^2$ is phenyl, cyclohexyl, tetrazolyl, naphthyl or acenaphthyl, each of said radicals may be unsubstituted or substituted by 1-3 $C_{1-8}$-alkanoyloxy-$C_{1-8}$-alkyl, $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxycarbonyl, $C_{1-8}$-alkoxycarbonyloxy-$C_{1-8}$-alkyl, $C_{1-8}$-alkyl, carboxy-$C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{1-8}$-alkylsulfanyl-$C_{1-8}$-alkyl, cyano, cyano-$C_{1-8}$-alkyl, $C_{3-8}$-cycloalkyl-$C_{0-6}$-alkoxy-$C_{1-8}$-alkoxy, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{0-6}$-alkoxy-$C_{1-8}$-alkyl, halo-$C_{1-8}$-alkyl, halogen, hydroxy-$C_{1-8}$-alkyl, hydroxyl, oxide, trifluoromethoxy or trifluoromethyl groups, or a $C_{1-8}$-alkylenedioxy group, and/or by an L1-T1-L2-T2-L3-T3-L4-T4-L5-U radical; or naphthyl or acenaphthyl;

L1, L2, L3, L4 and L5 are each independently a bond, $C_{1-8}$-alkylene, $C_{2-8}$-alkenylene or $C_{2-8}$-alkynylene, $C_{3-8}$-cycloalkene or are absent;

T1, T2, T3 and T4 are each independently (a) a bond, or are absent, or are one of the groups:

(b) —CH(OH)—;

(c) —CH(OR$^6$)—;

(d) —CH(NR$^5$R$^6$)—;

(e) —O—;

(f) —CR$^7$R$^8$;

(g) —O— or —NR$^6$—;

(h) —S(O)$_{0-2}$—;

(I) —SO$_2$NR$^6$—;

(j) —NR$^6$SO$_2$—;

(k) —CONR$^6$—;

(l) —NR$^6$CO—;

(m) —O—CO—;

(n) —CO—O—;

(o) —O—CO—O—;

(p) —O—CO—NR$^6$—;

(q) —N(R$^6$)—CO—N(R$^6$)—;

(r) —N(R$^6$)—CO—O—;

(s) pyrrolidinylene, piperidinylene or piperazinylene;

(t) —C(R$^{11}$)(R$^{12}$)—, wherein the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;

$R^3$ is hydrogen, hydroxyl, $C_{1-8}$-alkoxy or $C_{2-8}$-alkenyloxy;

$R^4$ is hydrogen, $C_{1-8}$-alkoxy, $C_{1-8}$-alkoxy-$C_{1-8}$-alkoxy, $C_{1-8}$-alkoxy-$C_{1-8}$-alkyl, $C_{1-8}$-alkyl, optionally (N—$C_{1-8}$-alkyl)-$C_{1-8}$-alkoxycarbonyl-amino-$C_{1-8}$-alkoxy, optionally (N—$C_{1-8}$-alkyl)-$C_{1-8}$-alkylcarbonyl-amino-$C_{1-8}$-alkoxy, optionally (N-mono- or N,N-di-$C_1$-$C_9$-alkyl)-amino-$C_{1-8}$-alkoxy, $C_{3-8}$-cycloalkyloxy, $C_{3-8}$-cycloalkyloxy-$C_{1-8}$-alkoxy, heterocyclyl-$C_{0-8}$-alkoxy, heterocyclyloxy-$C_{1-8}$-alkoxy, hydroxy, oxo or hydroxy-$C_{1-8}$-alkoxy-$C_{1-8}$-alkoxy;

$R^5$ and $R^6$ are each independently hydrogen, $C_{1-8}$-alkyl or acyl, or, together with the nitrogen atom to which they are bonded, are a 5- or 6-membered heterocyclic ring which may contain an additional nitrogen, oxygen or sulfur atom;

$R^7$ and $R^8$, together with the carbon atom to which they are bonded, are a 3-7-membered ring which may contain one or two —O— or —S— atoms;

$R^9$ is hydrogen, $C_{1-8}$-alkyl, acyl or arylalkyl;

U is hydrogen, $C_{1-8}$-alkyl, $C_{3-8}$-cycloalkyl, cyano, aryl or heterocyclyl;

Q is absent;
X is a bond, oxygen, sulfur or is a >$CHR^{11}$, >$CHOR^9$, —O—CO—, >CO or —O—CH—$R^{11}$—CO—$NR^9$— group;
W is oxygen or sulfur if $R^3$ is hydrogen;
Z is $C_{1-8}$-alkylene or -alk-O—; wherein, if X is a bond, Z is -alk-O—;
n is 0 or 1;
m is 0 or 1;
or a pharmaceutically useable salt thereof.

4. A compound according to claim 1, wherein
$R^2$ is phenyl or halophenyl each substituted by $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxy-$C_{1-8}$-alkyl-amino-$C_{1-8}$-alkyl, $C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{3-8}$-cycloalkylsulfanyl-$C_{1-8}$-alkyl, $C_{1-8}$-alkylsulfonyl-$C_{1-8}$-alkoxy-$C_{1-8}$-alkyl, $C_{3-8}$-cycloalkyl-$C_{0-6}$-alkoxy, $C_{3-8}$-cycloalkyl-$C_{0-6}$-alkoxy-$C_{1-8}$-alkoxy, $C_{3-8}$-cycloalkyl-$C_{0-6}$-alkoxy-$C_{1-8}$-alkyl, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{1-8}$-alkylamino-$C_{1-8}$-alkyl, halogen, heterocyclyl-$C_{0-6}$-alkoxy, heterocyclyl-$C_{0-6}$-alkoxy-$C_{1-8}$-alkyl, $C_{1-8}$-alkoxy-$C_{1-8}$-alkylamino-$C_{1-8}$-alkyl, N-(halo-phenyl)pyrrolidinyloxy, N-(halo-phenyl)pyrrolidinyloxy-$C_{1-8}$-alkyl, $C_{1-8}$-alkoxybenzyloxy-$C_{1-8}$-alkoxy, $C_{1-8}$-alkoxyphenoxy-$C_{1-8}$-alkoxy, $C_{1-8}$-alkoxyphenoxy-$C_{1-8}$-alkyl, $C_{1-8}$-alkoxyphenyl-$C_{1-8}$-alkoxy-$C_{1-8}$-alkoxy, halobenzyloxy-$C_{1-8}$-alkoxy, halophenoxy-$C_{1-8}$-alkoxy, halophenoxy-$C_{1-8}$-alkoxy-$C_{1-8}$-alkyl, halophenoxy-$C_{1-8}$-alkyl, halophenyl-$C_{1-8}$-alkoxy-$C_{1-8}$-alkoxy or $C_{1-8}$-alkylbenzyloxy-$C_{1-8}$-alkoxy, whereby at least one substituent is in the para-position relative to the bond of $R^2$ to the rest of the molecule.

5. A compound according to claim 1, wherein m is 0.

6. A pharmaceutical composition comprising a compound of the formula (I) according to claim 1, and a pharmaceutically inert excipient.

7. A compound according to claim 2, wherein
R is $C_{2-8}$-alkenyl, $C_{1-8}$-alkyl, $C_{2-8}$-alkynyl, $C_{0-8}$-alkyl-carbonyl-amino-$C_{1-8}$-alkyl, $C_{3-8}$-cycloalkyl-$C_{0-8}$-alkyl, $C_{1-8}$-alkyl-sulfonyl-$C_{0-8}$-alkyl, unalkylated or N-mono- or N,N-di-$C_{1-8}$-alkylated carbamoyl-$C_{0-8}$-alkyl, unalkylated or O—$C_{1-8}$-alkylated carboxyl-$C_{0-8}$-alkyl, unalkylated or N and/or N' mono-, di- or tri-$C_{1-8}$-alkylated ureido-$C_{0-8}$-alkyl or heterocyclylcarbonyl-$C_{0-8}$-alkyl, each of said radicals being substituted by 1-4 $C_{1-8}$-alkoxy or hydroxyl;
$R^1$ is benzoxazinyl;
$R^2$ is phenyl, cyclohexyl, tetrazolyl, naphthyl or acenaphthyl, each of said radicals may be unsubstituted or substituted by 1-3 $C_{1-8}$-alkanoyloxy-$C_{1-8}$-alkyl, $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxycarbonyl, $C_{1-8}$-alkoxycarbonyloxy-$C_{1-8}$-alkyl, $C_{1-8}$-alkyl, carboxy-$C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{1-8}$-alkylsulfanyl-$C_{1-8}$-alkyl, cyano, cyano-$C_{1-8}$-alkyl, $C_{3-8}$-cycloalkyl-$C_{0-6}$-alkoxy-$C_{1-8}$-alkoxy, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{0-6}$-alkoxy-$C_{1-8}$-alkyl, halo-$C_{1-8}$-alkyl, halogen, hydroxy-$C_{1-8}$-alkyl, hydroxyl, oxide, trifluoromethoxy or trifluoromethyl groups, or a $C_{1-8}$-alkylenedioxy group, and/or by an L1-T1-L2-T2-L3-T3-L4-T4-L5-U radical; or naphthyl or acenaphthyl;
L1, L2, L3, L4 and L5 are each independently a bond, $C_{1-8}$-alkylene, $C_{2-8}$-alkenylene or $C_{2-8}$-alkynylene, $C_{3-8}$-cycloalkene or are absent;
T1, T2, T3 and T4 are each independently
(a) a bond, or are absent, or are one of the groups:
(b) —CH(OH)—;
(c) —CH($OR^6$)—;
(d) —CH($NR^5R^6$)—;
(e) —CO—;
(f) —$CR^7R^8$—;
(g) —O— or —$NR^6$—;
(h) —$S(O)_{0-2}$—;
(I) —$SO_2NR^6$—;
(j) —$NR^6SO_2$—;
(k) —$CONR^6$—;
(l) —$NR^6CO$—;
(m) —O—CO—;
(n) —CO—O—;
(o) —O—CO—O—;
(p) —O—CO—$NR^6$—;
(q) —$N(R^6)$—CO—$N(R^6)$—;
(r) —$N(R^6)$—CO—O—;
(s) pyrrolidinylene, piperidinylene or piperazinylene;
(t) —$C(R^{11})(R^{12})$—,
wherein the bonds starting from (b)-(t) lead to a saturated or aromatic carbon atom of the adjacent group if the bond starts from a heteroatom, and where not more than two (b)-(f) groups, three (g)-(h) groups and one (i)-(t) group are present;
$R^3$ is hydrogen, hydroxyl, $C_{1-8}$-alkoxy or $C_{2-8}$-alkenyloxy;
$R^4$ is hydrogen, $C_{1-8}$-alkoxy, $C_{1-8}$-alkoxy-$C_{1-8}$-alkoxy, $C_{1-8}$-alkoxy-$C_{1-8}$-alkyl, $C_{1-8}$-alkyl, optionally (N—$C_{1-8}$-alkyl)-$C_{1-8}$-alkoxycarbonyl-amino-$C_{1-8}$-alkoxy, optionally (N—$C_{1-8}$-alkyl)-$C_{1-8}$-alkylcarbonyl-amino-$C_{1-8}$-alkoxy, optionally (N-mono- or N,N-di-$C_1$-$C_8$-alkyl)-amino-$C_{1-8}$-alkoxy, $C_{3-8}$-cycloalkyloxy, $C_{3-8}$-cycloalkyloxy-$C_{1-8}$-alkoxy, heterocyclyl-$C_{0-8}$-alkoxy, heterocyclyloxy-$C_{1-8}$-alkoxy, hydroxy, oxo or hydroxy-$C_{1-8}$-alkoxy-$C_{1-8}$-alkoxy;
$R^5$ and $R^6$ are each independently hydrogen, $C_{1-8}$-alkyl or acyl, or, together with the nitrogen atom to which they are bonded, are a 5- or 6-membered heterocyclic ring which may contain an additional nitrogen, oxygen or sulfur atom;
$R^7$ and $R^8$, together with the carbon atom to which they are bonded, are a 3-7-membered ring which may contain one or two —O— or —S— atoms;
$R^9$ is hydrogen, $C_{1-8}$-alkyl, acyl or arylalkyl;
U is hydrogen, $C_{1-8}$-alkyl, $C_{3-8}$-cycloalkyl, cyano, aryl or heterocyclyl;
Q is absent;
X is a bond, oxygen, sulfur or is a >$CHR^{11}$, >$CHOR^9$, —O—CO—, >CO or —O—CH—$R^{11}$—CO—$NR^9$— group;
W is oxygen or sulfur if $R^3$ is hydrogen;
Z is $C_{1-8}$-alkylene or -alk-O—; wherein, if X is a bond, Z is -alk-O—;
n is 0 or 1;
m is 0 or 1;
or a pharmaceutically useable salt thereof.

8. A compound according to claim 2, wherein
$R^2$ is phenyl or halophenyl each substituted by $C_{2-8}$-alkenyloxy, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxy-$C_{1-8}$-alkyl-amino -$C_{1-8}$-alkyl, $C_{1-8}$-alkyl, $C_{1-8}$-alkoxy-$C_{1-8}$-alkylsulfanyl, $C_{1-8}$-alkylsulfanyl, $C_{1-8}$-alkylsulfanyl-$C_{1-8}$-alkyl, $C_{1-8}$-alkylsulfanyl-$C_{1-8}$-alkoxy, $C_{1-8}$-alkylsulfanyl-$C_{1-8}$-alkoxy-$C_{1-8}$-alkyl, $C_{3-8}$-cycloalkylsulfanyl-$C_{1-8}$-alkyl, $C_{1-8}$-alkylsulfonyl-$C_{1-8}$-alkoxy-$C_{1-8}$-alkyl, $C_{3-8}$-cycloalkyl-$C_{0-6}$-alkoxy, $C_{3-8}$-cycloalkyl-$C_{0-6}$-alkoxy-$C_{1-8}$-alkoxy, $C_{3-8}$-cycloalkyl-$C_{0-6}$-alkoxy-$C_{1-8}$-alkyl, $C_{1-6}$-alkoxy-$C_{0-6}$-alkyl-$C_{3-8}$-cycloalkyl-$C_{0-6}$-alkoxy-$C_{1-8}$-alkyl, $C_{3-8}$-cycloalkyl-$C_{1-8}$-alkylamino-$C_{1-8}$-alkyl, halogen, heterocyclyl-$C_{0-6}$-alkoxy, heterocyclyl-$C_{0-6}$-alkoxy-$C_{1-8}$-alkyl, $C_{1-8}$-alkoxy-$C_{1-8}$-alkylamino-$C_{1-8}$-alkyl, N-(halo-phenyl)pyrrolidinyloxy, N-(halo-phenyl)pyrrolidinyloxy-$C_{1-8}$-alkyl, $C_{1-8}$-alkoxybenzyloxy-$C_{1-8}$-alkoxy, $C_{1-8}$-alkoxyphenoxy-$C_{1-8}$-alkoxy, $C_{1-8}$-alkoxyphenoxy-$C_{1-8}$-alkyl, $C_{1-8}$-alkoxyphenyl-$C_{1-8}$-alkoxy-$C_{1-8}$-alkoxy, halobenzyloxy-$C_{1-8}$-alkoxy, halophenoxy-$C_{1-8}$-alkoxy, halophenoxy-$C_{1-8}$-alkoxy-$C_{1-8}$-alkyl, halophenoxy-$C_{1-8}$-alkyl, halophenyl-$C_{1-8}$-alkoxy-$C_{1-8}$-alkoxy or $C_{1-8}$-alkylbenzyloxy-$C_{1-8}$-alkoxy, whereby at least one substituent is in the para-position relative to the bond of $R^2$ to the rest of the molecule.

9. A compound according to claim 2, wherein m is 0.

10. A pharmaceutical composition comprising a compound of the formula (IA) according to claim 2, and a pharmaceutically inert excipient.

11. A method for treating hypertension, glaucoma, cardiac infarction, or restenoses, which comprises administering a therapeutically effective amount of a compound of formula (I) according to claim 1 to a patient in need thereof.

12. A method for treating hypertension, glaucoma, cardiac infarction, or restenoses, which comprises administering a therapeutically effective amount of a compound of formula (IA) according to claim 2 to a patient in need thereof.

* * * * *